US012692259B2

(12) United States Patent
Liotta et al.

(10) Patent No.: US 12,692,259 B2
(45) Date of Patent: Jul. 28, 2026

(54) MORPHOLINE-CONTAINING AND PIPERAZINE-CONTAINING CXCR4 MODULATORS AND USES RELATED THERETO

(71) Applicant: Emory University, Atlanta, GA (US)

(72) Inventors: Dennis C. Liotta, Atlanta, GA (US); Edgars Jecs, Atlanta, GA (US); Yesim Altas Tahirovic, Atlanta, GA (US); Eric Miller, Atlanta, GA (US); Lawrence Wilson, Atlanta, GA (US)

(73) Assignee: Emory University, Atlanta, GA (US)

( * ) Notice: Subject to any disclaimer, the term of this patent is extended or adjusted under 35 U.S.C. 154(b) by 329 days.

(21) Appl. No.: 18/580,797

(22) PCT Filed: Jul. 19, 2022

(86) PCT No.: PCT/US2022/037568
§ 371 (c)(1),
(2) Date: Jan. 19, 2024

(87) PCT Pub. No.: WO2023/003862
PCT Pub. Date: Jan. 26, 2023

(65) Prior Publication Data

US 2024/0368146 A1 Nov. 7, 2024

Related U.S. Application Data

(60) Provisional application No. 63/223,387, filed on Jul. 19, 2021.

(51) Int. Cl.

| | |
|---|---|
| ***C07D 413/14*** | (2006.01) |
| ***A61K 31/4725*** | (2006.01) |
| ***A61K 31/496*** | (2006.01) |
| ***A61K 31/5377*** | (2006.01) |
| ***A61K 31/5383*** | (2006.01) |
| ***C07D 401/12*** | (2006.01) |
| ***C07D 401/14*** | (2006.01) |
| ***C07D 471/04*** | (2006.01) |
| ***C07D 471/14*** | (2006.01) |
| ***C07D 491/052*** | (2006.01) |
| ***C07D 491/08*** | (2006.01) |
| ***C07D 498/04*** | (2006.01) |

(52) U.S. Cl.
CPC ........ *C07D 413/14* (2013.01); *A61K 31/4725* (2013.01); *A61K 31/496* (2013.01); *A61K 31/5377* (2013.01); *A61K 31/5383* (2013.01); *C07D 401/12* (2013.01); *C07D 401/14* (2013.01); *C07D 471/04* (2013.01); *C07D 471/14* (2013.01); *C07D 491/052* (2013.01); *C07D 491/08* (2013.01); *C07D 498/04* (2013.01)

(58) Field of Classification Search
CPC .......................... C07D 413/14; A61K 31/5377
USPC ....................................... 544/128; 514/233.5
See application file for complete search history.

(56) References Cited

U.S. PATENT DOCUMENTS

| | | | |
|---|---|---|---|
| 7,354,934 | B2 | 4/2008 | Bridger et al. |
| 7,863,293 | B2 | 1/2011 | Bridger et al. |
| 8,008,312 | B2 | 8/2011 | Shim |
| 8,969,381 | B2 | 3/2015 | Wilson |
| 9,545,403 | B2 | 1/2017 | Wilson |
| 10,016,408 | B2 | 7/2018 | Wilson |
| 11,497,744 | B2 | 11/2022 | Liotta |
| 2010/0280010 | A1 | 11/2010 | Gunmundsson |
| 2023/0112832 | A1 | 4/2023 | Liotta |
| 2024/0316034 | A1 | 9/2024 | Liotta |

FOREIGN PATENT DOCUMENTS

| | | |
|---|---|---|
| CN | 102675305 | 11/2014 |
| CN | 103570683 | 4/2018 |
| WO | 20060020415 | 2/2006 |
| WO | 2006023400 | 3/2006 |
| WO | 2006026703 | 3/2006 |
| WO | 2007027999 | 3/2007 |
| WO | 2007087548 | 8/2007 |
| WO | 2007087549 | 8/2007 |
| WO | 2009121063 | 10/2009 |
| WO | 2012075362 | 6/2012 |
| WO | 2017011517 | 1/2017 |
| WO | 2017106291 | 6/2017 |

(Continued)

OTHER PUBLICATIONS

Balabanian et al. CXCR4-Tropic HIV-1 Envelope Glycoprotein Functions as a Viral Chemokine in Unstimulated Primary CD4+ T Lymphocytes, J Immunology, 2004, 173: 7150-7160.

(Continued)

*Primary Examiner* — Charanjit Aulakh

(74) *Attorney, Agent, or Firm* — Emory Patent Group

(57) ABSTRACT

CXCR4 antagonists and pharmaceutical formulations thereof are disclosed. The compounds and pharmaceutical formulations disclosed herein can be used to antagonize the CXCR4 pathway for mobilizing stem cells or treating a condition, disorder, or disease associated with the CXCR4 pathway. Exemplary conditions, disorders, and diseases relevant to this disclosure include HIV infections, WHIM syndrome, Waldenström macroglobulinemia, chronic neutropenia, primary immune-deficiency, aplastic anemia, hypoplastic myelodysplastic syndrome, acute respiratory distress syndrome (ARDS), ankylosing spondylitis, autoimmune diseases, and cancers.

12 Claims, No Drawings

(56) References Cited

FOREIGN PATENT DOCUMENTS

| | | | |
|---|---|---|---|
| WO | 2017223239 | 12/2017 | |
| WO | 2017223243 | 12/2017 | |
| WO | WO 2018-156595 A1 * | 8/2018 | ......... A61K 31/4709 |
| WO | 2019060860 | 3/2019 | |

OTHER PUBLICATIONS

Briz, et al., HIV entry inhibitors: mechanisms of action and resistance pathways, J Antimicrob Chemother, 2006, 57(4), 619-627.
Cameron, et al., Establishment of HIV-1 latency in resting CD4+ T cells depends on chemokine-induced changes in the actin cytoskeleton, PNAS USA, 2010, 107(39), 16934-16939.
Catalano, et al., Synthesis of a Novel Tricyclic 1,2,3,4,4a,5,6,10b-Octahydro-1,10-Phenanthroline Ring System and CXCR4 Antagonists with Potent Activity Against HIV-1, Bioorg. Med. Chem. Lett., 2010, 20, 2186-2190.
Challita-Eid, et al., Inhibition of HIV Type 1 Infection with a RANTES-IgG3 Fusion Protein, AIDS Research and Human Retroviruses, 1998, 14, 1617-1624.
Crane, et al., CXCR4 Receptor Expression on Human Retinal Pigment Epithelial Cells from the Blood-Retina Barrier Leads to Chemokine Secretion and Migration in Response to Stromal Cell-Derived Factor 1α, J. Immunol., 2000, 165, 4372-4278.
Debnath, et al., Small Molecule Inhibitors of CXCR4, Theranostics, 2013, 3(1), 47-75.
Dwinell, et al., Chemokine receptor expression by human intestinal epithelial cells, Gastroenterology, 1999, 117, 359-367.
Gudmundsson, et al., Amine Substituted N-(1H-Benzimidazol-2ylmethyl)-5,6,7,8-Tetrahydro-8-Quinolinamines as CXCR4 Antagonists with Potent Activity against HIV-1, Bioorg. Med. Chem. Lett., 2009, 19, 5048-5052.
Gudmundsson, et al., Imidazopyridine-5,6,7,8-tetrahydro-8-quinolinamine derivatives with potent activity against HIV-1, Bioorg. Med. Chem. Lett., 2009, 19, 6399-6403.
Gupta, et al., Chemokine receptors in human endothelial cells. Functional expression of CXCR4 and its transcriptional regulation by inflammatory cytokines, J Biol Chem., 1998, 273, 4282-4287.
Jecs, et al., Synthesis of Novel Tetrahydroisoquinoline CXCR4 Antagonists with Rigidified Side-Chains, ACS Med. Chem. Lett., 2018, 9(2), 89-93.
Jenkinson, et al., Blockade of X4-Tropic HIV-1 Cellular Entry by GSK812397, a Potent Noncompetitive CXCR4 Receptor Antagonist, Antimicrob. Agents Chemother, 2010, 54(2), 817-824.
Kang, et al., A multigenic program mediating breast cancer metastasis to bone, Cancer Cell, 2003, 3, 537-549.
Li, et al., Design, Synthesis, and Structure-Activity-Relationship of a Novel Series of CXCR4 Antagonists, Eur. J. Med. Chem., 2018, 149, 30-44.
Li, et al., Design, Synthesis, and Evaluation of Pyrrolidine Based CXCR4 Antagonists with in Vivo Anti-Tumor Metastatic Activity, Eur. J. Med. Chem., 2020, 205, 112537.
Lin, et al., Design, Synthesis, and Evaluation of Novel CXCR4 Antagonists Based on an Aminoquinoline Template, Bioorg. Chem., 2020, 99, 103824.
Lin, et al., Design, Synthesis, and Characterization of Novel CXCR4 Antagonists Featuring Cyclic Amines, ChemMedChem, 2020, 15, 1150-1162.
Miller, et al., Novel N-Substituted Benzimidazole CXCR4 Antagonists as Potential Anti-HIV Agents, Bioorg. Med. Chem. Lett., 2010, 20, 2125-2128.
Miller, et al., Synthesis and SAR of Novel Isoquinoline CXCR4 Antagonists with Potent Anti-HIV Activity, Bioorg. Med. Chem. Lett., 2010, 20, 3026-3030.
Miller, et al., Discovery of Tetrahydroisoquinoline-Containing CXCR4 Antagonists with Improved in Vitro ADMET Properties, J. Med. Chem., 2018, 61, 946-979.
Mitra, et al., CXCR4 mRNA expression in colon, esophageal and gastric cancers and hepatitis C infected liver, Int J Oncol, 1999, 14, 917-925.
Moyle, et al., Proof of activity with AMD11070, an orally bioavailable inhibitor of CXCR4-tropic HIV type 1, Clin Inf Diseases, 2009, 48(6), 798-805.
Muller, et al., Involvement of chemokine receptors in breast cancer metastasis, Nature, 2001, 410, 50-56.
Murdoch, et al., Functional expression of chemokine receptor CXCR4 on human epithelial cells, Immunology, 1998, 98 (1), 36-41.
Nguyen, et al., Design, Synthesis, and Pharmacological Evaluation of Second-Generation Tetrahydroisoquinoline-Based CXCR4 Antagonists with Favorable ADME Properties, J. Med. Chem. 2018, 61, 7168-7188.
Peng, et al., The Chemical Diversity and Structure-Based Evolution of Non-Peptide CXCR4 Antagonists with Diverse Therapeutic Potential, Eur. J. Med. Chem., 2018, 149, 148-169.
Sahin et al. Small molecule and peptide CXCR4 antagonists—A patent review from 2019 to 2024, Expert Opinion on Therapeutic Patents, 35:4, 357-369.
Skerlj, et al., Synthesis and SAR of Novel CXCR4 Antagonists That Are Potent Inhibitors of T-Tropic (X4) HIV-1 Replication, Bioorg. Med. Chem. Lett., 2011, 21, 1414-1418.
Skerlj, et al., Discovery of Novel Small Molecule Orally Bioavailable C-X-C Chemokine Receptor 4 Antagonists That Are Potent Inhibitors of T-Tropic (X4) HIV-1 Replication, J. Med. Chem., 2010, 53(8), 3376-3388.
Staller, et al., Chemokine receptor CXCR4 downregulated by von Hippel-Lindau tumour suppressor pVHL, Nature, 2003, 425, 307-311.
Tahirovic, et al., Discovery of N-Alkyl Piperazine Side Chain Based CXCR4 Antagonists with Improved Drug-like Properties, ACS Med. Chem. Lett., 2018, 9, 446-451.
Tahirovic, et al., Small Molecule and Peptide-Based CXCR4 Modulators as Therapeutic Agents. A Patent Review for the Period from 2010 to 2018, Expert Opin. Ther. Pat., 2020, 30(2), 87-10.
Truax, et al., Discovery of Tetrahydroisoquinoline-Based CXCR4 Antagonists, ACS Med. Chem. Lett., 2013, 4, 1025-1030.
Volin, et al., Chemokine Receptor CXCR4 Expression in Endothelium, Biochem Biophys Res Commnun, 1998, 242, 46-53.
Wald, et al., Involvement of the CXCL12/CXCR4 pathway in the advanced liver disease that is associated with hepatitis C virus or hepatitis B virus, Eur J Immun, 2004, 34(4), 1164-1174.
Westby, et al., Emergence of CXCR4-Using Human Immunodeficiency Virus Type 1 (HIV-1) Variants in a Minority of HIV-1-Infected Patients following Treatment with the CCR5 Antagonist Maraviroc Is from a Pretreatment CXCR4-Using Virus Reservoir, Journal of Virology, 2006, 80, 4909-4920.
Wilson, et al., Synthesis and SAR of 1,2,3,4-Tetrahydroisoquinoline-Based CXCR4 Antagonists, ACS Med. Chem. Lett., 2018, 9, 17-22.
Wu, et al., Chemokine Coreceptor Signaling in HIV-1 Infection and Pathogenesis, PLoS Pathogens, 2009, 5(12).
Zhang, et al., Discovery of non-peptide small molecular CXCR4 antagonists as anti-HIV agents: Recent advances and future opportunities, European Journal of Medicinal Chemistry, 114, 2016, 65-78.
Zhao, et al., Discovery of Novel N-Aryl Piperazine CXCR4 Antagonists, Bioorg. Med. Chem. Lett., 2015, 25, 4950-4955.
Zhu, et al., Structural Optimization of Aminopyrimidine-Based CXCR4 Antagonists, Eur. J. Med. Chem., 2020, 187, 111914.

* cited by examiner

MORPHOLINE-CONTAINING AND PIPERAZINE-CONTAINING CXCR4 MODULATORS AND USES RELATED THERETO

CROSS-REFERENCE TO RELATED APPLICATIONS

This application is the National Stage of International Application No. PCT/US2022/037568 filed Jul. 19, 2022, which claims the benefit of U.S. Provisional Application No. 63/223,387 filed Jul. 19, 2021. The entirety of each of these applications is hereby incorporated by reference for all purposes.

TECHNICAL FIELD

The present disclosure relates to CXCR4 modulators. It also relates to pharmaceutical formulations of the CXCR4 modulators and methods for treating conditions, disorders, or diseases using the CXCR4 modulators.

BACKGROUND

CXCR4 is a seven-transmembrane G protein-coupled receptor (GPCR) that responds to its endogenous ligand CXCL12 (SDF-1). CXCR4 is expressed in many cell types, including hematopoietic stem cells (HSCs), leukocytes, and endothelial cells. CXCR4 has been the center of intense study due to the vital roles it plays in immune system regulation. It has been implicated in the pathology of many human diseases. Initially, CXCR4 was discovered as a receptor required for T-tropic HIV entry. Further research showed that it also plays a critical role in an array of important biological processes, such as HSC quiescence and homing to the bone marrow, chemotaxis, and cell survival and proliferation.

Notably, CXCR4 is expressed in over 48 different types of cancers including various hematological malignancies (e.g., leukemias and lymphomas), as well as solid tumors, such as ovarian, breast, lung, colorectal, and prostate cancers (Chatterjee, et. al., *Adv Cancer Res.*, 2014, 124, 31-82; Mishan, et al., *Cell Biol. Int.*, 2016, 40, 955-967; Furusato, et al., *Pathol. Int.*, 2010, 60(7), 497-505; Domanska, et al., *Eur. J. Cancer,* 2013, 49(1), 219-230). Tumor-associated stromal cells constitutively express and secrete CXCL12, which is then available to stimulate CXCR4-expressing tumor cells. This paracrine signaling promotes the proliferation and survival of CXCR4-expressing tumor cells. Moreover, CXCR4-expressing tumor cells migrate along the CXCL12 gradient to distant organs showing peak levels of CXCL12 expression, leading to metastasis. For example, tumor cells utilize CXCR4 to access the CXCL12-rich bone marrow microenvironment that favors their growth and survival. High levels of CXCL12 secretion by bone marrow stromal cells are essential for homing of CXCR4-expressing tumor cells to this common site of metastatic expansion. Furthermore, high expression of CXCL12 by tumor cells and tumor-associated stromal cells forms a local gradient of the chemokine in the tumor region. CXCR4-expressing, pro-angiogenic and pro-vasculogenic cells are in turn recruited to the tumor, where they contribute to vasculogenesis by supporting newly formed blood vessels and releasing other pro-angiogenic factors.

CXCR4 antagonists can inhibit the crosstalk between tumor and stromal cells and mobilize cancer cells from protective stromal niches, thereby making them more sensitive to standard chemotherapy and radiation therapy. The development of CXCR4 antagonists began simultaneously with the discovery of the receptor itself. For example, AMD3100 (plerixafor) is the first CXCR4-targeting, FDA-approved drug. It was originally identified as an HIV-entry inhibitor and later developed into an HSC mobilization agent used for autologous stem cell transplantation in the treatment of non-Hodgkin's lymphoma and multiple myeloma. The next CXCR4 antagonist of clinical significance is AMD11070 (X4P-001 or mavorixafor). This compound was initially investigated for HIV infection (discontinued during Phase II clinical trials) but was recently revived for use in the emerging field of immuno-oncology. However, AMD3100 suffers from low oral bioavailability, and AMD11070 has poor metabolic stability and significant inhibition of the main CYP450 isoforms 3A4 and 2D6, leading to a significant risk of drug-drug interaction. They also suffer from cardiotoxicity and hepatotoxicity.

Accordingly, there is an urgent need for newer and safer CXCR4 antagonists with improved pharmacokinetic and therapeutic profiles.

SUMMARY

The present disclosure describes CXCR4 antagonists. Generally, the compounds contain an N-morpholine-substituted tetrahydroisoquinoline (THIQ) motif. In some embodiments, the compounds have potent activity against CXCR4, low or no CYP450 inhibition, high metabolic stability, and excellent cell permeability. The compounds can be used for mobilizing stem cells and treating a wide range of CXCR4-related diseases, disorders, and conditions.

Also disclosed are compositions containing a compound described herein, wherein the compound is in greater than 80%, 85%, 90%, or 95% enantiomeric or diastereomeric excess. In some embodiments, the compound in the compositions is in greater than 95% enantiomeric or diastereomeric excess.

Also disclosed are pharmaceutical formulations of the disclosed compounds or compositions. In general, the pharmaceutical formulations contain a pharmaceutically acceptable excipient. In some embodiments, the pharmaceutical formulations are in a form chosen from tablets, capsules, caplets, pills, beads, granules, particles, powders, gels, creams, solutions, suspensions, emulsions, and nanoparticulate formulations. In some embodiments, the pharmaceutical formulations are oral formulations. In some embodiments, the pharmaceutical formulations are intravenous formulations. In some embodiments, the pharmaceutical formulations are intramuscular formulations.

This disclosure also relates to (1) the compounds, compositions, and pharmaceutical formulations disclosed herein for treatment of a condition, disorder, or disease disclosed herein or use as a medicament, (2) the compounds, compositions, and pharmaceutical formulations disclosed herein for use in the treatment of a condition, disorder, or disease disclosed herein, or (3) the compounds, compositions, and pharmaceutical formulations disclosed herein for the manufacture of a medicament for treatment of a condition, disorder, or disease disclosed herein.

This disclosure also provides methods of treating a condition, disorder, or disease in a subject in need thereof. The method includes administering an effective amount of a compound, composition, or pharmaceutical formulation disclosed herein to the subject. In some embodiments, the compound, composition, or pharmaceutical formulation is administered orally, intravenously, or intramuscularly.

Exemplary conditions, disorders, and diseases relevant to this disclosure include, but are not limited to, such as HIV infections, WHIM syndrome, Waldenstrom macroglobulinemia, chronic neutropenia, primary immune-deficiency, aplastic anemia, hypoplastic myelodysplastic syndrome, acute respiratory distress syndrome (ARDS), ankylosing spondylitis, autoimmune diseases, and cancers.

DETAILED DESCRIPTION

The present disclosure describes CXCR4 antagonists and pharmaceutical formulations thereof. It also describes methods for mobilizing stem cells or treating a condition, disorder, or disease associated with the CXCR4 using the CXCR4 antagonists and pharmaceutical formulations thereof.

Before the present disclosure is described in greater detail, it is to be understood that this disclosure is not limited to the particular embodiments described herein, and as such, may vary in accordance with the scope of the present disclosure. Unless defined otherwise, all technical and scientific terms used herein have the same meaning as commonly understood by one of ordinary skill in the art to which this disclosure belongs.

All publications and patents cited in this specification are herein incorporated by reference as if each individual publication and patent were specifically and individually indicated to be incorporated by reference. They are incorporated by reference to disclose and describe the methods and/or materials in connection with which the publications and patents are cited.

As will be apparent to those of ordinary skill in the art upon reading this disclosure, each of the particular embodiments described and illustrated herein has discrete components and/or features that may be readily separated from or combined with one or more components and/or features of any of the other embodiments described herein, without departing from the scope or spirit of the present disclosure. Any recited method can be carried out in the order of events recited herein or in any other order that is logically possible.

Embodiments of the present disclosure will employ, unless otherwise indicated, techniques of medicine, organic chemistry, medicinal chemistry, biochemistry, molecular biology, pharmacology, neurology, and the like, which are within the skill of the art. Such techniques are explained fully in the literature, such as the publications and patents cited herein.

I. DEFINITIONS

As used herein, the singular forms "a," "an," and "the" include plural referents unless the context clearly dictates otherwise.

The terms "may," "may be," "can," and "can be," and related terms are intended to convey that the subject matter involved is optional (that is, the subject matter is present in some examples and is not present in other examples), not a reference to a capability of the subject matter or to a probability, unless the context clearly indicates otherwise.

The terms "optional" and "optionally" mean that the subsequently described event, circumstance, or material may or may not occur or be present, and that the description includes instances where the event, circumstance, or material occurs or is present as well as instances where it does not occur or is not present.

Use of the term "about" is intended to describe values either above or below the stated value in a range of approx. +/−10%; in other examples the values may range in value either above or below the stated value in a range of approx. +/−5%; in other examples the values may range in value either above or below the stated value in a range of approx. +/−2%; in other examples the values may range in value either above or below the stated value in a range of approx. +/−1%.

A carbon range (e.g., $C_1$-$C_{10}$) is intended to disclose individually every possible carbon value and/or sub-range encompassed within. For example, a carbon range of $C_1$-$C_{10}$ discloses $C_1$, $C_2$, $C_3$, $C_4$, $C_5$, $C_6$, $C_7$, $C_8$, $C_9$, and $C_{10}$, as well as sub-ranges encompassed therein, such as $C_2$-$C_9$, $C_3$-$C_8$, $C_1$-$C_5$, etc.

As used herein, the term "subject" refers to an animal, including human and non-human animals. Human subjects may include pediatric patients and adult patients. Non-human animals may include domestic pets, livestock and farm animals, and zoo animals. In some cases, the non-human animals may be non-human primates.

As used herein, the terms "prevent" and "preventing" include the prevention of the occurrence, onset, spread, and/or recurrence. It is not intended that the present disclosure is limited to complete prevention. For example, prevention is considered as achieved when the occurrence is delayed, the severity of the onset is reduced, or both.

As used herein, the terms "treat" and "treating" include medical management of a condition, disorder, or disease of a subject as would be understood by a person of ordinary skill in the art (see, for example, Stedman's Medical Dictionary). In general, treatment is not limited to cases where the subject is cured and the condition, disorder, or disease is eradicated. Rather, treatment also contemplates cases where a treatment regimen containing one of the compounds, compositions, or pharmaceutical formulations of the present disclosure provides an improved clinical outcome. The improved clinical outcome may include one or more of the following: abatement, lessening, and/or alleviation of one or more symptoms that result from or are associated with the condition, disorder, or disease to be treated; decreased occurrence of one or more symptoms; improved quality of life; diminishment of the extent of the condition, disorder, or disease; reaching or establishing a stabilized state (i.e., not worsening) of the condition, disorder, or disease; delay or slowing of the progression of the condition, disorder, or disease; amelioration or palliation of the state of the condition, disorder, or disease; partial or total remission; and improvement in survival (whether increase in the overall survival rate or prolonging of survival when compared to expected survival if the subject were not receiving the treatment).

The terms "derivative" and "derivatives" refer to chemical compounds/moieties with a structure similar to that of a parent compound/moiety but different from it in respect to one or more components, functional groups, atoms, etc. Optionally, the derivatives retain certain functional attributes of the parent compound/moiety. Optionally, the derivatives can be formed from the parent compound/moiety by chemical reaction(s). The differences between the derivatives and the parent compound/moiety can include, but are not limited to, replacement of one or more functional groups with one or more different functional groups or introducing or removing one or more substituents of hydrogen atoms.

The term "alkyl" refers to univalent groups derived from alkanes (i.e., acyclic saturated hydrocarbons) by removal of a hydrogen atom from any carbon atom. Alkyl groups can be linear or branched. Suitable alkyl groups can have one to 30 carbon atoms, i.e., $C_1$-$C_{30}$ alkyl. If the alkyl is branched, it is understood that at least three carbon atoms are present.

The term "alkenyl" refers to univalent groups derived from alkenes by removal of a hydrogen atom from any carbon atom. Alkenes are unsaturated hydrocarbons that contain at least one carbon-carbon double bond. Alkenyl groups can be linear or branched. Suitable alkenyl groups can have two to 30 carbon atoms, i.e., $C_2$-$C_{30}$ alkenyl. If the alkenyl is branched, it is understood that at least three carbon atoms are present.

The term "alkynyl" refers to univalent groups derived from alkynes by removal of a hydrogen atom from any carbon atom. Alkynes are unsaturated hydrocarbons that contain at least one carbon-carbon triple bond. Alkynyl groups can be linear or branched. Suitable alkynyl groups can have two to 30 carbon atoms, i.e., $C_2$-$C_{30}$ alkynyl. If the alkynyl is branched, it is understood that at least four carbon atoms are present.

The term "aryl" refers to univalent groups derived from arenes by removal of a hydrogen atom from a ring atom. Arenes are monocyclic or polycyclic aromatic hydrocarbons. In polycyclic arenes, the rings can be attached together in a pendant manner, a fused manner, or a combination thereof. Accordingly, in polycyclic aryl groups, the rings can be attached together in a pendant manner, a fused manner, or a combination thereof. Suitable aryl groups can have six to 30 carbon atoms, i.e., $C_6$-$C_{30}$ aryl. The number of "members" of an aryl group refers to the total number of carbon atoms in the ring(s) of the aryl group.

The term "heteroaryl" refers to univalent groups derived from heteroarenes by removal of a hydrogen atom from a ring atom. Heteroarenes are heterocyclic compounds derived from arenes by replacement of one or more methine (—C═) and/or vinylene (—CH═CH—) groups by trivalent or divalent heteroatoms, respectively, in such a way as to maintain the continuous π-electron system characteristic of aromatic systems and a number of out-of-plane π-electrons corresponding to the Hückel rule (4n+2). Heteroarenes can be monocyclic or polycyclic. In polycyclic heteroarenes, the rings can be attached together in a pendant manner, a fused manner, or a combination thereof. Accordingly, in polycyclic heteroaryl groups, the rings can be attached together in a pendant manner, a fused manner, or a combination thereof. Suitable heteroaryl groups can have one to 30 carbon atoms, i.e., $C_1$-$C_{30}$ heteroaryl. The number of "members" of a heteroaryl group refers to the total number of carbon atom(s) and heteroatom(s) in the ring(s) of the heteroaryl group.

"Carbocycle" or "carbocyclyl" refers to mono- and polycyclic ring systems containing only carbon atoms as ring atoms. The mono- and polycyclic ring systems may be aromatic, non-aromatic (saturated or unsaturated), or a mixture of aromatic and non-aromatic rings. Carbocyclyls are univalent, derived from carbocycles by removal of a hydrogen atom from a ring atom. Carbocycles include arenes; carbocyclyls include aryls. In polycyclic carbocycles or carbocyclyls, the rings can be attached together in a pendant manner (i.e., two rings are connected by a single bond), a spiro manner (i.e., two rings are connected through a defining single common atom), a fused manner (i.e., two rings share two adjacent atoms; in other words, two rings share one covalent bond), a bridged manner (i.e., two rings share three or more atoms, separating the two bridgehead atoms by a bridge containing at least one atom), or a combination thereof. Suitable carbocycle or carbocyclyl groups can have three to 30 carbon atoms, i.e., $C_3$-$C_{30}$ carbocycle or carbocyclyl. The number of "members" of a carbocycle or carbocyclyl group refers to the total number of carbon atoms in the ring(s) of the carbocycle or carbocyclyl group.

"Heterocycle" or "heterocyclyl" refers to mono- and polycyclic ring systems containing at least one carbon atom and one or more heteroatoms independently selected from elements like nitrogen, oxygen, and sulfur, as ring atoms. Optionally, the nitrogen and/or sulphur heteroatom(s) may be oxidized, and the nitrogen heteroatom(s) may be quaternized. The mono- and polycyclic ring systems may be aromatic, non-aromatic, or a mixture of aromatic and non-aromatic rings. Heterocyclyls are univalent, derived from heterocycles by removal of a hydrogen atom from a ring atom. Heterocycles include heteroarenes; heterocyclyls include heteroaryls. In polycyclic heterocycle or heterocyclyl groups, the rings can be attached together in a pendant manner (i.e., two rings are connected by a single bond), a spiro manner (i.e., two rings are connected through a defining single common atom), a fused manner (i.e., two rings share two adjacent atoms; in other words, two rings share one covalent bond), a bridged manner (i.e., two rings share three or more atoms, separating the two bridgehead atoms by a bridge containing at least one atom), or a combination thereof. Suitable heterocycle or heterocyclyl groups can have one to 30 carbon atoms, i.e., $C_1$-$C_{30}$ heterocycle or heterocyclyl. The number of "members" of a heterocycle or heterocyclyl group refers to the total number of carbon atom(s) and heteroatom(s) in the ring(s) of the heterocycle or heterocyclyl group.

As used herein, the terms "halogen" and "halo" refer to fluorine, chlorine, bromine, and iodine.

As used herein, "haloalkyl" refers to halogen-substituted alkyl groups. Optionally, the haloalkyl groups contain one halogen substituent. Optionally, the haloalkyl groups contain multiple halogen substituents, i.e., polyhaloalkyl. In some examples, the haloalkyl groups contain one or more fluorine substituents.

As used herein, "haloalkenyl" refers to halogen-substituted alkenyl groups. Optionally, the haloalkenyl groups contain one halogen substituent. Optionally, the haloalkenyl groups contain multiple halogen substituents. In some examples, the haloalkenyl groups contain one or more fluorine substituents.

As used herein, "haloalkynyl" refers to halogen-substituted alkynyl groups. Optionally, the haloalkynyl groups contain one halogen substituent. Optionally, the haloalkynyl groups contain multiple halogen substituents. In some examples, the haloalkynyl groups contain one or more fluorine substituents.

As used herein, "halocarbocyclyl" refers to halogen-substituted carbocyclyl groups. Optionally, the halocarbocyclyl groups contain one halogen substituent. Optionally, the halocarbocyclyl groups contain multiple halogen substituents. In some examples, the halocarbocyclyl groups contain one or more fluorine substituents.

As used herein, "haloheterocyclyl" refers to halogen-substituted heterocyclyl groups. Optionally, the haloheterocyclyl groups contain one halogen substituent. Optionally, the haloheterocyclyl groups contain multiple halogen substituents. In some examples, the haloheterocyclyl groups contain one or more fluorine substituents.

As used herein, "haloaryl" refers to halogen-substituted aryl groups. Optionally, the haloaryl groups contain one halogen substituent. Optionally, the haloaryl groups contain multiple halogen substituents. In some examples, the haloaryl groups contain one or more fluorine substituents.

As used herein, "haloheteroaryl" refers to halogen-substituted heteroaryl groups. Optionally, the haloheteroaryl groups contain one halogen substituent. Optionally, the haloheteroaryl groups contain multiple halogen substituents. In some examples, the haloheteroaryl groups contain one or more fluorine substituents.

The term "substituted," as used herein, means that the chemical group or moiety contains one or more substituents replacing the hydrogen atom(s) in the original chemical group or moiety.

It is understood that any substitution is in accordance with a permitted valence of the substituted atom and the substituent and that the substitution results in a stable compound, e.g., a compound that does not spontaneously undergo transformation such as by rearrangement, cyclization, elimination, etc., under room temperature. Unless otherwise specified, the substituents are R groups. The R groups, on each occurrence, can be independently selected from halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, haloheteroaryl, —OH, —SH, $—NH_2$, $—N_3$, —OCN, —NCO, $—ONO_2$, —CN, —NC, —ONO, $—CONH_2$, —NO, $—NO_2$, $—ONH_2$, —SCN, —SNCS, $—CF_3$, $—CH_2CF_3$, $—CH_2Cl$, $—CHCl_2$, $—CH_2NH_2$, —NHCOH, —CHO, —COOH, $—SO_3H$, $—CH_2SO_2CH_3$, $—PO_3H_2$, $—OPO_3H_2$, $—P(═O)(OR^{G1})(OR^{G2})$, $—OP(═O)(OR^{G1})(OR^{G2})$, $—BR^{G1}(OR^{G2})$, $—B(OR^{G1})(OR^{G2})$, $—Si(R^{G1})(R^{G2})(R^{G3})$, $—C(R^{G1})(R^{G2})(R^{G3})$, $—N[(R^{G1})(R^{G2})(R^{G3})]^+$, and $-GR^{G1}$, in which -G is —O—, —S—, $—NR^{G2}—$, —C═O—, —S(═O)—, $—SO_2—$, —C(═O)O—, $—C(═O)NR^{G2}—$, —OC(═O)—, $—NR^{G2}C(═O)—$, —OC(═O)O—, $—OC(═O)NR^{G2}—$, $—NR^{G2}C(═O)O—$, $—NR^{G2}C(═O)NR^{G3}$, —C(═S)—, —C(═S)S—, —SC(═S)—, —SC(═S)S—, $—C(═NR^{G2})—$, $—C(═NR^{G2})O—$, $—C(═NR^{G2})NR^{G3}—$, $—OC(═NR^{G2})—$, $—NR^{G2}C(═NR^{G3})—$, $—NR^{G2}SO_2—$, $—C(═NR^{G2})NR^{G3}—$, $—OC(═NR^{G2})—$, $—NR^{G2}C(═NR^{G3})—$, $—NR^{G2}SO_2—$, $—NR^{G2}SO_2NR^{G3}$, $—NR^{G2}C(═S)—$, $—SC(═S)NR^{G2}—$, $—NR^{G2}C(═S)S—$, $—NR^{G2}C(═S)NR^{G3}—$, $—SC(═NR^{G2})—$, $—C(═S)NR^{G2}—$, $—OC(═S)NR^{G2}—$, $—NR^{G2}C(═S)O—$, $—SC(═O)NR^{G2}—$, $—NR^{G2}C(═O)—$, —C(═O)S—, —S(═O)—, —SC(═O)S—, —C(═S)O—, —OC(═S)—, —OC(═S)O—, $—SO_2NR^{G2}—$, $—BR^{G2}—$, or $—PR^{G2}—$, wherein each occurrence of $R^{G1}$, $R^{G2}$, and $R^{G3}$ is independently selected from hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, and haloheteroaryl. Optionally, two R groups on the same atom can join together with that atom to form a cyclic moiety, such as a carbocycle or a heterocycle. Alternatively, two R groups on the same atom can merge into one oxygen (═O) or sulfur (═S) atom.

The term "optionally substituted," as used herein, means that substitution is optional, and therefore it is possible for the designated atom/chemical group/compound to be unsubstituted.

As used herein, "ester" refers to $—C(═O)OR^{g1}$ or $—OC(═O)R^{g2}$, wherein $R^{g1}$ and $R^{g2}$ are independently selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally and independently substituted by one or more R groups described above. Optionally, two R groups on the same atom can join together with that atom to form a cyclic moiety, such as a carbocycle or a heterocycle.

As used herein, "amino" refers to $—NR^{h1}R^2$, wherein $R^{h1}$ and $R^{h2}$ are independently selected from hydrogen, alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally and independently substituted by one or more R groups described above. Optionally, two R groups on the same atom can join together with that atom to form a cyclic moiety, such as a carbocycle or a heterocycle. When $R^{h1}$ and $R^{h2}$ are each hydrogen, the amino group is a primary amino group.

As used herein, "acyl" refers $—C(═O)R^1$, wherein $R^i$ is selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally substituted by one or more R groups described above. Optionally, two R groups on the same atom can join together with that atom to form a cyclic moiety, such as a carbocycle or a heterocycle.

As used herein, "amide" refers to $—C(═O)NR^{j1}R^{j2}$, wherein $R^{j1}$ and $R^{j2}$ are independently selected from hydrogen, alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally and independently substituted by one or more R groups described above. Optionally, two R groups on the same atom can join together with that atom to form a cyclic moiety, such as a carbocycle or a heterocycle. When $R^{j1}$ and $R^{j2}$ are each hydrogen, the amide group is a carbamoyl group.

As used herein, "thioacyl" refers $—C(═S)R^k$, wherein $R^k$ is selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally substituted by one or more R groups described above. Optionally, two R groups on the same atom can join together with that atom to form a cyclic moiety, such as a carbocycle or a heterocycle.

As used herein, "thioamide" refers $—C(═S)NR^{l1}R^{l2}$, wherein $R^{l1}$ and $R^{l2}$ are independently selected from hydrogen, alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally and independently substituted by one or more R groups described above. Optionally, two R groups on the same atom can join together with that atom to form a cyclic moiety, such as a carbocycle or a heterocycle. When $R^{l1}$ and $R^{l2}$ are each hydrogen, the amide group is a carbamoyl group.

As used herein, "sulfinyl" refers to $—S(═O)R^m$, wherein $R^m$ is selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally substituted by one or more R groups described above. Optionally, two R groups on the same atom can join together with that atom to form a cyclic moiety, such as a carbocycle or a heterocycle.

As used herein, "sulfonyl" refers to $—S(═O)_2R^n$, wherein $R^n$ is selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally substituted by one or more R groups described above. Optionally, two R groups on the same atom can join together with that atom to form a cyclic moiety, such as a carbocycle or a heterocycle.

As used herein, "thionoesters" refers to —C(═S)OR$^{o1}$, or —OC(═S)R$^{o2}$ wherein R$^{o1}$ and R$^{o2}$ are independently selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally and independently substituted by one or more R groups described above. Optionally, two R groups on the same atom can join together with that atom to form a cyclic moiety, such as a carbocycle or a heterocycle.

As used herein, "sulfonamide" refers to —S(═O)$_2$NR$^{p1}$R$^{p2}$, wherein R$^{p1}$ and R$^{p2}$ are independently selected from hydrogen, alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally and independently substituted by one or more R groups described above. Optionally, two R groups on the same atom can join together with that atom to form a cyclic moiety, such as a carbocycle or a heterocycle. When R$^{p1}$ and R$^{p2}$ are each hydrogen, the amide group is a sulfamoyl group.

As used herein, "sulfonic ester" refers to —S(═O)$_2$OR$^q$, wherein R$^q$ is selected from alkyl, alkenyl, alkynyl, carbocyclyl, heterocyclyl, aryl, and heteroaryl, wherein each of the alkyl, alkenyl, alkynyl, carbocyclyl, heterocyclyl, aryl, and heteroaryl can be optionally substituted by one or more R groups described above. Optionally, two R groups on the same atom can join together with that atom to form a cyclic moiety, such as a carbocycle or a heterocycle.

As used herein, "thiol" refers to the univalent radical —SH.

As used herein, "sulfonate" refers to —SO$_3^-$.

As used herein, the term "stereoisomer" refers to compounds made up of the same atoms having the same bond order but having different three-dimensional arrangements of atoms which are not interchangeable. As used herein, the term "enantiomer" refers to a pair of stereoisomers that are non-superimposable mirror images of one another. As used herein, the term "diastereomer" refers to two stereoisomers that are not mirror images but also not superimposable. The terms "racemate" and "racemic mixture" refer to a mixture of enantiomers. The term "chiral center" refers to a carbon atom to which four different groups are attached. Choice of the appropriate chiral column, eluent, and conditions necessary for effective separation of stereoisomers, such as a pair of enantiomers, is well known to one of ordinary skill in the art (e.g., Jacques et al., Enantiomers, Racemates, and Resolutions, John Wiley and Sons, Inc., 1981).

As used herein, the term "pharmaceutically acceptable" refers to compounds, materials, compositions, or formulations which are, within the scope of sound medical judgment, suitable for use in contact with the tissues of human beings and non-human animals without excessive toxicity, irritation, allergic response, or other problems or complications that commensurate with a reasonable benefit/risk ratio, in accordance with the guidelines of regulatory agencies of a certain country, such as the Food and Drug Administration (FDA) in the United States or its corresponding agencies in countries other than the United States (e.g., the European Medicines Agency (EMA) in Europe, the National Medical Products Administration (NMPA) in China).

As used herein, the term "salt" refers to acid or base salts of the original compound. In some cases, the salt is formed in situ during preparation of the original compound, i.e., the designated synthetic chemistry procedures produce the salt instead of the original compound. In some cases, the salt is obtained via modification of the original compound. In some cases, the salt is obtained via ion exchange with an existing salt of the original compound. Examples of salts include, but are not limited to, mineral or organic acid salts of basic residues such as amines, as well as alkali or organic salts of acidic residues such as carboxylic acids and phosphonic acids. For original compounds containing a basic residue, the salts can be prepared by treating the compounds with an appropriate amount of a non-toxic inorganic or organic acid; alternatively, the salts can be formed in situ during preparation of the original compounds. Exemplary salts of the basic residue include salts with an inorganic acid selected from hydrochloric, hydrobromic, sulfuric, sulfamic, phosphoric, and nitric acids or with an organic acid selected from acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic acids. For original compounds containing an acidic residue, the salts can be prepared by treating the compounds with an appropriate amount of a non-toxic base; alternatively, the salts can be formed in situ during preparation of the original compounds. Exemplary salts of the acidic residue include salts with a base selected from ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, and histidine. Optionally, the salts can be prepared by reacting the free acid or base form of the original compounds with a stoichiometric amount or more of an appropriate base or acid, respectively, in water or an aqueous solution, an organic solvent or an organic solution, or a mixture thereof. Lists of exemplary pharmaceutically acceptable salts can be found in Remington's Pharmaceutical Sciences, 20th Ed., Lippincott Williams & Wilkins, Baltimore, MD, 2000 as well as Handbook of Pharmaceutical Salts: Properties, Selection, and Use, Stahl and Wermuth, Eds., Wiley-VCH, Weinheim, 2002.

As used herein, the term "excipient" refers to any components present in the pharmaceutical formulations disclosed herein, other than the active ingredient (i.e., a compound or composition of the present disclosure).

As used herein, the term "effective amount" of a material refers to a nontoxic but sufficient amount of the material to provide the desired result. The exact amount required may vary from subject to subject, depending on the species, age, and general condition of the subject, the severity of the condition, disorder, or disease that is being treated, the active ingredient or therapy used, and the like.

II. COMPOUNDS

The present disclosure describes CXCR4 antagonists. Generally, the compounds contain an N-morpholine-substituted tetrahydroisoquinoline (THIQ) motif. In some embodiments, the compounds have potent activity against CXCR4, low or no CYP450 inhibition, high metabolic stability, and excellent cell permeability.

To the extent that chemical formulas described herein contain one or more unspecified chiral centers, the formulas are intended to encompass all stable stereoisomers, enantiomers, and diastereomers. Such compounds can exist as a single enantiomer, a racemic mixture, a mixture of diastereomers, or combinations thereof. It is also understood that the chemical formulas encompass all tautomeric forms if tautomerization occurs.

Methods of making exemplary compounds are disclosed in subsequent sections and exemplified by the Examples. The synthetic methods disclosed herein are compatible with a wide variety of functional groups and starting materials. Thus, a wide variety of compounds can be obtained from the disclosed methods.

Optionally, the alkyl groups described herein have 1-30 carbon atoms, i.e., $C_1$-$C_{30}$ alkyl. In some forms, the $C_1$-$C_{30}$ alkyl can be a linear $C_1$-$C_{30}$ alkyl or a branched $C_3$-$C_{30}$ alkyl. Optionally, the alkyl groups have 1-20 carbon atoms, i.e., $C_1$-$C_{20}$ alkyl. In some forms, the $C_1$-$C_{20}$ alkyl can be a linear $C_1$-$C_{20}$ alkyl or a branched $C_3$-$C_{20}$ alkyl. Optionally, the alkyl groups have 1-10 carbon atoms, i.e., $C_1$-$C_{10}$ alkyl. In some forms, the $C_1$-$C_{10}$ alkyl can be a linear $C_1$-$C_{10}$ alkyl or a branched $C_3$-$C_{10}$ alkyl. Optionally, the alkyl groups have 1-6 carbon atoms, i.e., $C_1$-$C_6$ alkyl. In some forms, the $C_1$-$C_6$ alkyl can be a linear $C_1$-$C_6$ alkyl or a branched $C_3$-$C_6$ alkyl. Representative straight chain alkyl groups include methyl, ethyl, n-propyl, n-butyl, n-pentyl, n-hexyl, n-heptyl, n-octyl, n-nonyl, and the like. Representative branched alkyl groups include isopropyl, sec-butyl, isobutyl, tert-butyl, isopentyl, and the like.

Optionally, the alkenyl groups described herein have 2-30 carbon atoms, i.e., $C_2$-$C_{30}$ alkenyl. In some forms, the $C_2$-$C_{30}$ alkenyl can be a linear $C_2$-$C_{30}$ alkenyl or a branched $C_3$-$C_{30}$ alkenyl. Optionally, the alkenyl groups have 2-20 carbon atoms, i.e., $C_2$-$C_{20}$ alkenyl. In some forms, the $C_2$-$C_{20}$ alkenyl can be a linear $C_2$-$C_{20}$ alkenyl or a branched $C_3$-$C_{20}$ alkenyl. Optionally, the alkenyl groups have 2-10 carbon atoms, i.e., $C_2$-$C_{10}$ alkenyl. In some forms, the $C_2$-$C_{10}$ alkenyl can be a linear $C_2$-$C_{10}$ alkenyl or a branched $C_3$-$C_{10}$ alkenyl. Optionally, the alkenyl groups have 2-6 carbon atoms, i.e., $C_2$-$C_6$ alkenyl. In some forms, the $C_2$-$C_6$ alkenyl can be a linear $C_2$-$C_6$ alkenyl or a branched $C_3$-$C_6$ alkenyl. Representative alkenyl groups include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

Optionally, the alkynyl groups described herein have 2-30 carbon atoms, i.e., $C_2$-$C_{30}$ alkynyl. In some forms, the $C_2$-$C_{30}$ alkynyl can be a linear $C_2$-$C_{30}$ alkynyl or a branched $C_4$-$C_{30}$ alkynyl. Optionally, the alkynyl groups have 2-20 carbon atoms, i.e., $C_2$-$C_{20}$ alkynyl. In some forms, the $C_2$-$C_{20}$ alkynyl can be a linear $C_2$-$C_{20}$ alkynyl or a branched $C_4$-$C_{20}$ alkynyl. Optionally, the alkynyl groups have 2-10 carbon atoms, i.e., $C_2$-$C_{10}$ alkynyl. In some forms, the $C_2$-$C_{10}$ alkynyl can be a linear $C_2$-$C_{10}$ alkynyl or a branched $C_4$-$C_{10}$ alkynyl. Optionally, the alkynyl groups have 2-6 carbon atoms, i.e., $C_2$-$C_6$ alkynyl. In some forms, the $C_2$-$C_6$ alkynyl can be a linear $C_2$-$C_6$ alkynyl or a branched $C_4$-$C_6$ alkynyl. Representative alkynyl groups include ethynyl, propynyl, 1-butynyl, 2-butynyl, 1-pentynyl, 2-pentynyl, 3-methyl-1-butynyl, and the like.

Optionally, the aryl groups described herein have 6-30 carbon atoms, i.e., $C_6$-$C_{30}$ aryl. Optionally, the aryl groups have 6-20 carbon atoms, i.e., $C_6$-$C_{20}$ aryl. Optionally, the aryl groups have 6-12 carbon atoms, i.e., $C_6$-$C_{12}$ aryl. Representative aryl groups include phenyl, naphthyl, and biphenyl.

Optionally, the heteroaryl groups described herein have 1-30 carbon atoms, i.e., $C_1$-$C_{30}$ heteroaryl. Optionally, the heteroaryl groups have 1-20 carbon atoms, i.e., $C_1$-$C_{20}$ heteroaryl. Optionally, the heteroaryl groups have 1-11 carbon atoms, i.e., $C_1$-$C_{11}$ heteroaryl. Optionally, the heteroaryl groups have 1-5 carbon atoms, i.e., $C_1$-$C_5$ heteroaryl. Optionally, the heteroaryl groups are 5-20 membered heteroaryl groups. Optionally, the heteroaryl groups are 5-12 membered heteroaryl groups. Optionally, the heteroaryl groups are 5 or 6 membered heteroaryl groups. Representative heteroaryl groups include furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

Optionally, the carbocyclyl groups described herein have 3-30 carbon atoms, i.e., $C_3$-$C_{30}$ carbocyclyl. Optionally, the carbocyclyl groups described herein have 3-20 carbon atoms, i.e., $C_3$-$C_{20}$carbocyclyl. Optionally, the carbocyclyl groups described herein have 3-12 carbon atoms, i.e., $C_3$-$C_{12}$ carbocyclyl. Representative saturated carbocyclyl groups include cyclopropyl, cyclobutyl, cyclopentyl, cyclohexyl, and the like. Representative unsaturated carbocyclyl groups include cyclopentenyl, cyclohexenyl, and the like.

Optionally, the heterocyclyl groups described herein have 1-30 carbon atoms, i.e., $C_1$-$C_{30}$ heterocyclyl. Optionally, the heterocyclyl groups described herein have 1-20 carbon atoms, i.e., $C_1$-$C_{20}$ heterocyclyl. Optionally, the heterocyclyl groups described herein have 1-11 carbon atoms, i.e., $C_1$-$C_{11}$ heterocyclyl. Optionally, the heterocyclyl groups described herein have 1-6 carbon atoms, i.e., $C_1$-$C_6$ heterocyclyl. Optionally, the heterocyclyl groups are 3-20 membered heterocyclyl groups. Optionally, the heterocyclyl groups are 3-12 membered heterocyclyl groups. Optionally, the heteroaryl groups are 4-7 membered heterocyclyl groups.

The optionally substituted groups described in the chemical formulas described herein (e.g., Formulas I-XIII and their sub-formulas), on each occurrence when not specified, may have one or more substituents in the form of the R groups described above.

The R groups, on each occurrence, can be independently selected from halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, haloheteroaryl, —OH, —SH, $—NH_2$, $—N_3$, —OCN, —NCO, $—ONO_2$, —CN, —NC, —ONO, $—CONH_2$, —NO, $—NO_2$, $—ONH_2$, —SCN, —SNCS, $—CF_3$, $—CH_2CF_3$, $—CH_2Cl$, $—CHCl_2$, $—CH_2NH_2$, —NHCOH, —CHO, —COOH, $—SO_3H$, $—CH_2SO_2CH_3$, $—PO_3H_2$, $—OPO_3H_2$, $—P(=O)(OR^{G1})(OR^{G2})$, $—OP(=O)(OR^{G1})(OR^{G2})$, $—BR^{G1}(OR^{G2})$, $—B(OR^{G1})(OR^{G2})$, $—Si(R^{G1})(R^{G2})(R^{G3})$, $—C(R^{G1})(R^{G2})(R^{G3})$, $—N[(R^{G1})(R^{G2})(R^{G3})]^+$, and $-GR^{G1}$, in which -G is —O—, —S—, $—NR^{G2}—$, —C=O—, —S(=O)—, $—SO_2—$, —C(=O)O—, $—C(=O)NR^{G2}—$, —C(O=)—, $—NR^{G2}C(=O)—$, —OC(=O)O—, $—OC(=O)NR^{G2}—$, $—NR^{G2}C(=O)O—$, $—NR^{G2}C(=O)NR^{G3}—$, —C(=S)—, —C(=S)S—, —SC(=S)—, —SC(=S)S—, $—C(=NR^{G2})—$, $—C(=NR^{G2})O—$, $—C(=NR^{G2})NR^{G3}—$, $—OC(=NR^{G2})—$, $—NR^{G2}C(=NR^{G3})—$, $—NR^{G2}SO_2—$, $—C(=NR^{G2})NR^{G3}—$, $—OC(=NR^{G2})—$, $—NR^{G2}C(=NR^{G3})—$, $—NR^{G2}SO_2—$, $—NR^{G2}SO_2NR^{G3}—$, $—NR^{G2}C(=S)—$, $—SC(=S)NR^{G2}—$, $—NR^{G2}C(=S)S—$, $—NR^{G2}C(=S)NR^{G3}—$, $—SC(=NR^{G2})—$, $—C(=S)NR^{G2}—$, $—OC(=S)NR^{G2}—$, $—NR^{G2}C(=S)O—$, $—SC(=O)NR^{G2}—$, $—NR^{G2}C(=O)S—$, —C(=)S—, —SC(=O)—, —C(=O)S—, —C(=S)O—, —OC(=S)—, —OC(=S)O—, $—SO_2NR^{G2}—$, —$BR^{G2}$—, or —$PR^{G2}$—, wherein each occurrence of $R^{G1}$, $R^{G2}$, and $R^{G3}$ is independently selected from hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, and haloheteroaryl. Optionally, two R groups on the same atom can join together with that atom to form a cyclic moiety, such as a carbocycle or a heterocycle. Alternatively, two R groups on the same atom can merge into one oxygen (═O) or sulfur (═S) atom.

In some examples, the R groups are independently selected from halogen, nitro, cyano, hydroxyl, formyl, carboxyl, thiol, ═O (counting as two R groups), ═S (counting as two R groups), sulfamoyl, alkyl (such as methyl, ethyl, isopropyl, tert-butyl), haloalkyl (such as trifluoromethyl), alkenyl, haloalkenyl, alkynyl, haloalkynyl, carbocyclyl, halocarbocyclyl, heterocyclyl, haloheterocyclyl, aryl, haloaryl, heteroaryl, haloheteroaryl, arylalkyl (such as benzyl), alkylaryl, alkyloxy (such as methoxy, ethoxy), haloalkyloxy (such as trifluoromethoxy), aryloxy, alkylcarbonyl (such as acetyl), arylcarbonyl (such as benzoyl), alkylcarbonyloxy (such as acetoxy), arylcarbonyloxy (such as benzoyloxy), alkyloxycarbonyl (such as methoxycarbonyl, ethoxycarbonyl, isopropoxycarbonyl), aryloxycarbonyl, primary amino, alkylamino (such as methylamino, ethylamino, dimethylamino, diethylamino, N-methyl-N-ethylamino), alkylammonium (such as trimethylammonium), alkylcarbonylamino (such as acetylamino), arylcarbonylamino (such as benzoylamino), carbamoyl, N-alkylcarbamoyl (such as N-methylcarbamoyl, N-ethylcarbamoyl, N,N-dimethylcarbamoyl, N,N-diethylcarbamoyl, N-methyl-N-ethylcarbamoyl), alkylthio (such as methylthio, ethylthio), alkylsulfinyl (such as methylsulfinyl, ethylsulfinyl), alkylsulfonyl (such as mesyl, ethylsulfonyl), and N-alkylsulfamoyl (such as N-methylsulfamoyl, N-ethylsulfamoyl, N,N-dimethylsulfamoyl, N,N-diethylsulfamoyl, N-methyl-N-ethylsulfamoyl).

In some examples, the R groups are independently selected from halogen, nitro, cyano, hydroxyl, trifluoromethyl, methoxy, ethoxy, trifluoromethoxy, primary amino, formyl, carboxyl, carbamoyl, thiol, ═O, ═S, sulfamoyl, acetyl, acetoxy, methoxycarbonyl, ethoxycarbonyl, isopropoxycarbonyl, methylamino, ethylamino, dimethylamino, diethylamino, N-methyl-N-ethylamino, trimethylammonium, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, alkyl, haloalkyl, alkenyl, haloalkenyl, alkynyl, haloalkynyl, carbocyclyl, halocarbocyclyl, heterocyclyl, haloheterocyclyl, aryl, haloaryl, heteroaryl, and haloheteroaryl.

In some examples, the R groups are independently selected from halogen, ═O, ═S, alkyl, haloalkyl, carbocyclyl, halocarbocyclyl, aryl, haloaryl, heterocyclyl, and haloheterocyclyl.

As used herein, "alkyloxy" refers to a hydroxyl group substituted by an alkyl group at the oxygen atom. Exemplary alkyloxy groups include, but are not limited to, methoxy, ethoxy, n-propoxy, i-propoxy, n-butoxy, s-butoxy, t-butoxy, n-pentoxy, and s-pentoxy.

As used herein, "haloalkyloxy" refers to a hydroxyl group substituted by a haloalkyl group at the oxygen atom. An example of haloalkyloxy is trifluoromethoxy.

As used herein, "aryloxy" refers to a hydroxyl group substituted by an aryl group at the oxygen atom.

As used herein, "alkylcarbonyl" refers to an alkyl group attached through a carbonyl bridge (—C(═O)—).

As used herein, "arylcarbonyl" refers to an aryl group attached through a carbonyl bridge.

As used herein, "alkylcarbonyloxy" refers to a hydroxyl group substituted by an alkylcarbonyl group at the oxygen atom of the hydroxyl group.

As used herein, "arylcarbonyloxy" refers to a hydroxyl group substituted by an arylcarbonyl group at the oxygen atom of the hydroxyl group.

As used herein, "alkyloxycarbonyl" refers to an alkyloxy group attached through a carbonyl bridge.

As used herein, "aryloxycarbonyl" refers to an aryloxy group attached through a carbonyl bridge.

As used herein, "alkylamino" refers to a primary amino group substituted by one or two alkyl groups. When the primary amino group is substituted by two alkyl groups, the two alkyl groups can be the same or different. An example of alkylamino is methylamino (i.e., —NH—$CH_3$).

As used herein, "alkylammonium" refers to a primary ammonium group substituted by one, two, or three alkyl groups. When the primary ammonium group is substituted by two or three alkyl groups, the two or three alkyl groups can be the same or different. An example of alkylammonium is trimethylammonium (i.e., —$N(CH_3)_3$).

As used herein, "alkylcarbonylamino" refers to a primary amino group substituted by one alkylcarbonyl group.

As used herein, "arylcarbonylamino" refers to a primary amino group substituted by one arylcarbonyl group.

As used herein, "N-alkylcarbamoyl" refers to a carbamoyl group (—C(═O)—$NH_2$) substituted by one or two alkyl groups at the nitrogen atom. When the carbamoyl group is substituted by two alkyl groups, the two alkyl groups can be the same or different.

As used herein, "alkylthio" refers to a thiol group substituted by an alkyl group at the sulfur atom. An example of alkylthio is methylthio (i.e., —S—$CH_3$).

As used herein, "alkylsulfinyl" refers to an alkyl group attached through a sulfinyl bridge (—S(═O)—).

As used herein, "alkylsulfonyl" refers to an alkyl group attached through a sulfonyl bridge (—$S(=O)_2$—).

As used herein, "N-alkylsulfamoyl" refers to a sulfamoyl group (—$S(=O)_2$—$NH_2$) substituted by one or two alkyl groups at the nitrogen atom. When the sulfamoyl group is substituted by two alkyl groups, the two alkyl groups can be the same or different.

A. Formula I

In some embodiments, the compounds have a structure of Formula I or a pharmaceutically acceptable salt, hydrate, or hydrated salt of Formula I, Formula I

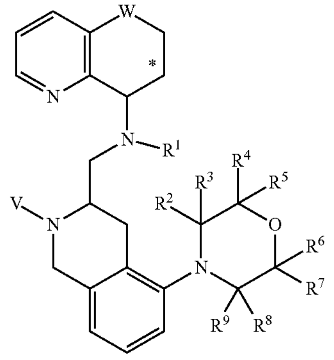

wherein W is $CH_2$ or O;

wherein V is hydrogen, an optionally substituted $C_1$-$C_4$ alkyl, or an optionally substituted $C_1$-$C_4$ haloalkyl;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, $R^6$ and $R^7$, and $R^8$ and $R^9$—are independently =O or =S; and optionally wherein two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond).

In some embodiments, Formula I is in the following configuration.

Formula I'

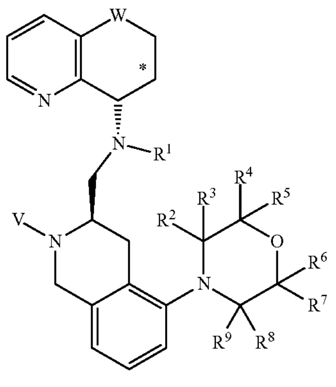

In some embodiments, W is $CH_2$. In some embodiments, W is O.

In some embodiments, V is hydrogen. In some embodiments, V is methyl.

In some embodiments, W is $CH_2$ and V is hydrogen.

1. The $R^1$ Moiety

Group I

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is —$R^{10}$—$R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$, $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

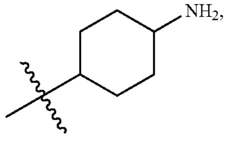

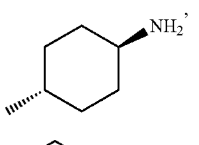

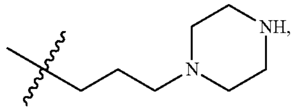

-continued
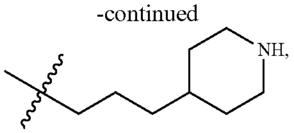
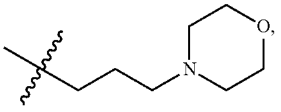
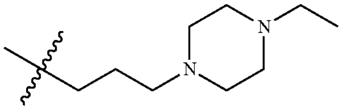
,
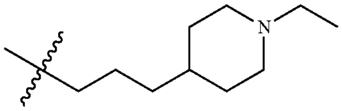
,
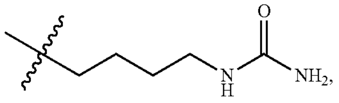
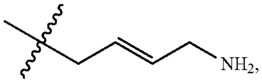
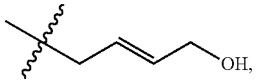
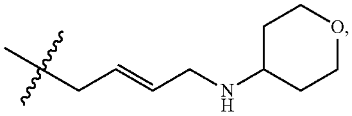
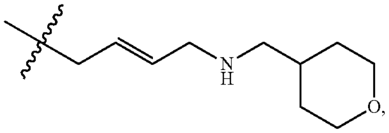
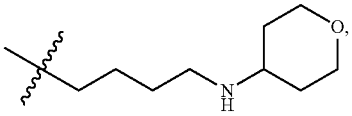
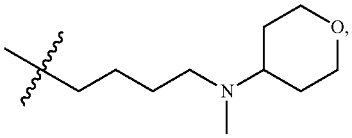
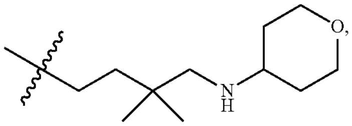
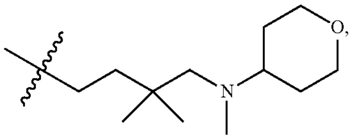
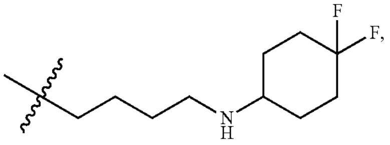
and
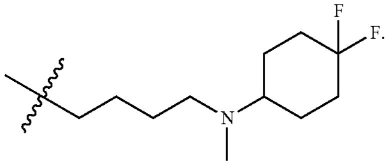
In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,
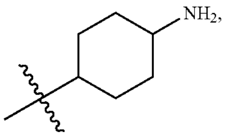
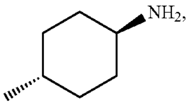
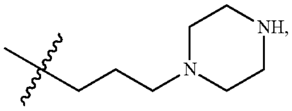
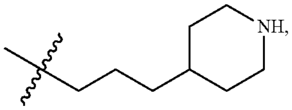
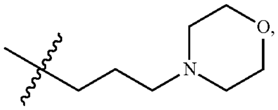
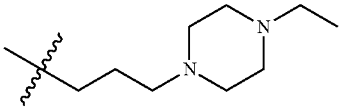
,
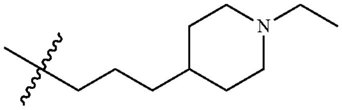
,
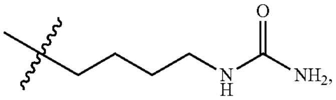
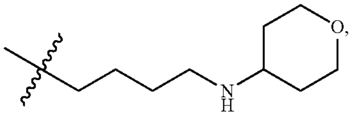
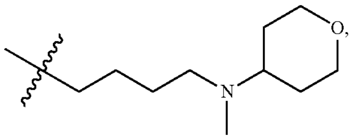
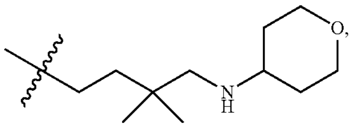
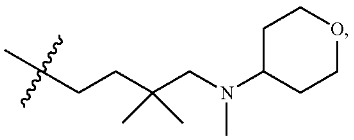
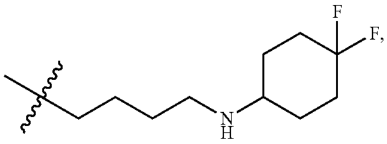
and -continued

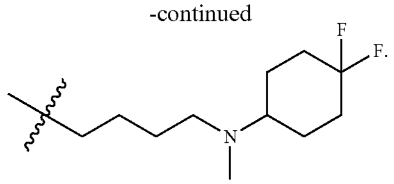

In some embodiments, —$R^{10}$—$R^{11}$ is $NH_2$ or

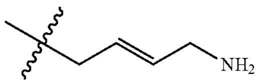

or

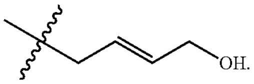

Group II

In some embodiments, $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle.

In some embodiments, the optionally substituted heterocycle is five- or six-membered. For example, the optionally substituted heterocycle is a six-membered heterocycle, such as piperidine.

2. The Morpholine Moiety

Group I

In some embodiments, $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, $R^2$, $R^3$, $R^4$, $R^5$, $R^6$, $R^7$, $R^8$, and $R^9$ are hydrogen.

In some embodiments, $R^2$, $R^3$, $R^4$, $R^5$, $R^6$, $R^7$, and $R^9$ are hydrogen and $R^8$ is halogen, amino, optionally substituted hydroxyl, optionally substituted alkyl, or optionally substituted haloalkyl. In some embodiments, $R^2$, $R^3$, $R^4$, $R^5$, $R^6$, $R^7$, and $R^9$ are hydrogen and $R^8$ is halogen, methyl, trifluoromethyl, or hydroxylmethyl. In some embodiments, $R^2$, $R^3$, $R^4$, $R^5$, $R^6$, $R^7$, and $R^9$ are hydrogen and $R^8$ is methyl. In some embodiments, $R^2$, $R^3$, $R^4$, $R^5$, $R^6$, $R^7$, and $R^9$ are hydrogen and $R^8$ is hydroxylmethyl.

In some embodiments, $R^2$, $R^3$, $R^4$, $R^5$, $R^7$, $R^8$, and $R^9$ are hydrogen and $R^6$ is halogen, amino, optionally substituted hydroxyl, optionally substituted alkyl, or optionally substituted haloalkyl.

In some embodiments, $R^2$, $R^3$, $R^4$, $R^5$, $R^7$, $R^8$, and $R^9$ are hydrogen and $R^6$ is halogen, methyl, trifluoromethyl, or hydroxylmethyl. In some embodiments, $R^2$, $R^3$, $R^4$, $R^5$, $R^7$, $R^8$, and $R^9$ are hydrogen and $R^6$ is methyl. In some embodiments, $R^2$, $R^3$, $R^4$, $R^5$, $R^7$, $R^8$, and $R^9$ are hydrogen and $R^6$ is hydroxylmethyl.

Group II

In some embodiments, one or more of the following pairs—$R^2$ and $R^3$, $R^4$ and $R^5$, $R^6$ and $R^7$, and $R^8$ and $R^9$—are independently =O or =S, wherein the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, the pair of $R^8$ and $R^9$ is =O or =S.

In some embodiments, the pair of $R^6$ and $R^7$ is =O or =S.

Group III

In some embodiments, two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond), whereas the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, two of $R^2$, $R^3$, $R^4$, $R^5$, $R^6$, $R^7$, $R^8$, and $R^9$ joint together to form a bridge on the morpholine ring. In some embodiments, the bridge is a single-member bridge, double-member bridge, or triple-member bridge. In some embodiments, the bridge is or contains a heteroatom, such as nitrogen, as a bridge member.

In some embodiments, $R^4$ and $R^6$ join together to form the bridge. In some embodiments, the bridge is a double-member bridge with both bridge members being carbon atoms. In some embodiments, the bridge is a triple-member bridge in the form of carbon-nitrogen-carbon.

In some embodiments, $R^2$ and $R^6$ join together to form the bridge. In some embodiments, the bridge is a single-member bridge with the bridge member being a carbon atom.

In some embodiments, $R^4$ and $R^8$ join together to form the bridge. In some embodiments, the bridge is a single-member bridge with the bridge member being a carbon atom.

For example, the

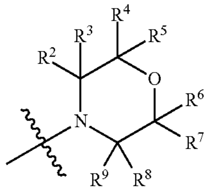

moiety in Formula I has a structure selected from:

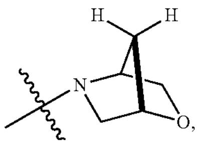

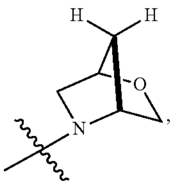

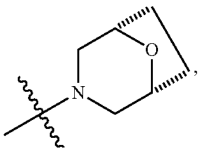

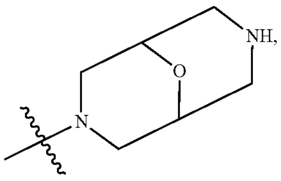

and

-continued
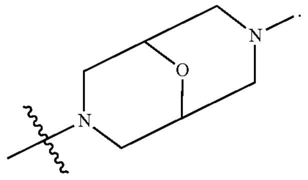
Exemplary compounds include, but are not limited to, the following:
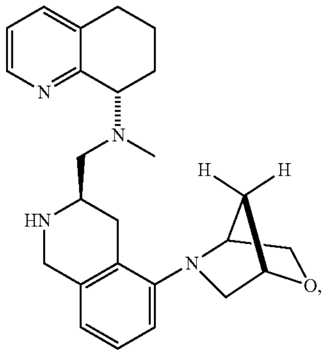
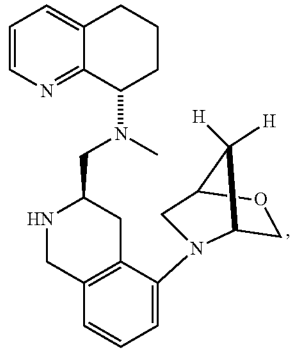
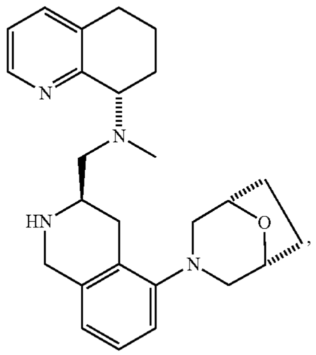
-continued
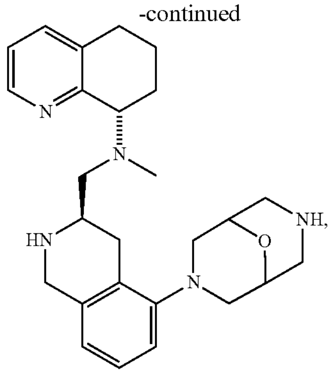
and
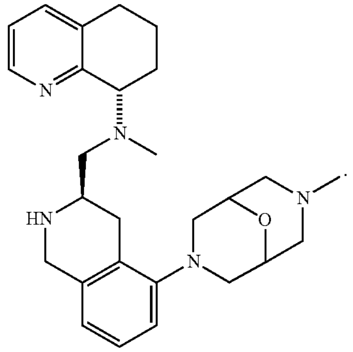
In some embodiments, the compound is
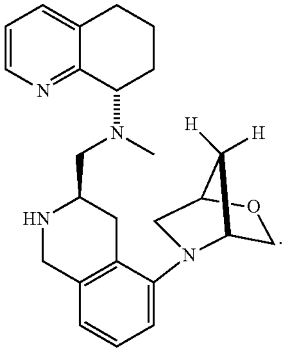
3. Exemplary Structures
Formula IA
In some embodiments, Formula I is Formula IA:
Formula IA
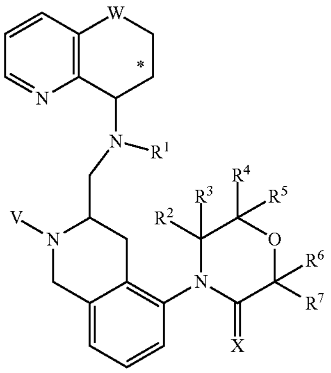

wherein X is O or S; and
wherein V, W, $R^1$, $R^2$, $R^3$, $R^4$, $R^5$, $R^6$, and $R^7$ are the same as those described above.
In some embodiments, Formula IA is in the following configuration.
Formula IA'
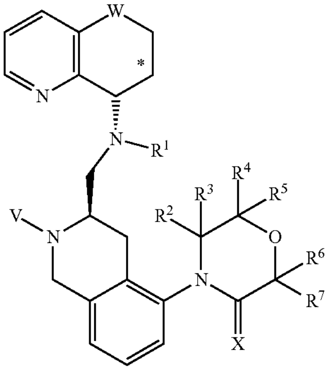
In some embodiments, X is O.
In some embodiments, $R^2$, $R^3$, $R^4$, $R^5$, $R^6$, and $R^7$ are hydrogen.
Exemplary compounds include, but are not limited to, the following:
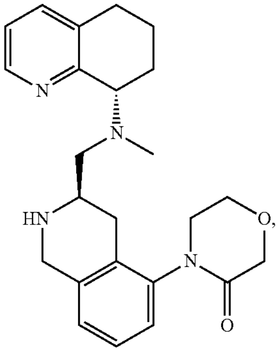
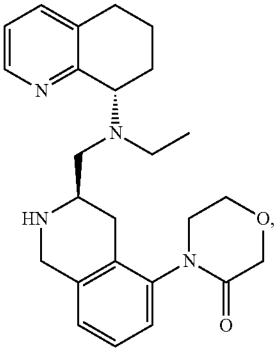
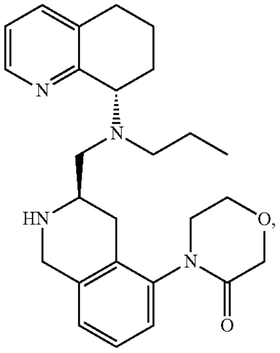
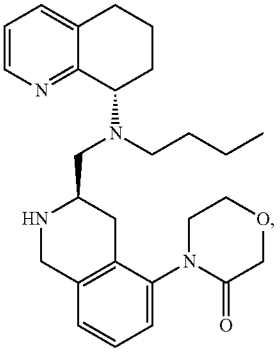
-continued
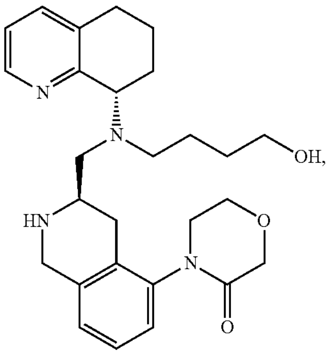
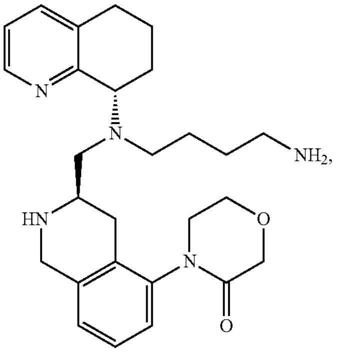
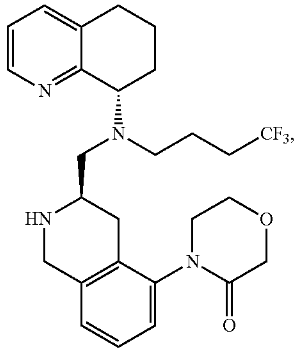
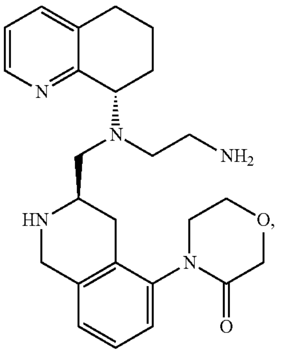

-continued
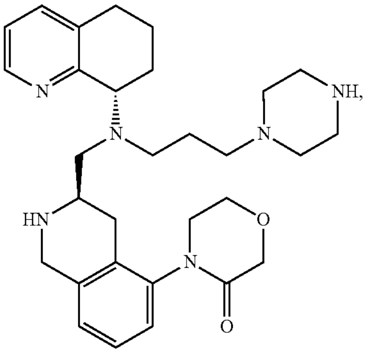
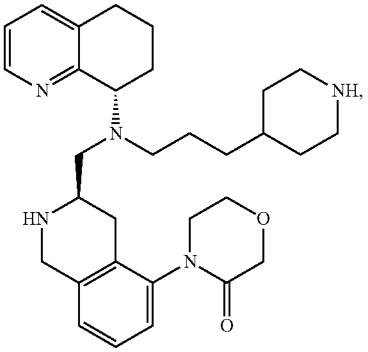
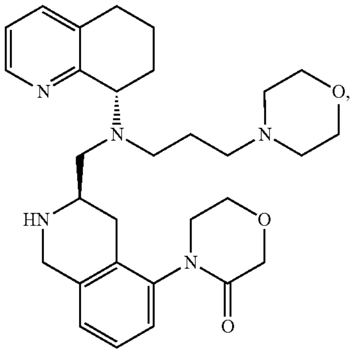
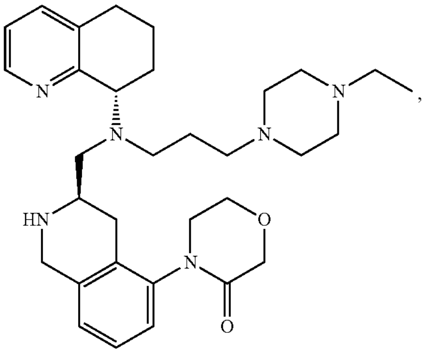
-continued
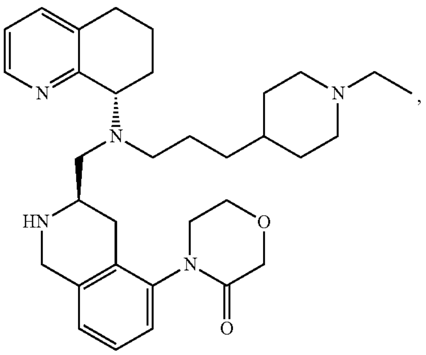
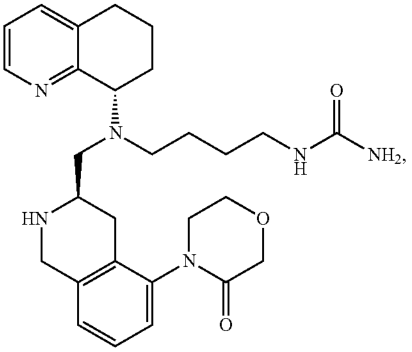
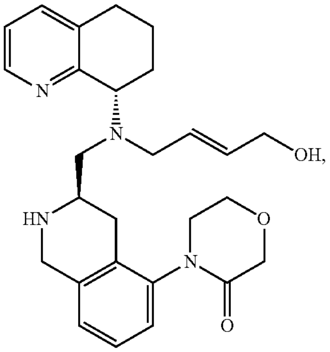
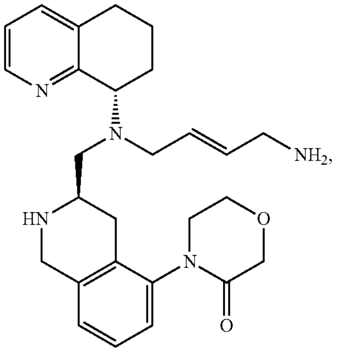

-continued
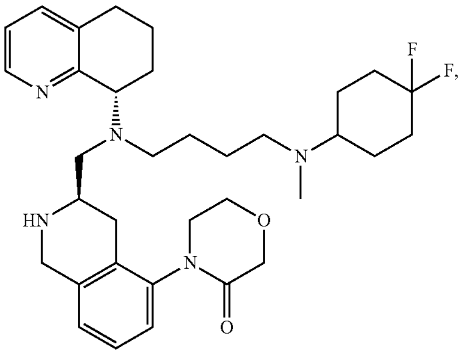
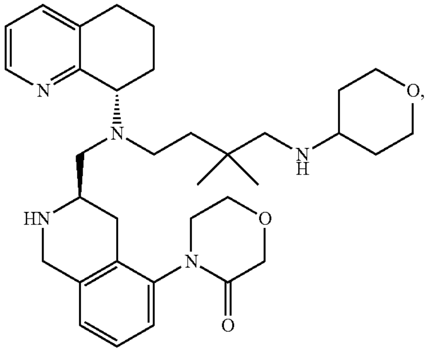
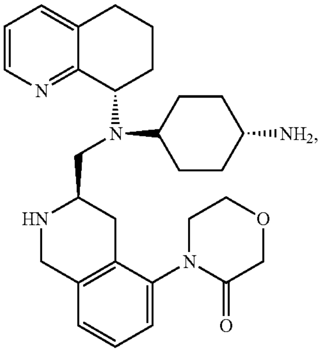
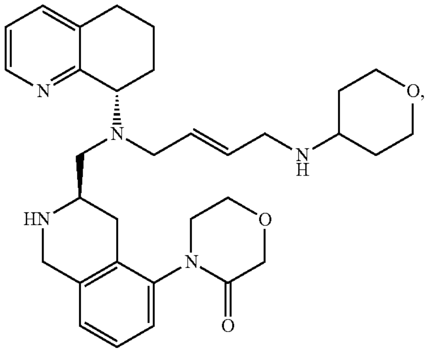
-continued
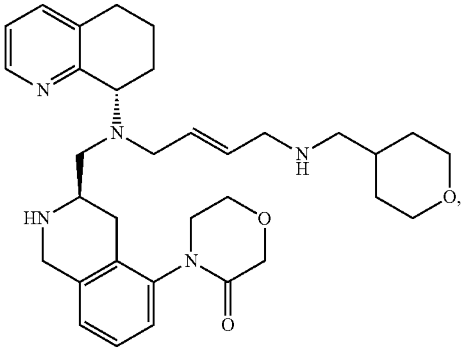
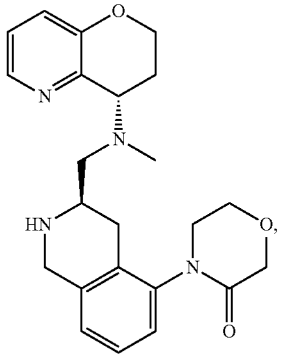
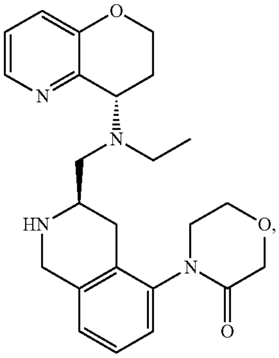
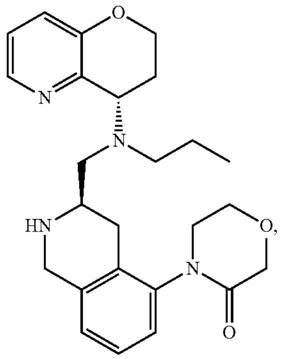
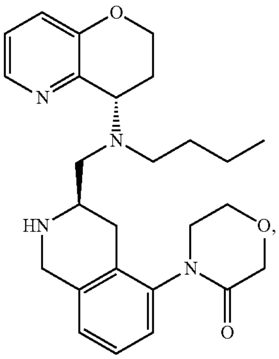
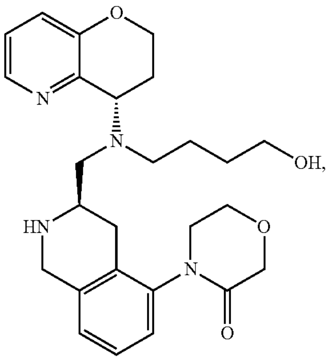

-continued
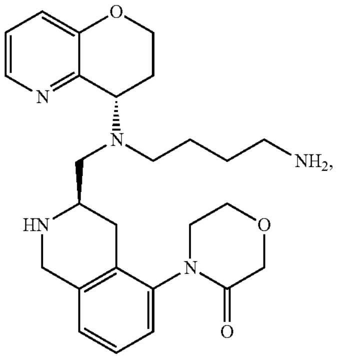
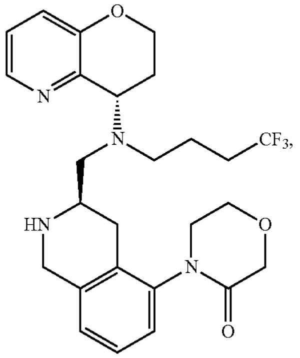
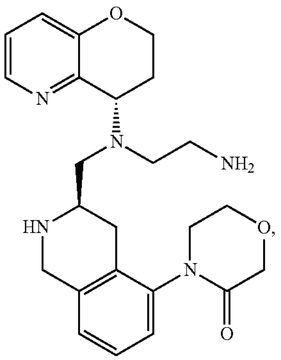
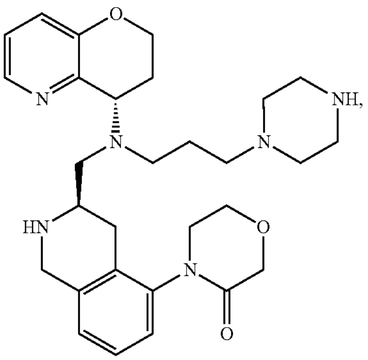
-continued
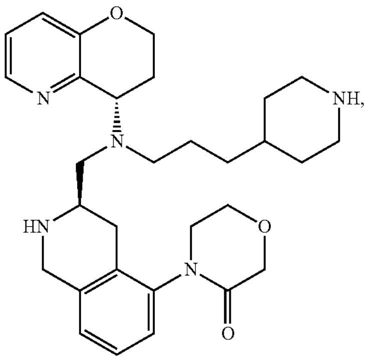
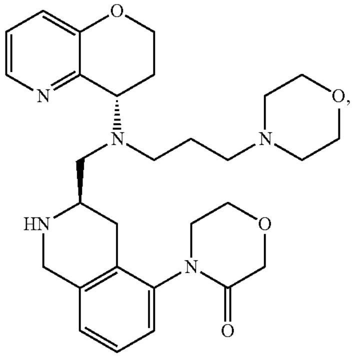
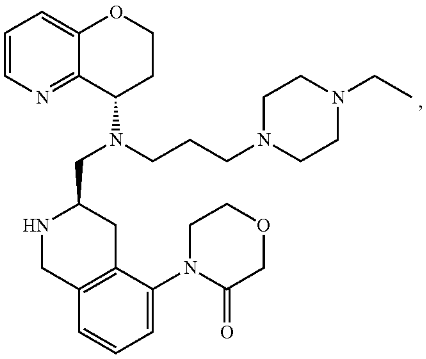
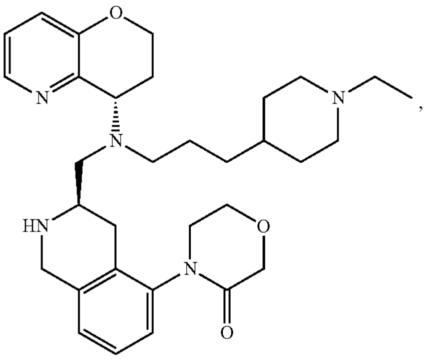

-continued
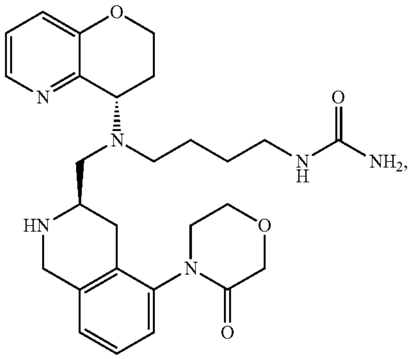
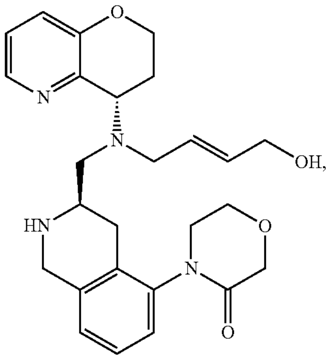
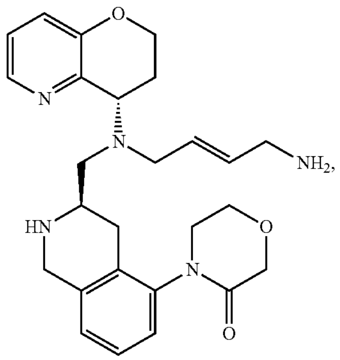
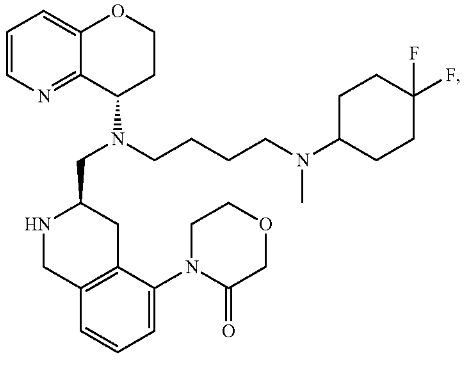
-continued
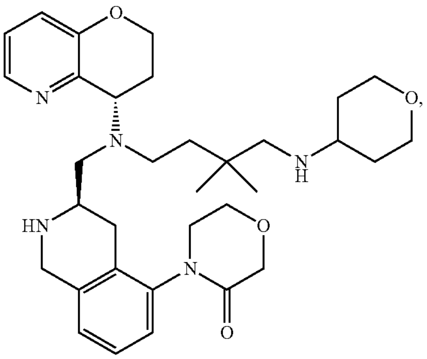
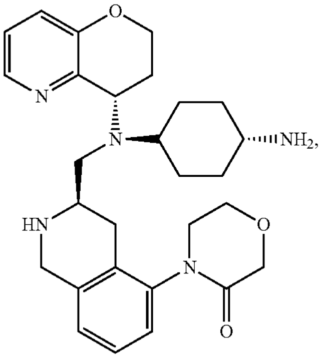
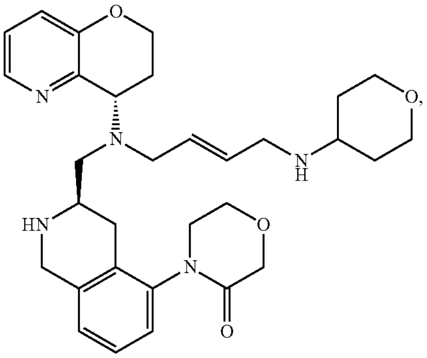
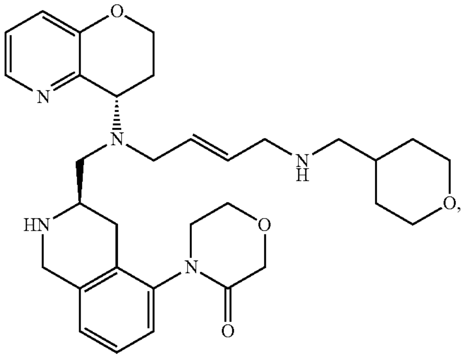

-continued

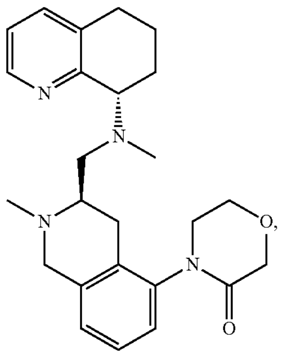

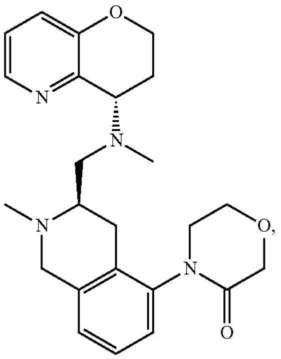

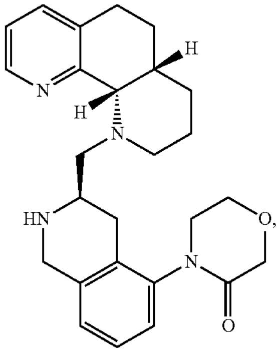

and

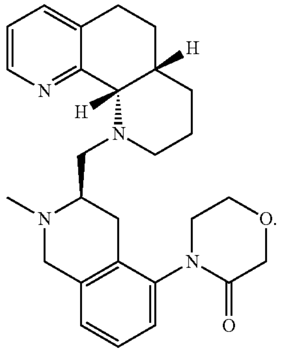

In some embodiments, the compound is

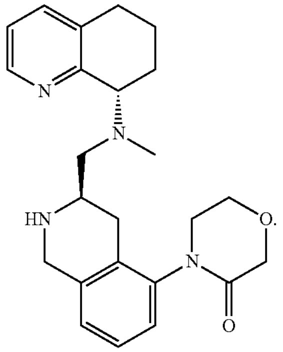 [SMILES: CN(C[C@H]1Cc2c(cccc2N2CCOCC2=O)CN1)[C@H]1CCCc2cccnc21]

In some embodiments, Formula I is Formula IB:

Formula IB

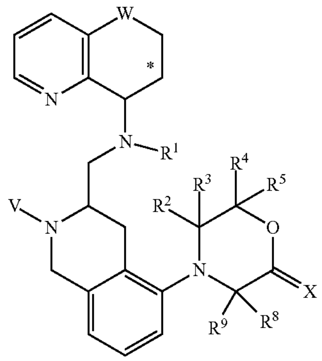

wherein X is O or S; and wherein V, W, $R^1$, $R^2$, $R^3$, $R^4$, $R^5$, $R^8$, and $R^9$ are the same as those described above.

In some embodiments, Formula IB is in the following configuration.

Formula IB′

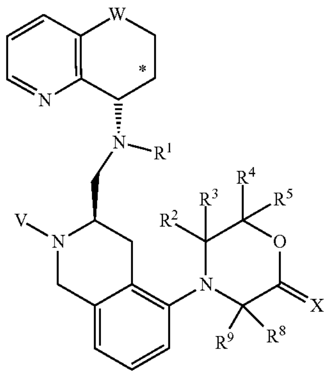

In some embodiments, X is O.

In some embodiments, $R^2$, $R^3$, $R^4$, $R^5$, $R^8$, and $R^9$ are hydrogen.

Exemplary compounds include, but are not limited to, the following:

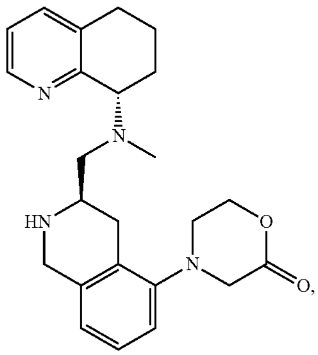

-continued

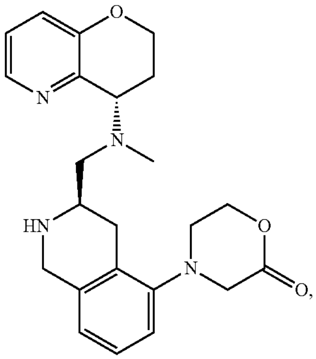

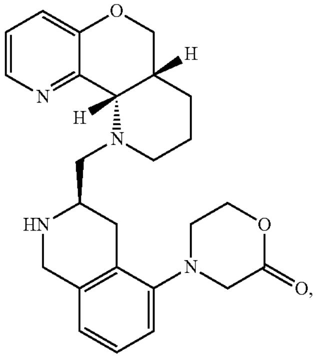

Formula IC

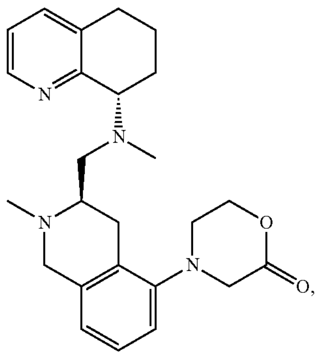

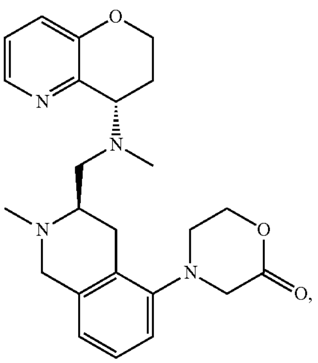

and

-continued

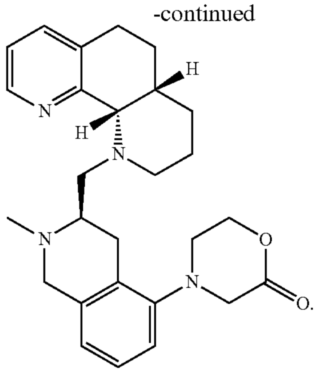

In some embodiments, Formula I is Formula IC:

Formula IC

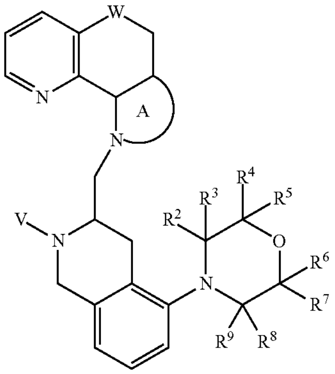

wherein ring A is an optionally substituted, five- or six-membered heterocycle, and wherein V, W, $R^2$, $R^3$, $R^4$, $R^5$, $R^6$, $R^7$, $R^8$, and $R^9$ are the same as those described above.

In some embodiments, Formula IC is in the following configuration.

Formula IC

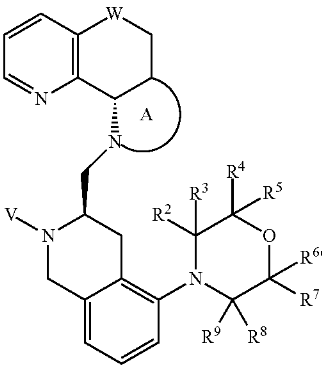

In some embodiments, ring A is a six-membered heterocycle, such as piperidine.

Formula ID

In some embodiments, Formula I is Formula ID:

Formula ID

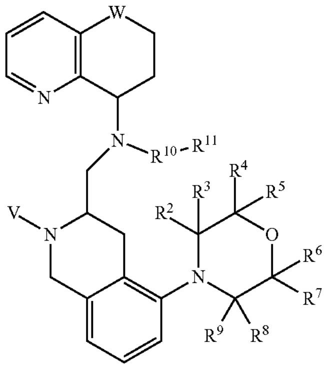

wherein $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge);

wherein $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, $—NR^aR^b$, $—NR^c[C(=O)R^d]$, or $—OR^f$;

wherein $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl; and wherein V, W, $R^2$, $R^3$, $R^4$, $R^5$, $R^6$, $R^7$, $R^8$, and $R^9$ are the same as those described above.

In some embodiments, Formula ID is in the following configuration.

Formula ID

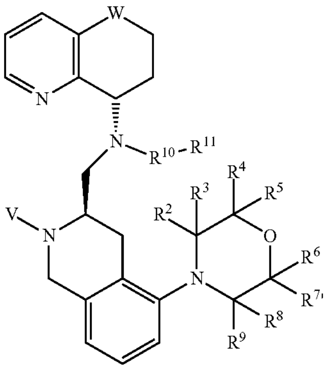

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, $—NR^aR^b$, $—NR^c[C(=O)R^d]$, or $—OR^f$.

In some embodiments, $—R^{10}—R^{11}$ is selected from ethyl, propyl, isopropyl, butyl, isobutyl, $—(CH_2)_2OH$, $—(CH_2)_2NH_2$, $—(CH_2)_3OH$, $—(CH_2)_3NH_2$, $—(CH_2)_4OH$, $—(CH_2)_3CF_3$,

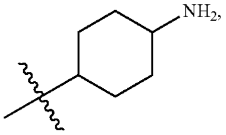

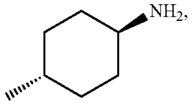

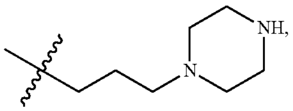

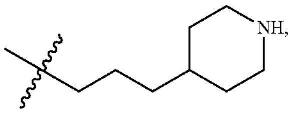

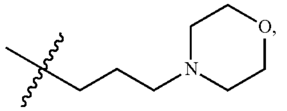

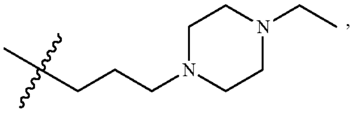

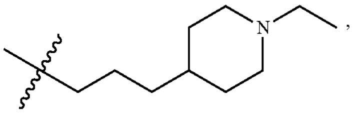

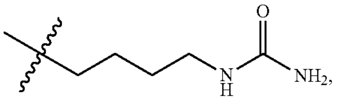

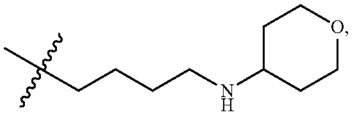

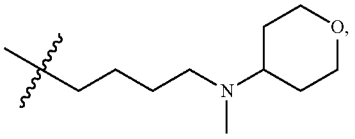

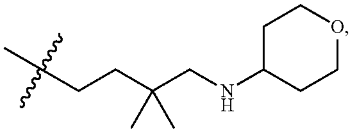

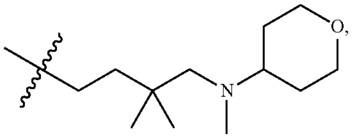

-continued
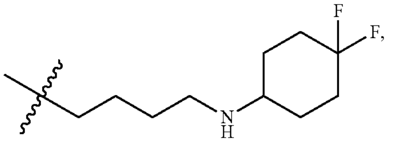
and
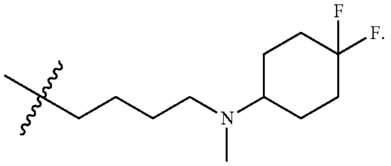
In some embodiments, —$R^{10}$—$R^{11}$ is
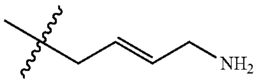
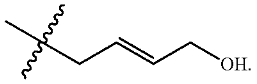
Exemplary compounds include, but are not limited to, the following:
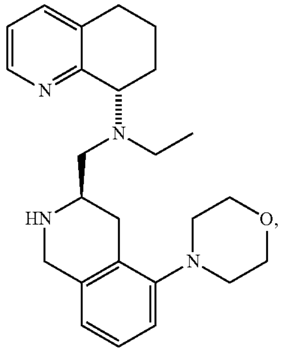
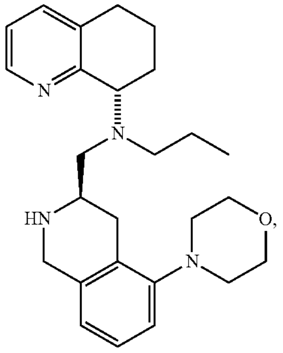
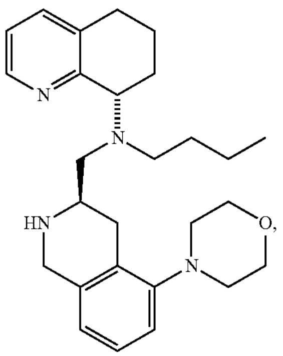
-continued
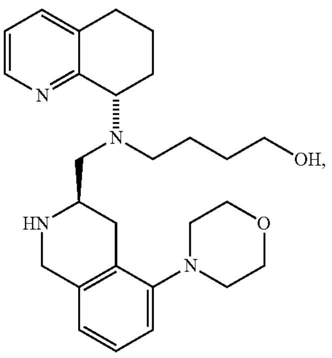
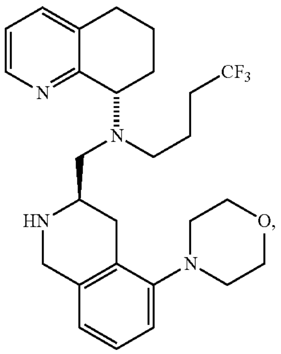
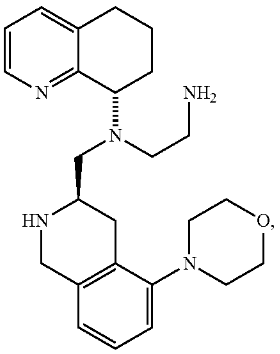
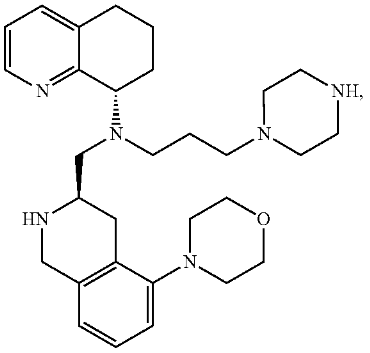
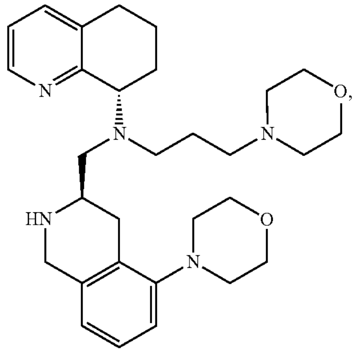

-continued
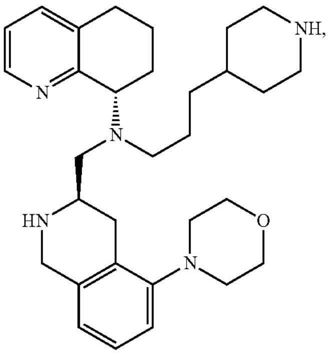
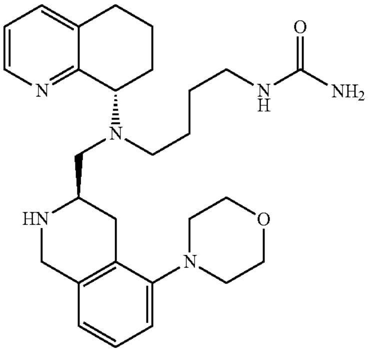
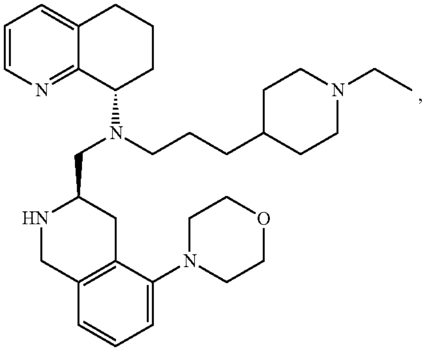
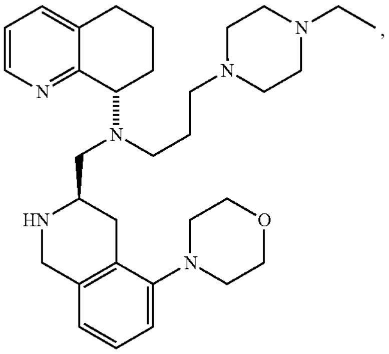
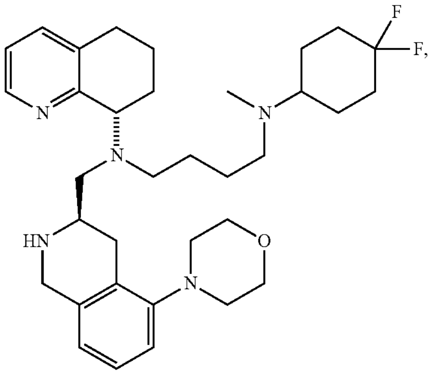
-continued
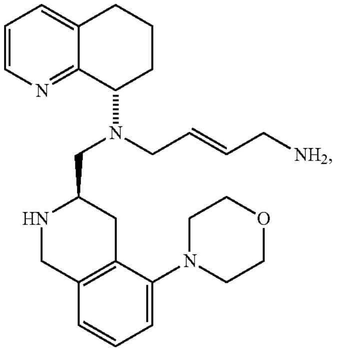
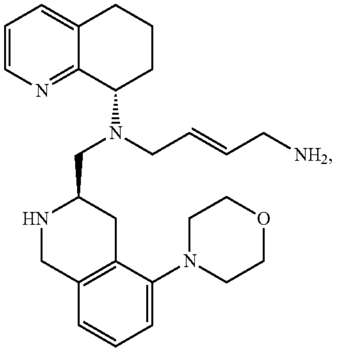
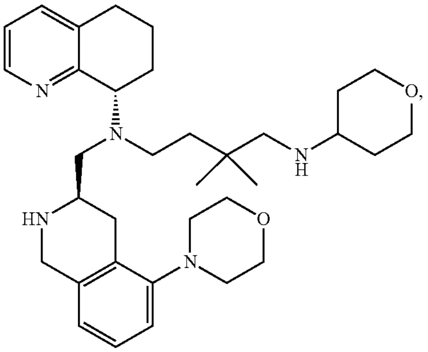

-continued
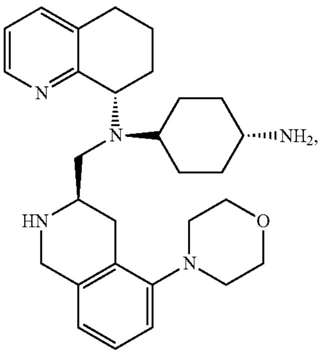
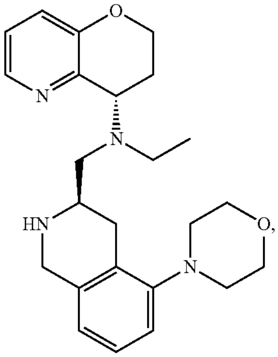
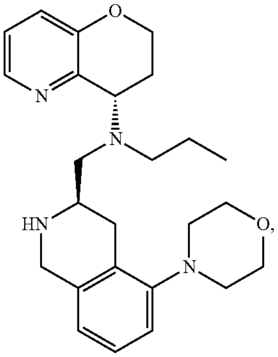
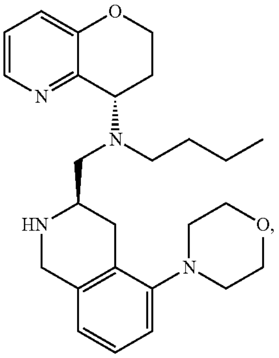
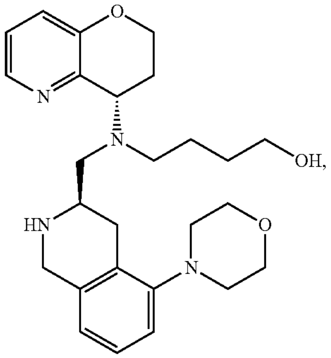
-continued
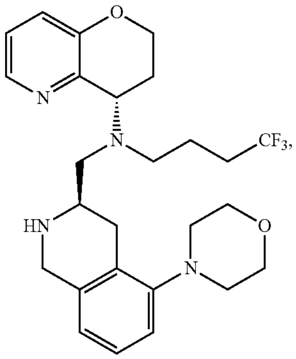
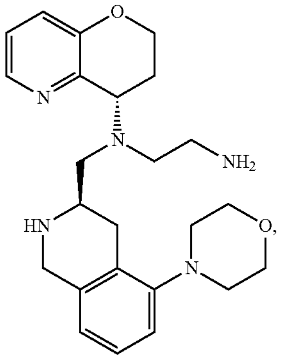
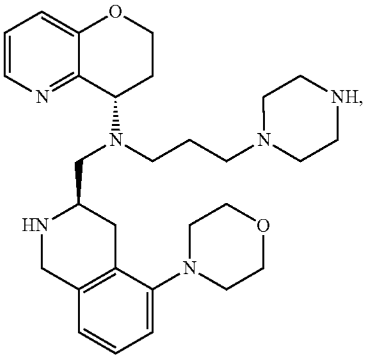
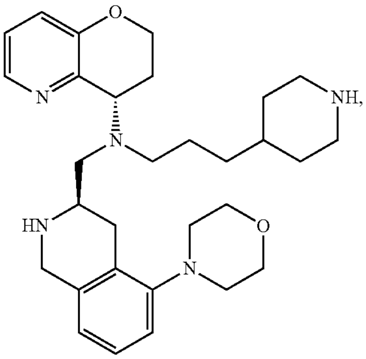

-continued
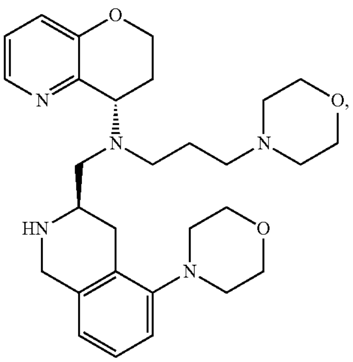
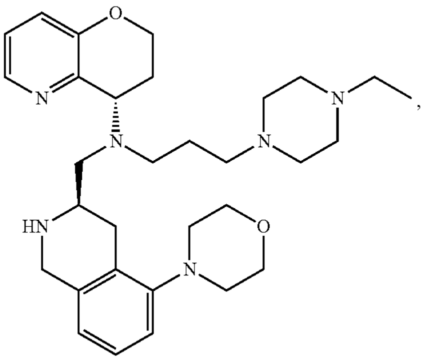
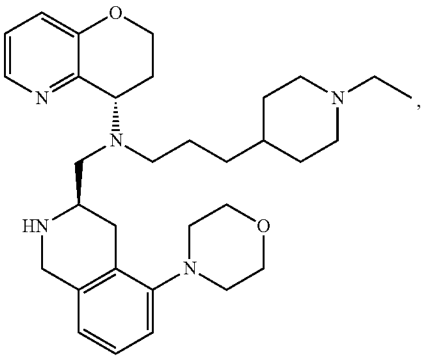
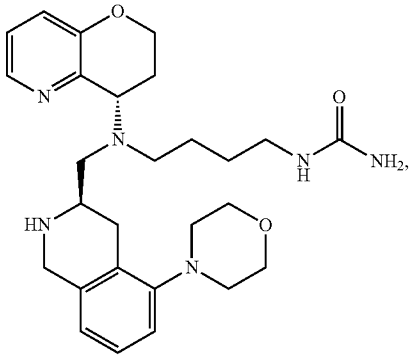
-continued
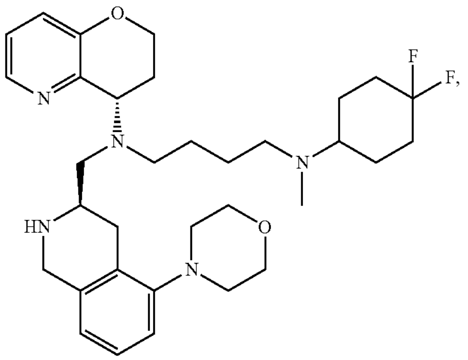
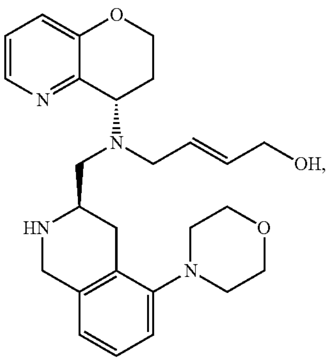
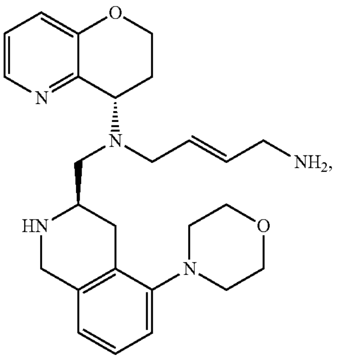
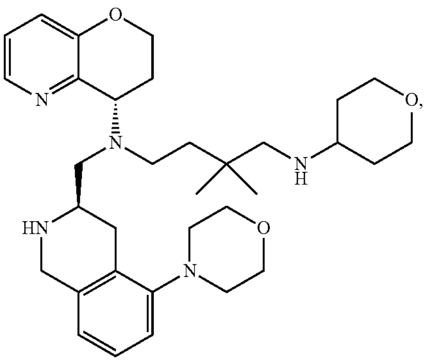
and -continued

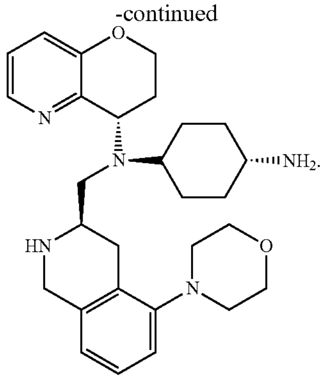

In some embodiments, the compound is

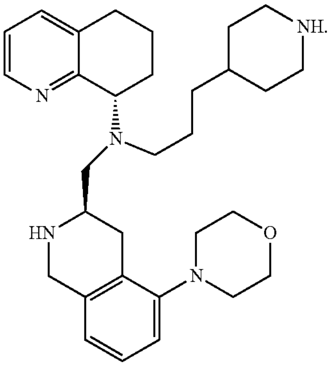 [SMILES: c1cnc2c(c1)CCC[C@@H]2N(CCCC1CCNCC1)C[C@H]1Cc2c(cccc2N2CCOCC2)CN1]

Formula IE and Formula IF

In some embodiments, Formula I is Formula IE:

Formula IE

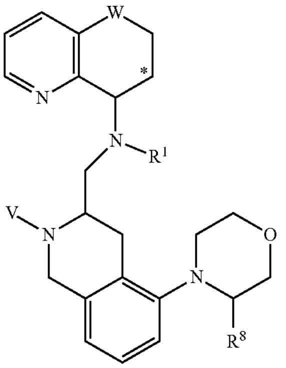

wherein V, W, $R^1$, and $R^8$ are the same as those described above.

In some embodiments, Formula IE is in the following configuration.

Formula IE

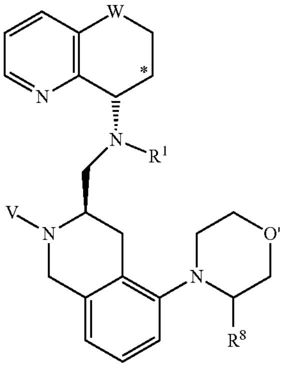

In some embodiments, $R^8$ is halogen, amino, optionally substituted hydroxyl, optionally substituted alkyl, or optionally substituted haloalkyl. In some embodiments, $R^8$ is halogen, methyl, trifluoromethyl, or hydroxylmethyl. In some embodiments, $R^8$ is methyl. In some embodiments, $R^8$ is hydroxylmethyl.

Exemplary compounds include, but are not limited to, the following:

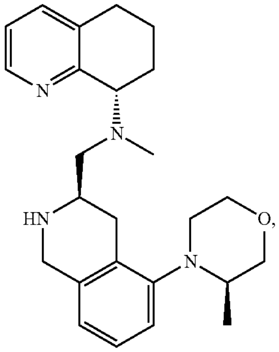

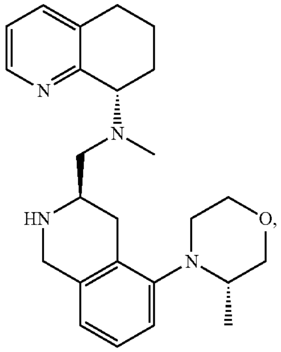

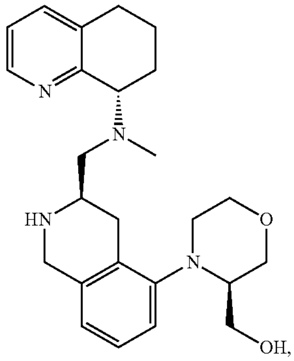

-continued
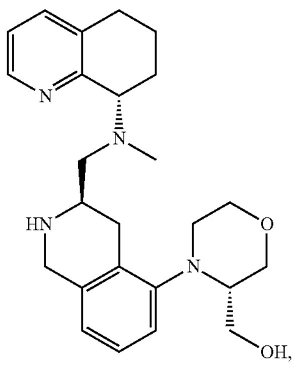
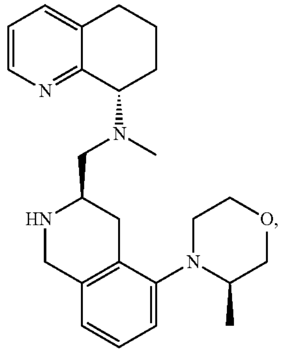
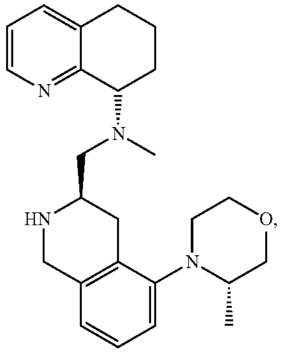
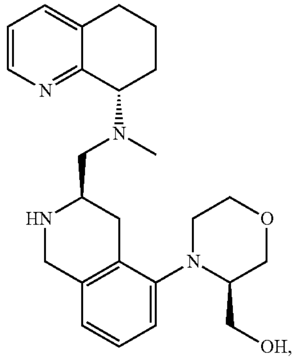
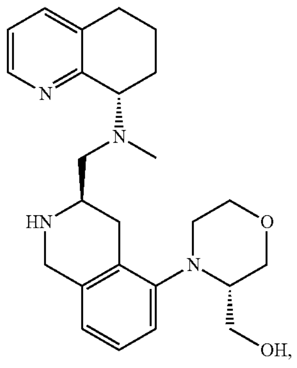
-continued
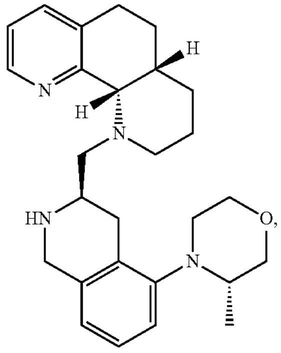
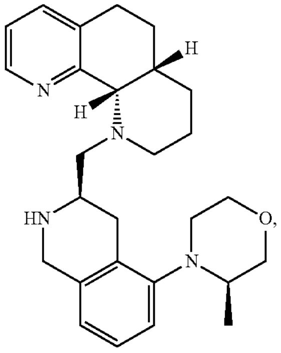
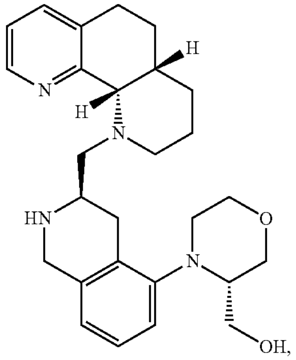
and
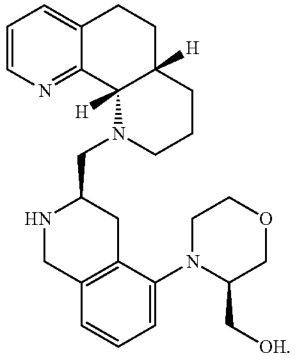 [SMILES: OC[C@@H]1COCCN1c1cccc2c1C[C@H](CN1CCC[C@H]3CCc4cccnc4[C@H]31)NC2]
In some embodiments, Formula I is Formula IF:
Formula IF
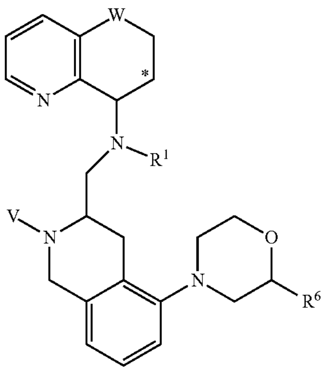
wherein V, W, $R^1$, and $R^6$ are the same as those described above.
In some embodiments, Formula IF is in the following configuration.

Formula IF

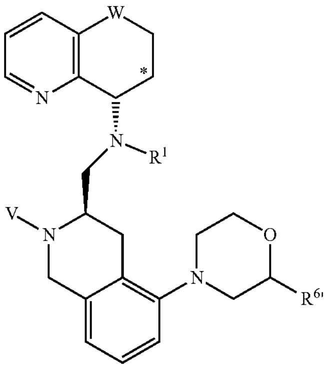

In some embodiments, $R^6$ is halogen, amino, optionally substituted hydroxyl, optionally substituted alkyl, or optionally substituted haloalkyl. In some embodiments, $R^6$ is halogen, methyl, trifluoromethyl, or hydroxylmethyl. In some embodiments, $R^6$ is methyl. In some embodiments, $R^6$ is hydroxylmethyl.

Exemplary compounds include, but are not limited to, the following:

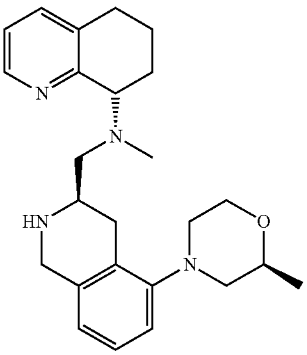

,

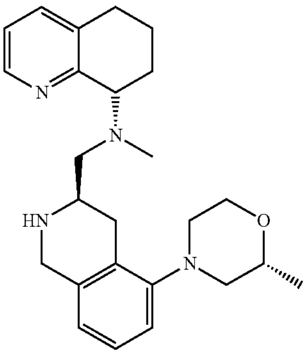

,

-continued

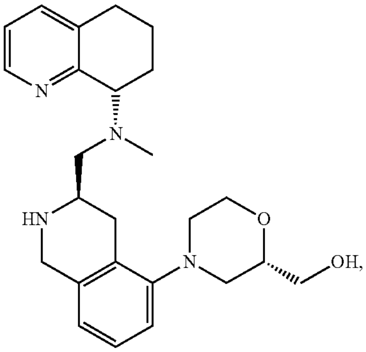

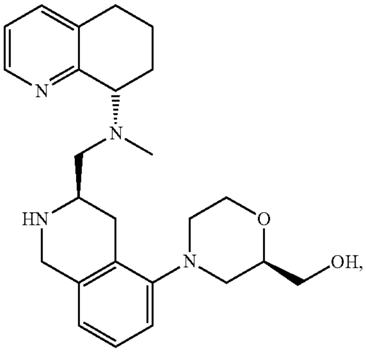

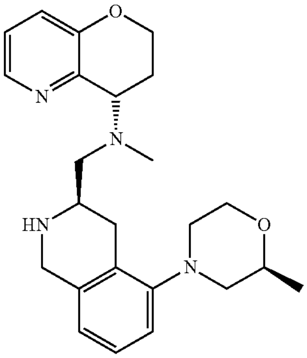

,

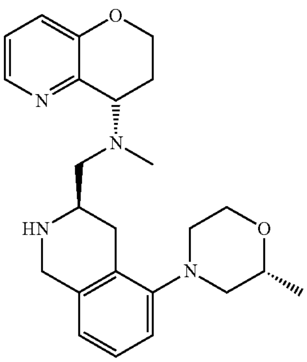

,

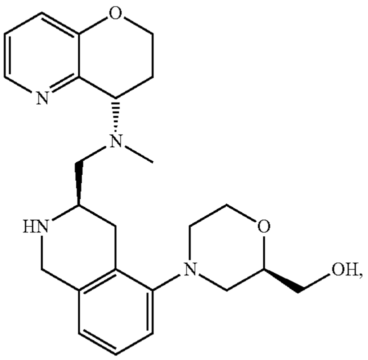
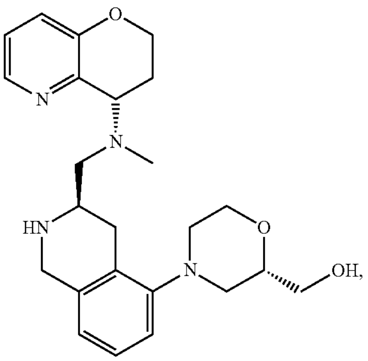
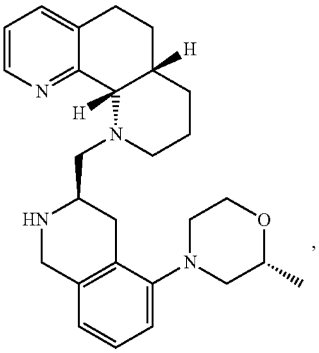
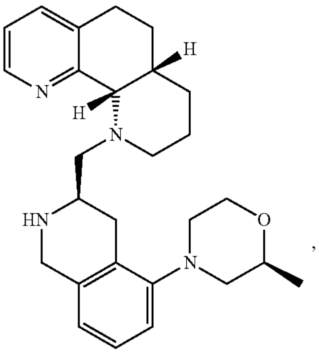
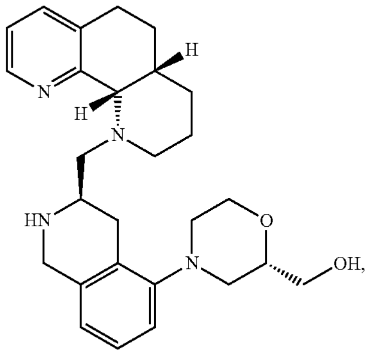
and
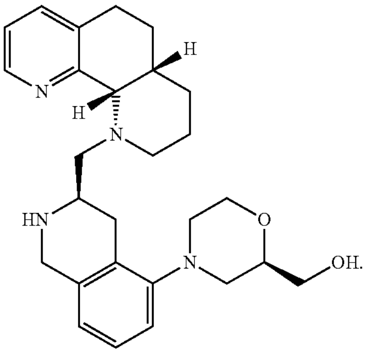
In some embodiments, the compound is
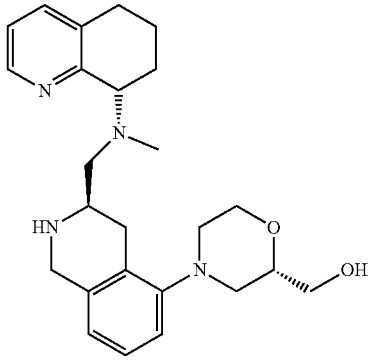
or
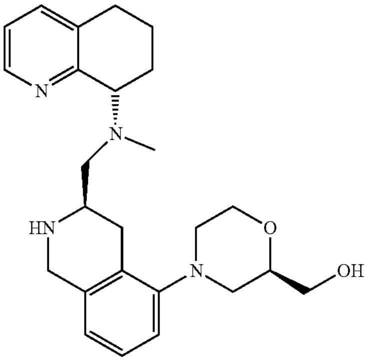
B. Formula II
In some embodiments, the compounds have a structure of Formula II or a pharmaceutically acceptable salt, hydrate, or hydrated salt of Formula II, Formula II

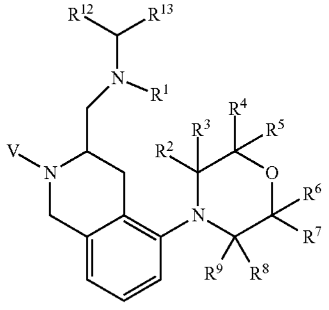

wherein V is hydrogen, an optionally substituted $C_1$-$C_4$ alkyl, or an optionally substituted $C_1$-$C_4$ haloalkyl;

wherein $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl;

wherein $R^{12}$ is an optionally substituted heterocyclyl;

wherein $R^{13}$ is hydrogen or optionally substituted $C_1$-$C_4$ alkyl;

wherein $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, $R^6$ and $R^7$, and $R^8$ and $R^9$—are independently =O or =S; and optionally wherein two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond).

In some wherein Formula II is in the following configuration.

Formula II

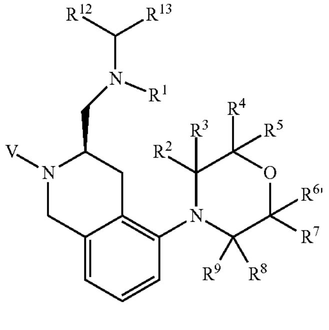

In some embodiments, V is hydrogen. In some embodiments, V is methyl.

In some embodiments, $R^{12}$ is selected from

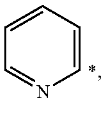, 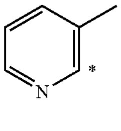, 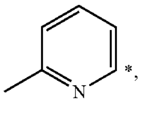, 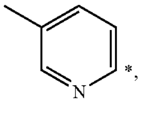,

-continued

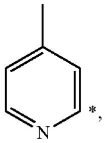, 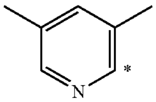, 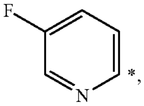,

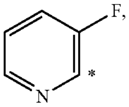, 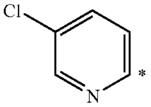, 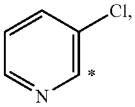

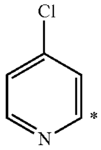, 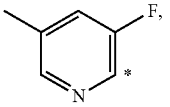, 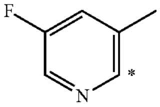,

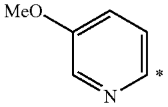, 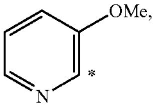, 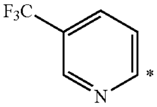,

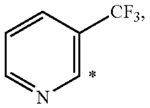, 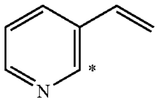, and

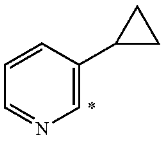.

In some embodiments, $R^{12}$ is selected from

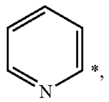, 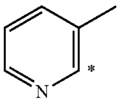, 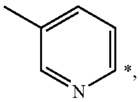,

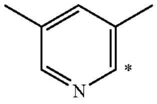, 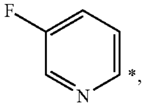, 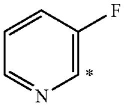,

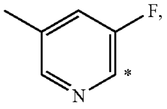, 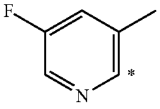, 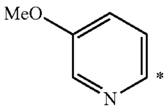,

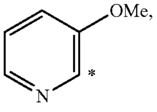, 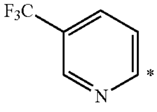, and 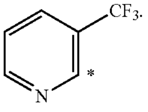.

In some embodiments, $R^{13}$ is selected from hydrogen, methyl, and trifluoromethyl. In some embodiments, $R^{13}$ is hydrogen.

1. The $R^1$ Moiety

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is $—R^{10}—R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, $—NR^aR^b$, $—NR^c[C(═O)R^d]$, or $—OR^f$. $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, $—NR^aR^b$, $—NR^c[C(═O)R^d]$, or $—OR^f$.

In some embodiments, $—R^{10}—R^{11}$ is selected from ethyl, propyl, isopropyl, butyl, isobutyl, $—(CH_2)_2OH$, $—(CH_2)_2NH_2$, $—(CH_2)_3OH$, $—(CH_2)_3NH_2$, $—(CH_2)_4OH$, $—(CH_2)_4NH_2$, $—(CH_2)_3CF_3$,

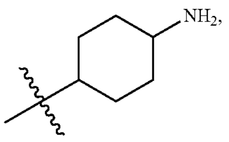
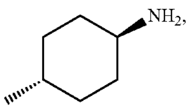
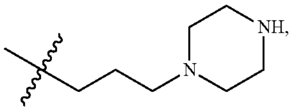
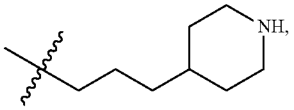
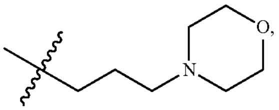
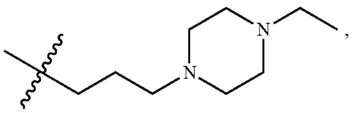
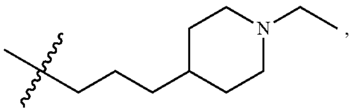
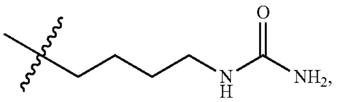

-continued

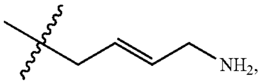
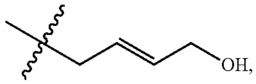
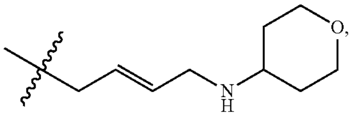
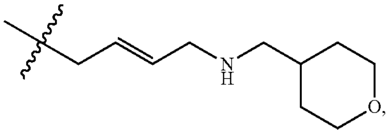
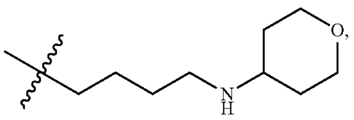
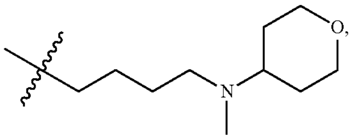
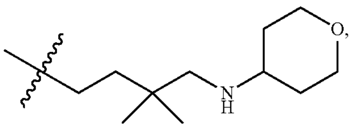
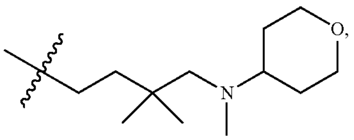
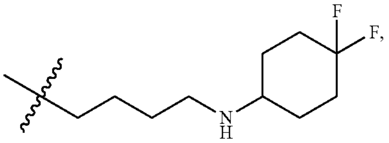
and
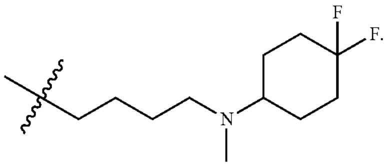

In some embodiments, $—R^{10}—R^{11}$ is selected from ethyl, propyl, isopropyl, butyl, isobutyl, $—(CH_2)_2OH$, $—(CH_2)_2NH_2$, $—(CH_2)_3OH$, $—(CH_2)_3NH_2$, $—(CH_2)_4OH$, $—(CH_2)_3CF_3$,

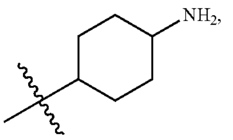
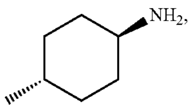
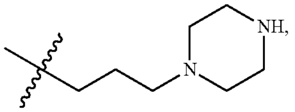
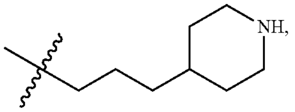

-continued

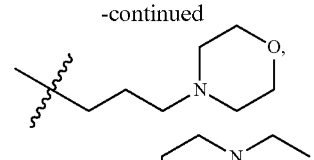

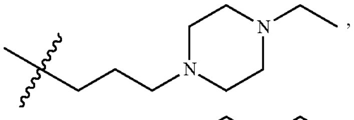

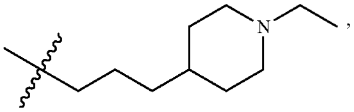

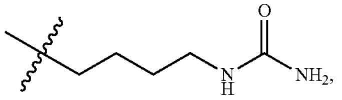

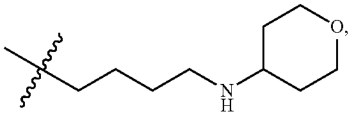

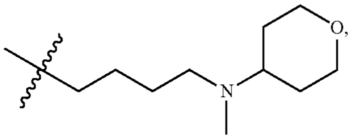

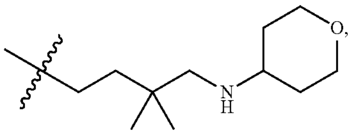

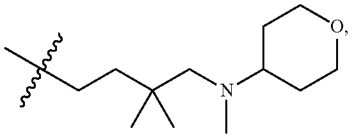

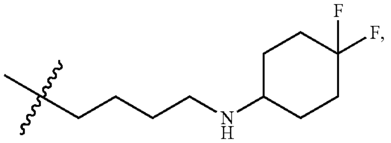

and

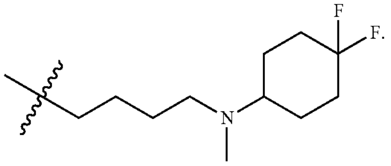

In some embodiments, —$R^{10}$—$R^{11}$ is

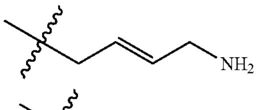

or

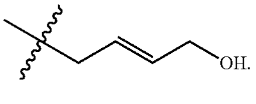

2. The Morpholine Moiety

Group I

In some embodiments, $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, $R^2$, $R^3$, $R^4$, $R^5$, $R^6$, $R^7$, $R^8$, and $R^9$ are hydrogen.

In some embodiments, $R^2$, $R^3$, $R^4$, $R^5$, $R^6$, $R^7$, and $R^9$ are hydrogen and $R^8$ is halogen, amino, optionally substituted hydroxyl, optionally substituted alkyl, or optionally substituted haloalkyl. In some embodiments, $R^2$, $R^3$, $R^4$, $R^5$, $R^6$, $R^7$, and $R^9$ are hydrogen and $R^8$ is halogen, methyl, trifluoromethyl, or hydroxylmethyl. In some embodiments, $R^2$, $R^3$, $R^4$, $R^5$, $R^6$, $R^7$, and $R^9$ are hydrogen and $R^8$ is methyl. In some embodiments, $R^2$, $R^3$, $R^4$, $R^5$, $R^6$, $R^7$, and $R^9$ are hydrogen and $R^8$ is hydroxylmethyl.

In some embodiments, $R^2$, $R^3$, $R^4$, $R^5$, $R^7$, $R^8$, and $R^9$ are hydrogen and $R^6$ is halogen, amino, optionally substituted hydroxyl, optionally substituted alkyl, or optionally substituted haloalkyl.

In some embodiments, $R^2$, $R^3$, $R^4$, $R^5$, $R^7$, $R^8$, and $R^9$ are hydrogen and $R^6$ is halogen, methyl, trifluoromethyl, or hydroxylmethyl. In some embodiments, $R^2$, $R^3$, $R^4$, $R^5$, $R^7$, $R^8$, and $R^9$ are hydrogen and $R^6$ is methyl. In some embodiments, $R^2$, $R^3$, $R^4$, $R^5$, $R^7$, $R^8$, and $R^9$ are hydrogen and $R^6$ is hydroxylmethyl.

Group II In some embodiments, one or more of the following pairs—$R^2$ and $R^3$, $R^4$ and $R^5$, $R^6$ and $R^7$, and $R^8$ and $R^9$—are independently =O or =S, wherein the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, the pair of $R^8$ and $R^9$ is =O or =S.

In some embodiments, the pair of $R^6$ and $R^7$ is =O or =S.

Group III

In some embodiments, two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond), whereas the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, two of $R^2$, $R^3$, $R^4$, $R^5$, $R^6$, $R^7$, $R^8$, and $R^9$ joint together to form a bridge on the morpholine ring. In some embodiments, the bridge is a single-member bridge, double-member bridge, or triple-member bridge. In some embodiments, the bridge is or contains a heteroatom, such as nitrogen, as a bridge member.

In some embodiments, $R^4$ and $R^6$ join together to form the bridge. In some embodiments, the bridge is a double-member bridge with both bridge members being carbon atoms. In some embodiments, the bridge is a triple-member bridge in the form of carbon-nitrogen-carbon.

In some embodiments, $R^2$ and $R^6$ join together to form the bridge. In some embodiments, the bridge is a single-member bridge with the bridge member being a carbon atom.

In some embodiments, $R^4$ and $R^8$ join together to form the bridge. In some embodiments, the bridge is a single-member bridge with the bridge member being a carbon atom.

For example, the
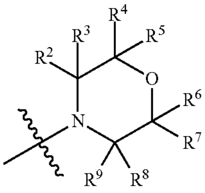
moiety in Formula II has a structure selected from:
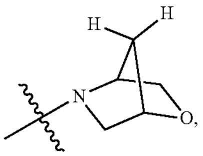
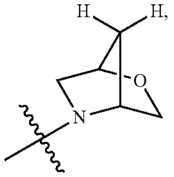
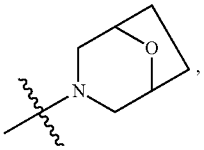
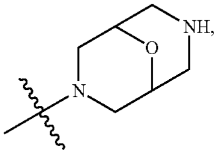
and
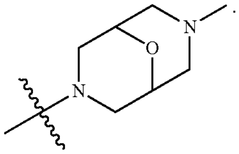
In some embodiments, V is hydrogen or methyl; $R^{12}$ is selected from
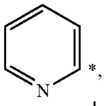
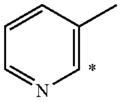
,
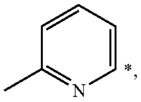
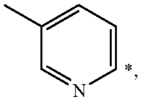
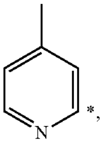
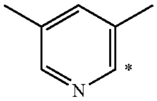
,
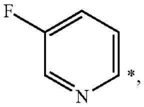
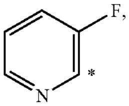
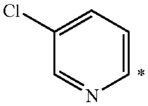
,
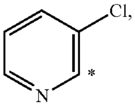
-continued
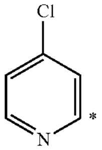
,
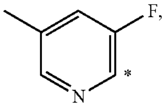
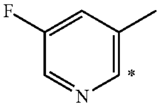
,
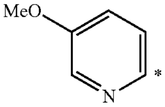
,
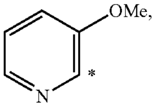
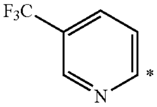
,
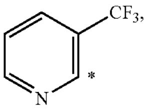
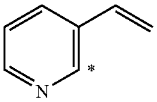
, and
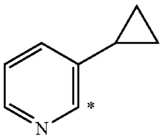
;
$R^{13}$ is selected from hydrogen, methyl, and trifluoromethyl; and the
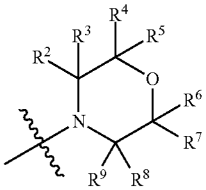
moiety in Formula II has a structure selected from
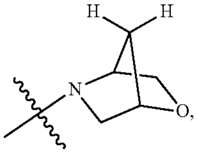
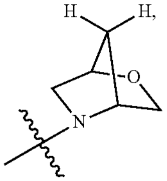
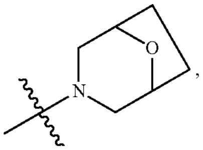
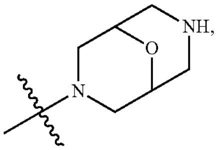
and -continued
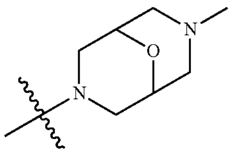.
In some embodiments, V is hydrogen; $R^{12}$ is selected from
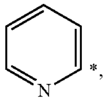, 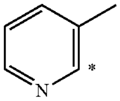, 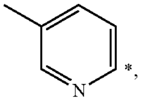,
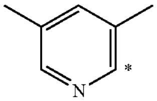, 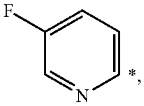, 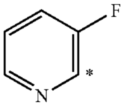,
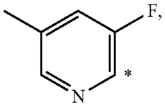, 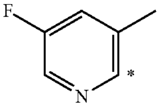, 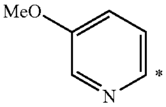,
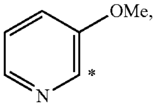, 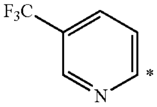, and 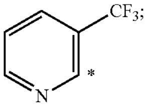;
$R^{13}$ is hydrogen; and the
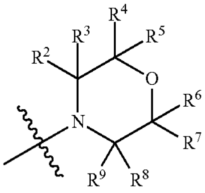
moiety in Formula II has a structure selected from
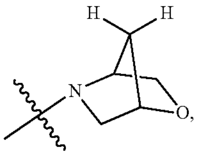,
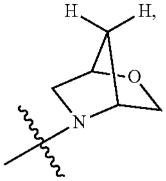,
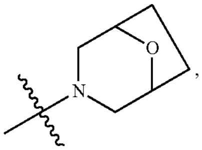,
-continued
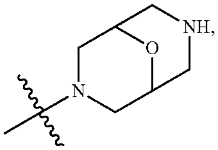, and
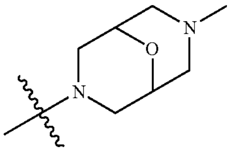.
In some embodiments, V is hydrogen; $R^1$ is methyl; $R^{12}$ is selected from
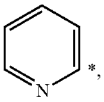, 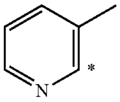, 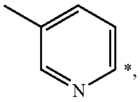,
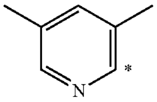, 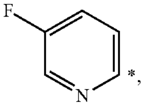, 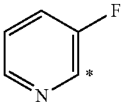,
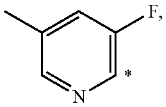, 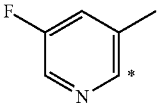, 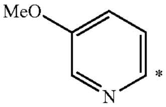,
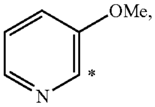, 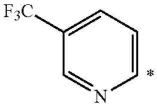, and 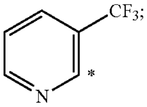;
$R^{13}$ is hydrogen; and the
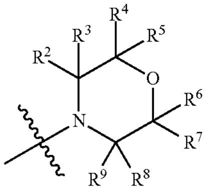
moiety in Formula II has a structure selected from
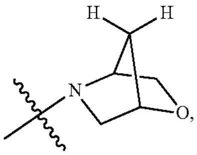,
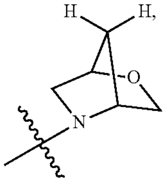

-continued

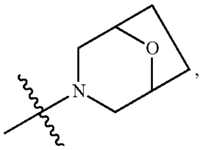

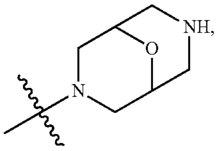

and

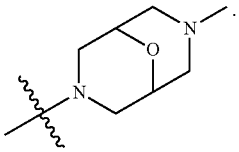

3. Exemplary Structures

Formula IIA

In some embodiments, Formula II is Formula IIA:

Formula IIA

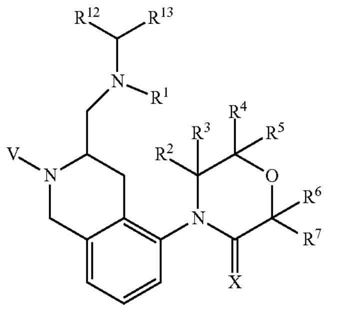

wherein X is O or S; and wherein V, $R^1$, $R^{12}$, $R^{13}$, $R^2$, $R^3$, $R^4$, $R^5$, $R^6$, and $R^7$ are the same as those described above.

In some embodiments, Formula IIA is in the following configuration.

Formula IIA

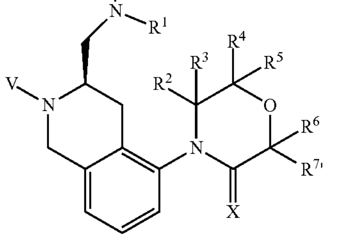

In some embodiments, X is O.

In some embodiments, V is hydrogen or methyl; $R^{12}$ is selected from

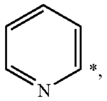 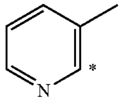, 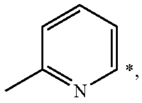 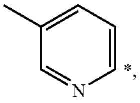

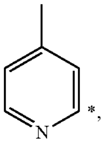 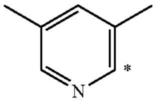, 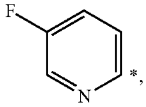

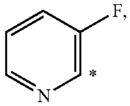 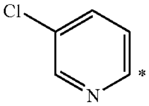, 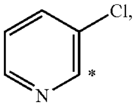

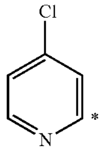, 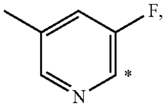 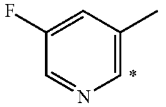,

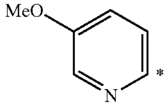, 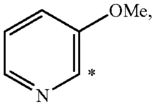 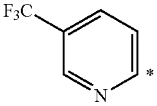,

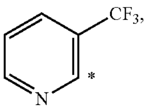 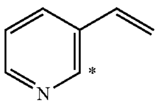, and

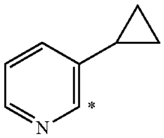;

$R^{13}$ is selected from hydrogen, methyl, and trifluoromethyl; X is O; and $R^2$, $R^3$, $R^4$, $R^5$, $R^6$, and $R^7$ are hydrogen.

In some embodiments, V is hydrogen; $R^{12}$ is selected from

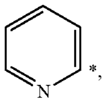 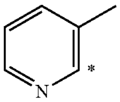, 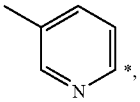

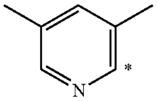, 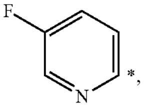 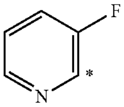,

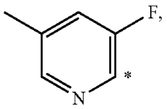 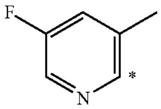, 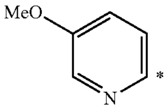,

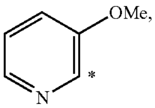 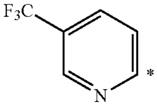, and 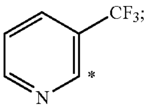

$R^{13}$ is hydrogen; X is O; and $R^2$, $R^3$, $R^4$, $R^5$, $R^6$, and $R^7$ are hydrogen.

In some embodiments, V is hydrogen; $R^1$ is methyl; $R^{12}$ is selected from

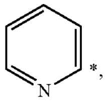, 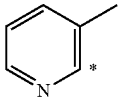, 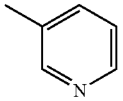,
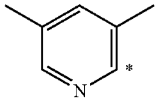, 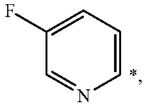, 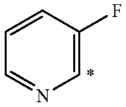,
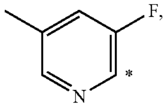, 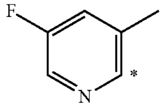, 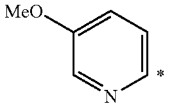,
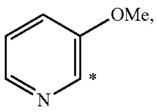, 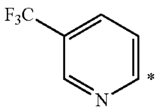, and 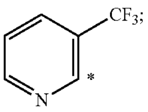;

$R^{13}$ is hydrogen; X is O; and $R^2$, $R^3$, $R^4$, $R^5$, $R^6$, and $R^7$ are hydrogen.

Formula IIB

In some embodiments, Formula II is Formula IIB:

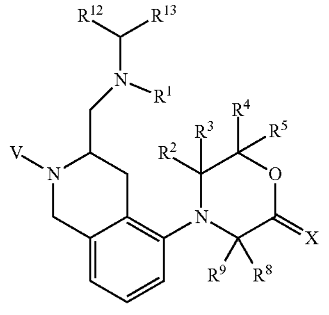

Formula IIB wherein X is O or S; and wherein V, $R^1$, $R^{12}$, $R^{13}$, $R^2$, $R^3$, $R^4$, $R^5$, $R^8$, and $R^9$ are the same as those described above.

In some embodiments, Formula IIB is in the following configuration.

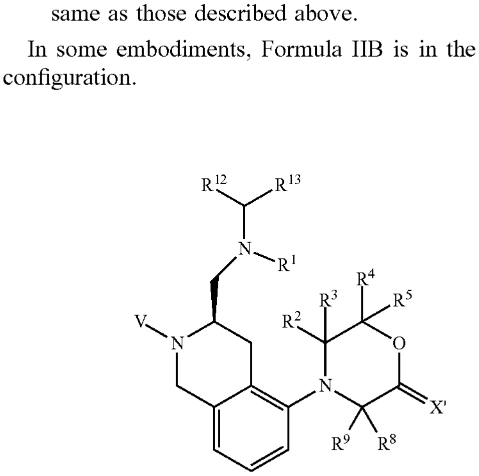

Formula IIB

In some embodiments, X is O.

In some embodiments, V is hydrogen or methyl; $R^2$ is selected from

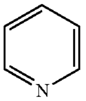, 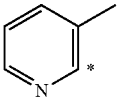, 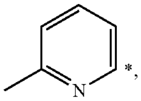, 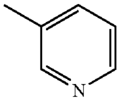,
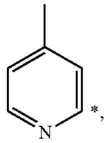, 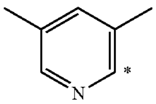, 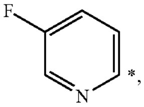,
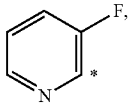, 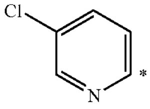, 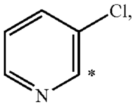,
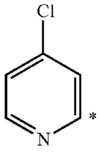, 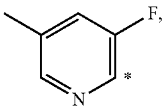, 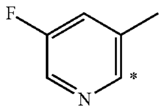,
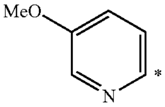, 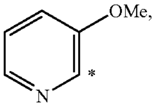, 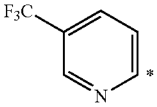,
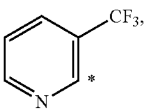, 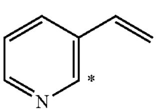, and
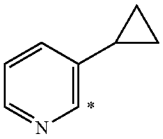;

$R^{13}$ is selected from hydrogen, methyl, and trifluoromethyl; X is O; and $R^2$, $R^3$, $R^4$, $R^5$, $R^8$, and $R^9$ are hydrogen.

In some embodiments, V is hydrogen; $R^{12}$ is selected from

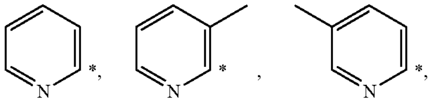,
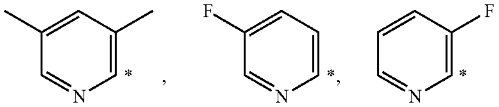,
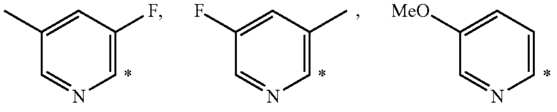,
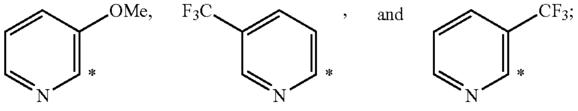
, and ;

$R^{13}$ is hydrogen; X is O; and $R^2$, $R^3$, $R^4$, $R^5$, $R^8$, and $R^9$ are hydrogen.

In some embodiments, V is hydrogen; $R^1$ is methyl; $R^{12}$ is selected from

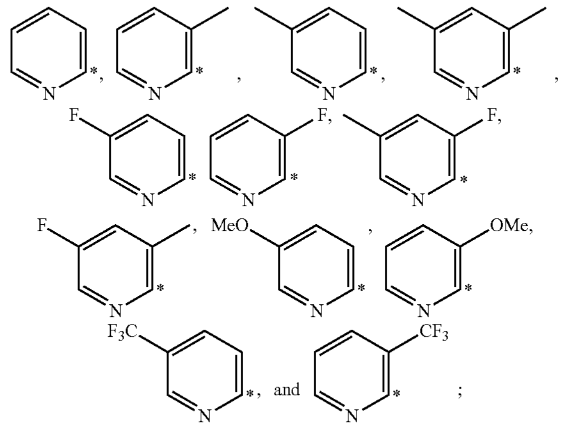

$R^{13}$ is hydrogen; X is O; and $R^2$, $R^3$, $R^4$, $R^5$, $R^8$, and $R^9$ are hydrogen.

Formula IIC

In some embodiments, Formula II is Formula IIC:

Formula IIC

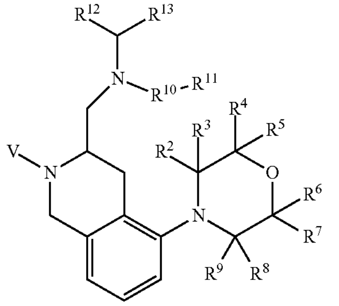

wherein $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge);

wherein $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$;

wherein $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl; and wherein V, $R^{12}$, $R^{13}$, $R^2$, $R^3$, $R^4$, $R^5$, $R^6$, $R^7$, $R^8$, and $R^9$ are the same as those described above.

In some embodiments, Formula IIC is in the following configuration.

Formula IIC

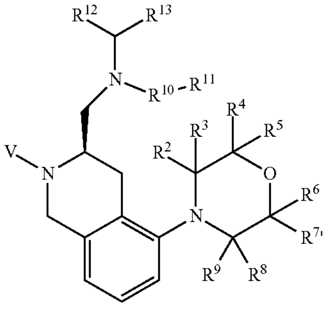

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,

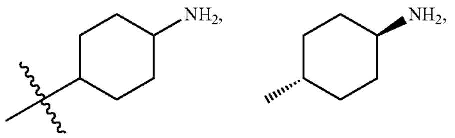

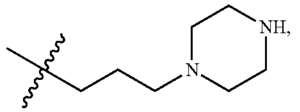

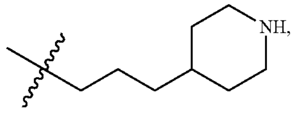

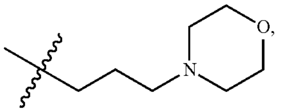

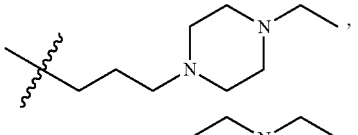

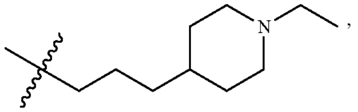

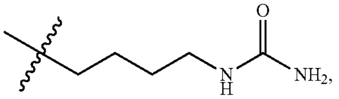

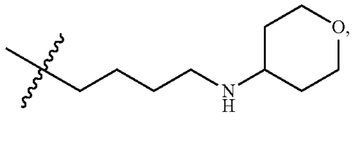

-continued

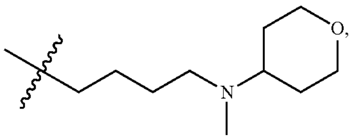

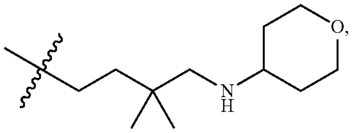

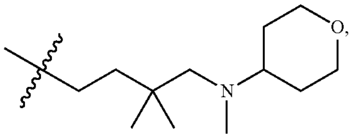

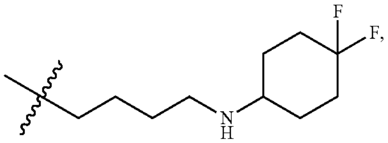

and

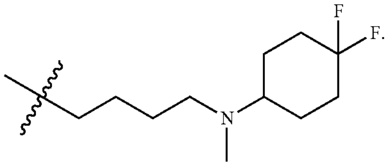

In some embodiments, —$R^{10}$—$R^{11}$ is or

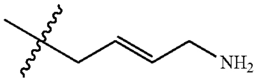

or

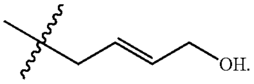

In some embodiments, V is hydrogen or methyl; $R^{12}$ is selected from

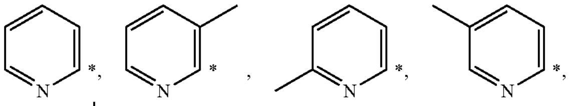

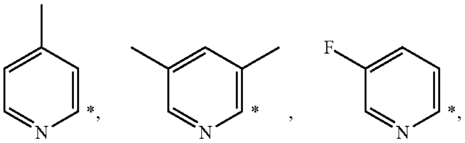

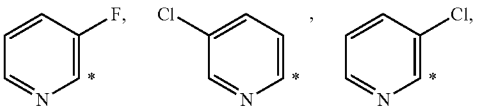

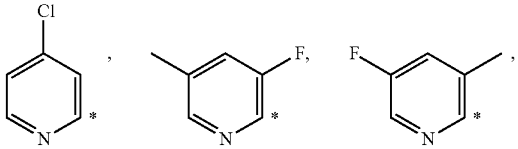

-continued

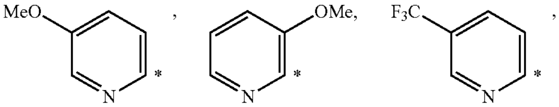

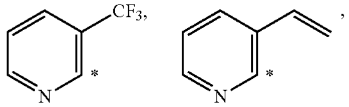

and

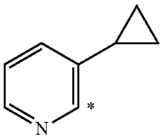

;

$R^{13}$ is selected from hydrogen, methyl, and trifluoromethyl; and $R^2$, $R^3$, $R^4$, $R^5$, $R^6$, $R^7$, $R^8$, and $R^9$ are hydrogen.

In some embodiments, V is hydrogen; $R^{12}$ is selected from

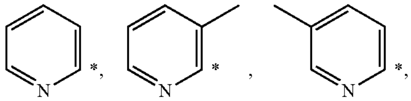

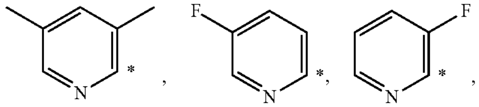

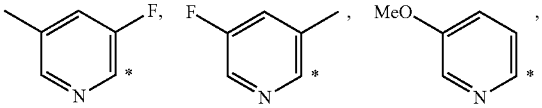

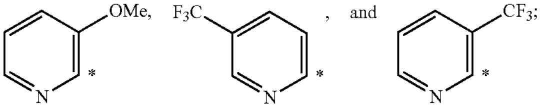

and $R^{13}$ is hydrogen; and $R^2$, $R^3$, $R^4$, $R^5$, $R^6$, $R^7$, $R^8$, and $R^9$ are hydrogen.

In some embodiments, V is hydrogen or methyl; $R^{12}$ is selected from

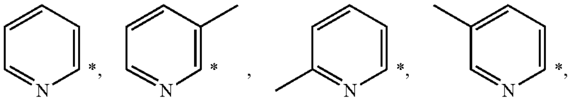

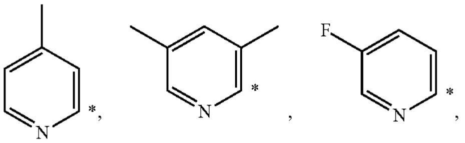

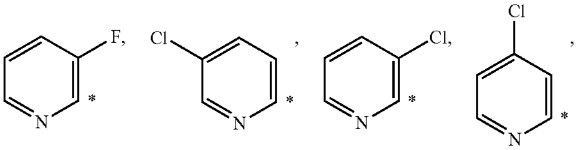

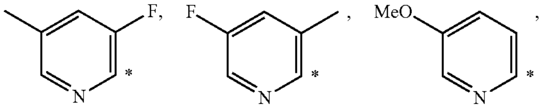

-continued

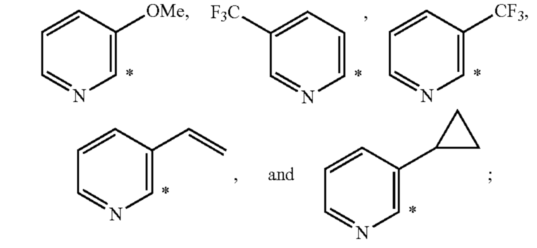

$R^{13}$ is selected from hydrogen, methyl, and trifluoromethyl; $R^6$ and $R^7$ form =O; and $R^2$, $R^3$, $R^4$, $R^5$, $R^8$, and $R^9$ are hydrogen.

In some embodiments, V is hydrogen; $R^{12}$ is selected from

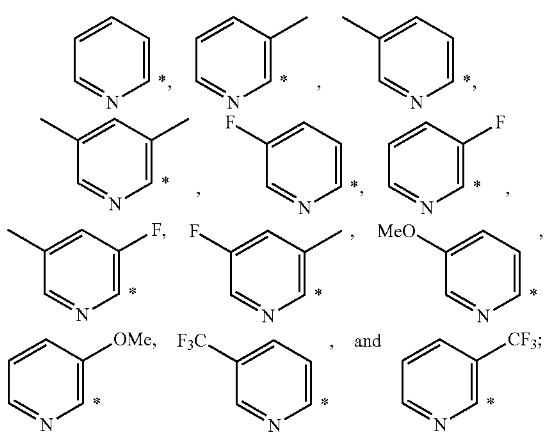

$R^{13}$ is hydrogen; $R^6$ and $R^7$ form =O; and $R^2$, $R^3$, $R^4$, $R^5$, $R^8$, and $R^9$ are hydrogen.

In some embodiments, V is hydrogen or methyl; $R^{12}$ is selected from

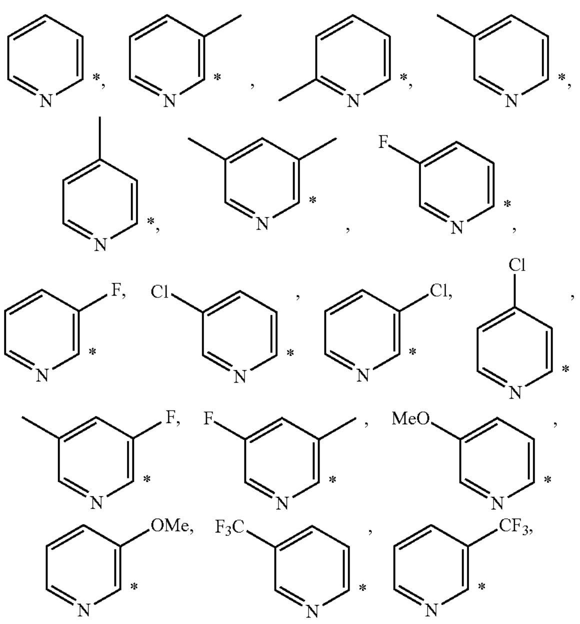

-continued

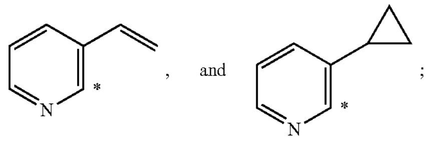

$R^{13}$ is selected from hydrogen, methyl, and trifluoromethyl; $R^8$ and $R^9$ form =O; and $R^2$, $R^3$, $R^4$, $R^5$, $R^6$, and $R^7$ are hydrogen.

In some embodiments, V is hydrogen; $R^{12}$ is selected from

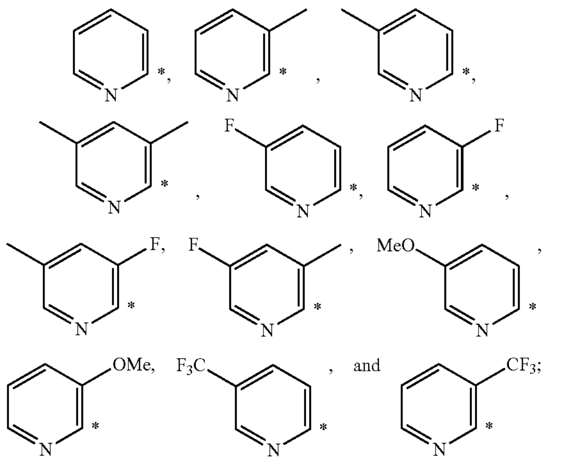

$R^{13}$ is hydrogen; $R^8$ and $R^9$ form =O; and $R^2$, $R^3$, $R^4$, $R^5$, $R^6$, and $R^7$ are hydrogen.

In some embodiments, V is hydrogen or methyl; $R^{12}$ is selected from

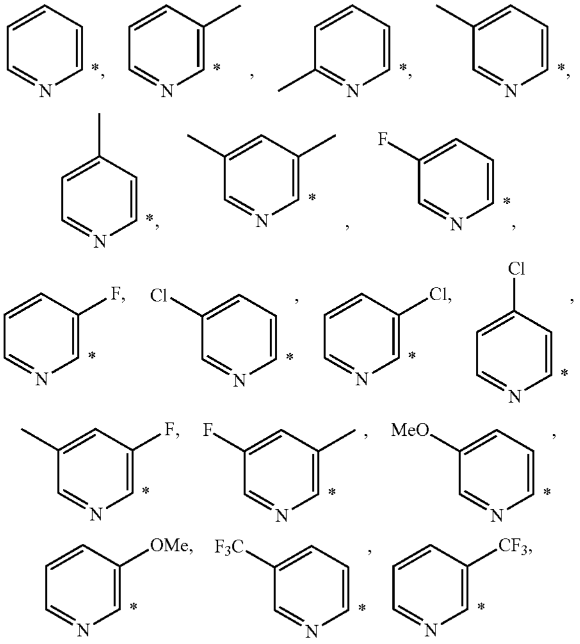

-continued

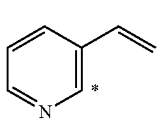, and 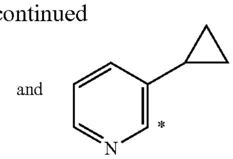;

$R^{13}$ is selected from hydrogen, methyl, and trifluoromethyl; and the

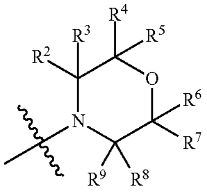

moiety has a structure selected from

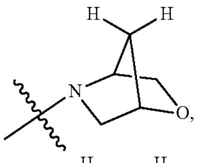

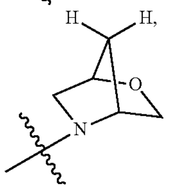

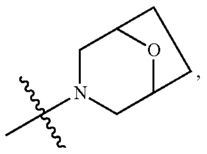

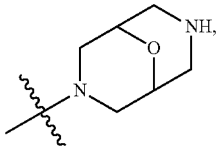 and

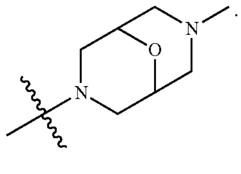

In some embodiments, V is hydrogen; $R^{12}$ is selected from

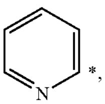 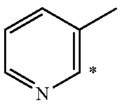, 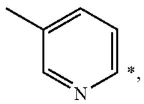

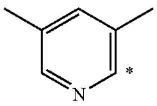, 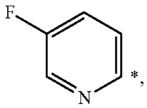 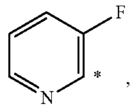,

-continued

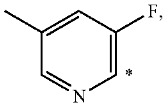 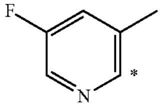, 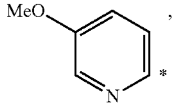,

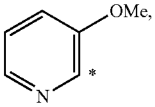 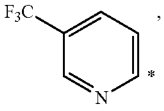, and 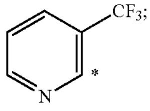

$R^{13}$ is hydrogen; and the

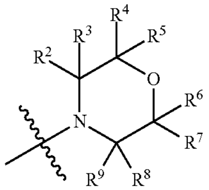

moiety has a structure selected from

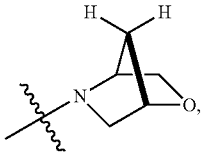 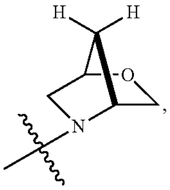

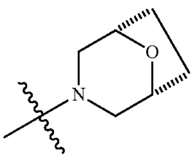, 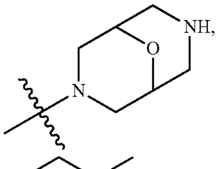 and

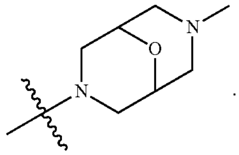.

Formula IID and Formula IIE

In some embodiments, Formula II is Formula IID:

Formula IID

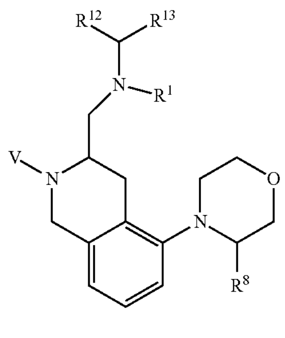

wherein V, $R^1$, $R^{12}$, and $R^{13}$ are the same as those described above.

In some embodiments, Formula IID is in the following configuration.

Formula IID′

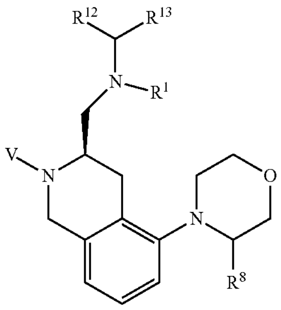

In some embodiments, $R^8$ is halogen, amino, optionally substituted hydroxyl, optionally substituted alkyl, or optionally substituted haloalkyl. In some embodiments, $R^8$ is halogen, methyl, trifluoromethyl, or hydroxylmethyl. In some embodiments, $R^8$ is methyl. In some embodiments, $R^8$ is hydroxylmethyl.

In some embodiments, V is hydrogen or methyl; $R^{12}$ is selected from

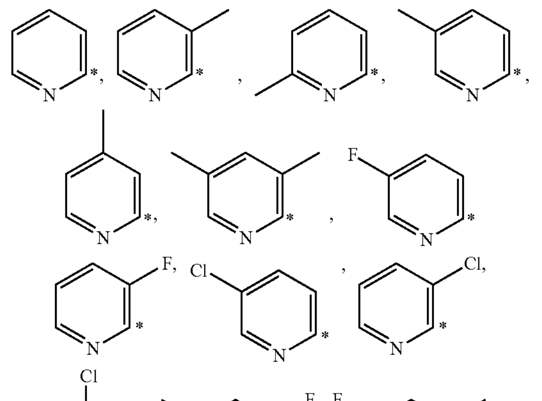

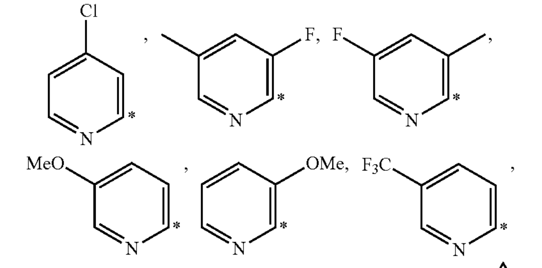

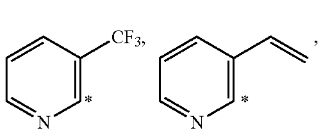

and

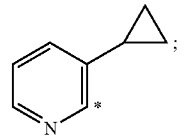

and $R^{13}$ is selected from hydrogen, methyl, and trifluoromethyl.

In some embodiments, V is hydrogen; $R^{12}$ is selected from

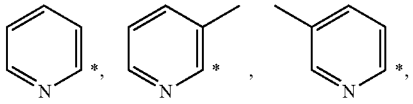

-continued

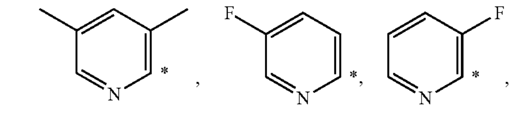

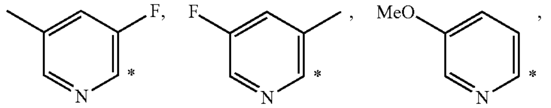

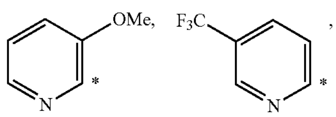

and

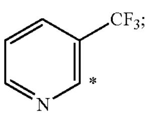

and $R^{13}$ is hydrogen.

In some embodiments, V is hydrogen; $R^1$ is methyl; $R^{12}$ is selected from

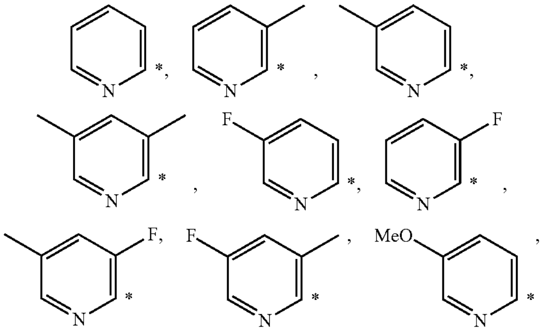

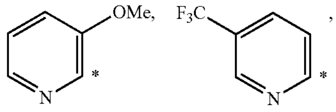

and

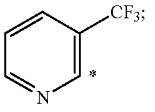

$R^{13}$ is hydrogen.

In some embodiments, Formula II is Formula IIE:

Formula IIE

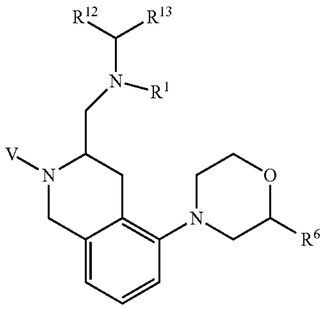

wherein V, $R^1$, $R^{12}$, and $R^{13}$ are the same as those described above.

In some embodiments, Formula IE is in the following configuration.

Formula IIE'

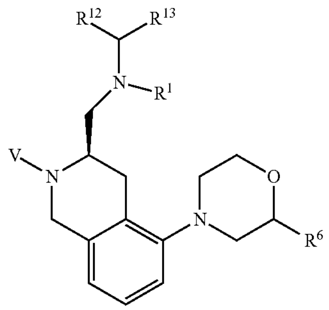

In some embodiments, $R^6$ is halogen, amino, optionally substituted hydroxyl, optionally substituted alkyl, or optionally substituted haloalkyl. In some embodiments, $R^8$ is halogen, methyl, trifluoromethyl, or hydroxylmethyl. In some embodiments, $R^8$ is methyl. In some embodiments, $R^6$ is hydroxylmethyl.

In some embodiments, V is hydrogen or methyl; $R^{12}$ is selected from

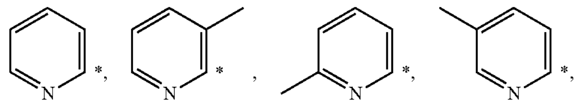

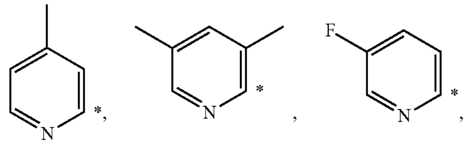

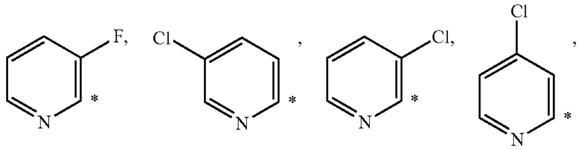

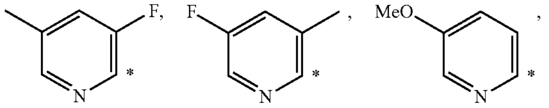

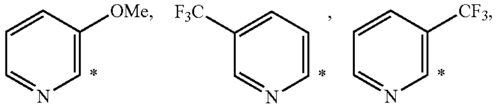

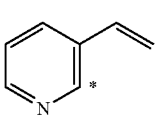

, and

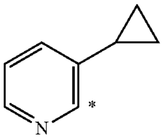

;

and $R^{13}$ is selected from hydrogen, methyl and trifluoromethyl.

In some embodiments, V is hydrogen $R^{12}$ is selected from

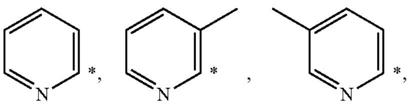

-continued

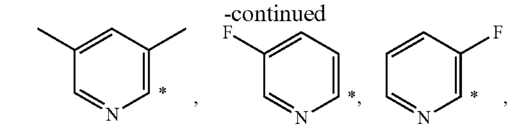

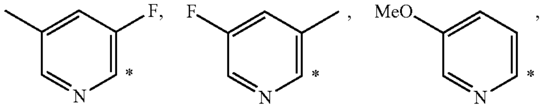

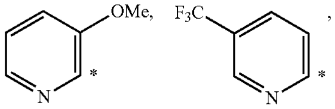

, and

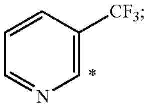

and $R^{13}$ is hydrogen.

In some embodiments V is hydrogen; $R^1$ is methyl; $R^{12}$ is selected from

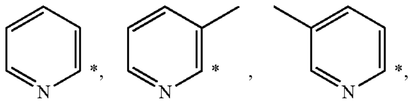

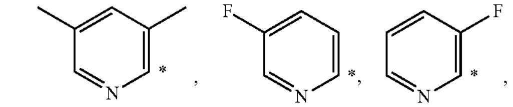

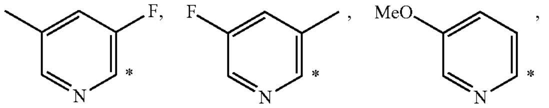

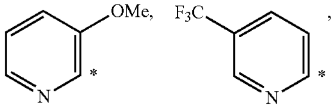

, and

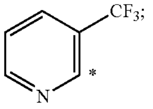

and $R^{13}$ is hydrogen.

C. Formula III

In some embodiments, the compounds have a structure of Formula III or a pharmaceutically acceptable salt, hydrate, or hydrated salt of Formula III, Formula III

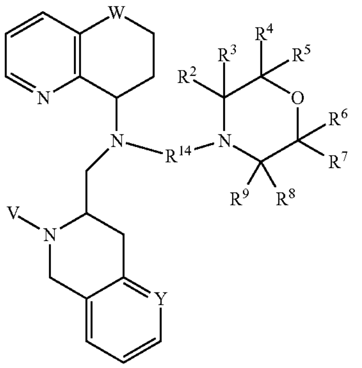

wherein W is $CH_2$ or O;

wherein V is hydrogen, an optionally substituted $C_1$-$C_4$ alkyl, or an optionally substituted $C_1$-$C_4$ haloalkyl;

wherein Y is N or C—$R^e$, wherein $R^e$ is hydrogen, alkyl, haloalkyl, alkenyl, haloalkenyl, alkynyl, haloalkynyl, carbocyclyl, halocarbocyclyl, heterocyclyl, haloheterocyclyl, aryl, haloaryl, heteroaryl, haloheteroaryl, hydroxyl, or amino, wherein each of the foregoing chemical groups for $R^e$ can be optionally substituted;

wherein $R^{14}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge);

wherein $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, $R^6$ and $R^7$, and $R^8$ and $R^9$—are independently =O or =S; and optionally wherein two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond).

In some embodiments, Formula III is in the following configuration.

Formula III'

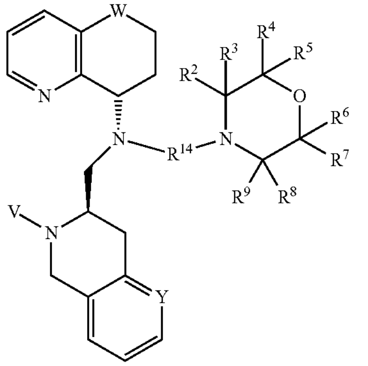

In some embodiments, W is $CH_2$. In some embodiments, W is O.

In some embodiments, V is hydrogen. In some embodiments, V is methyl.

In some embodiments, W is $CH_2$ and V is hydrogen.

In some embodiments, Y is CH. In some embodiments, Y is N.

In some embodiments, W is $CH_2$, V is hydrogen, and Y is CH. In some embodiments, W is $CH_2$, V is hydrogen, and Y is N.

In some embodiments, $R^{14}$ is an optionally substituted, bridging $C_1$-$C_4$ alkylene (alkyl bridge). In some embodiments, $R^{14}$ is a bridging $C_1$-$C_4$ alkylene (alkyl bridge). In some embodiments, $R^{14}$ is a bridging $C_3$ alkylene (alkyl bridge). In some embodiments, $R^{14}$ is a bridging $C_4$ alkylene (alkyl bridge).

In some embodiments, $R^{14}$ is an optionally substituted, bridging $C_1$-$C_4$ alkenylene (alkenyl bridge). In some embodiments, $R^{14}$ is a bridging $C_1$-$C_4$ alkenylene (alkenyl bridge). In some embodiments, $R^{14}$ is a bridging $C_3$ alkenylene (alkenyl bridge). In some embodiments, $R^{14}$ is a bridging $C_4$ alkenylene (alkenyl bridge).

Exemplary compounds include, but are not limited to, the following:

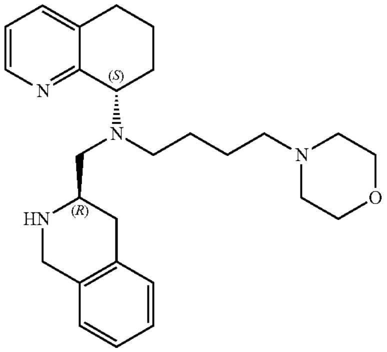

and

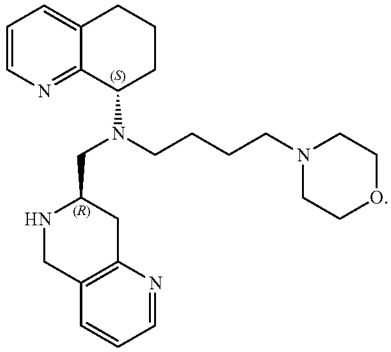

.

1. The Morpholine Moiety

Group I

In some embodiments, $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, $R^2$, $R^3$, $R^4$, $R^5$, $R^6$, $R^7$, $R^8$, and $R^9$ are hydrogen.

In some embodiments, $R^2$, $R^3$, $R^4$, $R^5$, $R^6$, $R^7$, and $R^9$ are hydrogen and $R^8$ is halogen, amino, optionally substituted hydroxyl, optionally substituted alkyl, or optionally substituted haloalkyl. In some embodiments, $R^2$, $R^3$, $R^4$, $R^5$, $R^6$, $R^7$, and $R^9$ are hydrogen and $R^8$ is halogen, methyl, trifluoromethyl, or hydroxylmethyl. In some embodiments, $R^2$, $R^3$, $R^4$, $R^5$, $R^6$, $R^7$, and $R^9$ are hydrogen and $R^8$ is methyl. In some embodiments, $R^2$, $R^3$, $R^4$, $R^5$, $R^6$, $R^7$, and $R^9$ are hydrogen and $R^8$ is hydroxylmethyl.

In some embodiments, $R^2$, $R^3$, $R^4$, $R^5$, $R^7$, $R^8$, and $R^9$ are hydrogen and $R^6$ is halogen, amino, optionally substituted hydroxyl, optionally substituted alkyl, or optionally substituted haloalkyl.

In some embodiments, $R^2$, $R^3$, $R^4$, $R^5$, $R^7$, $R^8$, and $R^9$ are hydrogen and $R^6$ is halogen, methyl, trifluoromethyl, or hydroxylmethyl. In some embodiments, $R^2$, $R^3$, $R^4$, $R^5$, $R^7$, $R^8$, and $R^9$ are hydrogen and $R^6$ is methyl. In some embodiments, $R^2$, $R^3$, $R^4$, $R^5$, $R^7$, $R^8$, and $R^9$ are hydrogen and $R^6$ is hydroxylmethyl.

Group II

In some embodiments, one or more of the following pairs—$R^2$ and $R^3$, $R^4$ and $R^5$, $R^6$ and $R^7$, and $R^8$ and $R^9$—are independently =O or =S, wherein the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, the pair of $R^8$ and $R^9$ is =O or =S.

In some embodiments, the pair of $R^6$ and $R^7$ is =O or =S.

Group III

In some embodiments, two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond), whereas the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, two of $R^2$, $R^3$, $R^4$, $R^5$, $R^6$, $R^7$, $R^8$, and $R^9$ joint together to form a bridge on the morpholine ring. In some embodiments, the bridge is a single-member bridge, double-member bridge, or triple-member bridge. In some embodiments, the bridge is or contains a heteroatom, such as nitrogen, as a bridge member.

In some embodiments, $R^4$ and $R^6$ join together to form the bridge. In some embodiments, the bridge is a double-member bridge with both bridge members being carbon atoms. In some embodiments, the bridge is a triple-member bridge in the form of carbon-nitrogen-carbon.

In some embodiments, $R^2$ and $R^6$ join together to form the bridge. In some embodiments, the bridge is a single-member bridge with the bridge member being a carbon atom.

In some embodiments, $R^4$ and $R^8$ join together to form the bridge. In some embodiments, the bridge is a single-member bridge with the bridge member being a carbon atom.

For example, the

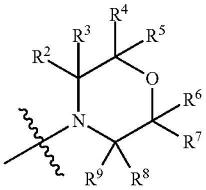

moiety in Formula III has a structure selected from:

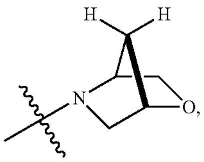

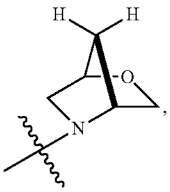

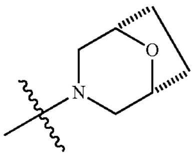

,

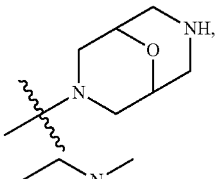

and

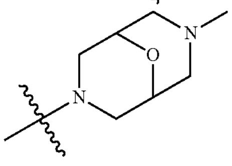

.

D. Formula IV

In some embodiments, the compounds have a structure of Formula IV or a pharmaceutically acceptable salt, hydrate, or hydrated salt of Formula IV, Formula IV

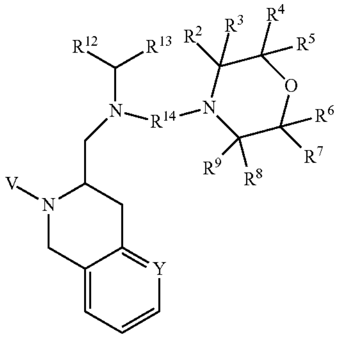

wherein V is hydrogen, an optionally substituted $C_1$-$C_4$ alkyl, or an optionally substituted $C_1$-$C_4$ haloalkyl;

wherein Y is N or C—$R^e$, wherein $R^e$ is hydrogen, alkyl, haloalkyl, alkenyl, haloalkenyl, alkynyl, haloalkynyl, carbocyclyl, halocarbocyclyl, heterocyclyl, haloheterocyclyl, aryl, haloaryl, heteroaryl, haloheteroaryl, hydroxyl, or amino, wherein each of the foregoing chemical groups for $R^e$ can be optionally substituted;

wherein $R^{12}$ is an optionally substituted heterocyclyl;

wherein $R^{13}$ is hydrogen or optionally substituted $C_1$-$C_4$ alkyl;

wherein $R^{14}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge);

wherein $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, $R^6$ and $R^7$, and $R^8$ and $R^9$—are independently =O or =S; and optionally wherein two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond).

In some embodiments, Formula IV is in the following configuration.

Formula IV'

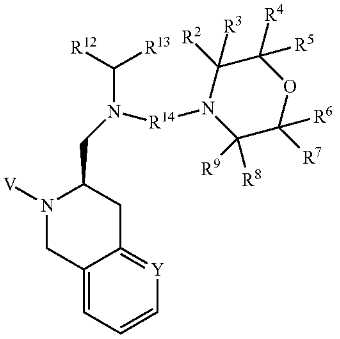

In some embodiments, V is hydrogen. In some embodiments, V is methyl.

In some embodiments, Y is CH. In some embodiments, Y is N.

In some embodiments, V is hydrogen and Y is CH. In some embodiments, V is hydrogen and Y is N.

In some embodiments, $R^{12}$ is selected from

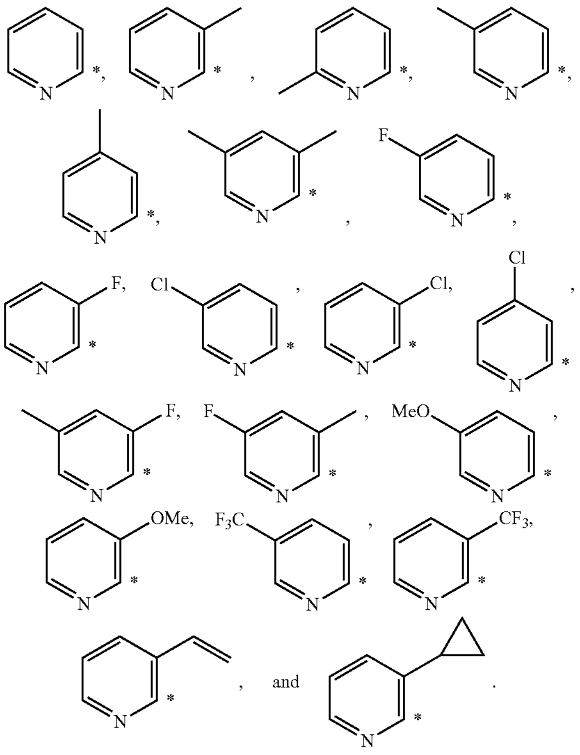

In some embodiments, $R^{12}$ is selected from

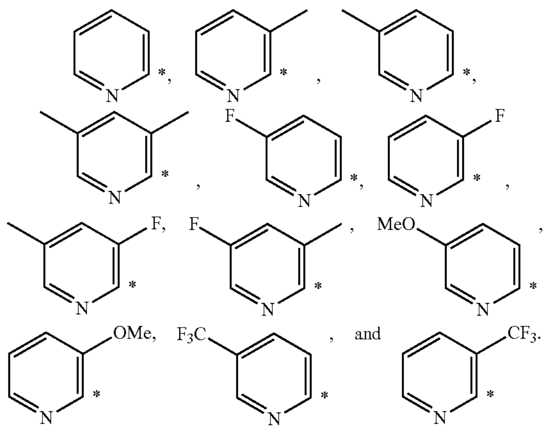

In some embodiments, $R^{13}$ is selected from hydrogen, methyl, and trifluoromethyl. In some embodiments, $R^{13}$ is hydrogen.

In some embodiments, $R^{14}$ is an optionally substituted, bridging $C_1$-$C_4$ alkylene (alkyl bridge). In some embodiments, $R^{14}$ is a bridging $C_1$-$C_4$ alkylene (alkyl bridge). In some embodiments, $R^{14}$ is a bridging $C_3$ alkylene (alkyl bridge). In some embodiments, $R^{14}$ is a bridging $C_4$ alkylene (alkyl bridge).

In some embodiments, $R^{14}$ is an optionally substituted, bridging $C_1$-$C_4$ alkenylene (alkenyl bridge). In some embodiments, $R^{14}$ is a bridging $C_1$-$C_4$ alkenylene (alkenyl bridge). In some embodiments, $R^{14}$ is a bridging $C_3$ alkenylene (alkenyl bridge). In some embodiments, $R^{14}$ is a bridging $C_4$ alkenylene (alkenyl bridge).

1. The Morpholine Moiety

Group I

In some embodiments, $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, $R^2$, $R^3$, $R^4$, $R^5$, $R^6$, $R^7$, $R^8$, and $R^9$ are hydrogen.

In some embodiments, $R^2$, $R^3$, $R^4$, $R^5$, $R^6$, $R^7$, and $R^9$ are hydrogen and $R^8$ is halogen, amino, optionally substituted hydroxyl, optionally substituted alkyl, or optionally substituted haloalkyl. In some embodiments, $R^2$, $R^3$, $R^4$, $R^5$, $R^6$, $R^7$, and $R^9$ are hydrogen and $R^8$ is halogen, methyl, trifluoromethyl, or hydroxylmethyl. In some embodiments, $R^2$, $R^3$, $R^4$, $R^5$, $R^6$, $R^7$, and $R^9$ are hydrogen and $R^8$ is methyl. In some embodiments, $R^2$, $R^3$, $R^4$, $R^5$, $R^6$, $R^7$, and $R^9$ are hydrogen and $R^8$ is hydroxylmethyl.

In some embodiments, $R^2$, $R^3$, $R^4$, $R^5$, $R^7$, $R^8$, and $R^9$ are hydrogen and $R^6$ is halogen, amino, optionally substituted hydroxyl, optionally substituted alkyl, or optionally substituted haloalkyl. In some embodiments, $R^2$, $R^3$, $R^4$, $R^5$, $R^7$, $R^8$, and $R^9$ are hydrogen and $R^6$ is halogen, methyl, trifluoromethyl, or hydroxylmethyl. In some embodiments, $R^2$, $R^3$, $R^4$, $R^5$, $R^7$, $R^8$, and $R^9$ are hydrogen and $R^6$ is methyl. In some embodiments, $R^2$, $R^3$, $R^4$, $R^5$, $R^7$, $R^8$, and $R^9$ are hydrogen and $R^6$ is hydroxylmethyl.

Group II

In some embodiments, one or more of the following pairs—$R^2$ and $R^3$, $R^4$ and $R^5$, $R^6$ and $R^7$, and $R^8$ and $R^9$—are independently =O or =S, wherein the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, the pair of $R^8$ and $R^9$ is =O or =S.

In some embodiments, the pair of $R^6$ and $R^7$ is =O or =S.

Group III

In some embodiments, two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond), whereas the rest of $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl.

In some embodiments, two of $R^2$, $R^3$, $R^4$, $R^5$, $R^6$, $R^7$, $R^8$, and $R^9$ joint together to form a bridge on the morpholine ring. In some embodiments, the bridge is a single-member bridge, double-member bridge, or triple-member bridge. In some embodiments, the bridge is or contains a heteroatom, such as nitrogen, as a bridge member.

In some embodiments, $R^4$ and $R^6$ join together to form the bridge. In some embodiments, the bridge is a double-member bridge with both bridge members being carbon atoms. In some embodiments, the bridge is a triple-member bridge in the form of carbon-nitrogen-carbon.

In some embodiments, $R^2$ and $R^6$ join together to form the bridge. In some embodiments, the bridge is a single-member bridge with the bridge member being a carbon atom.

In some embodiments, $R^4$ and $R^8$ join together to form the bridge. In some embodiments, the bridge is a single-member bridge with the bridge member being a carbon atom.

For example, the

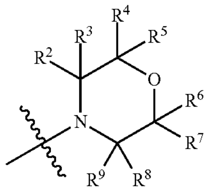

moiety in Formula IV has a structure selected from:

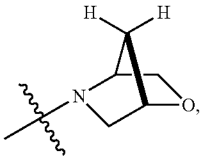,

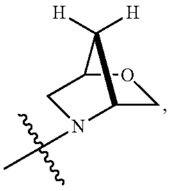,

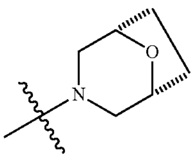,

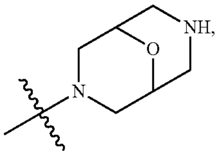, and

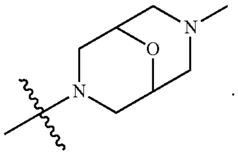.

E. Formula V

In some embodiments, the compounds have a structure of Formula V or a pharmaceutically acceptable salt, hydrate, or hydrated salt of Formula V, Formula V

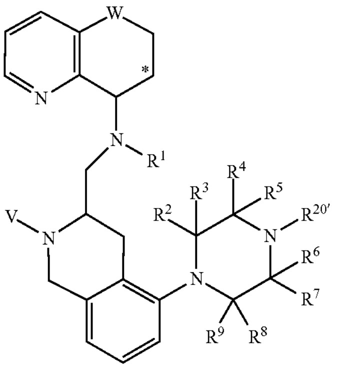

wherein W is $CH_2$ or O;

wherein V is hydrogen, an optionally substituted $C_1$-$C_4$ alkyl, or an optionally substituted $C_1$-$C_4$ haloalkyl;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein $R^2$, $R^3$, $R^4$, $R^5$, $R^6$, $R^7$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, $R^6$ and $R^7$, and $R^8$ and $R^9$—are independently =O or =S;

optionally wherein two of $R^2$, $R^3$, $R^4$, $R^5$, $R^6$, $R^7$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond);

$R^{20'}$ is trifluoromethyl, trifluoroethyl, —$SF_5$, acyl, thioacyl, ester, thionoester, amide, thioamide, sulfinyl, sulfonyl, sulfonic ester, or sulfamide.

In some embodiments, Formula V is in the following configuration.

Formula V'

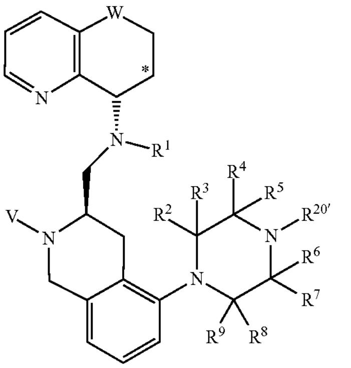

In some embodiments, W is $CH_2$. In some embodiments, W is O.

In some embodiments, V is hydrogen. In some embodiments, V is methyl.

In some embodiments, W is $CH_2$ and V is hydrogen.

1. The $R^1$ Moiety

Group I

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is —$R^{10}$—$R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C({=}O)R^d]$, or —$OR^f$. $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C({=}O)R^d]$, or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

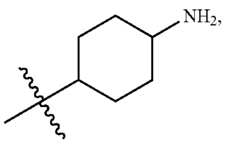
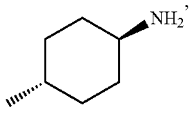
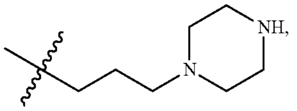
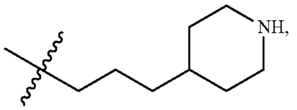
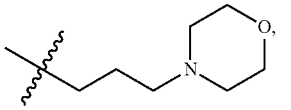
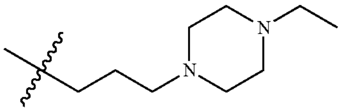
,
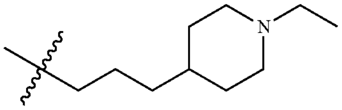
, -continued

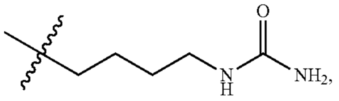
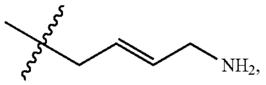
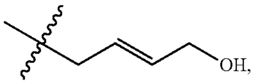
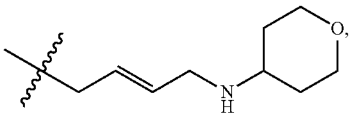
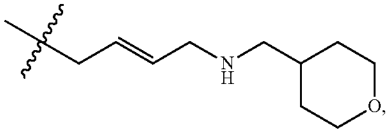
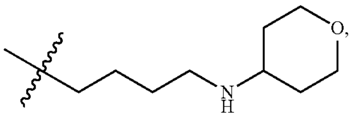
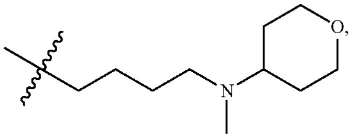
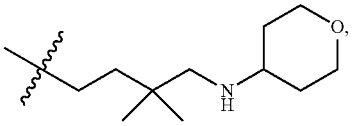
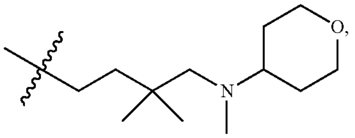
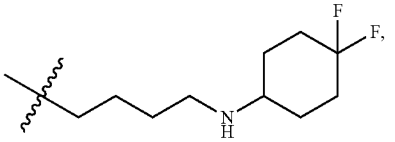
and
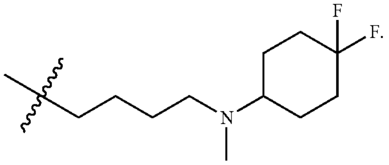

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,

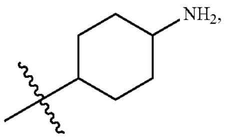
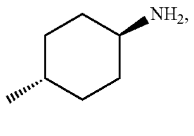
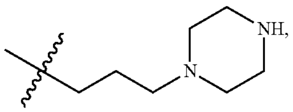

-continued

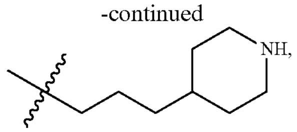
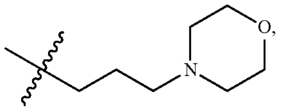
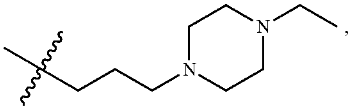
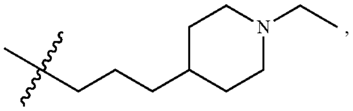
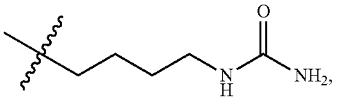
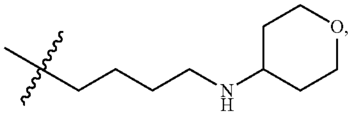
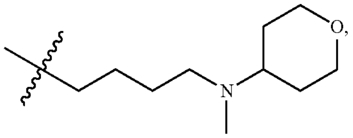
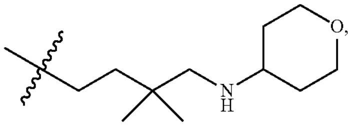
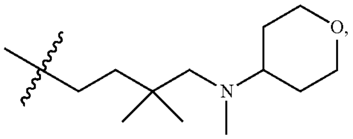
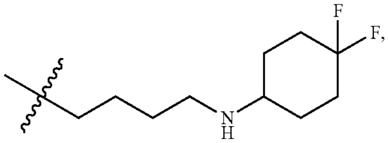 and
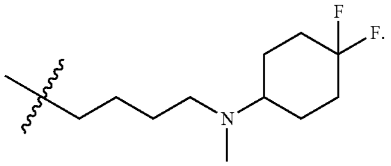

In some embodiments, —$R^{10}$—$R^{11}$ is

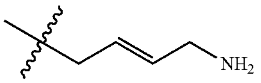 or 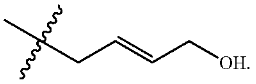

Group II

In some embodiments, $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle.

In some embodiments, the optionally substituted heterocycle is five- or six-membered. For example, the optionally substituted heterocycle is a six-membered heterocycle, such as piperidine.

2. The Piperazine Moiety

In some embodiments, $R^2$, $R^3$, $R^4$, $R^5$, $R^6$, $R^7$, $R^8$, and $R^9$ are hydrogen.

In some embodiments, $R^{20'}$ is acyl, thioacyl, ester, thionoester, amide, thioamide, sulfinyl, sulfonyl, sulfonic ester, or sulfamide.

In some embodiments, $R^{20'}$ is —C(=O)$R^i$, —C(=S)$R^k$, —C(=O)O$R^{g1}$, —C(=S)O$R^{o1}$, —C(=O)N$R^{j1}R^{j2}$, —C(=S)N$R^{l1}R^{l2}$, —S(=O)$R^m$, —S(=O)$_2R^n$, —S(=O)$_2$N$R^{p1}R^{p2}$, or —S(=O)$_2$O$R^q$, wherein $R^i$, $R^k$, $R^{g1}$, $R^{o1}$, $R^{j1}$, $R^{j2}$, $R^{l1}$, $R^{l2}$, $R^m$, $R^n$, $R^{p1}$, $R^{p2}$, and $R^q$ are the same as those defined herein (see the Definitions section).

In some embodiments, $R^i$, $R^k$, $R^{g1}$, $R^{o1}$, $R^{j1}$, $R^{j2}$, $R^{l1}$, $R^{l2}$, $R^m$, $R^n$, $R^{p1}$, $R^{p2}$, and $R^q$ are independently selected from hydrogen, $C_{1-4}$ alkyl, phenyl, and benzyl. In some embodiments, $R^i$, $R^k$, $R^{g1}$, $R^{o1}$, $R^{j1}$, $R^{j2}$, $R^{l1}$, $R^{l2}$, $R^m$, $R^n$, $R^{p1}$, $R^{p2}$, and $R^q$ are independently selected from hydrogen, methyl, ethyl, isopropyl, phenyl, and benzyl.

In some embodiments, the piperazine moiety

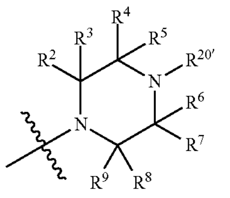

has one of the following structures:

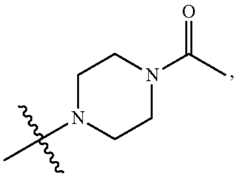
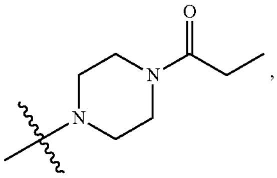
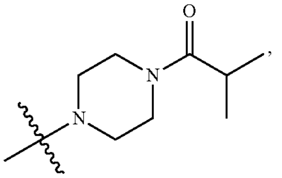
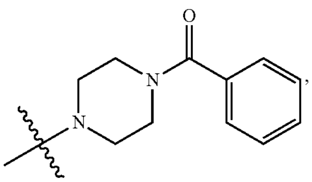
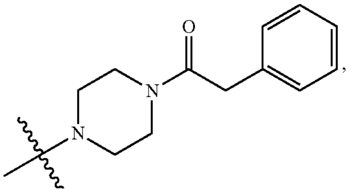

-continued
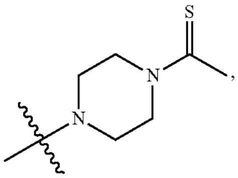,
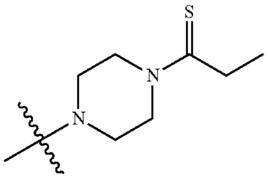,
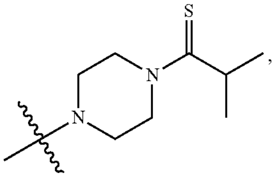,
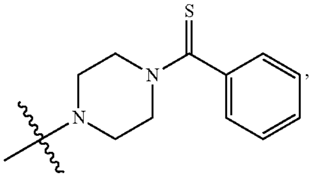,
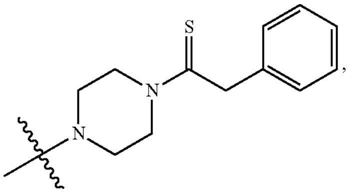,
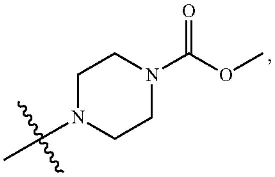,
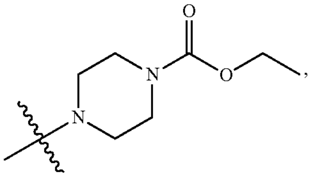,
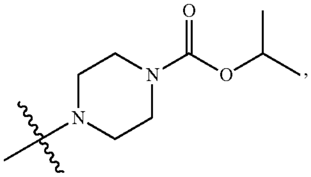,
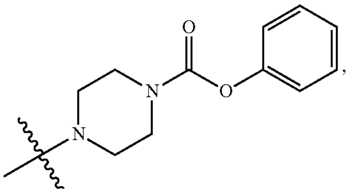,
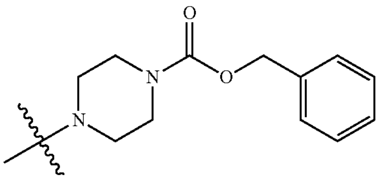,
-continued
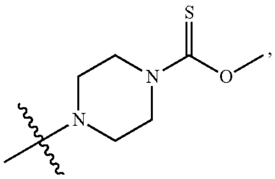,
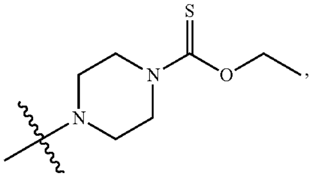,
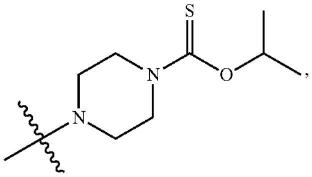,
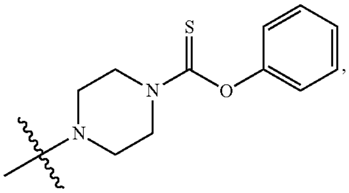,
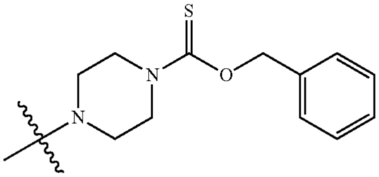,
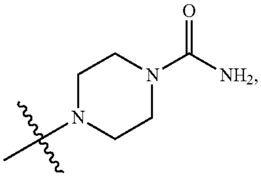,
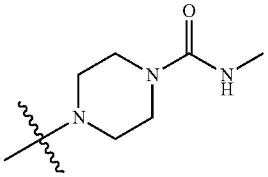,
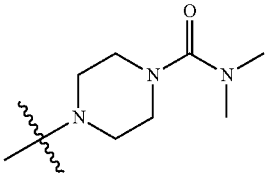,
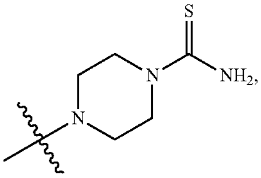,
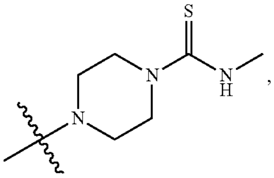,
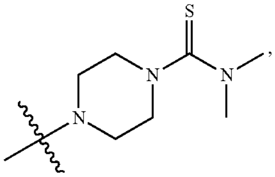,
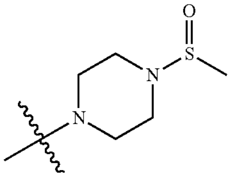, -continued
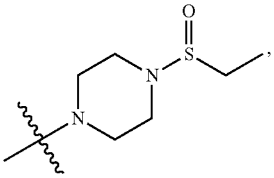
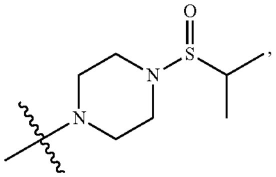
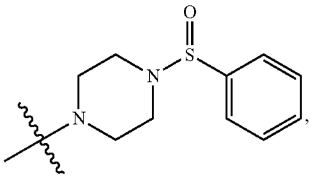
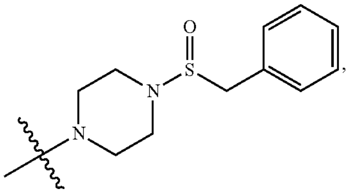
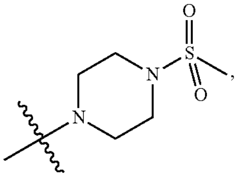
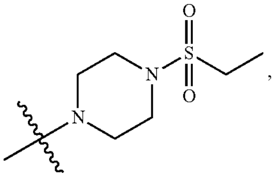
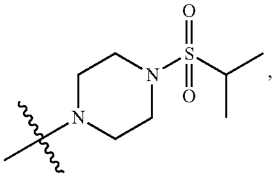
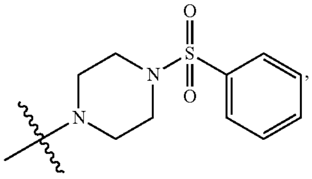
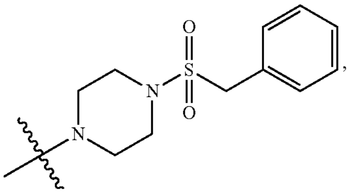
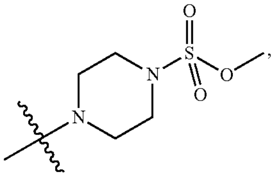
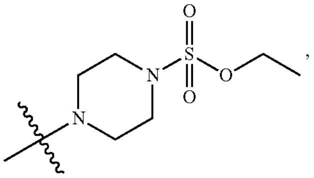
-continued
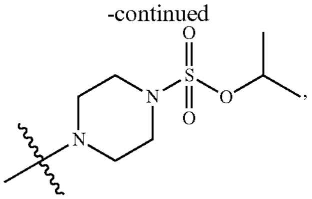
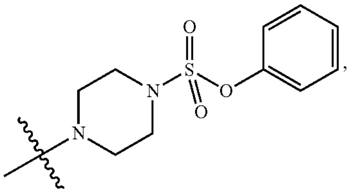
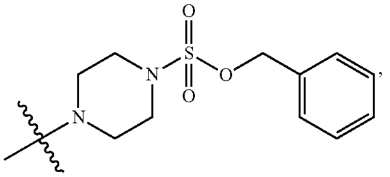
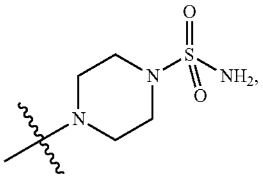
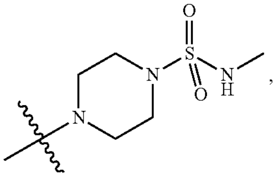
and
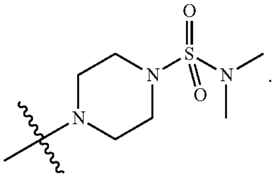
3. Exemplary Structures
In some embodiments, Formula V is Formula VA:
Formula VA
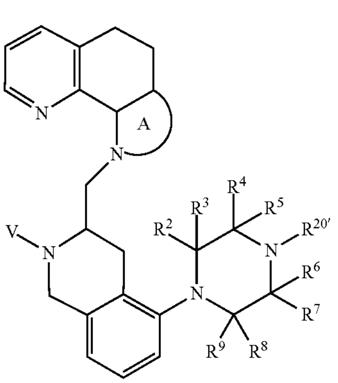
wherein ring A is an optionally substituted, five- or six-membered heterocycle, and
wherein V, $R^2$, $R^3$, $R^4$, $R^5$, $R^6$, $R^7$, $R^8$, $R^9$, and $R^{20'}$ are the same as those described above.

In some embodiments, Formula VA is in the following configuration.

Formula VA'

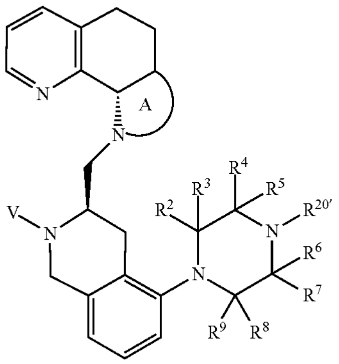

In some embodiments, ring A is a six-membered heterocycle, such as piperidine.

In some embodiments, Formula V has the following structure.

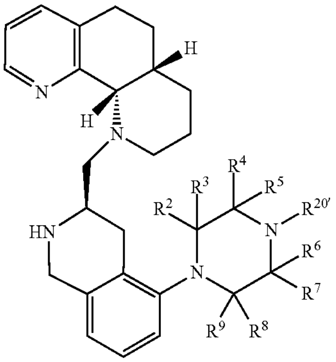

In some embodiments, Formula V has the following structure.

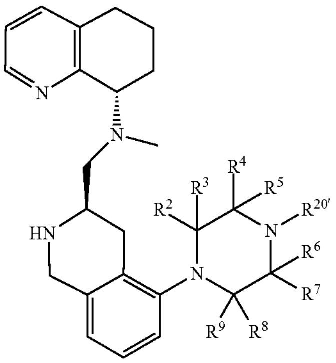

In some embodiments, Formula V has the following structure.

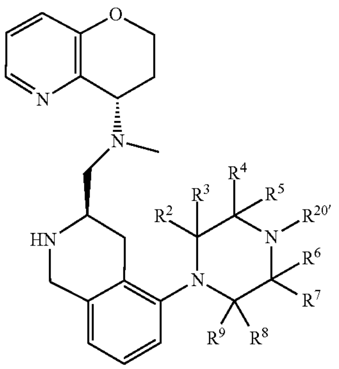

Exemplary structures include, but are not limited to, the following:

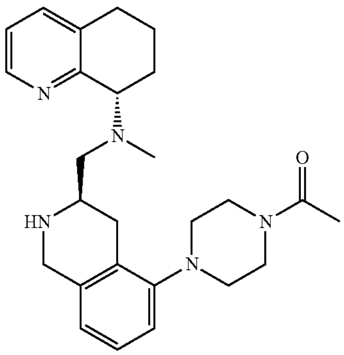

,

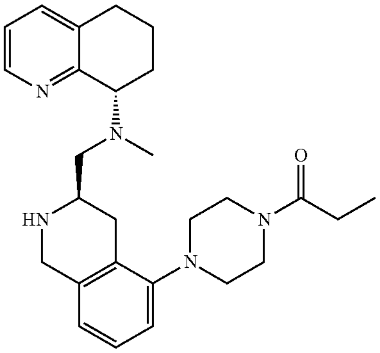

,

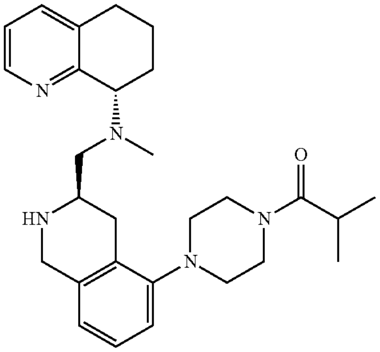

,

-continued
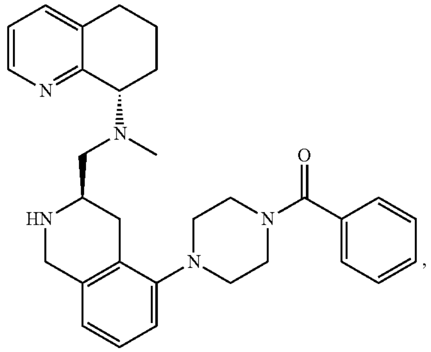
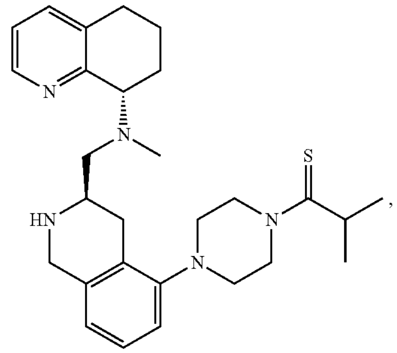
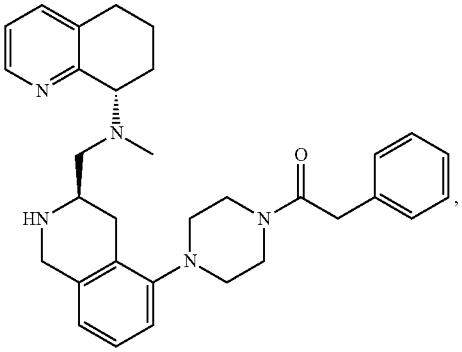
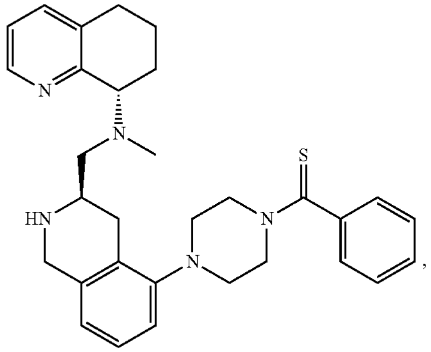
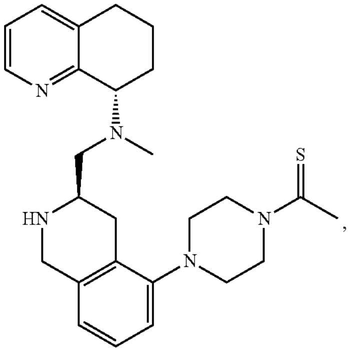
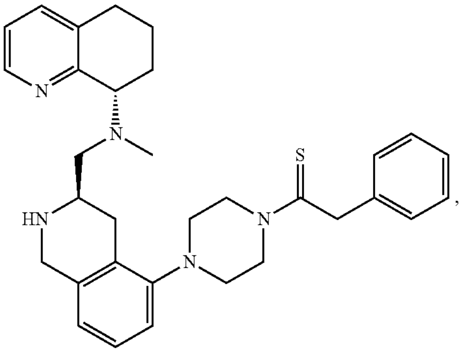
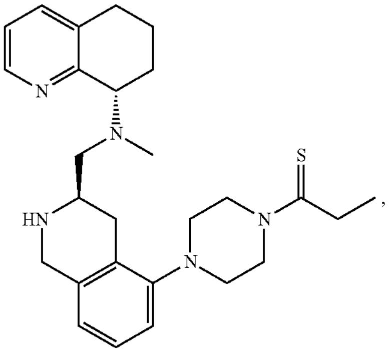
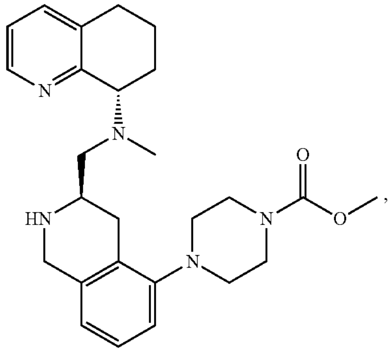

-continued
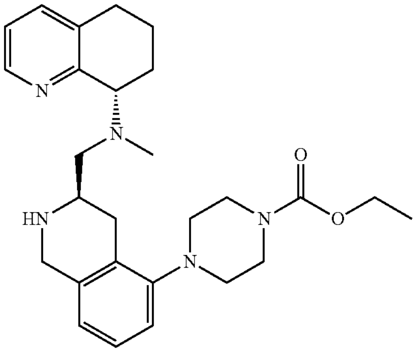
,
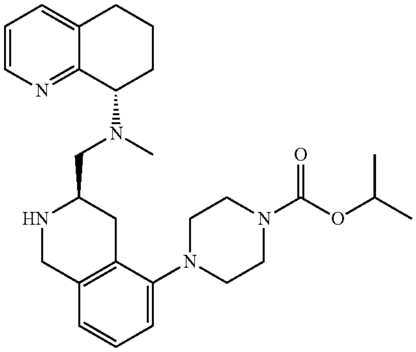
,
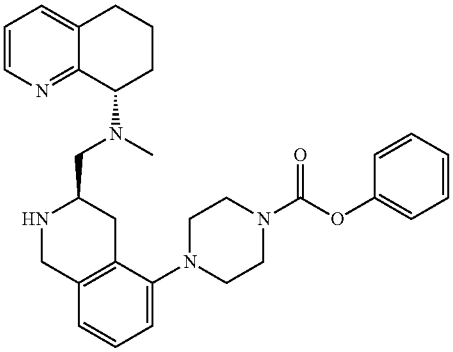
,
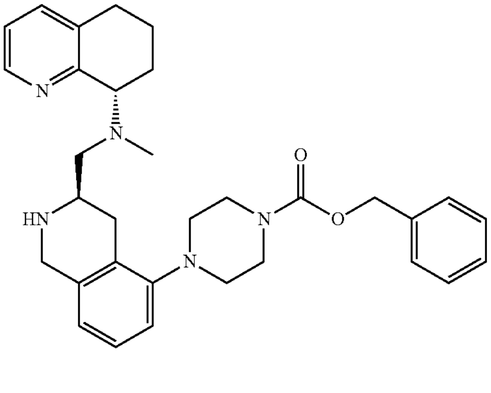
,
-continued
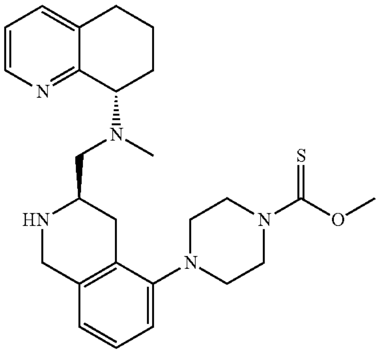
,
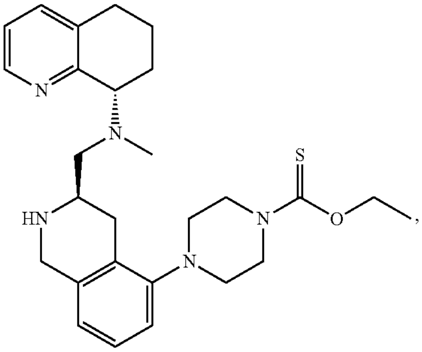
,
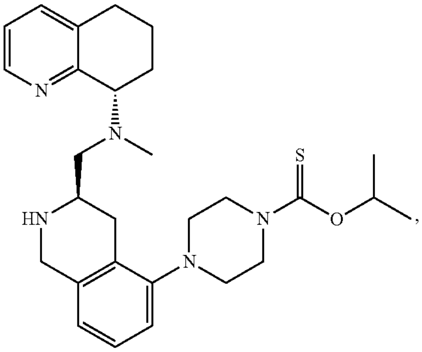
,
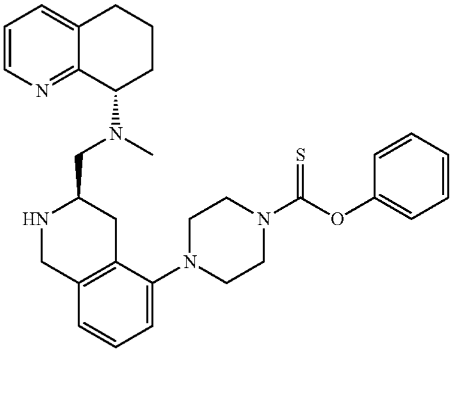
, -continued
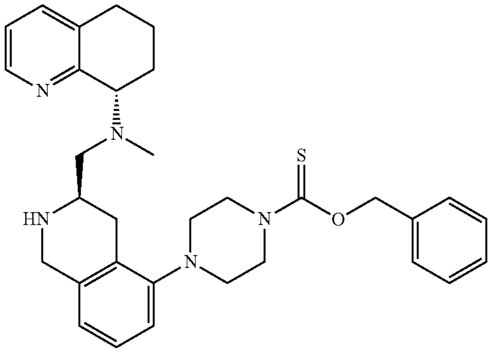
,
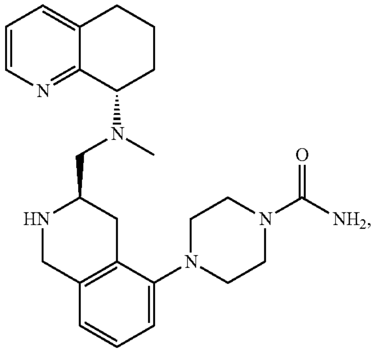
,
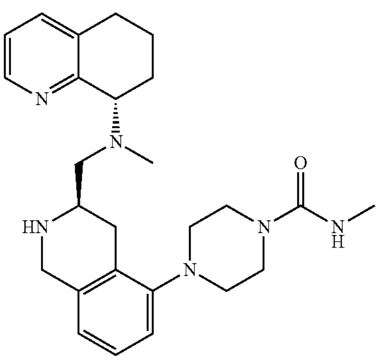
,
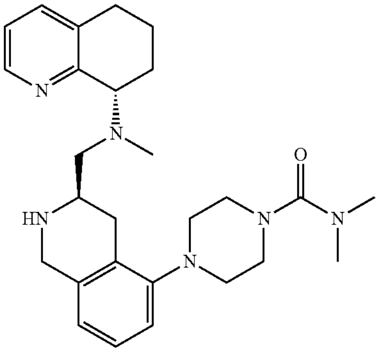
,
-continued
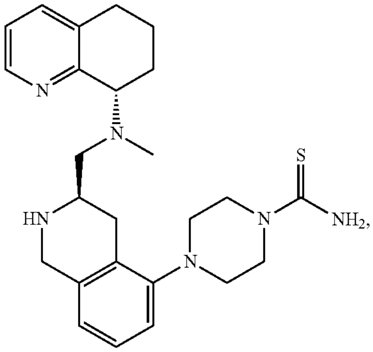
,
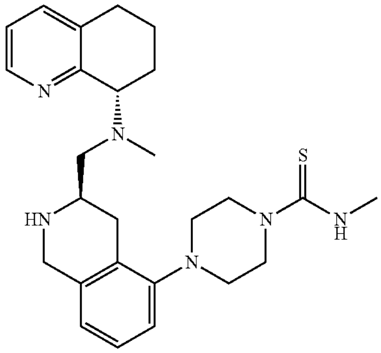
,
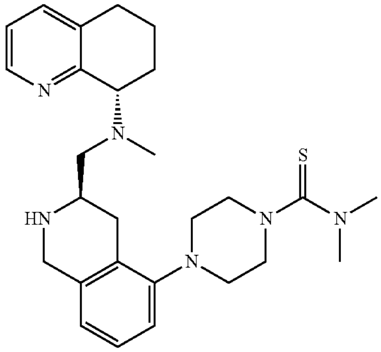
,
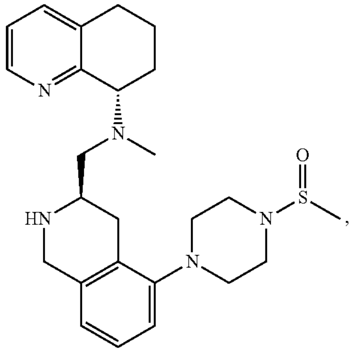
, -continued
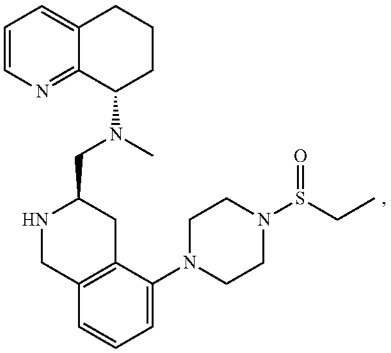
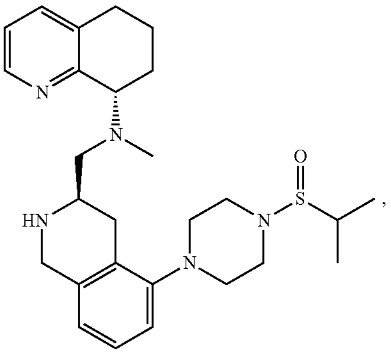
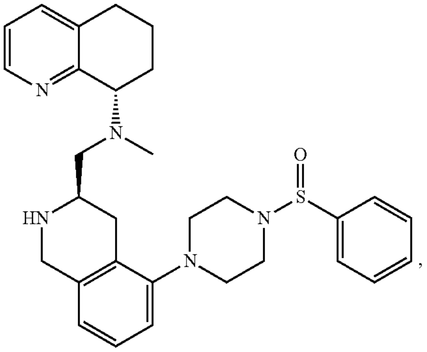
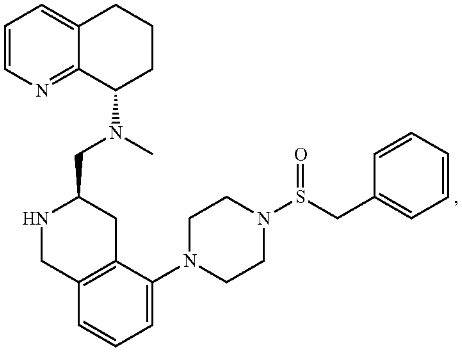
-continued
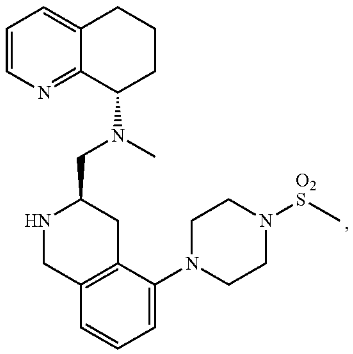
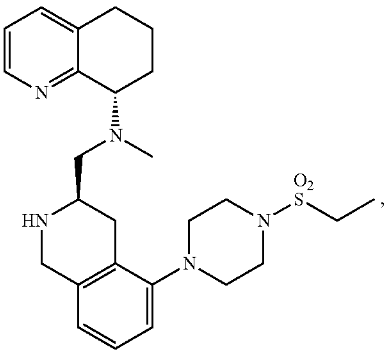
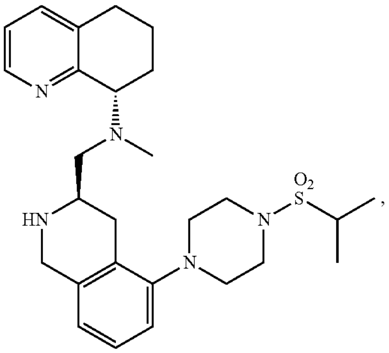
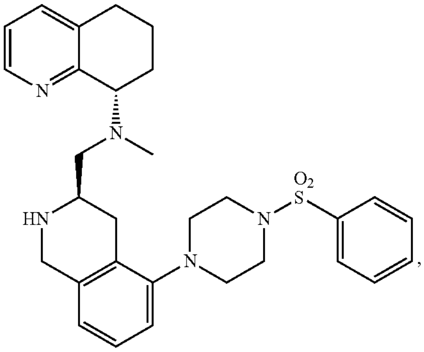

-continued
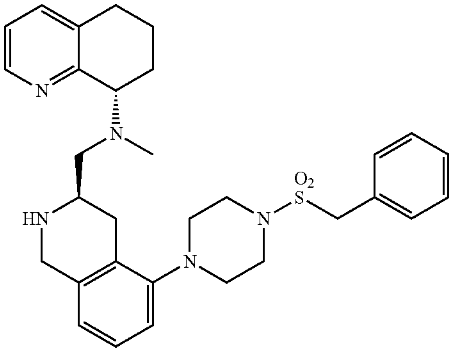
,
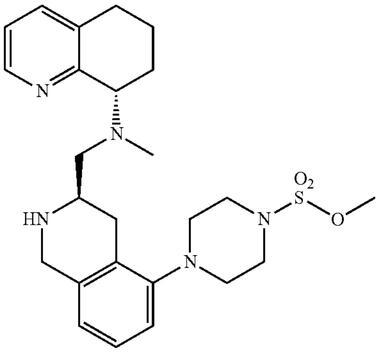
,
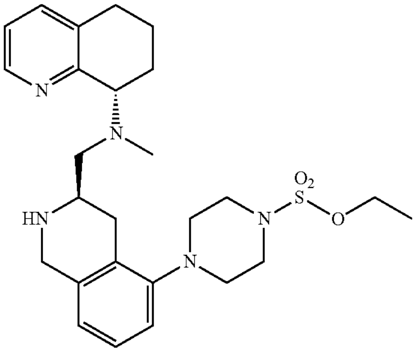
,
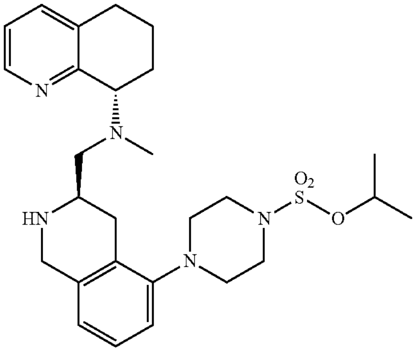
,
-continued
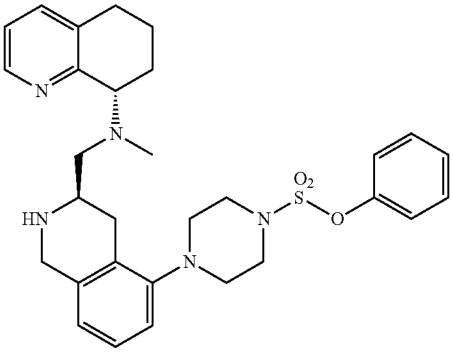
,
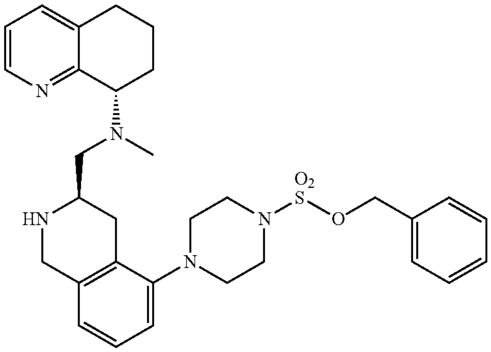
,
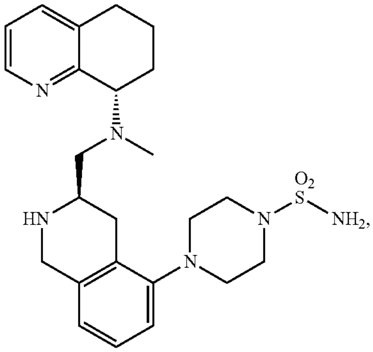
,
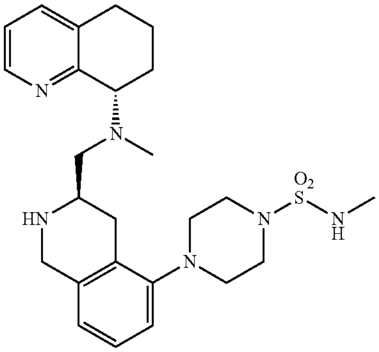
, and -continued

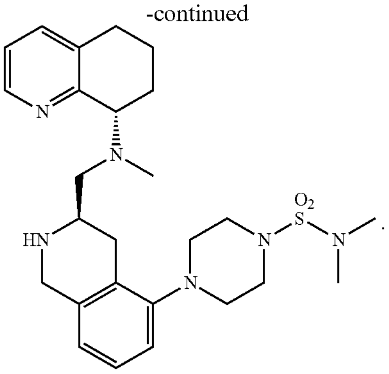

F. Formula VI

In some embodiments, the compounds have a structure of Formula VI or a pharmaceutically acceptable salt, hydrate, or hydrated salt of Formula VI, Formula VI

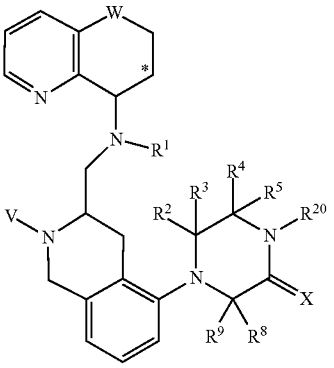

wherein W is $CH_2$ or O;

wherein V is hydrogen, an optionally substituted $C_1$-$C_4$ alkyl, or an optionally substituted $C_1$-$C_4$ haloalkyl;

wherein X is O or S;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein $R^2$, $R^3$, $R^4$, $R^5$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, and $R^8$ and $R^9$—are independently =O or =S;

optionally wherein two of $R^2$, $R^3$, $R^4$, $R^5$, $R^8$, and $R^9$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond);

$R^{20}$ is hydrogen, optionally substituted alkyl, optionally substituted haloalkyl, optionally substituted alkenyl, optionally substituted haloalkenyl, optionally substituted alkynyl, optionally substituted haloalkynyl, optionally substituted carbocyclyl, optionally substituted halocarbocyclyl, optionally substituted heterocyclyl, optionally substituted haloheterocyclyl, optionally substituted aryl, optionally substituted haloaryl, optionally substituted heteroaryl, optionally substituted haloheteroaryl, trifluoromethyl, trifluoroethyl, —$SF_5$, acyl, thioacyl, ester, thionoester, amide, thioamide, sulfinyl, sulfonyl, sulfonic ester, or sulfamide; and optionally wherein $R^4$ or $R^5$ join $R^{20}$ to form an optionally substituted heterocycle.

In some embodiments, Formula VI is in the following configuration.

Formula VI'

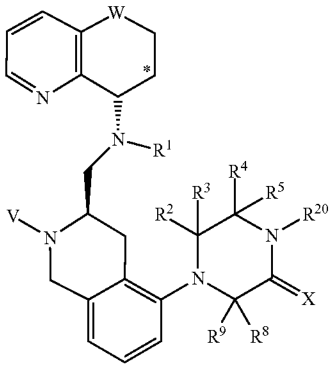

In some embodiments, W is $CH_2$. In some embodiments, W is O.

In some embodiments, V is hydrogen. In some embodiments, V is methyl.

In some embodiments, W is $CH_2$ and V is hydrogen.

1. The $R^1$ Moiety

Group I

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is —$R^{10}$—$R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c$[C(═O)$R^d$], or —$OR^f$. $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c$[C(═O)$R^d$], or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

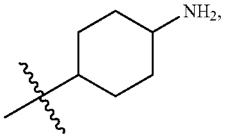
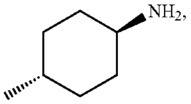
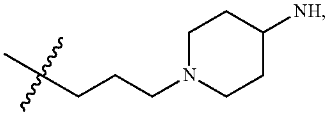
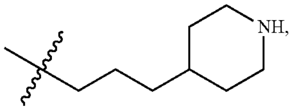
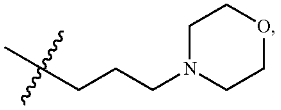
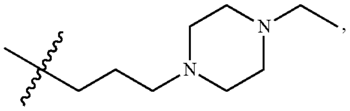
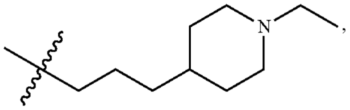
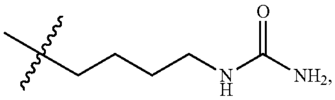
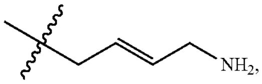
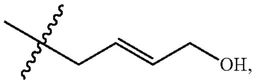
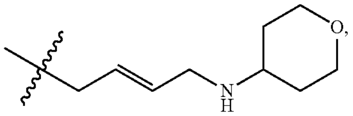

-continued

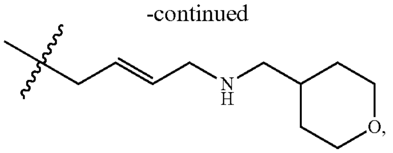
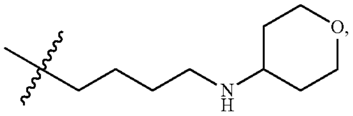
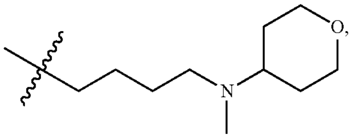
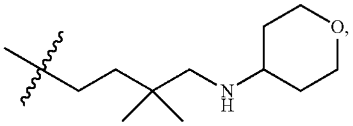
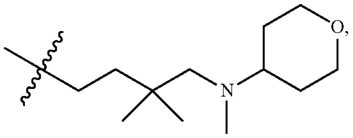
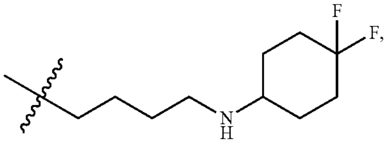
and
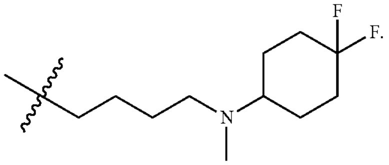

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,

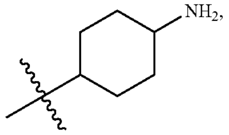
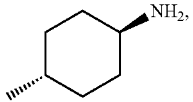
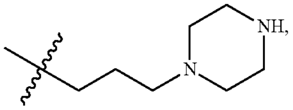
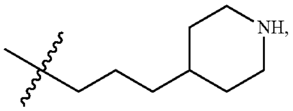
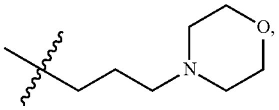
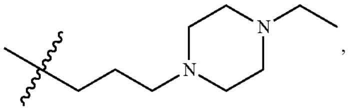
,

-continued

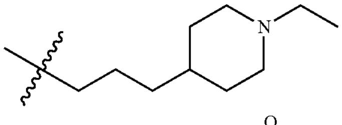

,

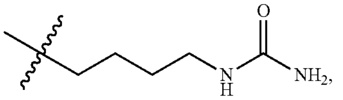

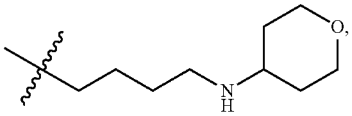

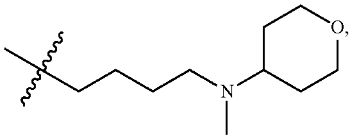

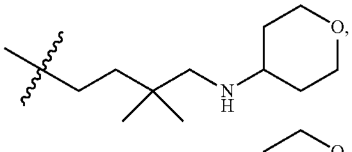

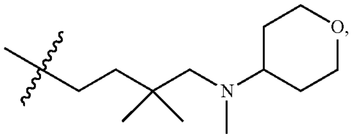

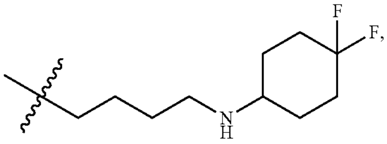

and

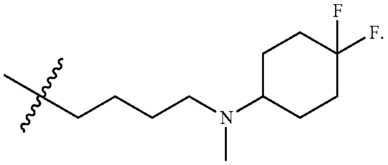 [SMILES: *CCCCN(C)C1CCC(F)(F)CC1]

In some embodiments, —$R^{10}$—$R^{11}$ is

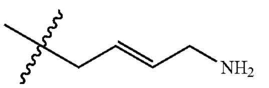

or

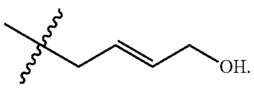

Group II

In some embodiments, $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle.

In some embodiments, the optionally substituted heterocycle is five- or six-membered. For example, the optionally substituted heterocycle is a six-membered heterocycle, such as piperidine.

2. The Piperazine Moiety

In some embodiments, X is O.

In some embodiments, $R^2$, $R^3$, $R^4$, $R^5$, $R^8$, and $R^9$ are hydrogen.

In some embodiments, $R^{20}$ is hydrogen, optionally substituted alkyl, optionally substituted haloalkyl, optionally substituted alkenyl, optionally substituted haloalkenyl, optionally substituted alkynyl, optionally substituted haloalkynyl, optionally substituted carbocyclyl, optionally substituted halocarbocyclyl, optionally substituted heterocyclyl, optionally substituted haloheterocyclyl, optionally substituted aryl, optionally substituted haloaryl, optionally substituted heteroaryl, or optionally substituted haloheteroaryl. In some embodiments, $R^{20}$ is hydrogen, alkyl, or haloalkyl. In some embodiments, $R^{20}$ is methyl.

In some embodiments, the piperazine moiety

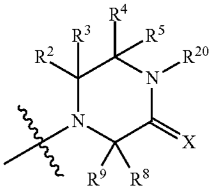

has one of the following structures:

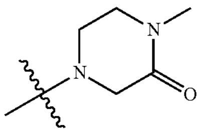

and

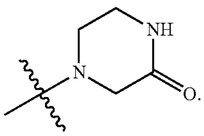

G. Formula VII

In some embodiments, the compounds have a structure of Formula VII or a pharmaceutically acceptable salt, hydrate, or hydrated salt of Formula VII, Formula VII

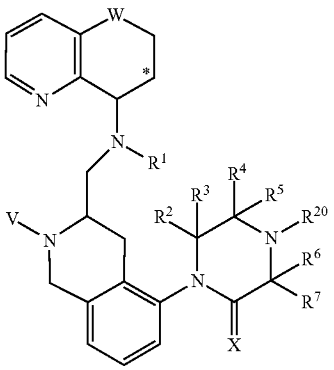

wherein W is $CH_2$ or O;

wherein V is hydrogen, an optionally substituted $C_1$-$C_4$ alkyl, or an optionally substituted $C_1$-$C_4$ haloalkyl;

wherein X is O or S;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein $R^2$, $R^3$, $R^4$, $R^5$, $R^6$, and $R^7$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, and $R^6$ and $R^7$—are independently =O or =S;

optionally wherein two of $R^2$, $R^3$, $R^4$, $R^5$, $R^6$, and $R^7$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond);

$R^{20}$ is hydrogen, optionally substituted alkyl, optionally substituted haloalkyl, optionally substituted alkenyl, optionally substituted haloalkenyl, optionally substituted alkynyl, optionally substituted haloalkynyl, optionally substituted carbocyclyl, optionally substituted halocarbocyclyl, optionally substituted heterocyclyl, optionally substituted haloheterocyclyl, optionally substituted aryl, optionally substituted haloaryl, optionally substituted heteroaryl, optionally substituted haloheteroaryl, trifluoromethyl, trifluoroethyl, —$SF_5$, acyl, thioacyl, ester, thionoester, amide, thioamide, sulfinyl, sulfonyl, sulfonic ester, or sulfamide; and optionally wherein $R^4$ or $R^5$ join $R^{20}$ to form an optionally substituted heterocycle.

In some embodiments, Formula VII is in the following configuration.

Formula VII'

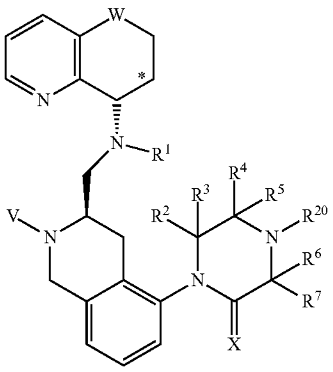

In some embodiments, W is $CH_2$. In some embodiments, W is O.

In some embodiments, V is hydrogen. In some embodiments, V is methyl.

In some embodiments, W is $CH_2$ and V is hydrogen.

1. The $R^1$ Moiety

Group I

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is —$R^{10}$—$R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$. $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

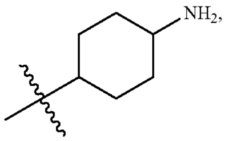 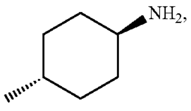

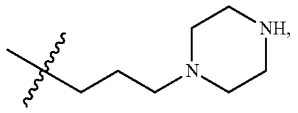

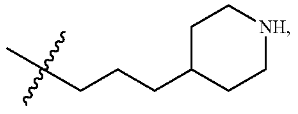

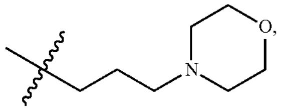

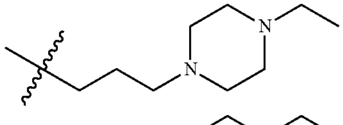 ,

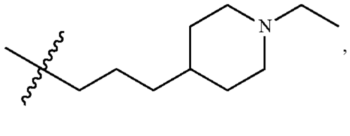 ,

-continued

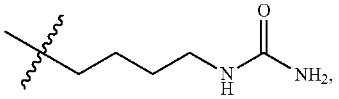

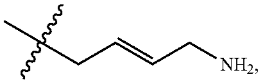

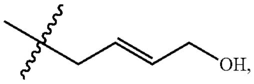

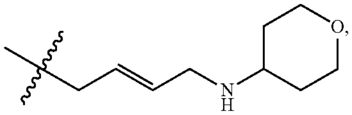

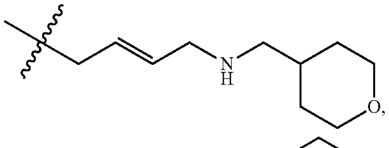

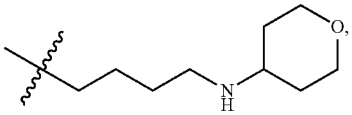

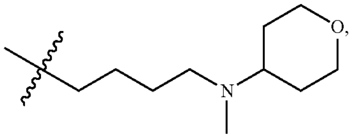

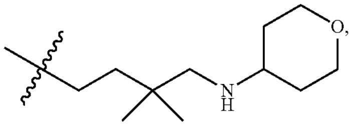

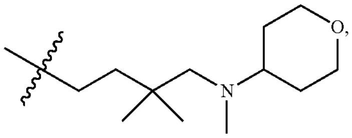

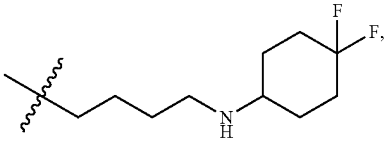

and

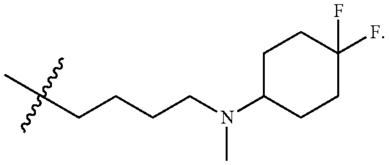 [SMILES: *CCCCN(C)C1CCC(F)(F)CC1]

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,

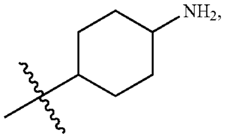

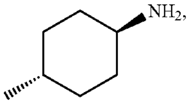

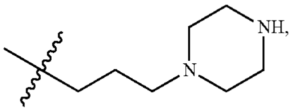

-continued

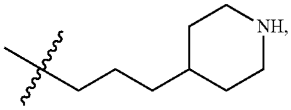

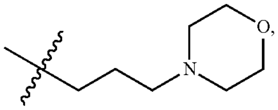

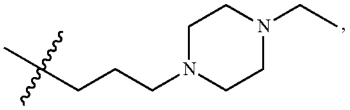

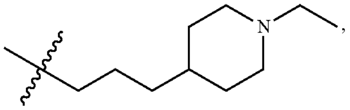

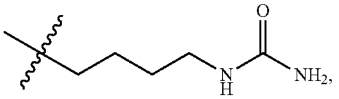

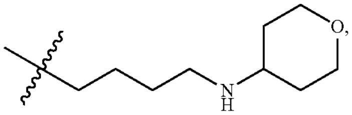

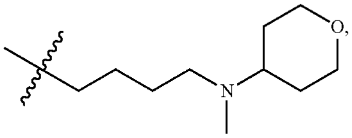

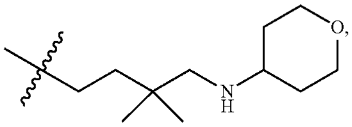

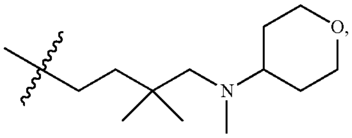

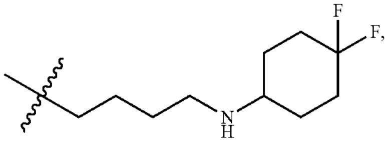

and

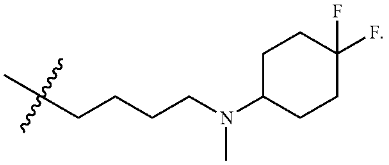 [SMILES: *CCCCN(C)C1CCC(F)(F)CC1]

In some embodiments, —$R^{10}$—$R^{11}$ is

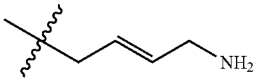

or

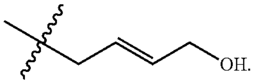

Group II

In some embodiments, $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle.

In some embodiments, the optionally substituted heterocycle is five- or six-membered. For example, the optionally substituted heterocycle is a six-membered heterocycle, such as piperidine.

2. The Piperazine Moiety

In some embodiments, X is O.

In some embodiments, $R^2$, $R^3$, $R^4$, $R^5$, $R^6$, and $R^7$ are hydrogen.

In some embodiments, $R^{20}$ is hydrogen, optionally substituted alkyl, optionally substituted haloalkyl, optionally substituted alkenyl, optionally substituted haloalkenyl, optionally substituted alkynyl, optionally substituted haloalkynyl, optionally substituted carbocyclyl, optionally substituted halocarbocyclyl, optionally substituted heterocyclyl, optionally substituted haloheterocyclyl, optionally substituted aryl, optionally substituted haloaryl, optionally substituted heteroaryl, or optionally substituted haloheteroaryl. In some embodiments, $R^{20}$ is hydrogen, alkyl, or haloalkyl. In some embodiments, $R^{20}$ is methyl.

In some embodiments, the piperazine moiety

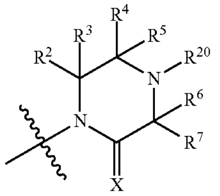

has one of the following structures:

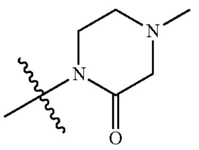

and

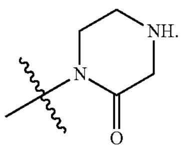

In some embodiments, $R^{20}$ is —C(=O)$R^i$, —C(=S)$R^k$, —C(=O)O$R^{g1}$, —C(=S)O$R^{o1}$, —C(=O)N$R^{j1}R^{j2}$, —C(=S)N$R^{l1}R^{l2}$, —S(=O)$R^m$, —S(=O)$_2R^n$, —S(=O)$_2$N$R^{p1}R^{p2}$, or —S(=O)$_2$O$R^q$, wherein $R^i$, $R^k$, $R^{g1}$, $R^{o1}$, $R^{j1}$, $R^{j2}$, $R^{l1}$, $R^{l2}$, $R^m$, $R^n$, $R^{p1}$, $R^{p2}$, and $R^q$ are the same as those defined herein (see the Definitions section).

In some embodiments, $R^i$, $R^k$, $R^{g1}$, $R^{o1}$, $R^{j1}$, $R^{j2}$, $R^{l1}$, $R^{l2}$, $R^m$, $R^n$, $R^{p1}$, $R^{p2}$, and $R^q$ are independently selected from hydrogen, $C_{1-4}$ alkyl, phenyl, and benzyl. In some embodiments, $R^i$, $R^k$, $R^{g1}$, $R^{o1}$, $R^{j1}$, $R^{j2}$, $R^{l1}$, $R^{l2}$, $R^m$, $R^n$, $R^{p1}$, $R^{p2}$, and $R^q$ are independently selected from hydrogen, methyl, ethyl, isopropyl, phenyl, and benzyl.

H. Formula X

In some embodiments, the compounds have a structure of Formula X or a pharmaceutically acceptable salt, hydrate, or hydrated salt of Formula X, Formula X

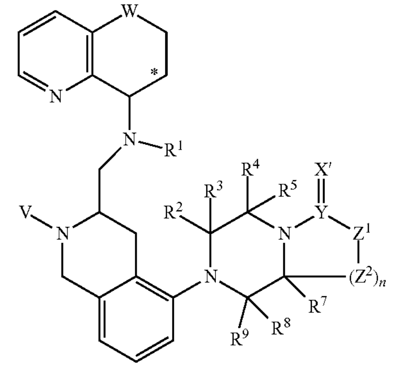

wherein W is $CH_2$ or O;

wherein V is hydrogen, an optionally substituted $C_1$-$C_4$ alkyl, or an optionally substituted $C_1$-$C_4$ haloalkyl;

wherein X' is O or S and Y is C, S, or S=O, wherein when X' is S, Y is C;

wherein n is 1 or 2;

wherein $Z^1$ is —[C($R^rR^s$)]—, —O—, or —[N($R^t$)]— and $Z^2$ is —[C($R^uR^v$)]—;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein $R^2$, $R^3$, $R^4$, $R^5$, $R^7$, $R^8$, and $R^9$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, and $R^8$ and $R^9$—are independently =O or =S; and $R^r$, $R^s$, $R^t$, $R^u$, and $R^v$, in each occurrence, are independently hydrogen, optionally substituted alkyl, optionally substituted haloalkyl, optionally substituted alkenyl, optionally substituted haloalkenyl, optionally substituted alkynyl, optionally substituted haloalkynyl, optionally substituted carbocyclyl, optionally substituted halocarbocyclyl, optionally substituted heterocyclyl, optionally substituted haloheterocyclyl, optionally substituted aryl, optionally substituted haloaryl, optionally substituted heteroaryl, or optionally substituted haloheteroaryl.

In some embodiments, Formula X is in the following configuration.

Formula X'

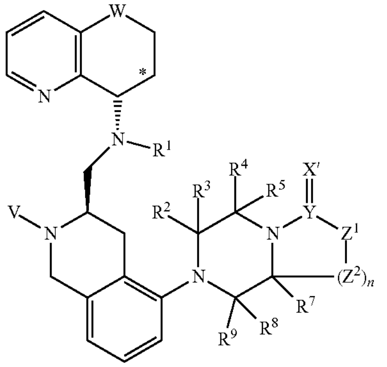

In some embodiments, W is $CH_2$. In some embodiments, W is O.

In some embodiments, V is hydrogen. In some embodiments, V is methyl.

In some embodiments, W is $CH_2$ and V is hydrogen.

1. The $R^1$ Moiety

Group I

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is —$R^{10}$—$R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —OR. $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

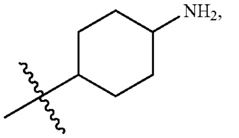,
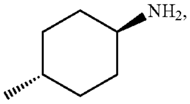,

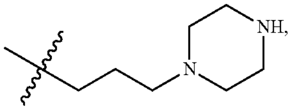,

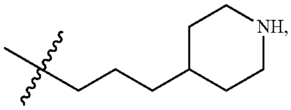,

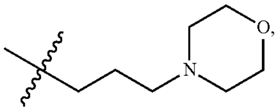,

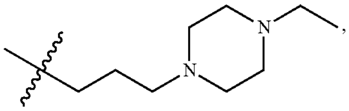,

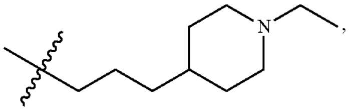,

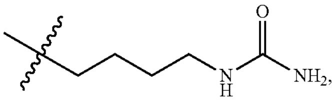,

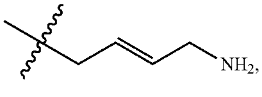,
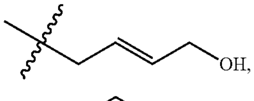,

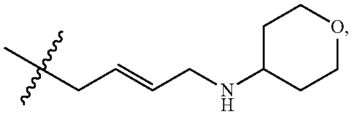,

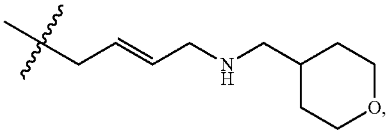,

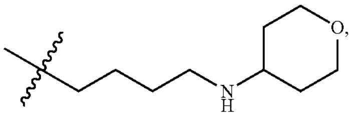,

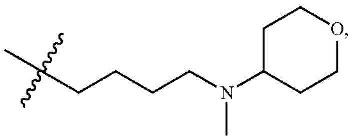

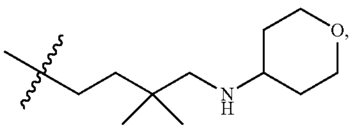

-continued

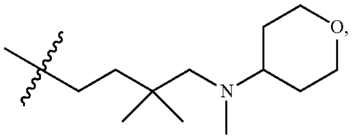

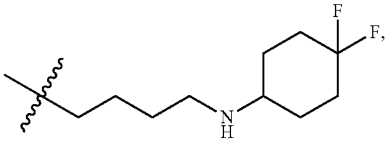

and

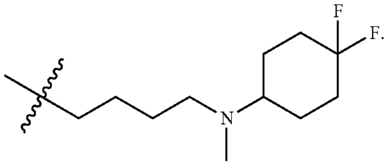

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,

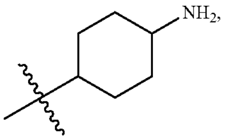

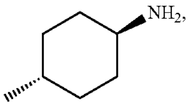

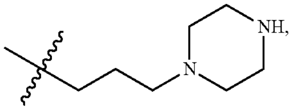

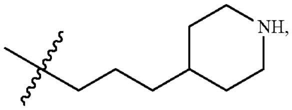

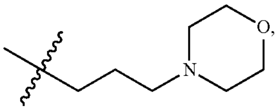

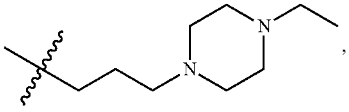

,

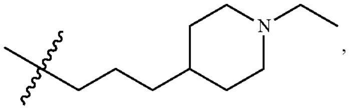

,

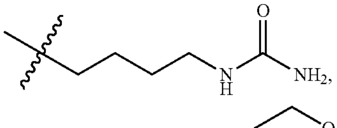

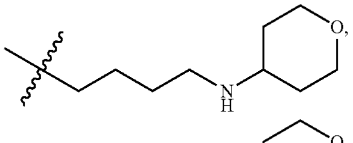

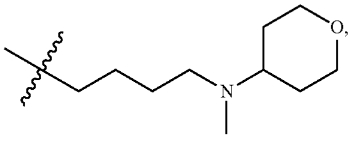

-continued

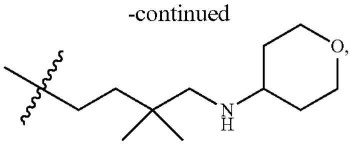

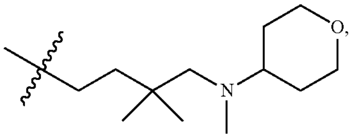

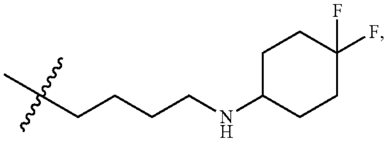

and

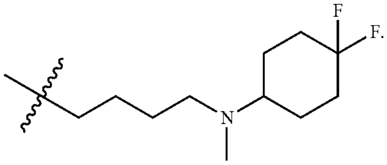 [SMILES: *CCCCN(C)C1CCC(F)(F)CC1]

In some embodiments, —$R^{10}$—$R^{11}$ is

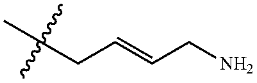

or

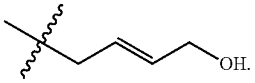

Group II

In some embodiments, $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle.

In some embodiments, the optionally substituted heterocycle is five- or six-membered. For example, the optionally substituted heterocycle is a six-membered heterocycle, such as piperidine.

2. The Piperazine Moiety

In some embodiments, $R^2$, $R^3$, $R^4$, $R^5$, $R^7$, $R^8$, and $R^9$ are hydrogen.

In some embodiments, X' is S and Y is C.

In some embodiments, X' is O and Y is C, S, or S═O. In some embodiments, X' is O and Y is C.

In some embodiments, n is 1. In some embodiments, n is 2.

In some embodiments, $Z^1$ is —$CH_2$—. In some embodiments, $Z^1$ is —O—. In some embodiments, $Z^1$ is —NH— or —$N(CH_3)$—.

In some embodiments, $Z^2$, in each occurrence, is —$CH_2$—.

In some embodiments, the piperazine moiety

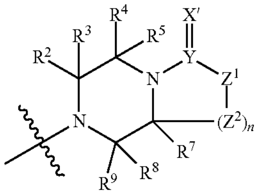

has one of the following structures:
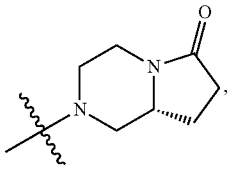
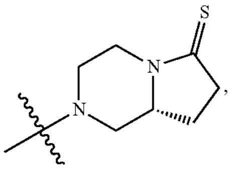
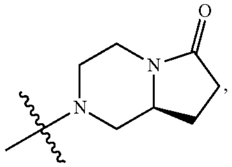
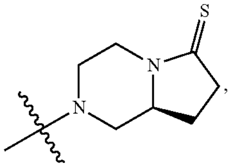
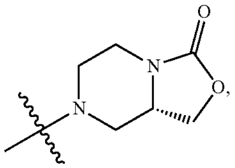
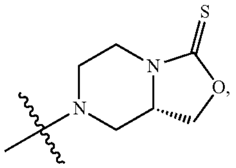
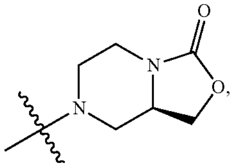
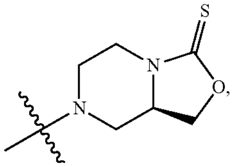
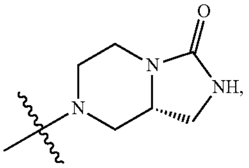
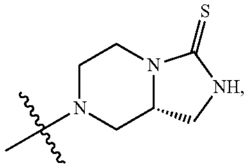
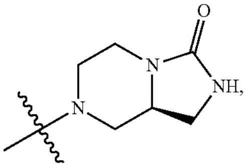
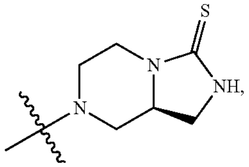
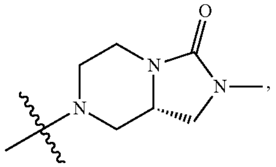
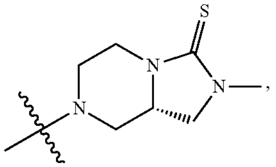
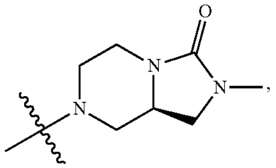
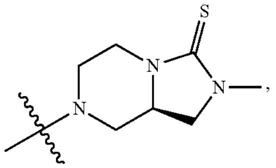
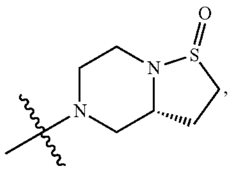
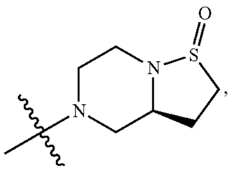
-continued
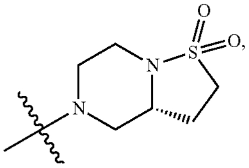
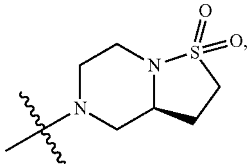
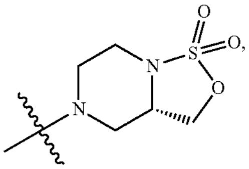
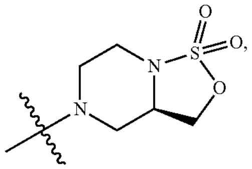
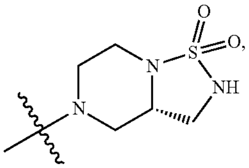
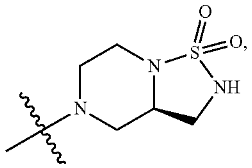
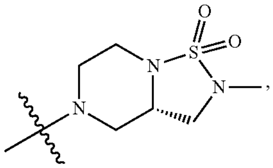
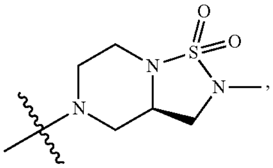
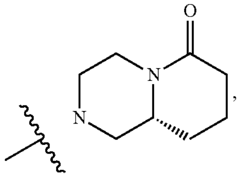
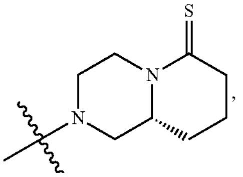
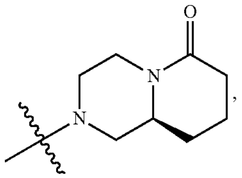
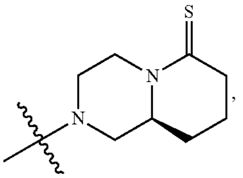
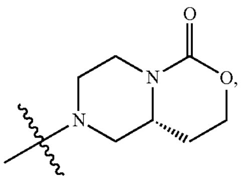
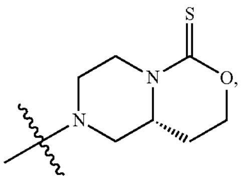
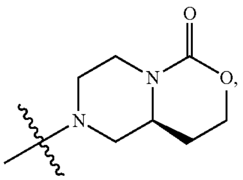
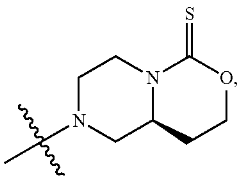
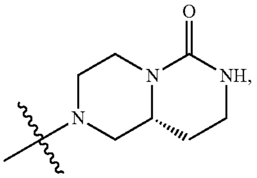
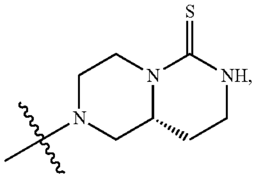

-continued
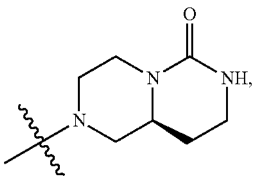
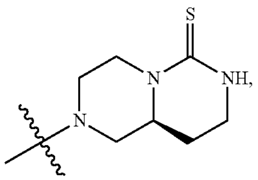
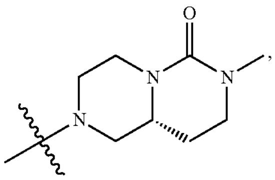
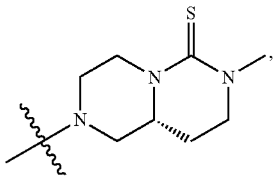
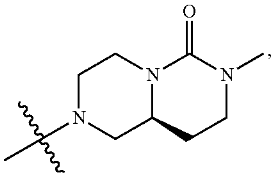
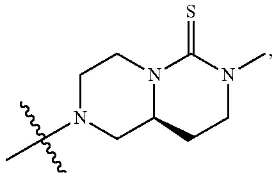
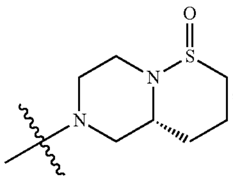
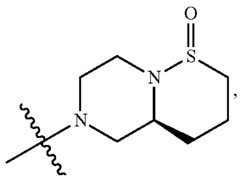
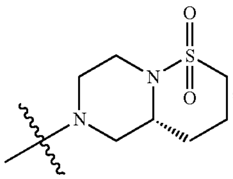
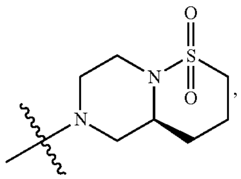
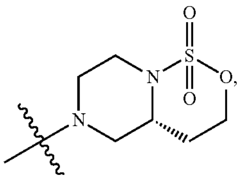
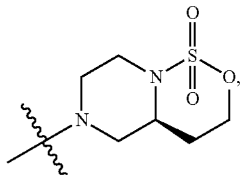
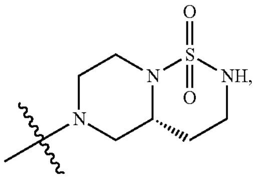
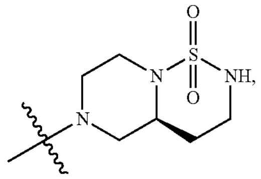
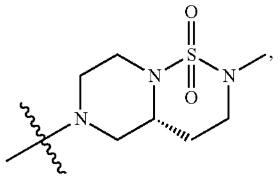
and
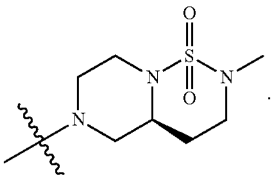
3. Exemplary Structures
In some embodiments, Formula X has the following structure.
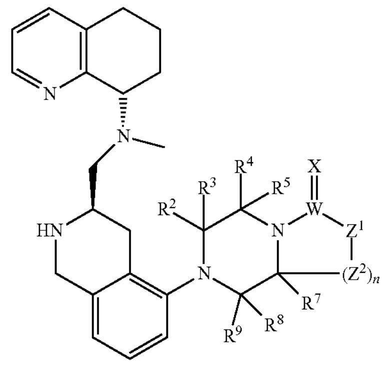
In some embodiments, Formula X has the following structure.
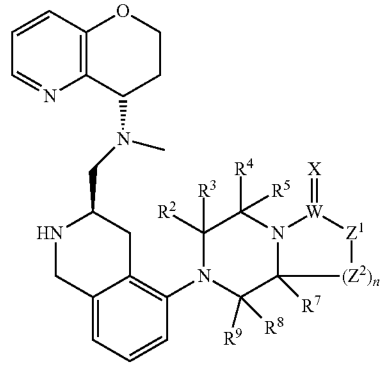
In some embodiments, Formula X has the following structure.
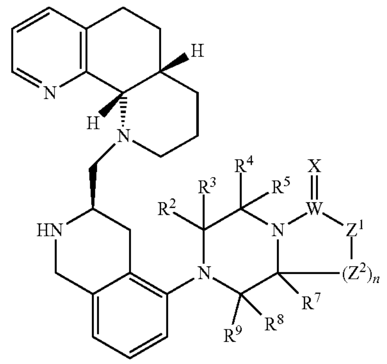
Exemplary structures include, but are not limited to, the following.

-continued
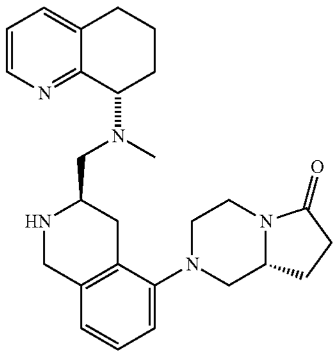,
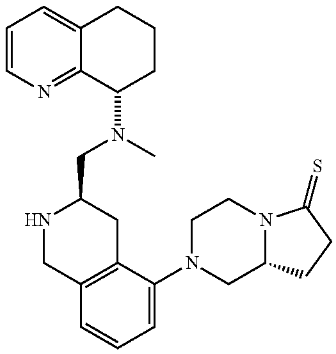,
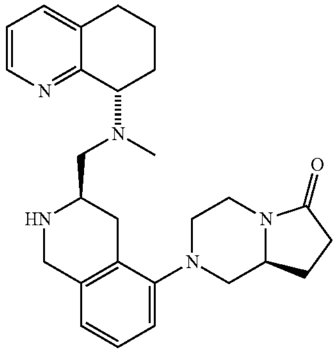,
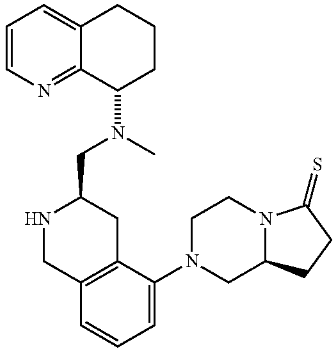,
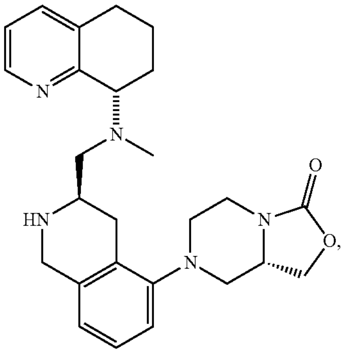,
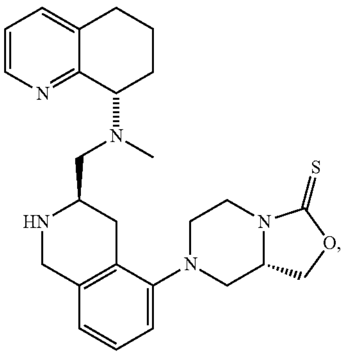,
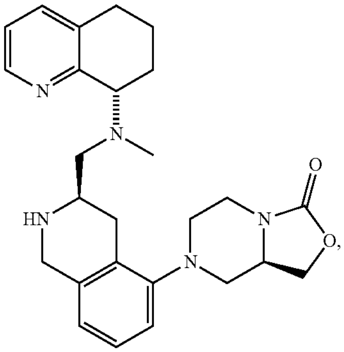,
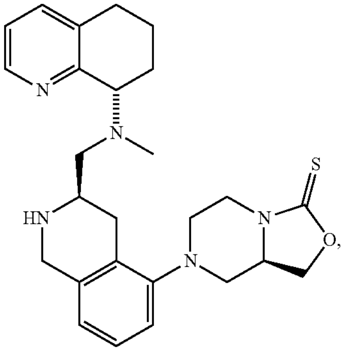, -continued
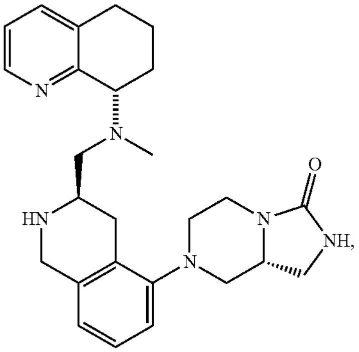
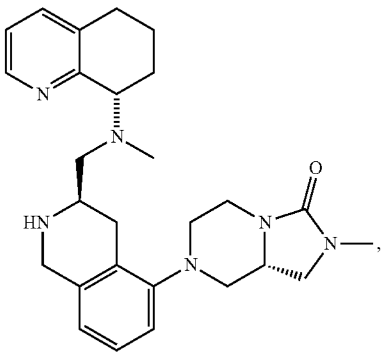
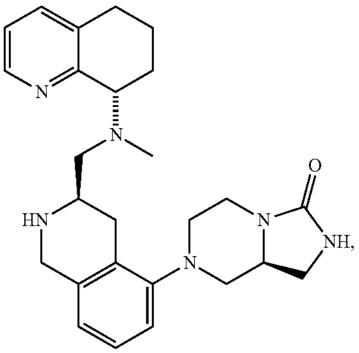
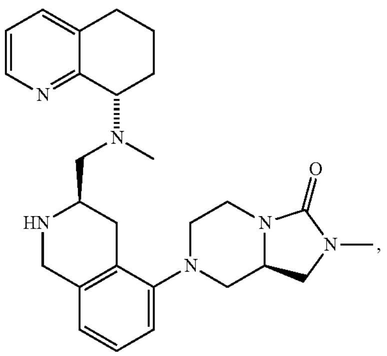
-continued
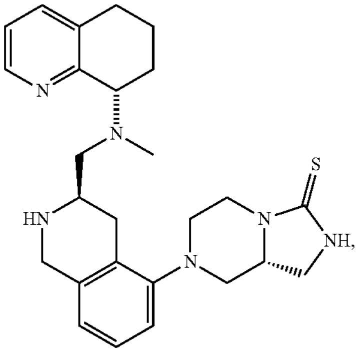
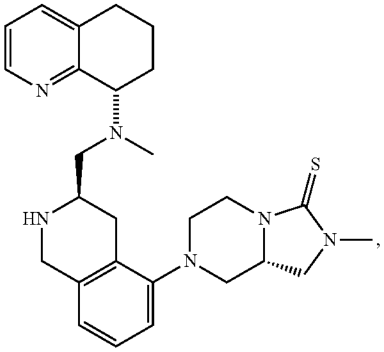
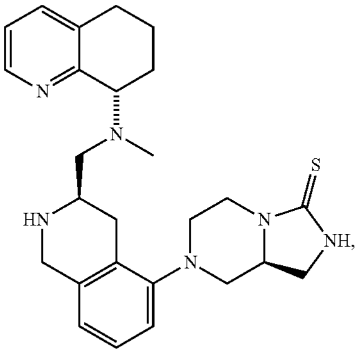
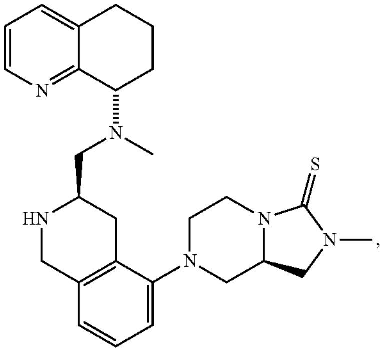

-continued
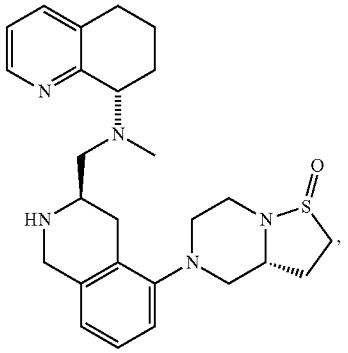
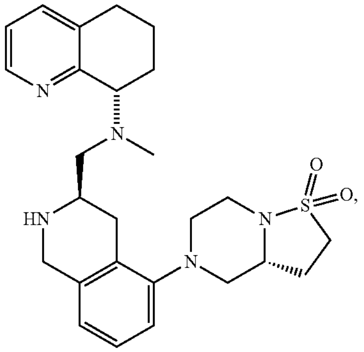
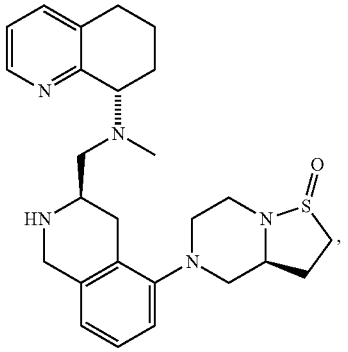
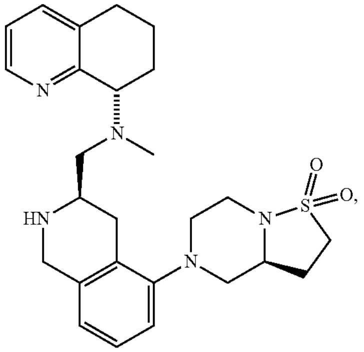
-continued
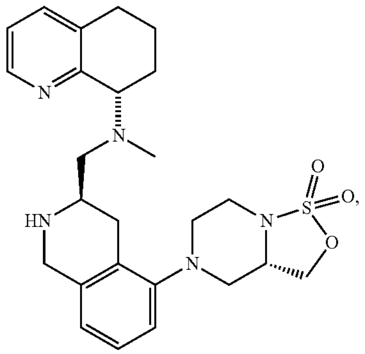
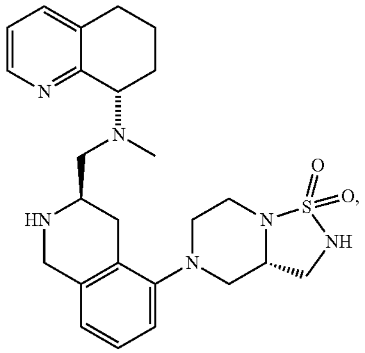
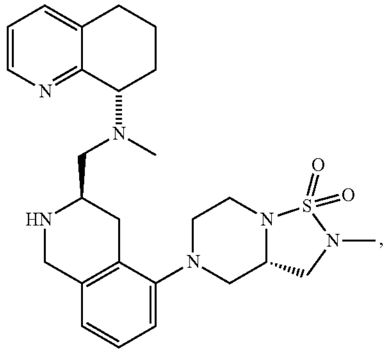
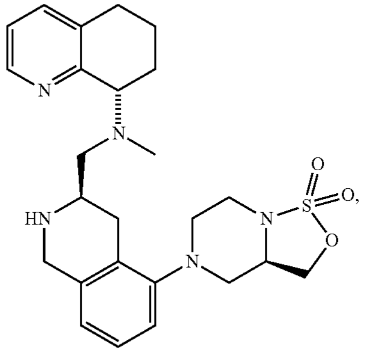

-continued
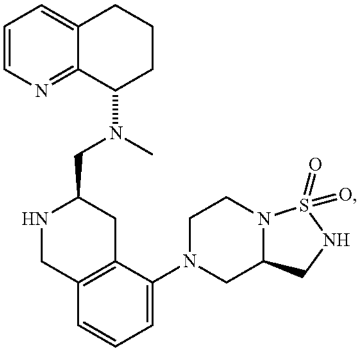
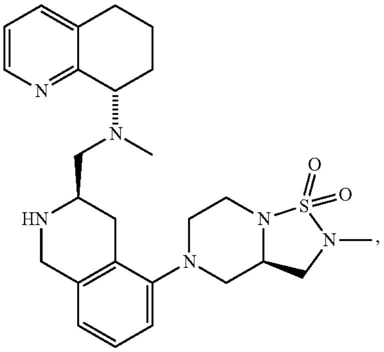
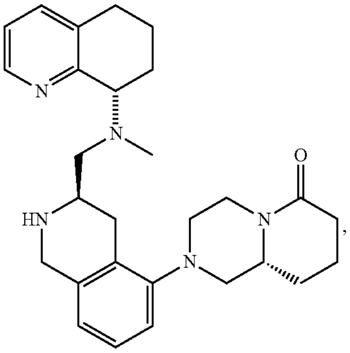
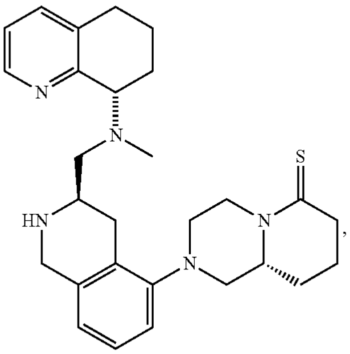
-continued
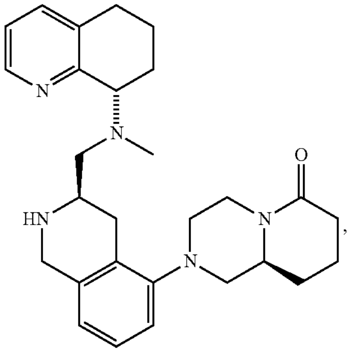
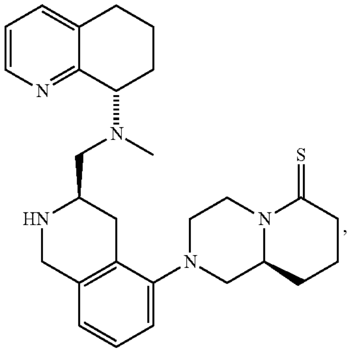
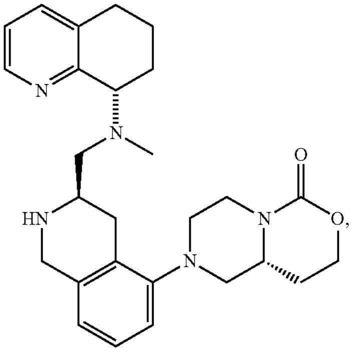
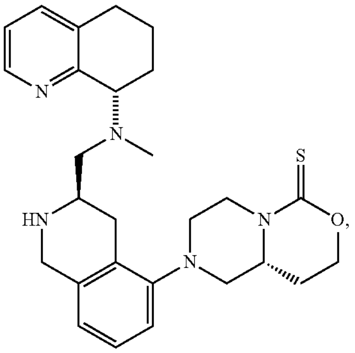

-continued
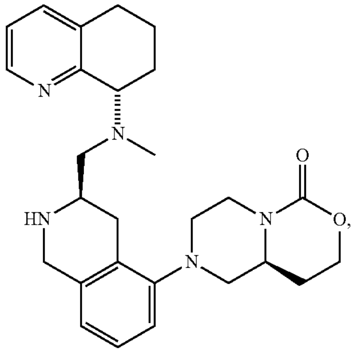
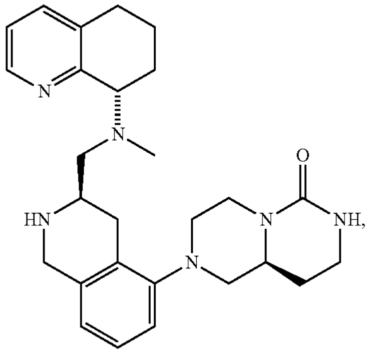
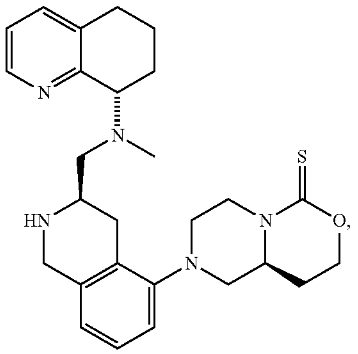
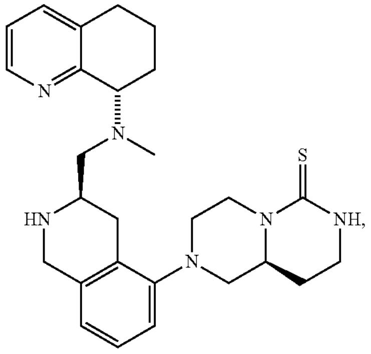
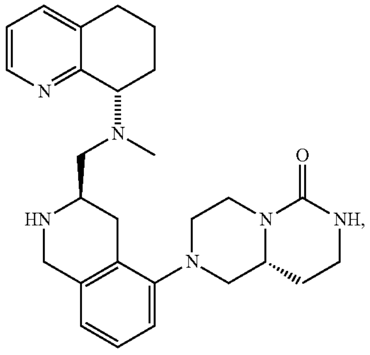
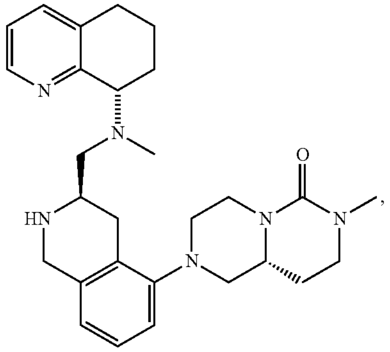
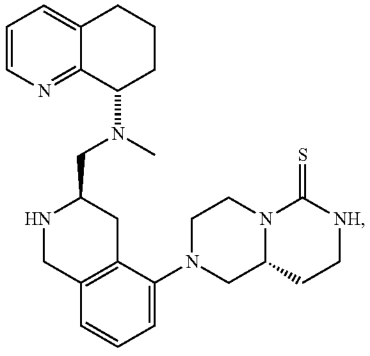
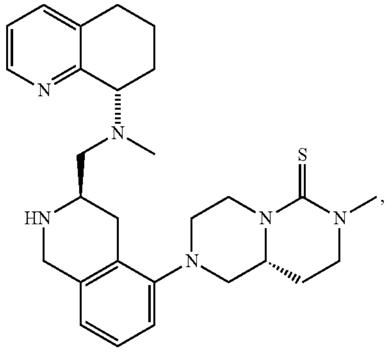

-continued
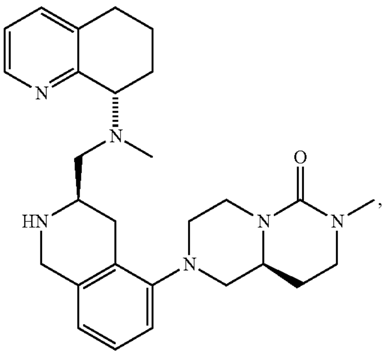
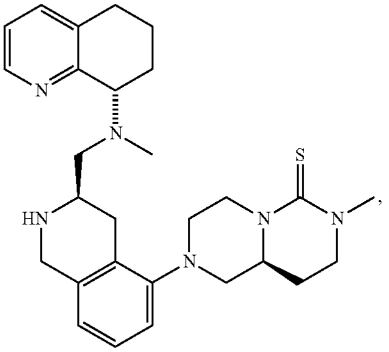
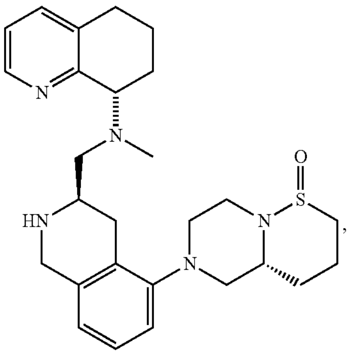
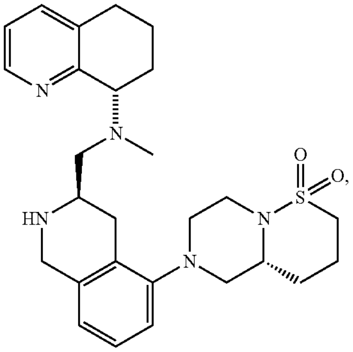
-continued
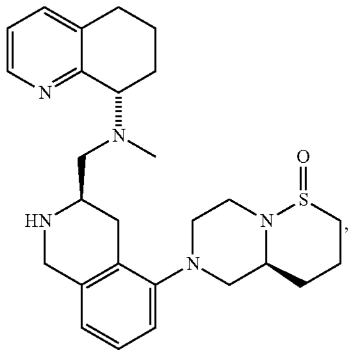
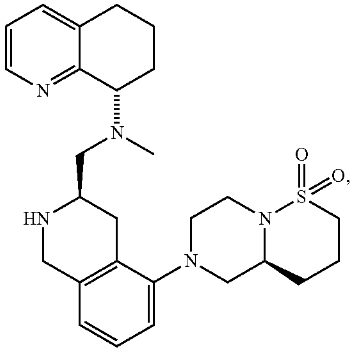
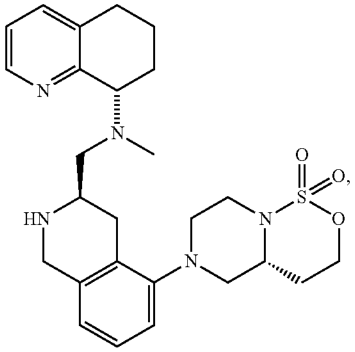
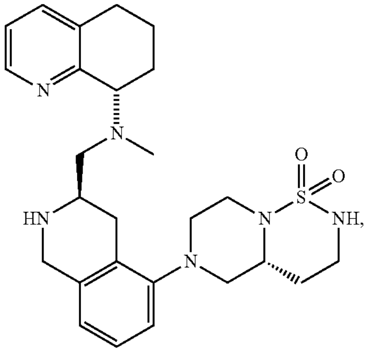

-continued

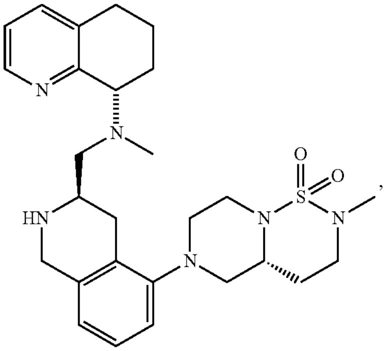

,

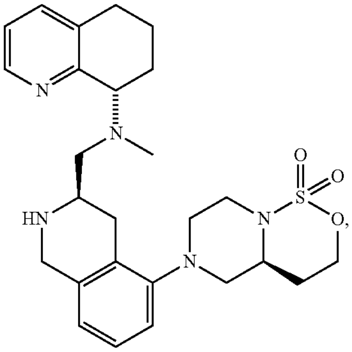

,

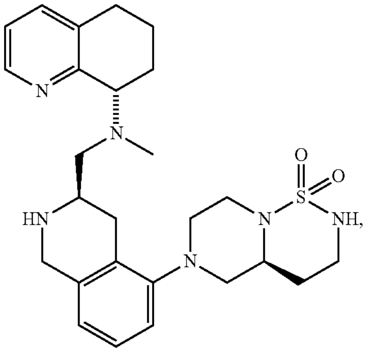

and

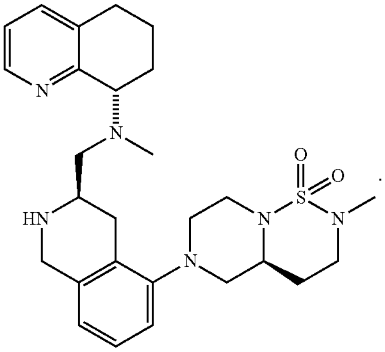

.

I. Formula XII

In some embodiments, the compounds have a structure of Formula XII or a pharmaceutically acceptable salt, hydrate, or hydrated salt of Formula XII, Formula XII

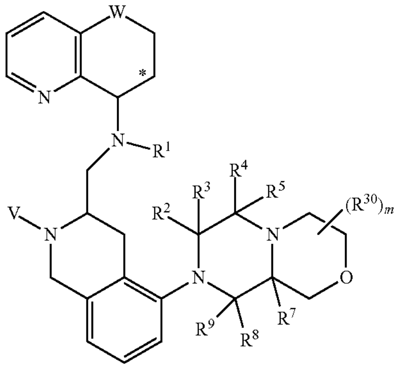

wherein W is $CH_2$ or O;

wherein V is hydrogen, an optionally substituted $C_1$-$C_4$ alkyl, or an optionally substituted $C_1$-$C_4$ haloalkyl;

wherein m is 0, 1, 2, 3, or 4;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein $R^2$, $R^3$, $R^4$, $R^5$, $R^7$, $R^8$, $R^9$, and $R^{30}$, on each occurrence, are independently hydrogen, halogen, amino, optionally substituted hydroxyl, optionally substituted alkyl, or optionally substituted haloalkyl; and optionally wherein one or more of the following pairs—$R^2$ and $R^3$, $R^4$ and $R^5$, and $R^8$ and $R^9$—are independently =O or =S.

In some embodiments, Formula XII is in the following configuration.

Formula XII'

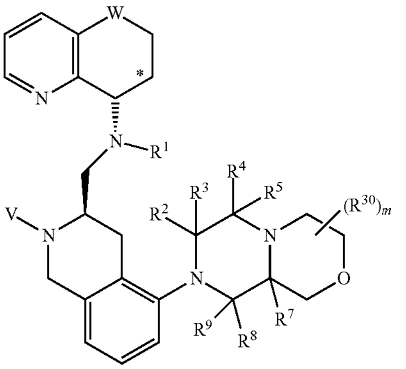

In some embodiments, W is $CH_2$. In some embodiments, W is O.

In some embodiments, V is hydrogen. In some embodiments, V is methyl.

In some embodiments, W is $CH_2$ and V is hydrogen.

1. The $R^1$ Moiety

Group I

In some embodiments, $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl.

In some embodiments, $R^1$ is methyl.

In some embodiments, $R^1$ is an optionally substituted $C_2$-$C_4$ alkyl, an optionally substituted $C_2$-$C_4$ haloalkyl, an optionally substituted $C_2$-$C_4$ alkenyl, an optionally substituted $C_2$-$C_4$ haloalkenyl, an optionally substituted carbocyclyl, or an optionally substituted halocarbocyclyl.

In some embodiments, $R^1$ is —$R^{10}$—$R^{11}$. $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge). $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(═O)R^d]$, or —$OR^f$. $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

In some embodiments, $R^{10}$ is an optionally substituted, bridging $C_2$-$C_4$ alkylene (alkyl bridge), an optionally substituted, bridging $C_2$-$C_4$ haloalkylene (haloalkyl bridge), an optionally substituted, bridging carbocyclylene (carbocyclyl bridge), or an optionally substituted, bridging halocarbocyclylene (halocarbocyclyl bridge).

In some embodiments, $R^{11}$ is hydrogen, halogen, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(═O)R^d]$, or —$OR^f$.

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

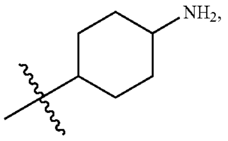
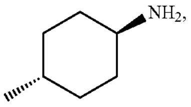
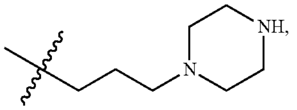
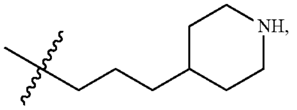
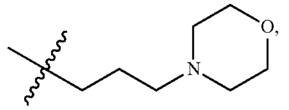

-continued

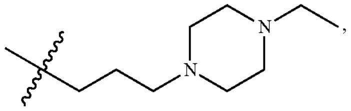
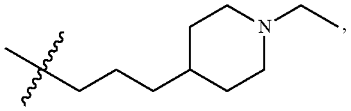
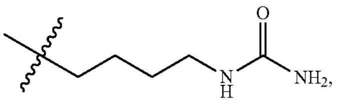
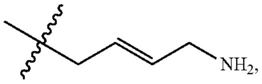
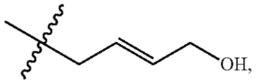
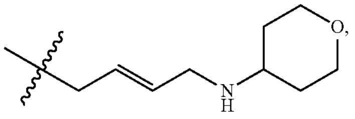
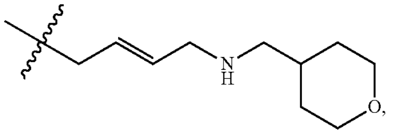
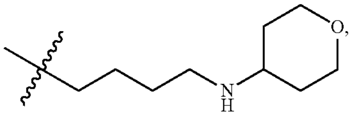
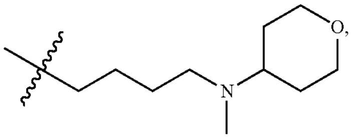
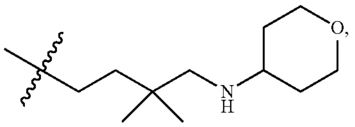
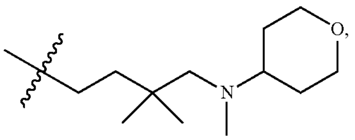
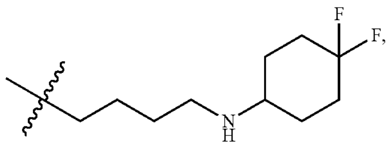
and
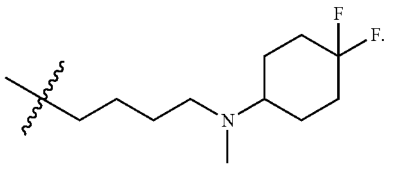 [SMILES: *CCCCN(C)C1CCC(F)(F)CC1]

In some embodiments, —$R^{10}$—$R^{11}$ is selected from ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_3CF_3$,

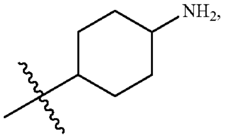

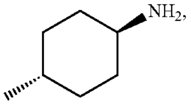

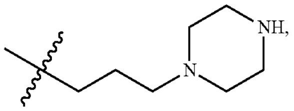

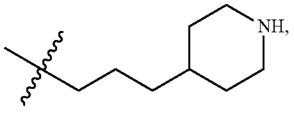

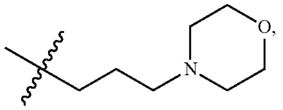

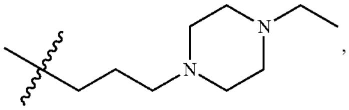

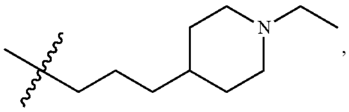

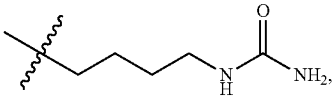

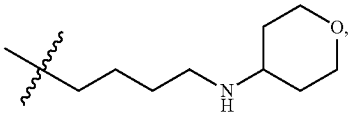

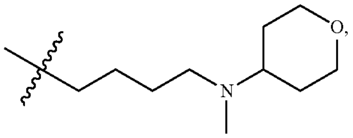

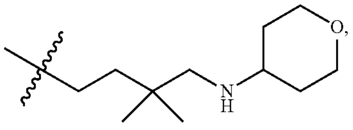

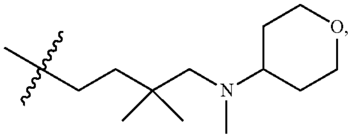

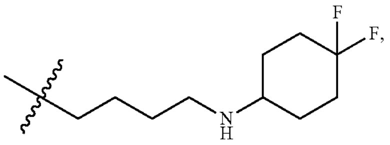

and

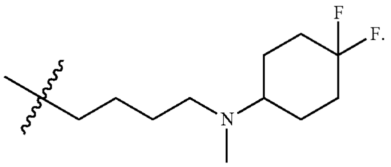

In some embodiments, —$R^{10}$—$R^{11}$ is

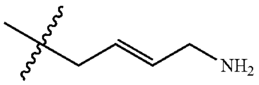

or

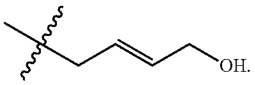

Group II

In some embodiments, $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle.

In some embodiments, the optionally substituted heterocycle is five- or six-membered. For example, the optionally substituted heterocycle is a six-membered heterocycle, such as piperidine.

2. The Piperazine Moiety

In some embodiments, m is 0.

In some embodiments, $R^2$, $R^3$, $R^4$, $R^5$, $R^7$, $R^8$, and $R^9$ are hydrogen.

In some embodiments, the piperazine moiety

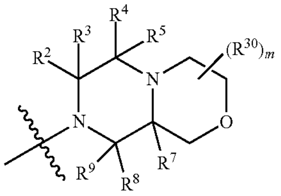

R has one of the following structures:

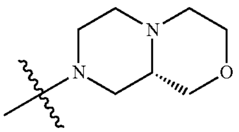

and

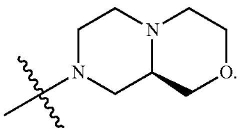

3. Exemplary Structures

In some embodiments, Formula XII has the following structure.

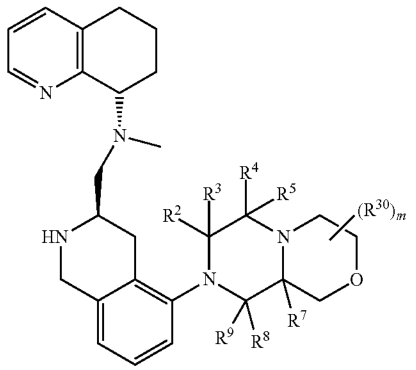

In some embodiments, Formula XII has the following structure.

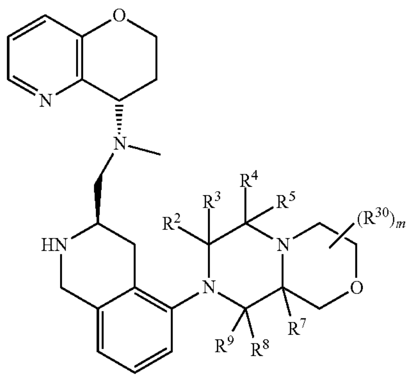

In some embodiments, Formula XII has the following structure.

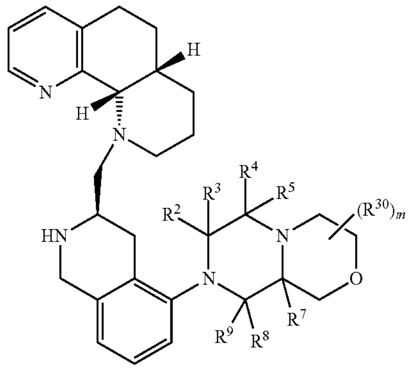

Exemplary structures include, but are not limited to, the following:

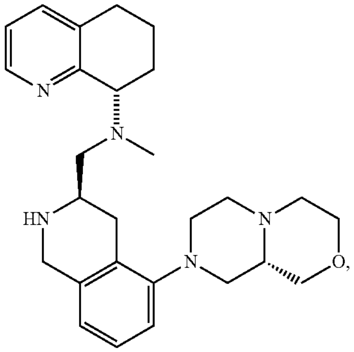

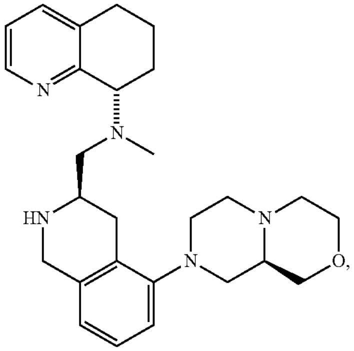

-continued

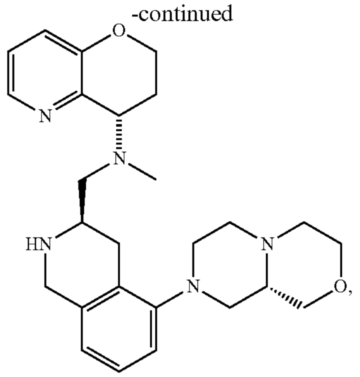

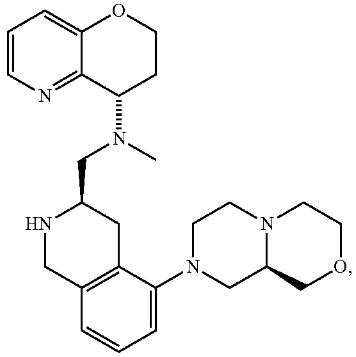

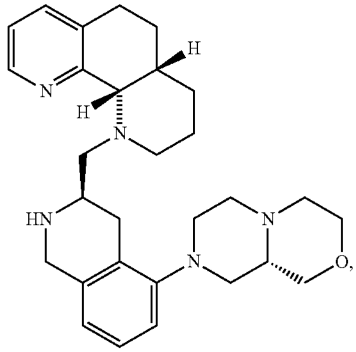

and

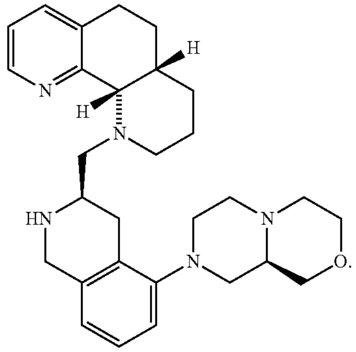

III. COMPOSITIONS

Disclosed are compositions containing a compound disclosed herein. In some embodiments, the compound in the composition is in greater than 80%, 85%, 90%, or 95% enantiomeric or diastereomeric excess. In some embodiments, the compound in the composition is in greater than 95% enantiomeric or diastereomeric excess.

In some embodiments, the compositions contain a compound having a structure of Formula I or a pharmaceutically acceptable salt, hydrate, or hydrated salt of Formula I, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula II or a pharmaceutically acceptable salt, hydrate, or hydrated salt of Formula II, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula III or a pharmaceutically acceptable salt, hydrate, or hydrated salt of Formula III, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula IV or a pharmaceutically acceptable salt, hydrate, or hydrated salt of Formula IV, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula V or a pharmaceutically acceptable salt, hydrate, or hydrated salt of Formula V, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula VI or a pharmaceutically acceptable salt, hydrate, or hydrated salt of Formula VI, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula VII or a pharmaceutically acceptable salt, hydrate, or hydrated salt of Formula VII, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula X or a pharmaceutically acceptable salt, hydrate, or hydrated salt of Formula X, wherein the compound is in greater than 80%, 85%, 90%, or 95% enantiomeric or diastereomeric excess. In some embodiments, the compound is in greater than 95% enantiomeric or diastereomeric excess.

In some embodiments, the compositions contain a compound having a structure of Formula XII or a pharmaceutically acceptable salt, hydrate, or hydrated salt of Formula XII, wherein the compound is in greater than 80%, 85%, 90%, or 95% enantiomeric or diastereomeric excess. In some embodiments, the compound is in greater than 95% enantiomeric or diastereomeric excess.

The disclosed compounds may be present in a mixture of a salt form and a non-salt form. In some embodiments, more than 50%, 60%, 70%, 80%, 90%, 95%, or 98% of the compound in the mixture may be in the non-salt form, calculated as the ratio of the weight of the non-salt form to the total weight of the mixture. In some embodiments, more than 90% of the compound in the mixture may be in the non-salt form. In some embodiments, more than 50%, 60%, 70%, 80%, 90%, 95%, or 98% of the compound in the mixture may be in the salt form, calculated as the ratio of the weight of the salt form to the total weight of the mixture. In some embodiments, more than 90% of the compound in the mixture may be in the salt form.

IV. FORMULATIONS

Disclosed are pharmaceutical formulations containing a compound or composition described herein. Generally, the pharmaceutical formulations also contain one or more pharmaceutically acceptable excipients.

The pharmaceutical formulations can be in a form chosen from tablets, capsules, caplets, pills, powders, beads, granules, particles, creams, gels, solutions (such as aqueous solutions, e.g., buffer, saline, and buffered saline), emulsions, suspensions (including nano- and micro-suspensions), nanoparticulate formulations, etc. In some embodiments, the pharmaceutical formulations are formulated for oral administration. In some embodiments, the pharmaceutical formulations are formulated for intravenous administration. In some embodiments, the pharmaceutical formulations are formulated for intramuscular administration.

As used herein, "emulsion" refers to a mixture of non-miscible components homogenously blended together. In some forms, the non-miscible components include a lipophilic component and an aqueous component. For example, an emulsion may be a preparation of one liquid distributed in small globules throughout the body of a second liquid. The dispersed liquid is the discontinuous phase, and the dispersion medium is the continuous phase. When oil or an oleaginous substance is the dispersed liquid and water or an aqueous solution is the continuous phase, it is known as an oil-in-water emulsion, whereas when water or an aqueous solution is the dispersed phase and oil or an oleaginous substance is the continuous phase, it is known as a water-in-oil emulsion.

As used herein, "biocompatible" refers to materials that are neither themselves toxic to the host (e.g., a non-human animal or human), nor degrade (if the material degrades) at a rate that produces monomeric or oligomeric subunits or other byproducts at toxic concentrations in the host.

As used herein, "biodegradable" refers to degradation or breakdown of a polymeric material into smaller (e.g., non-polymeric) subunits or digestion of the material into smaller subunits.

As used herein, "enteric polymers" refers to polymers that become soluble in the higher pH environment of the lower gastrointestinal tract or slowly erode as they pass through the gastrointestinal tract.

As used herein, "nanoparticulate formulations" generally refers to formulations containing nanoparticles, which are particles having a diameter from about 1 nm to about 1000 nm, from about 10 nm to about 1000 nm, from about 100 nm to about 1000 nm, or from about 250 nm to about 1000 nm. In some embodiments, "nanoparticulate formulations" can also refer to formulations containing microparticles, which are particles having a diameter from about 1 micron to about 100 microns, from about 1 to about 50 microns, from about 1 to about 30 microns, from about 1 micron to about 10 microns. In some embodiments, the nanoparticulate formulation may contain a mixture of nanoparticles, as defined above, and microparticles, as defined above.

As used herein, "surfactant" refers to any agent which preferentially absorbs to an interface between two immiscible phases, such as the interface between water (or aqueous solution) and an organic solvent (or organic solution), between water (or aqueous solution) and air, or between organic solvent (or organic solution) and air. Surfactants generally possess a hydrophilic moiety and a lipophilic moiety.

As used herein, "gel" is a semisolid system containing a dispersion of the active ingredient, i.e., a compound or composition according to the present disclosure, in a liquid vehicle that is rendered semisolid by the action of a thickening agent or polymeric material dissolved or suspended in the liquid vehicle. The liquid vehicle may include a lipophilic component, an aqueous component or both.

As used herein, "hydrogel" refers to a swollen, water-containing network of finely-dispersed polymer chains that are water-insoluble, where the polymer molecules are in the external or dispersion phase and water (or an aqueous solution) forms the internal or dispersed phase. The polymer chains can be chemically cross-linked (chemical gels) or physically cross-linked (physical gels). Chemical gels possess polymer chains connected through covalent bonds, whereas physical gels have polymer chains linked by non-covalent interactions, such as van der Waals interactions, ionic interactions, hydrogen bonding interactions, and hydrophobic interactions.

As used herein, "beads" refers to beads made with the active ingredient (i.e., a compound or composition according to the present disclosure) and one or more pharmaceutically acceptable excipients. The beads can be produced by applying the active ingredient to an inert support, e.g., inert sugar core coated with the active ingredient. Alternatively, the beads can be produced by creating a "core" comprising both the active ingredient and at least one of the one or more pharmaceutically acceptable excipients. As used herein, "granules" refers to a product made by processing particles of the active ingredient (i.e., a compound or composition according to the present disclosure) that may or may not include one or more pharmaceutical acceptable excipients.

Typically, granules do not contain an inert support and are bigger in size compared to the particles used to produce them. Although beads, granules and particles may be formulated to provide immediate release, beads and granules are usually employed to provide delayed release.

As used herein, "enzymatically degradable polymers" refers to polymers that are degraded by bacterial enzymes present in the intestines and/or lower gastrointestinal tract.

A. Physical Forms and Unit Dosages

Depending upon the administration route, the compounds or compositions described herein may be formulated in a variety of ways. The pharmaceutical formulations can be prepared in various forms, such as tablets, capsules, caplets, pills, granules, powders, nanoparticle formulations, solutions (such as aqueous solutions, e.g., buffer, saline, and buffered saline), suspensions (including nano- and micro-suspensions), emulsions, creams, gels, and the like.

In some embodiments, the pharmaceutical formulations are in a solid dosage form suitable for simple administration of precise dosages. For example, the solid dosage form may be selected from tablets, soft or hard gelatin or non-gelatin capsules, and caplets for oral administration. Optionally, the solid dosage form is a lyophilized powder that can be readily dissolved and converted to a liquid dosage form for intravenous or intramuscular administration. In some embodiments, the lyophilized powder is manufactured by dissolving the active ingredient (i.e., a compound or composition disclosed herein) in an aqueous medium followed by lyophilization. In some embodiments, the aqueous medium is water, normal saline, PBS, or an acidic aqueous medium such as an acetate buffer.

In some embodiments, the pharmaceutical formulations are in a liquid dosage form suitable for intravenous or intramuscular administration. Exemplary liquid dosage forms include, but are not limited to, solutions, suspensions, and emulsions. In some embodiments, the pharmaceutical formulations are in the form of a sterile aqueous solution. In some embodiments, the sterile aqueous solution is a sterile normal saline solution. In some embodiments, the sterile aqueous solution is a sterile PBS solution. In some embodiments, the sterile aqueous solution is an acidic, sterile aqueous solution such as a sterile acetate buffer. In some embodiments, the sterile aqueous solution is manufactured by dissolving a lyophilized powder containing the active ingredient (i.e., a compound or composition disclosed herein) in an aqueous medium. For example, the sterile aqueous solution can be prepared by dissolving the lyophilized powder containing the active ingredient in a dose-appropriate volume of sterile water, sterile normal saline, sterile PBS, or acidic, sterile aqueous medium such as a sterile acetate buffer. In some embodiments, the lyophilized powder containing the active ingredient is the same as those described in the paragraph above.

In some embodiments, the pharmaceutical formulations are in a unit dosage form, and may be suitably packaged, for example, in a box, blister, vial, bottle, syringe, sachet, ampoule, or in any other suitable single-dose or multi-dose holder or container, optionally with one or more leaflets containing product information and/or instructions for use.

B. Pharmaceutically Acceptable Excipients

Exemplary pharmaceutically acceptable excipients include, but are not limited to, diluents, binders, lubricants, disintegrants, pH-modifying or buffering agents, salts (such as NaCl), preservatives, antioxidants, solubility enhancers, wetting or emulsifying agents, plasticizers, colorants (such as pigments and dyes), flavoring or sweetening agents, thickening agents, emollients, humectants, stabilizers, glidants, solvents or dispersion mediums, surfactants, pore formers, and coating or matrix materials.

In some embodiments, the powders described herein, including the lyophilized powders, contain one or more of the following pharmaceutically acceptable excipients: pH-modifying or buffering agents, salts (such as NaCl), and preservatives.

In some embodiments, the tablets, beads, granules, and particles described herein contain one or more of the following pharmaceutically acceptable excipients: coating or matrix materials, diluents, binders, lubricants, disintegrants, pigments, stabilizers, and surfactants. If desired, the tablets, beads, granules, and particles may also contain a minor amount of nontoxic auxiliary substances such as wetting or emulsifying agents, dyes, pH-buffering agents, and preservatives.

Examples of the coating or matrix materials include, but are not limited to, cellulose polymers (such as methylcellulose, ethyl cellulose, cellulose acetate, cellulose acetate phthalate, hydroxypropyl cellulose, hydroxyethyl cellulose, hydroxymethyl cellulose, hydroxypropyl methylcellulose, hydroxypropyl methylcellulose phthalate, hydroxypropyl methylcellulose acetate succinate, cellulose acetate trimellitate, and carboxymethylcellulose sodium), vinyl polymers and copolymers (such as polyvinyl pyrrolidone, polyvinyl acetate, polyvinyl acetate phthalate, vinyl acetate-crotonic acid copolymer, and ethylene-vinyl acetate copolymer), acrylic acid polymers and copolymers (such as those formed from acrylic acid, methacrylic acid, methyl acrylate, ethyl acrylate, methyl methacrylate, or ethyl methacrylate, as well as methacrylic resins that are commercially available under the tradename EUDRAGIT®), enzymatically degradable polymers (such as azo polymers, pectin, chitosan, amylose, and guar gum), zein, shellac, and polysaccharides. In some embodiments, the coating or matrix materials may contain one or more excipients such as plasticizers, colorants, glidants, stabilizers, pore formers, and surfactants.

In some embodiments, the coating or matrix materials are pH-sensitive or pH-responsive polymers, such as the enteric polymers commercially available under the tradename EUDRAGIT®. For example, EUDRAGIT® L30D-55 and L100-55 are soluble at pH 5.5 and above; EUDRAGIT® L100 is soluble at pH 6.0 and above; EUDRAGIT® S is soluble at pH 7.0 and above.

In some embodiments, the coating or matrix materials are water-insoluble polymers having different degrees of permeability and expandability, such as EUDRAGIT® NE, RL, and RS.

Depending on the coating or matrix materials, the decomposition/degradation or structural change of the pharmaceutical formulations may occur at different locations of the gastrointestinal tract. In some embodiments, the coating or matrix materials are selected such that the pharmaceutical formulations can survive exposure to gastric acid and release the active ingredient in the intestines after oral administration.

Diluents can increase the bulk of a solid dosage formulation so that a practical size is provided for compression of tablets or formation of beads, granules, or particles. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, powdered sugar, and combinations thereof.

Binders are used to impart cohesive qualities to a solid dosage formulation, and thus ensure that a tablet, bead, granule, or particle remains intact after the formation of the solid dosage formulation. Suitable binders include, but are not limited to, starch, pregelatinized starch, gelatin, sugars (such as sucrose, glucose, dextrose, lactose, and sorbitol), polyethylene glycol, waxes, natural and synthetic gums (such as acacia, tragacanth, and sodium alginate), cellulose (such as hydroxypropylmethylcellulose, hydroxypropylcellulose, and ethylcellulose), veegum, and synthetic polymers (such as acrylic acid copolymers, methacrylic acid copolymers, methyl methacrylate copolymers, aminoalkyl methacrylate copolymers, polyacrylic acid, polymethacrylic acid, and polyvinylpyrrolidone), and combinations thereof.

Lubricants are used to facilitate tablet manufacture. Suitable lubricants include, but are not limited to, magnesium stearate, calcium stearate, stearic acid, glycerol behenate, polyethylene glycol, talc, and mineral oil.

Disintegrants are used to facilitate disintegration or "breakup" of a solid dosage formulation after administration. Suitable disintegrants include, but are not limited to, starch, sodium starch glycolate, sodium carboxymethyl starch, sodium carboxymethylcellulose, hydroxypropyl cellulose, pregelatinized starch, clays, cellulose, gums, and cross-linked polymers, such as cross-linked polyvinylpyrrolidone (e.g., POLYPLASDONE® XL).

Plasticizers are normally present to produce or promote plasticity and flexibility and to reduce brittleness. Examples of plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil, and acetylated monoglycerides.

Stabilizers are used to inhibit or retard decomposition reactions of the active ingredient in the pharmaceutical formulations or stabilize particles in a dispersion. For example, when the decomposition reactions involve an oxidation reaction of the active ingredient in the pharmaceutical formulations, the stabilizer can be an antioxidant or a reducing agent. Stabilizers also include nonionic emulsifiers such as sorbitan esters, polysorbates, and polyvinylpyrrolidone.

Glidants are used to reduce sticking effects during film formation and drying. Exemplary glidants include, but are not limited to, talc, magnesium stearate, and glycerol monostearates.

Preservatives can inhibit the deterioration and/or decomposition of a pharmaceutical formulation. Deterioration or decomposition can be brought about by one or more of microbial growth, fungal growth, and undesirable chemical or physical changes. Suitable preservatives include benzoate salts (e.g., sodium benzoate), ascorbic acid, methyl hydroxybenzoate, ethyl p-hydroxybenzoate, n-propyl p-hydroxybenzoate, n-butyl p-hydroxybenzoate, potassium sorbate, sorbic acid, propionate salts (e.g., sodium propionate), chlorobutanol, benzyl alcohol, and combinations thereof.

Surfactants may be anionic, cationic, amphoteric, or nonionic surface-active agents. Exemplary anionic surfactants include, but are not limited to, those containing a carboxylate, sulfonate, or sulfate ion. Examples of anionic surfactants include sodium, potassium, and ammonium salts of long-chain (e.g., 13-21) alkyl sulfonates (such as sodium lauryl sulfate), alkylaryl sulfonates (such as sodium dodecylbenzene sulfonate), and dialkyl sulfosuccinates (such as sodium bis-(2-ethylthioxyl)-sulfosuccinate). Examples of cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, poloxamers (such as poloxamer 401), stearoyl monoisopropanolamide, and polyoxyethylene hydrogenated tallow amide. Examples of amphoteric surfactants include, but are not limited to, sodium N-dodecyl-β-alanine, sodium N-lauryl-β-iminodipropionate, myristoamphoacetate, lauryl betaine, and lauryl sulfobetaine.

Pharmaceutical formulations in the liquid dosage forms typically contain a solvent or dispersion medium such as water, aqueous solution (e.g., buffer, saline, buffered saline), ethanol, polyol (such as glycerol, propylene glycol, and polyethylene glycol), oil (such as vegetable oil, e.g., peanut oil, corn oil, sesame oil), and combinations thereof. In some embodiments, the pharmaceutical formulations in the liquid dosage forms are aqueous formulations. Suitable solvents or dispersion mediums for aqueous formulations include, but are not limited to, water, buffers (such as acidic buffers), salines (such as normal saline), buffered salines (such as PBS), and Ringer's solution.

C. Pharmaceutical Acceptable Carriers

In some embodiments, the pharmaceutical formulations are prepared using a pharmaceutically acceptable carrier, which encapsulates, embeds, entraps, dissolves, disperses, absorbs, and/or binds to a compound or composition disclosed herein. The pharmaceutical acceptable carrier is composed of materials that are considered safe and can be administered to a subject without causing undesirable biological side effects or unwanted interactions. Preferably, the pharmaceutically acceptable carrier does not interfere with the effectiveness of the compound or composition in performing its function. The pharmaceutically acceptable carrier can be formed of biodegradable materials, non-biodegradable materials, or combinations thereof. One or more of the pharmaceutical acceptable excipients described above may be present in the pharmaceutical acceptable carrier.

In some embodiments, the pharmaceutical acceptable carrier is a controlled-release carrier, such as delayed-release carriers, sustained-release (extended-release) carriers, and pulsatile-release carriers.

In some embodiments, the pharmaceutical acceptable carrier is pH-sensitive or pH-responsive. In some forms, the pharmaceutical acceptable carrier can decompose or degrade in a certain pH range. In some forms, the pharmaceutical acceptable carrier can experience a structural change when experiencing a change in the pH.

Exemplary pharmaceutical acceptable carriers include, but are not limited to: nanoparticles, microparticles, and combinations thereof, liposomes; hydrogels; polymer matrices; and solvent systems.

In some embodiments, the pharmaceutical acceptable carrier is nanoparticles, microparticles, or a combination thereof. In some embodiments, the compound or composition is embedded in the matrix formed by the materials of the nanoparticles, microparticles, or combination thereof.

The nanoparticles, microparticles, or combination thereof can be biodegradable, and optionally are capable of biodegrading at a controlled rate for delivery of the compound or composition. The nanoparticles, microparticles, or combination thereof can be made of a variety of materials. Both inorganic and organic materials can be used. Both polymeric and non-polymeric materials can be used.

For example, the nanoparticles, microparticles, or combination thereof are formed of one or more biocompatible polymers. In some forms, the biocompatible polymers are biodegradable. In some forms, the biocompatible polymers are non-biodegradable. In some forms, the nanoparticles, microparticles, or combination thereof are formed of a mixture of biodegradable and non-biodegradable polymers. The polymers used to form the nanoparticles, microparticles, or combination thereof may be tailored to optimize different characteristics of the nanoparticles, microparticles, or combination thereof, including: (i) interactions between the active ingredient and the polymer to provide stabilization of the active ingredient and retention of activity upon delivery; (ii) rate of polymer degradation and, thereby, rate of release; (iii) surface characteristics and targeting capabilities; and (iv) particle porosity.

Exemplary polymers include, but are not limited to, polymers prepared from lactones (such as poly(caprolactone) (PCL)), polyhydroxy acids and copolymers thereof (such as poly(lactic acid) (PLA), poly(glycolic acid) (PGA), and poly(lactic acid-co-glycolic acid) (PLGA)), polyalkyl cyanoacralate, polyurethanes, polyamino acids (such as poly-L-lysine (PLL), poly(valeric acid), and poly-L-glutamic acid), hydroxypropyl methacrylate (HPMA), polyanhydrides, polyorthoesters, poly(ester amides), polyamides, poly(ester ethers), polycarbonates, ethylene vinyl acetate polymer (EVA), polyvinyl alcohols (PVA), polyvinyl ethers, polyvinyl esters (such as poly(vinyl acetate)), polyvinyl halides (such as poly(vinyl chloride) (PVC)), polyvinylpyrrolidone, polysiloxanes, polystyrene (PS), celluloses and derivatized celluloses (such as alkyl celluloses, hydroxyalkyl celluloses, cellulose ethers, cellulose esters, nitro celluloses, hydroxypropylcellulose, and carboxymethylcellulose), polymers of acrylic acids (such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), and poly(octadecyl acrylate)), polydioxanone, polyhydroxyalkanoates, polypropylene fumarate, polyoxymethylene, poloxamers, poly(butyric acid), polyphosphazenes, polysaccharides, polypeptides, and blends thereof.

In some embodiments, the one or more biocompatible polymers forming the nanoparticles, microparticles, or combination thereof include an FDA-approved biodegradable polymer such as polyhydroxy acids (e.g., PLA, PGA, and PLGA), polyanhydrides, and polyhydroxyalkanoate (e.g., poly(3-butyrate) and poly(4-butyrate)).

Materials other than polymers may be used to form the nanoparticles, microparticles, or combination thereof. Suitable materials include surfactants. The use of surfactants in the nanoparticles, microparticles, or combination thereof may improve surface properties by, for example, reducing particle-particle interactions, and render the surface of the particles less adhesive. Both naturally occurring surfactants and synthetic surfactants can be incorporated into the nanoparticles, microparticles, or combination thereof. Exemplary surfactants include, but are not limited to, phosphoglycerides such as phosphatidylcholines (e.g., L-α-phosphatidylcholine dipalmitoyl), diphosphatidyl glycerol, hexadecanol, fatty alcohols, polyoxyethylene-9-lauryl ether, fatty acids such as palmitic acid and oleic acid, sorbitan trioleate, glycocholate, surfactin, poloxomers, sorbitan fatty acid esters such as sorbitan trioleate, tyloxapol, and phospholipids.

The nanoparticles, microparticles, or combination thereof may contain a plurality of layers. The layers can have similar or different release kinetic profiles for the active ingredient. For example, the nanoparticles, microparticles, or combination thereof can have a controlled-release core surrounded by one or more additional layers. The one or more additional layers can include an instant-release layer, preferably on the surface of the nanoparticles, microparticles, or combination thereof. The instant-release layer can provide a bolus of the active ingredient shortly after administration.

The composition and structure of the nanoparticles, microparticles, or combination thereof can be selected such that the nanoparticles, microparticles, or combination thereof are pH-sensitive or pH-responsive. In some embodiments, the nanoparticles, microparticles, or combination thereof are formed of one or more pH-sensitive or pH-responsive polymers such as the enteric polymers commercially available under the tradename EUDRAGIT®, as described above. Depending on the particle materials, the decomposition/degradation or structural change of the nanoparticles, microparticles, or combination thereof may occur at different locations of the gastrointestinal tract. In some embodiments, the particle materials are selected such that the nanoparticles, microparticles, or combination thereof can survive exposure to gastric acid and release the active ingredient in the intestines after oral administration.

D. Controlled Release

In some embodiments, the pharmaceutical formulations can be controlled-release formulations. Examples of controlled-release formulations include extended-release formulations, delayed-release formulations, and pulsatile-release formulations.

1. Extended Release

In some embodiments, the extended-release formulations are prepared as diffusion or osmotic systems, for example, as described in "Remington—The science and practice of pharmacy" (20th Ed., Lippincott Williams & Wilkins, 2000).

A diffusion system is typically in the form of a matrix, generally prepared by combining the active ingredient with a slowly dissolving, pharmaceutically acceptable carrier, optionally in a tablet form. Suitable materials used in the preparation of the matrix include plastics, hydrophilic polymers, and fatty compounds. Suitable plastics include, but are not limited to, acrylic polymer, methyl acrylate-methyl methacrylate copolymer, polyvinyl chloride, and polyethylene. Suitable hydrophilic polymers include, but are not limited to, cellulosic polymers such as methyl ethyl cellulose, hydroxyalkylcelluloses (such as hydroxypropylcellulose and hydroxypropylmethylcellulose), sodium carboxymethylcellulose, CARBOPOL® 934, polyethylene oxides, and combinations thereof. Suitable fatty compounds include, but are not limited to, various waxes such as carnauba wax and glyceryl tristearate, wax-type substances such as hydrogenated castor oil and hydrogenated vegetable oil, and combinations thereof.

In some embodiments, the plastic is a pharmaceutically acceptable acrylic polymer. In some embodiments, the pharmaceutically acceptable acrylic polymer is chosen from acrylic acid and methacrylic acid copolymers, methyl methacrylate copolymers, ethoxyethyl methacrylate copolymers, cyanoethyl methacrylate copolymers, aminoalkyl methacrylate copolymers, poly(acrylic acid), poly(methacrylic acid), methacrylic acid alkylamine copolymers, poly(methyl methacrylate), poly(methacrylic acid), polymethacrylate, polyacrylamide, poly(methacrylic acid anhydride), and glycidyl methacrylate copolymers.

In some embodiments, the pharmaceutically acceptable acrylic polymer can be an ammonio methacrylate copolymer. Ammonio methacrylate copolymers are well known in the art and are described as fully polymerized copolymers of acrylic and methacrylic acid esters with a low content of quaternary ammonium groups.

In some embodiments, the pharmaceutically acceptable acrylic polymer is an acrylic resin lacquer such as those commercially available under the tradename EUDRAGIT®. In some embodiments, the pharmaceutically acceptable acrylic polymer contains a mixture of two acrylic resin lacquers, EUDRAGIT® RL (such as EUDRAGIT® RL30D) and EUDRAGIT® RS (such as EUDRAGIT® RS30D). EUDRAGIT® RL30D and EUDRAGIT® RS30D are copolymers of acrylic and methacrylic acid esters with a low content of quaternary ammonium groups, the molar ratio of ammonium groups to the remaining neutral methacrylic esters being 1:20 in EUDRAGIT® RL30D and 1:40 in EUDRAGIT® RS30D. The code designations RL (high permeability) and RS (low permeability) refer to the permeability properties of these polymers. EUDRAGIT® RL/RS mixtures are insoluble in water and in digestive fluids. However, multi-particulate systems formed to include the same are swellable and permeable in aqueous solutions and digestive fluids. The EUDRAGIT® RL/RS mixtures may be prepared in any desired ratio in order to ultimately obtain a sustained-release formulation having a desirable release profile. Suitable sustained-release, multi-particulate systems may be obtained, for instance, from 90% EUDRAGIT® RL+10% EUDRAGIT® RS, to 50% EUDRAGIT® RL+50% EUDRAGIT® RS, and to 10% EUDRAGIT® RL+90% EUDRAGIT® RS. In some embodiments, the pharmaceutically acceptable acrylic polymer can also be or include other acrylic resin lacquers, such as EUDRAGIT® S-100, EUDRAGIT® L-100, and mixtures thereof.

Matrices with different release mechanisms or profiles can be combined in a final dosage form containing single or multiple units. Examples of multiple units include, but are not limited to, multilayer tablets and capsules containing beads, granules, and/or particles of the active ingredient. An immediate release portion can be added to the extended-release system by means of either applying an immediate release layer on top of the extended-release core using a coating or compression process or in a multiple unit system such as a capsule containing both extended- and immediate-release beads.

Extended-release tablets containing one or more of the hydrophilic polymers can be prepared by techniques commonly known in the art such as direct compression, wet granulation, and dry granulation.

Extended-release tablets containing one or more of the fatty compounds can be prepared using methods known in the art such as direct blend methods, congealing methods, and aqueous dispersion methods. In the congealing methods, the active ingredient is mixed with the fatty compound(s) and congealed.

Alternatively, the extended-release formulations can be prepared using osmotic systems or by applying a semi-permeable coating to a solid dosage form. In the latter case, the desired release profile can be achieved by combining low permeable and high permeable coating materials in suitable proportions.

2. Delayed Release

Delayed-release formulations can be prepared by coating a solid dosage form with a coating. In some embodiments, the coating is insoluble and impermeable in the acidic environment of the stomach, and becomes soluble or permeable in the less acidic environment of the intestines and/or the lower GI tract. In some embodiments, the solid dosage form is a tablet for incorporation into a capsule, a tablet for use as an inner core in a "coated-core" dosage form, or a plurality of beads, granules, and/or particles containing the active ingredient, for incorporation into either a tablet or capsule.

Suitable coating materials may be bioerodible polymers, gradually hydrolysable polymers, gradually water-dissolvable polymers, and enzymatically degradable polymers. In some embodiments, the coating material is or contains enteric polymers. Combinations of different coating materials may also be used. Multilayer coatings using different coating materials may also be applied.

The coating may also contain one or more additives, such as plasticizers as described above (optionally representing about 10 wt % to 50 wt % relative to the dry weight of the coating), colorants as described above, stabilizers as described above, glidants as described above, etc.

3. Pulsatile Release

Pulsatile-release formulations release a plurality of doses of the active ingredient at spaced-apart time intervals. Generally, upon administration, such as oral administration, of the pulsatile-release formulations, release of the initial dose is substantially immediate, e.g., the first release "pulse" occurs within about three hours, two hours, or one hour of administration. This initial pulse may be followed by a first time-interval (lag time) during which very little or no active ingredient is released from the formulations, after which a second dose may be released. Similarly, a second lag time (nearly release-free interval) between the second and third release pulses may be designed. The duration of the lag times will vary depending on the formulation design, especially on the length of the dosing interval, e.g., a twice daily dosing profile, a three-time daily dosing profile, etc.

For pulsatile-release formulations providing a twice daily dosage profile, they deliver two release pulses of the active ingredient. In some embodiments, the one nearly release-free interval between the first and second release pulses may have a duration of between 3 hours and 14 hours.

For pulsatile-release formulations providing a three daily dosage profile, they deliver three release pulses of the active ingredient. In some embodiments, the two nearly release-free interval between two adjacent pulses may have a duration of between 2 hours and 8 hours.

In some embodiments, the pulsatile-release formulations contain a plurality of pharmaceutically acceptable carriers with different release kinetics.

In some embodiments, the pulsatile-release formulations contain a pharmaceutically acceptable carrier with a plurality of layers loaded with the active ingredient. In some embodiments, the layers may have different release kinetics. In some embodiments, the layers may be separated by a delayed-release coating. For example, the pulsatile-release formulations may have a first layer loaded with the active ingredient on the surface for the first release pulse and a second layer, e.g., a core loaded with the active ingredient, for the second release pulse; the second layer may be surrounded by a delayed-release coating, which creates a lag time between the two release pulses.

In some embodiments, the pulsatile-release profile is achieved with formulations that are closed and optionally sealed capsules housing at least two "dosage units" wherein each dosage unit within the capsules provides a different release profile. In some embodiments, at least one of the dosage units is a delayed-release dosage unit. Control of the delayed-release dosage unit(s) may be accomplished by a controlled-release polymer coating on the dosage unit(s) or by incorporation of the active ingredient in a controlled-release polymer matrix. In some embodiments, each dosage unit may comprise a compressed or molded tablet, wherein each tablet within the capsule provides a different release profile.

E. Exemplary Formulations for Different Routes of Administration

A subject suffering from a condition, disorder, or disease as described herein, can be treated by either targeted or systemic administration, via oral, inhalation, topical, trans- or sub-mucosal, subcutaneous, intramuscular, intravenous, or transdermal administration of a pharmaceutical formulation containing a compound or composition described herein. In some embodiments, the pharmaceutical formulation is suitable for oral administration. In some embodiments, the pharmaceutical formulation is suitable for subcutaneous, intravenous, or intramuscular administration. In some embodiments, the pharmaceutical formulation is suitable for inhalation or intranasal administration. In some embodiments, the pharmaceutical formulation is suitable for transdermal or topical administration.

In some embodiments, the pharmaceutical formulation is an oral pharmaceutical formulation. In some embodiments, the active ingredient may be incorporated with one or more pharmaceutically acceptable excipients as described above and used in the form of tablets, pills, caplets, or capsules. For example, the corresponding oral pharmaceutical formulation may contain one or more of the following pharmaceutically acceptable excipients or those of a similar nature: a binder as described above, a disintegrant as described above, a lubricant as described above, a glidant as described above, a sweetening agent (such as sucrose and saccharin), and a flavoring agent (such as methyl salicylate and fruit flavorings). In some embodiments, when the oral pharmaceutical formulation is in the form of capsules, it may contain, in addition to the material(s) listed above, a liquid carrier (such as a fatty oil). In some embodiments, when the oral pharmaceutical formulation is in the form of capsules, each capsule may contain a plurality of beads, granules, and/or particles of the active ingredient. In some embodiments, the oral pharmaceutical formulation may contain one or more other materials which modify the physical form or one or more pharmaceutical properties of the dosage unit, for example, coatings of polysaccharides, shellac, or enteric polymers as described in previous sections.

In some embodiments, the oral pharmaceutical formulation can be in the form of an elixir, suspension, syrup, wafer, chewing gum or the like. A syrup may contain, in addition to the active ingredient, one or more sweetening agents (such as sucrose and saccharine), one or more flavoring agents, one or more preservatives, and/or one or more dyes or colorings.

In some embodiments, the pharmaceutical formulation is a subcutaneous, intramuscular, or intravenous pharmaceutical formulation. In some embodiments, the subcutaneous, intramuscular, or intravenous pharmaceutical formulation can be enclosed in an ampoule, syringe, or a single or multiple dose vial made of glass or plastic. In some embodiments, the subcutaneous, intramuscular, or intravenous pharmaceutical formulation contains a liquid pharmaceutically acceptable carrier for the active ingredient. Suitable liquid pharmaceutically acceptable carriers include, but are not limited to, water, buffer, saline, buffered saline (such as PBS), and combinations thereof.

In some embodiments, the pharmaceutical formulation is a topical pharmaceutical formulation. Suitable forms of the topical pharmaceutical formulation include lotions, suspensions, ointments, creams, gels, tinctures, sprays, powders, pastes, slow-release transdermal patches, and suppositories for application to rectal, vaginal, nasal, or oral mucosa. In some embodiments, thickening agents, emollients (such as mineral oil, lanolin and its derivatives, and squalene), humectants (such as sorbitol), and/or stabilizers can be used to prepare the topical pharmaceutical formulations. Examples of thickening agents include petrolatum, beeswax, xanthan gum, and polyethylene.

In some embodiments, the pharmaceutical formulation is an intranasal pharmaceutical formulation. In some embodiments, the intranasal pharmaceutical formulation is in the form of an aqueous suspension, which can be optionally placed in a pump spray bottle. Other than water, the aqueous suspension may contain one or more pharmaceutically acceptable excipients, such as suspending agents (e.g., microcrystalline cellulose, sodium carboxymethylcellulose, hydroxypropyl-methyl cellulose), humectants (e.g., glycerol, propylene glycol), acids, bases, and/or pH-buffering agents for adjusting the pH (e.g., citric acid, sodium citrate, phosphoric acid, sodium phosphate, and combinations thereof), surfactants (e.g., polysorbate 80), and preservatives (e.g., benzalkonium chloride, phenylethyl alcohol, potassium sorbate).

In some embodiments, the pharmaceutical formulation is an inhalation pharmaceutical formulation. In some embodiments, the inhalation pharmaceutical formulation may be in the form of an aerosol suspension, a dry powder, or a liquid suspension. The inhalation pharmaceutical formulation may be prepared for delivery as a nasal spray or an inhaler, such as a metered dose inhaler (MDI). In some embodiments, MDIs can deliver aerosolized particles suspended in chlorofluorocarbon propellants such as CFC-11 and CFC-12, or non-chlorofluorocarbons or alternate propellants such as fluorocarbons (e.g., HFC-134A, HFC-227), with or without surfactants or suitable bridging agents. Dry-powder inhalers can also be used, either breath activated or delivered by pressure.

In some embodiments, the active ingredient is prepared with a pharmaceutically acceptable carrier that will protect it against rapid degradation or elimination from the body of the subject after administration, such as the controlled-release formulations described in previous sections.

V. METHODS OF USE

Disclosed are methods of mobilizing stem cells or treating a condition, disorder, or disease in a subject in need thereof. The methods include administering an effective amount of a compound, composition, or pharmaceutical formulation disclosed herein to the subject.

The compound, composition, or pharmaceutical formulation can be administered in a variety of manners, depending on whether local or systemic administration is desired. In some embodiments, the compound, composition, or pharmaceutical formulation is directly administered to a specific bodily location of the subject, e.g., topical administration and intranasal administration. In some embodiments, the compound, composition, or pharmaceutical formulation is administered in a systemic manner, such as enteral administration (e.g., oral administration) and parenteral administration (e.g., injection, infusion, and implantation). Exemplary administration routes include oral administration, intravenous administration such as intravenous injection or infusion, intramuscular administration such as intramuscular injection, intranasal administration, and topical administration. In some embodiments, the compound, composition, or pharmaceutical formulation is administered orally. In some embodiments, the compound, composition, or pharmaceutical formulation is administered intravenously. In some embodiments, the compound, composition, or pharmaceutical formulation is administered intramuscularly.

In some embodiments, the subject is a human. In some embodiments, the subject is a non-human animal, such as domestic pets, livestock and farm animals, and zoo animals. In some embodiments, the non-human animal may be a non-human primate.

The compounds, compositions, or pharmaceutical formulations disclosed herein can be used to antagonize the CXCR4 pathway for mobilizing stem cells, such as hematopoietic stem cells (HSCs). In some embodiments, the compounds, compositions, or pharmaceutical formulations can be used to mobilize stem cells for autologous, allogeneic, and haploidentical transplantations in patients. In some embodiments, the patients have a hematological malignancy. Exemplary hematological malignancies include, but are not limited to, multiple myeloma, acute myelogenous leukemia, acute lymphoblastic leukemia, chronic myelogenous leukemia, non-Hodgkin lymphoma, Hodgkin disease, chronic lymphocytic leukemia, myelodysplastic syndrome, and myeloproliferative neoplasm.

The compounds, compositions, or pharmaceutical formulations disclosed herein can be used to antagonize the CXCR4 pathway for treating a condition, disorder, or disease associated with the CXCR4 pathway. Exemplary conditions, disorders, and diseases include, but are not limited to, HIV infections, respiratory infections (e.g., SARS-CoV-2, respiratory syncytial virus (RSV), and others), WHIM syndrome, chronic neutropenia (SCN/CN), primary immune-deficiency (PID), acute respiratory distress syndrome (ARDS), myocardial infarction, diseases associated with hematopoiesis, inflammation, neuroinflammation, Alzheimer's disease, Parkinson's disease, amyotrophic lateral sclerosis (ALS), multiple sclerosis (MS), allergic diseases, asthma, allergic pneumonia, interstitial lung disease, lupus erythematosus, ankylosing spondylitis, multiple sclerosis, systemic sclerosis, polymyositis, rheumatoid arthritis, ankylosing spondylitis, myasthenia gravis, juvenile diabetes, glomerulonephritis, autoimmune thyroiditis, graft rejection, inflammatory bowel disease, gout, Crohn's disease, ulcerative colitis, scleroderma, psoriasis, dermatitis, retinitis pigmentosa, proliferative vitreoretinopathy, Best's vitelliform macular degeneration, eczema, urticaria, vasculitis, eosinophilic fasciitis, wet and dry age-related macular degeneration (ARMD), diabetic retinopathy, retinopathy of prematurity (ROP), diabetic macular edema, uveitis, retinal vein occlusion, cystic macular edema, glaucoma, vein branch occlusion, chronic and non-progressive anemia, aplastic anemia, spontaneous or primary thrombocytosis, idiopathic myelofibrosis, pulmonary fibrosis, renal fibrosis, liver fibrosis, cirrhosis, diabetic retinopathy, myelodysplastic syndrome, hypoplastic myelodysplastic syndrome, myeloproliferative disorders, renal diseases induced or exacerbated by lupus (lupus nephritis), diabetes, or HIV, acute kidney diseases, renal microtubule or microvascular dysfunction, acute renal failure, and cancers (such as breast cancer, lung cancer (small cell and non-small cell), bladder cancer, pancreatic cancer, kidney cancer, renal cell carcinoma, liver cancer, hepatocellular carcinoma, head and neck cancers including squamous cell carcinoma and nasopharyngeal cancer, laryngeal and hypopharyngeal squamous-cell cancer, oral squamous cell cancer, salivary gland cancer, squamous cell carcinoma of the tongue, Merkel cell carcinoma, thyroid cancer, sarcoma, osteosarcoma, desmofibroma, rhabdomyosarcoma, soft tissue sarcoma, melanoma, prostate cancer, colon cancer, rectal cancer, urothelial cancer, ductal carcinoma in situ, endometrial cancer, Ewing sarcoma, gallbladder cancer, gastrointestinal stromal tumors (GIST), colorectal cancer, ovarian cancer, cervical cancer, testicular tumors, thymoma, esophageal cancer, gastric cancer, adrenocortical carcinoma, atypical ductal hyperplasia, basal cell carcinoma, cholangiocarcinoma, myeloma, multiple myeloma, lymphoma, mantle cell lymphoma, non-Hodgkin's lymphoma, Hodgkin's lymphoma, primary CNS lymphoma, cutaneous T cell lymphoma, lymphoblastic lymphoma, T-acute lymphoblastic lymphoma, macroglobulinemia, Waldenstrom macroglobulinemia (WM), leukemia, acute lymphoblastic leukemia (ALL), chronic leukemia, lymphoblastic leukemia, T-acute lymphoblastic leukemia, acute myeloid leukemia (AML), chronic lymphocytic leukemia (CLL), chronic myelogenous leukemia (CML), T cell leukemia, encephaloma, astrocytoma, medulloblastoma, schwannoma, primary neuroectodermal tumor, glioblastoma, neuroblastoma, glioma, adamanti-nomatous craniopharyngioma, mesothelioma, and pituitary adenoma).

In some embodiments, the condition, disorder, or disease is HIV infections. In some embodiments, the condition, disorder, or disease is WHIM syndrome. In some embodiments, the condition, disorder, or disease is Waldenstrom macroglobulinemia. In some embodiments, the condition, disorder, or disease is chronic neutropenia (SCN/CN). In some embodiments, the condition, disorder, or disease is primary immune-deficiency (PID). In some embodiments, the condition, disorder, or disease is aplastic anemia. In some embodiments, the condition, disorder, or disease is hypoplastic myelodysplastic syndrome. In some embodiments, the condition, disorder, or disease is acute respiratory distress syndrome (ARDS), such as those secondary to COVID-19 and other respiratory viral infections (e.g., RSV infections). In some embodiments, the condition, disorder, or disease is ankylosing spondylitis (Cui, et al., *Sci. Adv.,* 2022, 8, eab18054). In some embodiments, the condition, disorder, or disease is a cancer have an upregulation of CXCR4, its natural ligand CXCL12, or both.

A. Exemplary Indications

1. Virology

The compounds, compositions, and pharmaceutical formulations described herein can be used to treat or prevent viral infections where the virus utilizes CXCR4 to infect host cells. In this context, the compounds, compositions, and pharmaceutical formulations can function as antiviral, pre-exposure prophylaxis (PrEP), or both. In some embodiments, the viral infections are HIV infections.

In some embodiments, the disclosure relates to a method of treating or preventing HIV infections and/or reduction of one or more symptoms associated with AIDS. The method includes administering an effective amount of a compound, composition, or pharmaceutical formulation disclosed herein to a subject in need thereof. The subject may have contracted HIV, be diagnosed with HIV infection, or have a risk of HIV exposure. In some embodiments, the method is prophylactic in nature, e.g., for the prevention of HIV infection or reduction of symptoms associated with AIDS.

In some embodiments, the disclosure relates to a method of treating HIV-associated neurocognitive disorder (HAND) and HIV-induced renal insufficiency and failure. The method includes administering an effective amount of a compound, composition, or pharmaceutical formulation disclosed herein to a subject suffering from one or more of these conditions.

In some embodiments, the disclosure relates to treating the pathology caused by SARS-Cov-2 infections. The method may specifically refer to treatment of lung pathology involving dysregulation of T-cell subsets in the overall immune response after SARS-Cov-2 infections (Neidleman et. al., *Cell Reports,* 2021, 36, 109414). Boosting SARS-CoV-2-specific CD4+ T effector responses while diminishing CXCR4-mediated homing can help recovery from severe disease associated with SARS-CoV-2 infections. The method includes administering an effective amount of a compound, composition, or pharmaceutical formulation disclosed herein to a subject suffering from COVID-19.

2. Abnormal Cell Proliferation and Cancers

The compounds, compositions, and pharmaceutical formulations described herein can also be used to treat other disorders of abnormal cell proliferation or hyperproliferation. In some embodiments, these disorders of abnormal cell proliferation or hyperproliferation have an upregulation of CXCR4, its natural ligand CXCL12, or both.

There are a number of skin disorders associated with cellular hyperproliferation. Psoriasis, for example, is a benign disease of human skin generally characterized by plaques covered by thickened scales. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma, and squamous cell carcinoma.

Other hyperproliferative cell disorders include blood vessel proliferation disorders, fibrotic disorders, autoimmune disorders, graft-versus-host rejection, and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock, and inflammation in general.

In certain embodiments, the compound disclosed herein can be used to treat or prevent hyperplastic disorders including, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, verrucous hyperplasia, leukemia (including acute leukemia (e.g., acute lymphocytic leukemia, acute myelocytic leukemia (including myeloblasts, promyelocyte, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and, carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

Mechanistically, upregulation of the CXCR4/CXCL12 axis promotes cancer progression in at least three key ways: (1) Cancer-associated fibroblasts (CAFs) secrete CXCL12, which stimulates protective tumor-stromal interactions and secretion of pro-angiogenic cytokines; (2) CXCR4+ RCC and PC cells can escape into circulation and migrate along CXCL12 concentration gradients to alternative stromal niches (e.g., bone, lung, liver, and lymph nodes) to initiate metastases; and (3) CAFs establish intratumoral CXCL12 gradients that drive infiltration of CXCR4+ $T_{Regs}$ and MDSCs, which combat anti-tumor immune responses by inhibiting CD8+ T cell recruitment and function. Accordingly, CXCR4 antagonists can combat these consequences of CXCR4/CXCL12 upregulation.

In some embodiments, the compounds, compositions, and pharmaceutical formulations described herein can be used to treat cancers. In some embodiments, the cancers have an upregulation of CXCR4, its natural ligand CXCL12, or both. An exemplary list of CXCR4-associated cancers can be found in the lists of cancers above as well as in (1) Chatterjee, et. al; *Adv Cancer Res.,* 2014, 124, 31-82, (2) Mishan, et al., *Cell Biol. Int.,* 2016, 40, 955-967, (3) Furusato, et al., *Pathol. Int.,* 2010, 60(7), 497-505, and (4) Domanska, et al., *Eur. J. Cancer,* 2013, 49(1), 219-230.

In some embodiments, the disclosure relates to a method of treating a CXCR4-associated cancer. The method includes administering an effective amount of a compound, composition, or pharmaceutical formulation disclosed herein to a subject diagnosed with the cancer. The cancer can be selected from the lists of cancers above. In some embodiments, the cancer is renal cell carcinoma. In some embodiments, the cancer is prostate cancer. In some embodiments, the cancer is lung cancer, such as non-small cell lung cancer. In some embodiments, the cancer is pancreatic cancer, such as metastatic pancreatic adenocarcinoma. In some embodiments, the cancer is Waldenstrom macroglobulinemia. In some embodiments, the cancer is acute myeloid leukemia. In some embodiments, the cancer is lymphoblastic leukemia or lymphoblastic lymphoma.

3. Other Indications

The compounds, compositions, and pharmaceutical formulations described herein can be used to antagonize the CXCR4 pathway for treating other indications associated with the CXCR4 pathway.

In some embodiments, the disclosure relates to a method for the treatment of or reducing the severity of a CXCR4-related primary immune-deficiency (PID). The method includes administering an effective amount of a compound, composition, or pharmaceutical formulation disclosed herein to a subject diagnosed with the CXCR4-related PID. In some embodiments, the CXCR4-related PID is the WHIM syndrome, which is caused by gain-of-function mutations in the CXCR4 gene.

In some embodiments, the disclosure relates to a method for the treatment of or reducing the severity of chronic neutropenia. The method includes administering an effective amount of a compound, composition, or pharmaceutical formulation disclosed herein to a subject diagnosed with chronic neutropenia. Chronic neutropenia is often caused by gain-of-function mutations in the CXCR4 gene or increased neutrophil CXCR4 expression.

In some embodiments, the disclosure relates to a method for the treatment of or reducing the severity of aplastic anemia. The method includes administering an effective amount of a compound, composition, or pharmaceutical formulation disclosed herein to a subject diagnosed with aplastic anemia. Aplastic anemia is often caused by T cells migrating to and attacking bone marrow in response to chemokines like CXCR4.

In some embodiments, the disclosure relates to a method for the treatment of or reducing the severity of hypoplastic myelodysplastic syndrome. The method includes administering an effective amount of a compound, composition, or pharmaceutical formulation disclosed herein to a subject diagnosed with hypoplastic myelodysplastic syndrome.

In some embodiments, the disclosure relates to a method for the treatment of or reducing the severity of acute respiratory distress syndrome (ARDS). The method includes administering an effective amount of a compound, composition, or pharmaceutical formulation disclosed herein to a subject in need thereof. In some embodiments, the ARDS is secondary to COVID-19 or other respiratory viral infections.

In some embodiments, the disclosure relates to a method for the treatment of or reducing the severity of liver damages associated with a flavivirus or pestivirus infection, such as a hepatitis virus infection. The method includes administering an effective amount of a compound, composition, or pharmaceutical formulation disclosed herein to a subject diagnosed with the hepatitis virus infection. Chronic hepatitis C virus (HCV) and hepatitis B virus (HBC) infections are accompanied by inflammation and fibrosis eventually leading to cirrhosis. The CXCR4 pathway plays an important role in recruitment and retention of immune cells in the liver during chronic HCV and HBV infections (Wald et al., *European Journal of Immunology,* 2004, 34(4), 1164-1174). High levels of CXCR4 and TGFβ have been detected in liver samples obtained from patients infected with HCV (Mitra et al., *Int. J. Oncol.,* 1999, 14, 917-925).

In some embodiments, the disclosure relates to a method for the treatment of or reducing the severity of age-related macular degeneration (ARMD) and other pathogenic states involving macular retinal pigment epithelial (RPE). The method includes administering an effective amount of a compound, composition, or pharmaceutical formulation disclosed herein to a subject diagnosed with ARMD or other pathogenic states involving RPE. The CXCR4 pathway plays an important role in ocular diseases involving the retina such as ARMD. The retinal pigment epithelium has a major role in the physiological renewal of photoreceptor outer segments in the provision of a transport and storage system for nutrients essential to the photoreceptor layer. The RPE cells predominantly express CXCR4 (Crane, et al., *J. Immunol.,* 2000, 165, 4372-4278). CXCR4 expression on human RPE cells from the blood-retina barrier leads to chemokine secretion and migration in response to stromal cell-derived factor Ia. RPE cells also migrated in response to CXCL12, indicating that CXCR4/CXCL12 interactions modulate the effects of chronic inflammation and subretinal neovascularization at the RPE site of the blood-retina barrier.

In some embodiments, the disclosure relates to a method for the treatment of or reducing the severity of inflammatory disease states, neovascularization, and wound healing. The method includes administering an effective amount of a compound, composition, or pharmaceutical formulation disclosed herein to a subject in need thereof. Vascular endothelial cells express a multitude of chemokine receptors, with CXCR4 being particularly prominent (Gupta, et al., *J. Biol. Chem.,* 1998, 273, 4282; Volin, et al., *Biochem. Biophys. Res. Commnun.,* 1998, 242, 46). CXCR4 is expressed not only in primary cultures and transformed type II alveolar epithelial cells (pneumocytes) but also in a number of epithelial cell lines derived from various other tissues (Murdoch, et al., *Immunology,* 1998, 98(1), 36-41). Unlike with endothelial cells, CXCR4 is the only chemokine receptor expressed on epithelial cells and playing a functional role in epithelial pathology. CXCR4 expressed on the epithelium facilitates the recruitment of phagocytic cells to sites of inflammation by direct effects on epithelial cells. CXCR4 also has other functional roles within the immune response or participates in wound healing or neovascularization. CXCR4 is also involved in the pathophysiology of several acute or chronic inflammatory disease states associated with the epithelium.

In a particular embodiment, the compounds of the disclosure can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines.

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells). Neuroinflammation is a key driver of neurodegeneration and the development of Alzheimer's disease, Parkinson's disease, amyotrophic lateral sclerosis (AML), amongst other neurodegenerative conditions. Importantly, the CXCR4/CXCL12 axis is an important disease-associated pathway that can be targeted with small molecule therapeutics to slow or even prevent neurodegenerative onset.

In one embodiment, compounds, compositions and methods of treatment of respiratory disorders comprising administering a compound as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g., cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the compounds of the disclosure are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the disclosure is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the disclosure is directed to methods of treating animal subjects, in particular, veterinary and human patients, who are defective in white blood cell (WBQ 8 count, or who would benefit from elevation of WBC levels using the compounds disclosed herein. Moreover, the disclosure is directed to methods of effecting regeneration of cardiac tissue in a subject in need of such regeneration using the disclosed compounds.

The compounds of the disclosure may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round disclosure thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the disclosure targets a broad spectrum of conditions characterized by a deficiency in white blood cell count, or which would benefit from elevation of said WBC count.

In some embodiments, the compounds, compositions, and pharmaceutical formulations of this disclosure can be used to treat the condition known as febrile neutropenia, which occurs in patients receiving chemotherapy and also in elderly patients with neutropenia caused by hematopoietic disorders and neutrophil deficiencies.

B. Dosing and Administration

In some embodiments, the compound, composition, or pharmaceutical formulation disclosed herein is administered for a sufficient time period to alleviate one or more undesired symptoms and/or one or more clinical signs associated with the condition, disorder, or disease being treated. In some embodiments, the compound, composition, or pharmaceutical formulation is administered less than three times daily. In some embodiments, the compound, composition, or pharmaceutical formulation is administered once or twice daily. In some embodiments, the compound, composition, or pharmaceutical formulation is administered once daily. In some embodiments, the compound, composition, or pharmaceutical formulation is administered in a single oral dosage once a day. In some embodiments, the compound, composition, or pharmaceutical formulation is administered in a single intravenous dosage once a day. In some embodiments, the compound, composition, or pharmaceutical formulation is administered in a single intramuscular dosage once a day.

In cases of acute brain injuries, such as stroke, concussion, and traumatic brain injury, the compound, composition, or pharmaceutical formulation may be administered under emergency care via intramuscular injection to minimize the onset of action.

In cases of chronic or non-acute illnesses, such as depression and postpartum depression, the compound, composition, or pharmaceutical formulation may be administered via oral administration or intravenous infusion.

C. Combination Therapies

In certain embodiments, the disclosure relates combination therapies that include a compound, composition, or pharmaceutical formulation disclosed herein and at least another therapeutic agent.

1. Combination Therapies for HIV

HIV is typically treated or prevented (pre-exposure prophylaxis or PrEP) with a combination of antiviral agents. In some embodiments, the disclosure relates to administering to a subject suffering from or having a risk of contracting HIV a compound disclosed herein in combination with at least another therapeutic agent, such as another HIV antiviral. The combination therapy may be a two-drug combination, three-drug combination, or four-drug combination.

Exemplary therapeutic agents include, but are not limited to: abacavir, acyclovir, acyclovir, adefovir, amantadine, amprenavir, ampligen, arbidol, atazanavir, atripla, boceprevir, cidofovir, caboregravir, combivir, darunavir, delavirdine, didanosine, docosanol, dolutegravir, doravirine, edoxudine, efavirenz, emtricitabine, enfuvirtide, entecavir, etravirine, famciclovir, fomivirsen, fostemsavir, fosamprenavir, foscarnet, fosfonet, ganciclovir, ibacitabine, ibalizumab-uiyk, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rilpivirine, rimantadine, ritonavir, pyramidine, saquinavir, stavudine, tenofovir, tenofovir disoproxil, tenofovir alafenamide, tipranavir, trifluridine, trizivir, tromantadine, truvada, valaciclovir, valganciclovir, vicriviroc, vidarabine, viramidine zalcitabine, zanamivir, and zidovudine.

Common types of HIV antivirals include: nucleoside reverse transcriptase inhibitors (NRTIs), such as abacavir, emtricitabine, lamivudine, tenofovir and prodrugs thereof (tenofovir disoproxil and tenofovir alafenamide), zidovudine; non-nucleoside reverse transcriptase inhibitors (NNRTIs), such as doravirine, efavirenz, etravirine, nevirapine, rilpivirine; HIV protease inhibitors, such as atazanavir, darunavir, fosamprenavir, ritonavir, tipranavir; HIV fusion inhibitors, such as enfuvirtide; CCR5 antagonists, such as maraviroc; HIV integrase inhibitors, such as caboregravir, dolutegravir, raltegravir; HIV attachment inhibitors, such as fostemsavir; and post-attachment inhibitors, such as ibalizumab-uiyk.

In some embodiments, the disclosure relates to treating a subject suffering from or having a risk of contracting HIV by administering a compound disclosed herein in combination with at least one NRTI. For example, the disclosure relates to treating a subject suffering from or having a risk of contracting HIV by administering a compound disclosed herein in combination with two NRTIs.

In some embodiments, the disclosure relates to treating a subject suffering from or having a risk of contracting HIV by administering a compound disclosed herein in combination with at least one NNRTI.

In some embodiments, the disclosure relates to treating a subject suffering from or having a risk of contracting HIV by administering a compound disclosed herein in combination with at least another therapeutic agent that inhibits HIV's cellular entry through a mechanism not dependent on CXCR4. In some embodiments, the mechanism involves CCR5, gp120, gp41 or CD4. Exemplary agents include, but are not limited to, maraviroc, enfuvirtide, TNX-355, PRO 250, BMS-488043, theaflavin, vicriviroc, gruffithsin, DCM205, ESN196, TBR220, TMB355, nifeviroc, BMS663068, CYT107, sifuvirtide, PF232798, SP01A, and BanLec.

In some embodiments, the disclosure relates to treating a subject suffering from or having a risk of contracting HIV by administering a compound disclosed herein in combination with at least one CCR5 antagonist, such as maraviroc. Such combination therapies can block cellular entry of both the T-tropic HIV strains (also termed as X4 strains), which target host CXCR4 for cellular entry, and the M-tropic HIV strains (also termed as R5 strains), which target host CCR5 for cellular entry. In the context of HIV, they are useful as not only therapeutics but also pre-exposure prophylaxis or PrEP.

2. Combination Therapies for Cancers

Cancer treatment using a compound disclosed herein may be combined with radiation therapy, chemotherapy, and/or immunotherapy.

In some embodiments, the disclosure relates to treating a subject suffering from cancer by administering a compound disclosed herein in combination with a chemotherapeutic agent. Exemplary chemotherapeutic agents include, but are not limited to, the following categories:

(i) antiproliferative/antineoplastic drugs and combinations thereof, as used in medical oncology, such as alkylating agents (for example, cisplatin, carboplatin, cyclophosphamide, nitrogen mustard, melphalan, chlorambucil, busulfan and nitrosoureas); antimetabolites (for example, antifolates such as fluoropyrimidines like 5-fluorouracil and gemcitabine, tegafur, raltitrexed, methotrexate, cytosine arabinoside and hydroxyurea); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, *vinca* alkaloids like vincristine, vinblastine, vindesine and vinorelbine and taxoids like taxol and taxotere); topoisomerase inhibitors (for example, epipodophyllotoxins like etoposide and teniposide, amsacrine, topotecan and camptothecin); and proteosome inhibitors (for example, bortezomib); anegrilide; and alpha-interferon;

(ii) cytostatic agents such as antioestrogens (for example, tamoxifen, toremifene, raloxifene, droloxifene and iodoxyfene), oestrogen receptor down regulators (for example, fulvestrant), antiandrogens (for example, bicalutamide, flutamide, nilutamide and cyproterone acetate), LHRH antagonists or LHRH agonists (for example, goserelin, leuprorelin and buserelin), progestogens (for example, megestrol acetate), aromatase inhibitors (for example, anastrozole, letrozole, vorazole and exemestane) and inhibitors of 5α-reductase such as finasteride; (iii) agents which inhibit cancer cell invasion (for example, metalloproteinase inhibitors like marimastat and inhibitors of urokinase plasminogen activator receptor function); (iv) inhibitors of growth factor function such as growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors, serine/threonine kinase inhibitors, inhibitors of the epidermal growth factor family (for example, EGFR family tyrosine kinase inhibitors such as gefitinib, erlotinib, and CI 1033), inhibitors of vascular endothelial growth factor receptors (for example, axitinib), inhibitors of the platelet-derived growth factor family, inhibitors of the hepatocyte growth factor family, inhibitors of phosphotidylinositol 3-kinase (PI3K), inhibitors of mitogen activated protein kinase kinase (MEK1/2), inhibitors of protein kinase B (PKB/Akt), inhibitors of Src tyrosine kinase family, inhibitors of Abelson (AbI) tyrosine kinase family (for example, dasatinib (BMS-354825), imatinib mesylate, nilotinib), and agents that modify STAT signaling;

(v) antiangiogenic agents such as those which inhibit the effects of vascular endothelial growth factor (for example the anti-vascular endothelial cell growth factor antibody bevacizumab) and compounds that work by other mechanisms (for example, linomide, inhibitors of integrin ocvβ3 function and angiostatin);

(vi) vascular damaging agents such as combretastatin A4;

(vii) antisense therapies, for example those which are directed to the targets listed above, such as an anti-ras antisense; and (viii) synthetic lethality agents, such as inhibitors of poly-ADP ribose polymerase (PARP) including but not limited to olarparib, rucaparib, niraparib, and talazoparib.

In some embodiments, the compound disclosed herein is used in combination with a vascular endothelial growth factor receptor (VEGFR) inhibitor. For example, the VEGFR inhibitor is axitinib.

In some embodiments, the disclosure relates to treating a subject suffering from cancer by administering a compound disclosed herein in combination with an immunotherapy. Exemplary immunotherapies include, but are not limited to, the following categories:

(i) immune checkpoint inhibitors such as CTLA-4 inhibitors (for example, ipilimumab), PD-1 inhibitors (for example, nivolumab, pembrolizumab, cemiplimab, spartalizumab), PD-L1 inhibitors (for example, atezolizumab, avelumab, duvalumab);

(ii) ex vivo and in vivo approaches to increase the immunogenicity of patient tumor cells, such as T-cell transfer therapies, transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines, approaches using anti-idiotypic antibodies, and approaches using the immunomodulatory drugs thalidomide and lenalidomide;

(iii) cancer treatment vaccines; and (iv) chimeric antigen receptor T (CAR-T) cell therapy.

In some embodiments, the compound disclosed herein is used in combination with an immune checkpoint inhibitor. In some embodiments, the immune checkpoint inhibitor is a PD-1 inhibitor. In some embodiments, the immune checkpoint inhibitor is a PD-L1 inhibitor. In some embodiments, the immune checkpoint inhibitor is selected from ipilimumab, nivolumab, pembrolizumab, cemiplimab, spartalizumab, atezolizumab, avelumab, and duvalumab. In some embodiments, the immune checkpoint inhibitor is pembrolizumab.

EXAMPLES

The examples below describe the synthesis and evaluation of exemplary CXCR4 antagonists.

General Information for Synthetic Chemistry:

All solvents and reagents were purchased from commercial suppliers and used without further purification. Analytical thin layer chromatography was carried out on silica pre-coated glass plates from Merck KGaA (silica gel 60 $F_{254}$, 0.25 mm thickness) and visualized with UV light at 254 nm and/or with phosphomolybdic acid or idodine. Automated flash chromatography was performed on Teledyne ISCO CombiFlash $R_f$ 200 system with RediSep $R_f$ prepacked silica cartridges (60 Å, 40-63 m particle size). Concentration refers to rotary evaporation under reduced pressure.

$^1H$ and $^{13}C$ NMR spectra were recorded on Varian INOVA or VNMR spectrometer operating at 400 or 500 MHz at ambient temperature with $CDCl_3$ or methanol-$d_4$ as solvents. Data for $^1H$ NMR were recorded as follows: δ chemical shift (ppm), multiplicity (s, singlet; d, doublet; dd=doublet of doublet; t, triplet; q, quartet; m, multiplet; br, broad), coupling constant (Hz), integration. Chemical shifts are reported in parts per million relative to internal reference $CDCl_3$ ($^1H$ NMR: δ 7.26; $^{13}C$ NMR: δ 77.16), methanol-$d_4$ ($^1H$ NMR, δ 4.87, 3.31; $^{13}C$ NMR, δ 49.00), and TMS ($^1H$ NMR: δ 0.00).

Liquid chromatography/mass spectrometry (LC-MS) data was obtained to verify molecular mass and analyze purity of products. Typical specifications of the LC-MS instrument are the following: Agilent 1200 HPLC coupled to a 6120 quadrupole mass spectrometer (ESI-API), UV detection at 254 and 210 nm, Agilent Zorbax XDB-18 C18 column (50 mm×4.6 mm, 3.5 μm), gradient mobile phase consisting of MeOH/water with 0.1% formic acid, and a flow rate of 1.00 mL/min. The chemical purity of all final compounds was determined by LC-MS and confirmed to be ≥95%.

High resolution mass-spectra (HRMS) were acquired on a VG 70-S Nier Johnson or JEOL mass spectrometer.

General procedures for Boc deprotection, Buchwald-Hartwig coupling, and reductive amination are described below. The experimental conditions for these general procedures may be optimized or adjusted for each compound.

Procedure A—General Procedure for Boc Deprotection:

To a 20-mL scintillation vial equipped with a Teflon-coated magnetic stir bar was charged with Boc-protected substrate (1 equiv) and DCM (0.13 M). Trifluoroacetic acid (36 equiv) was added dropwise, and the resulting mixture was stirred at room temperature overnight. Upon the completion of the reaction as judged by LC-MS analysis, the mixture was diluted with DCM, cooled in an ice-bath, and quenched by addition of 3M NaOH until pH>12. The biphasic mixture was transferred to a separatory funnel. The aqueous layer was separated and extracted with DCM (three times). The combined organic extract was dried over anhydrous sodium sulfate and concentrated under reduced pressure to a crude material which was purified by the CombiFlash system using a gradient of solvent A (DCM) to solvent B (8:2:0.6 DCM/MeOH/$NH_3$ (7 N in MeOH)) as eluent on a silica gel column to afford the final product.

Procedure B—General Procedure for Buchwald-Hartwig Coupling:

An oven-dried microwave vial equipped with a magnetic stir bar was charged with bromo-substituted starting material (1 equiv), $Pd_2(dba)_3$ (0.05 equiv, 5 mol %), rac-BINAP (0.15 equiv, 15 mol %), cesium carbonate (1.4 equiv), and amine (if solid) (1.2 equiv). The vial was sealed with a Teflon-lined septum and purged with argon for five minutes. Degassed toluene (0.2 M) and amine (if liquid) (1.2 equiv) were added successively via a syringe, and the vessel was degassed with argon for another five minutes. The resulting mixture was heated at 120° C. for 24 hours. Upon the completion of the reaction as judged by TLC and/or LC-MS, the mixture was allowed to cool to room temperature, filtered through a celite pad, and concentrated to a crude material which was purified by the CombiFlash system using a gradient of solvent A (DCM) to solvent B (MeOH) as eluent on a RediSep Rf GOLD silica column to afford the Boc-protected product.

Procedure C—General Procedure for Reductive Amination:

A 20 mL scintillation vial equipped with a magnetic stir bar was charged with amine (1.0 equiv), sodium triacetoxyborohydride (STAB, 1.8 equiv), and 1,2-dichloroethane (DCE, 0.1 M). After the solution was stirred for five min, aldehyde or ketone (1.2-3.0 equiv) was added in one portion. The resulting mixture was stirred at room temperature for 24-72 h. Additional equivalents of aldehyde/ketone might be added to drive the reaction to completion. Upon the completion of the reaction as judged by TLC and/or LC-MS, the mixture was quenched with 1 N NaOH. The biphasic mixture was transferred to a separatory funnel. The aqueous layer was separated and extracted with DCM three times. The combined organic extract was dried over anhydrous sodium sulfate and concentrated under reduced pressure to a crude material, which was purified by a CombiFlash system using a gradient of solvent A (DCM) to solvent B (MeOH) as eluent on a RediSep Rf GOLD silica column to afford the Boc-protected product.

Example 1. Exemplary Reaction Schemes

Exemplary synthetic routes for EMU-250, EMU-271, EMU-272, EMU-277, EMU-278, EMU-273, EMU-279, and EMU-282 are shown in the scheme below.

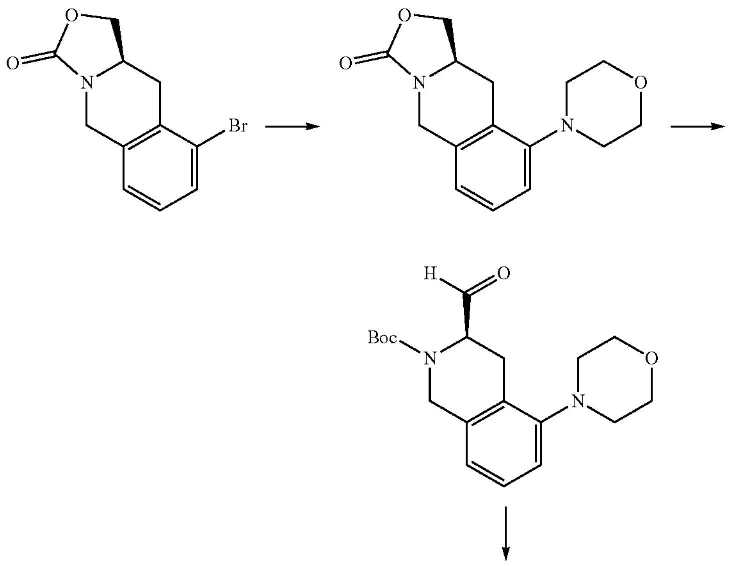

-continued
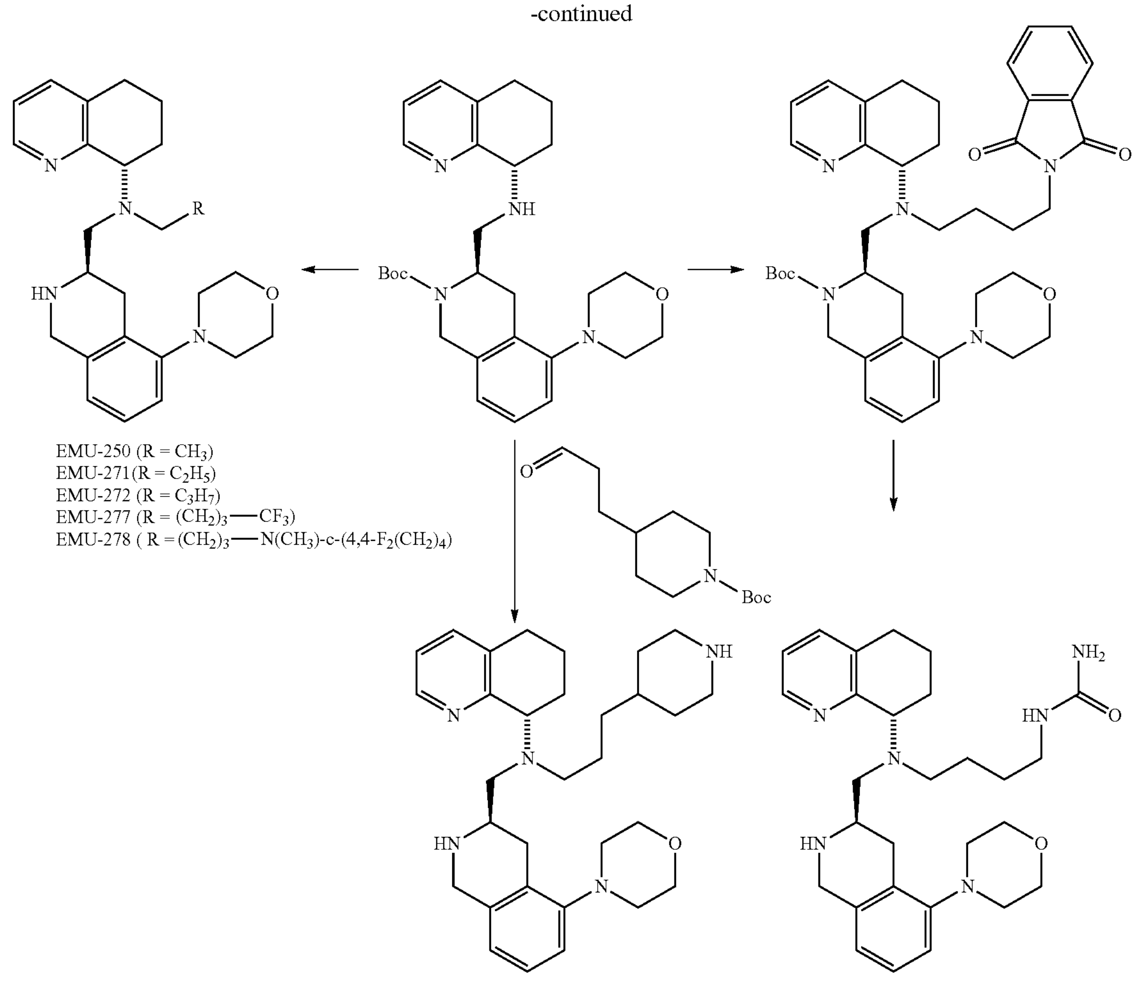
EMU-250 (R = $CH_3$)
EMU-271(R = $C_2H_5$)
EMU-272 (R = $C_3H_7$)
EMU-277 (R = $(CH_2)_3$—$CF_3$)
EMU-278 ( R = $(CH_2)_3$—$N(CH_3)$-c-(4,4-$F_2(CH_2)_4$)
EMU-279
EMU-282
Exemplary synthetic routes for EMU-184, EMU-274, and EMU-275 are shown in the scheme below.
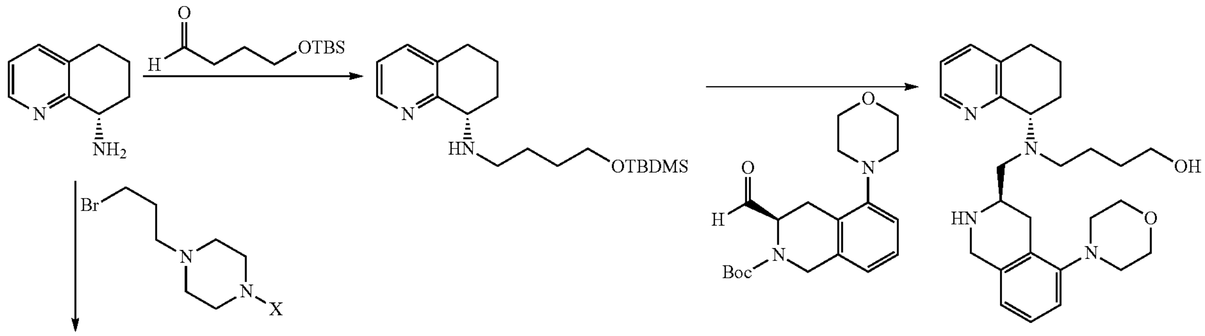
EMU-274

-continued
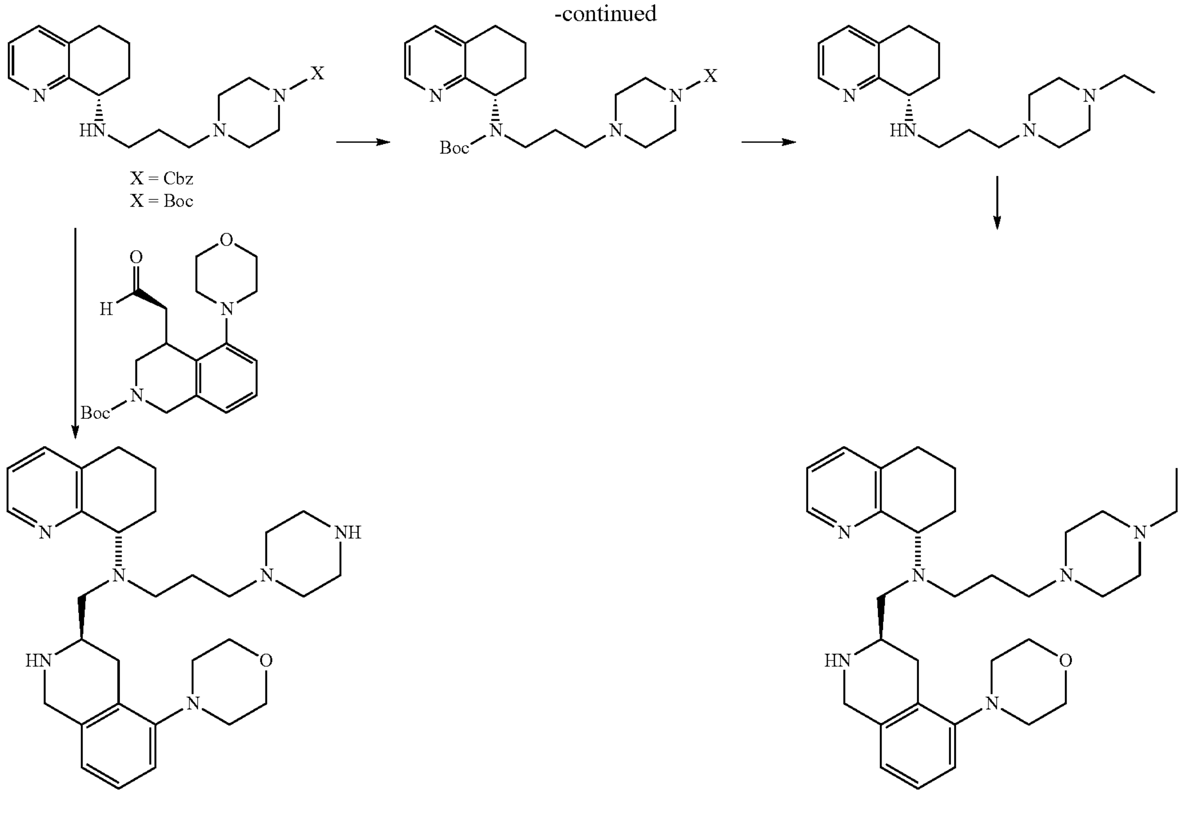
EMU-184 EMU-275
Exemplary synthetic routes for EMU-172, EMU-317, EMU-318, EMU-339, EMU-338, EMU-247, EMU-295, EMU-308, EMU-322, EMU-266, EMU-325, and EMU-324 are shown in the scheme below.
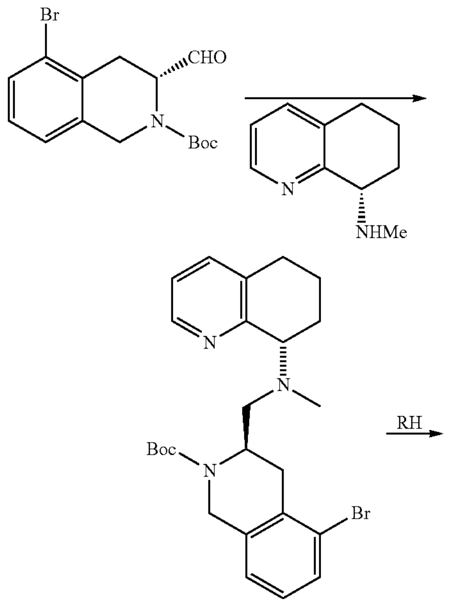
-continued
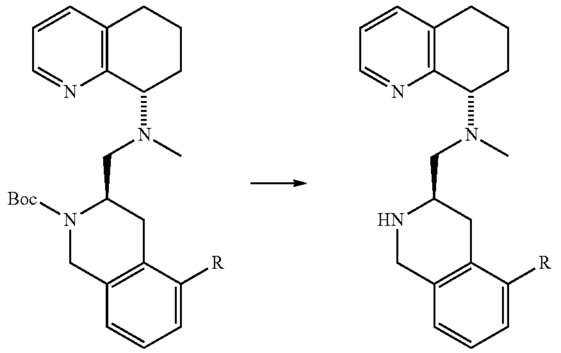
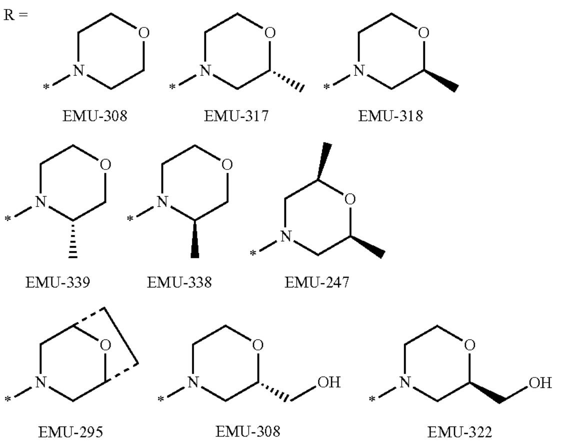

-continued
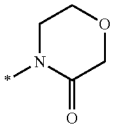
EMU-266
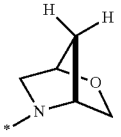
EMU-325
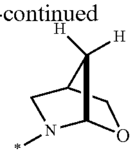
EMU-324
Exemplary synthetic routes for EMU-260, EMU-340, EMU-319, EMU-341, EMU-321, and EMU-342 are shown in the scheme below.
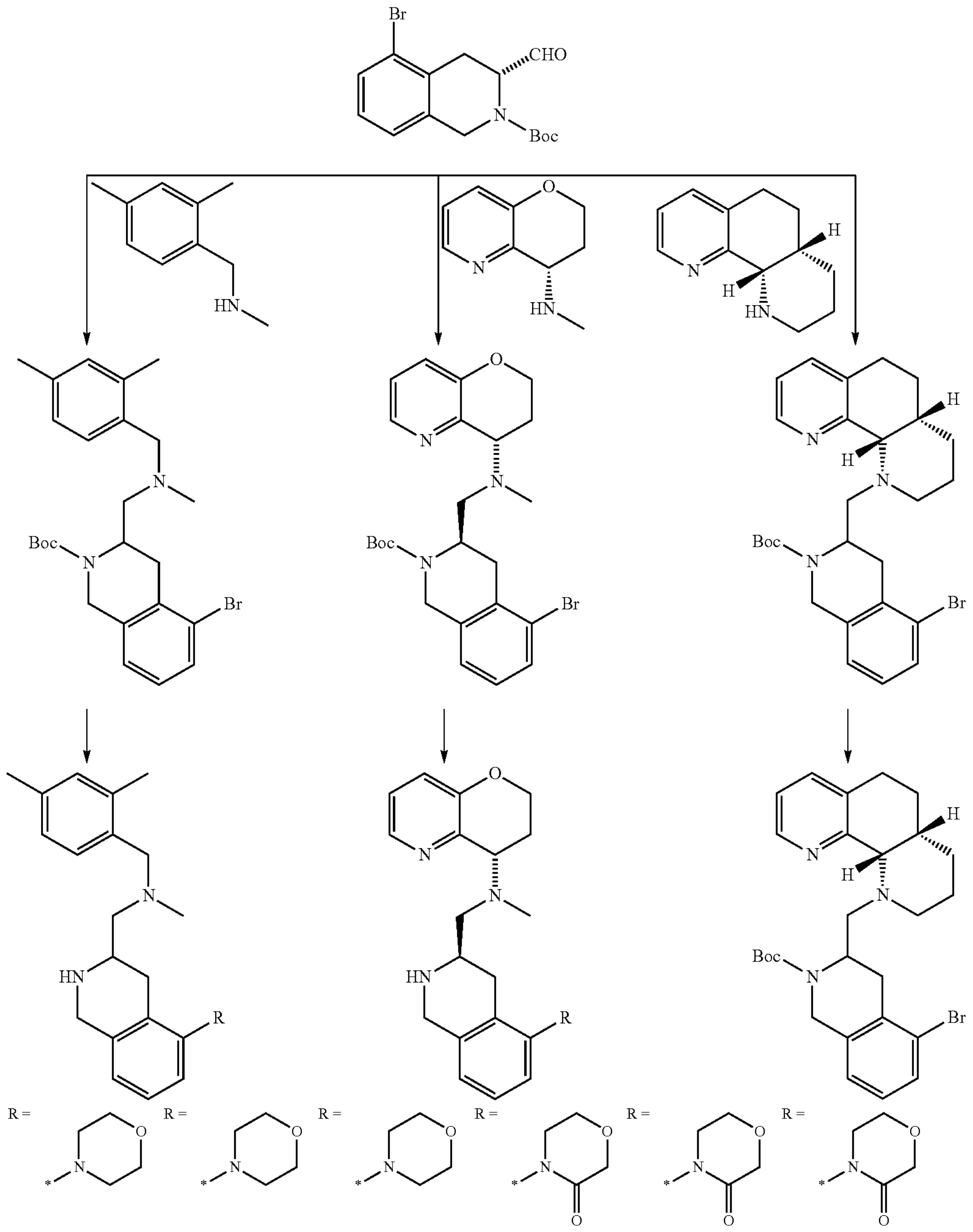
EMU-260 EMU-319 EMU-321 EMU-340 EMU-341 EMU-342

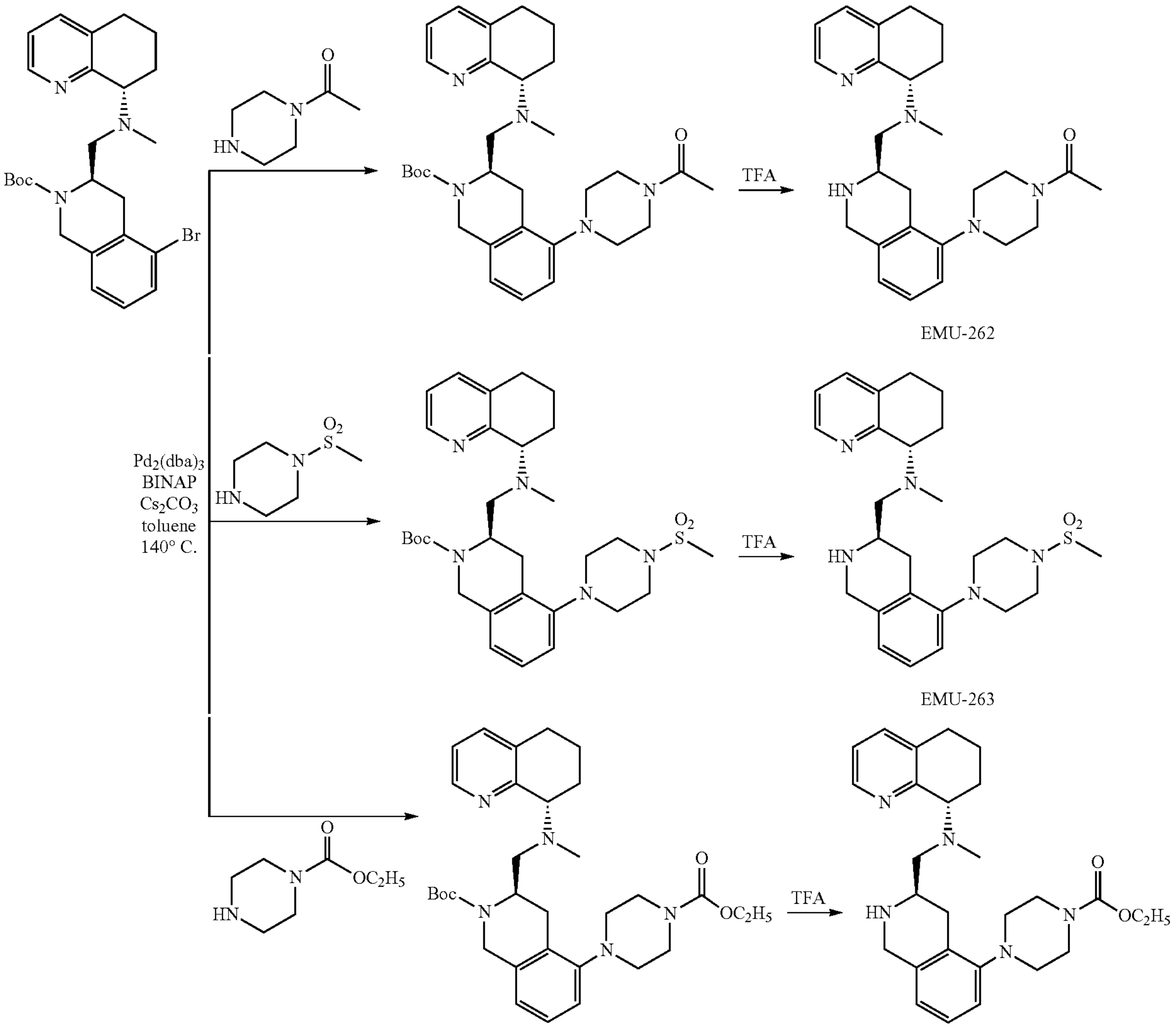
EMU-262
EMU-263
EMU-261
An exemplary synthetic route for EMU-326 is shown in the scheme below.
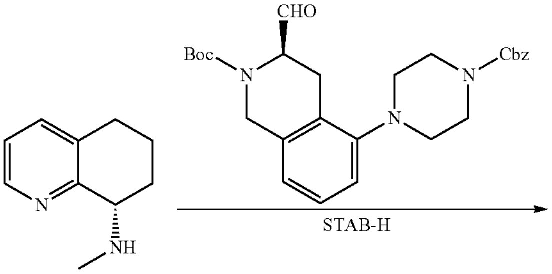

-continued
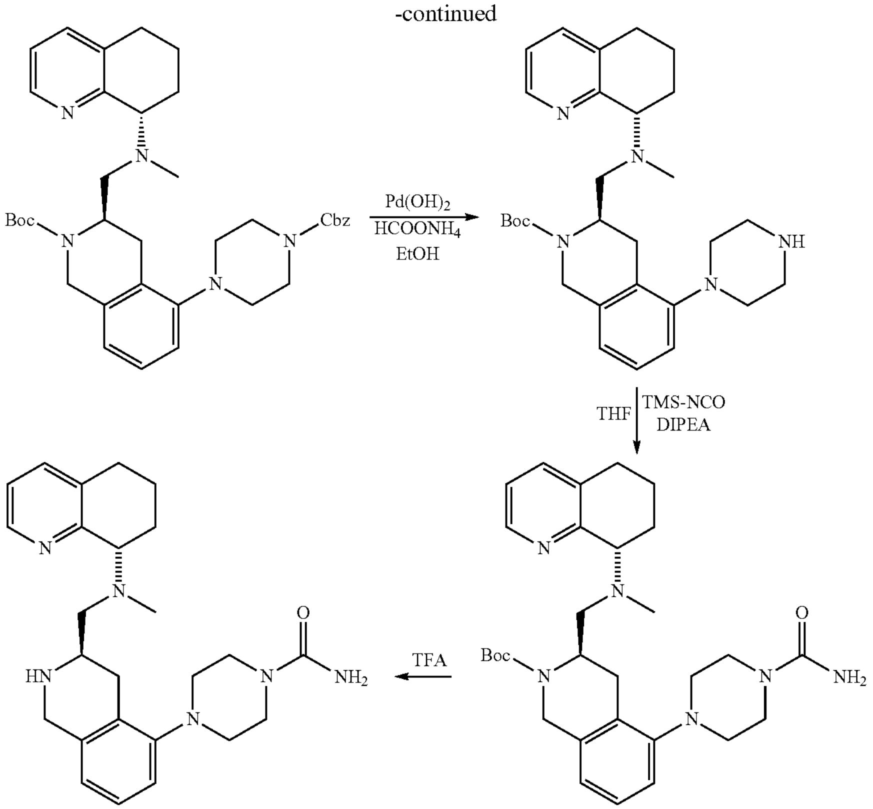
EMU-326
An exemplary synthetic route for EMU-327 is shown in the scheme below.
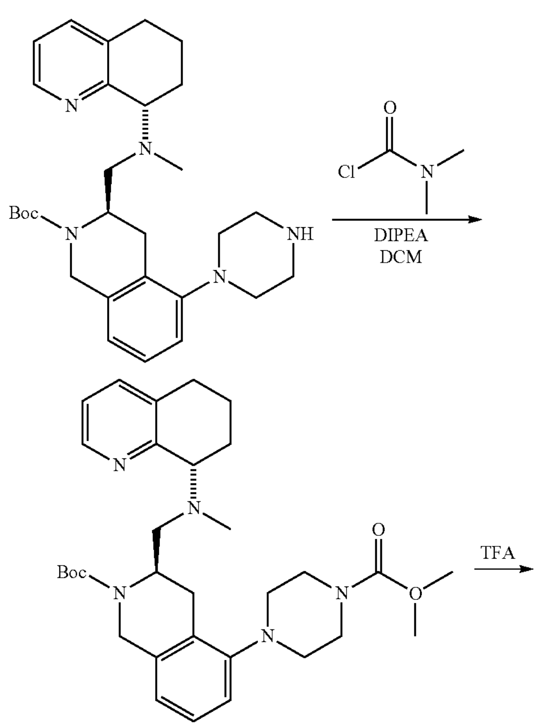
-continued
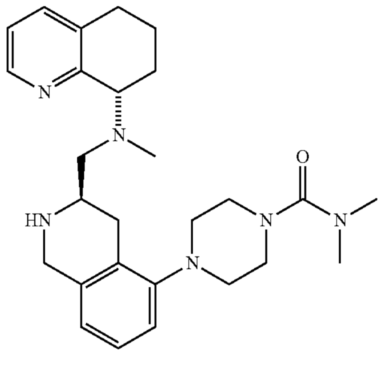
EMU-327
An exemplary synthetic route for EMU-251 is shown in the scheme below.

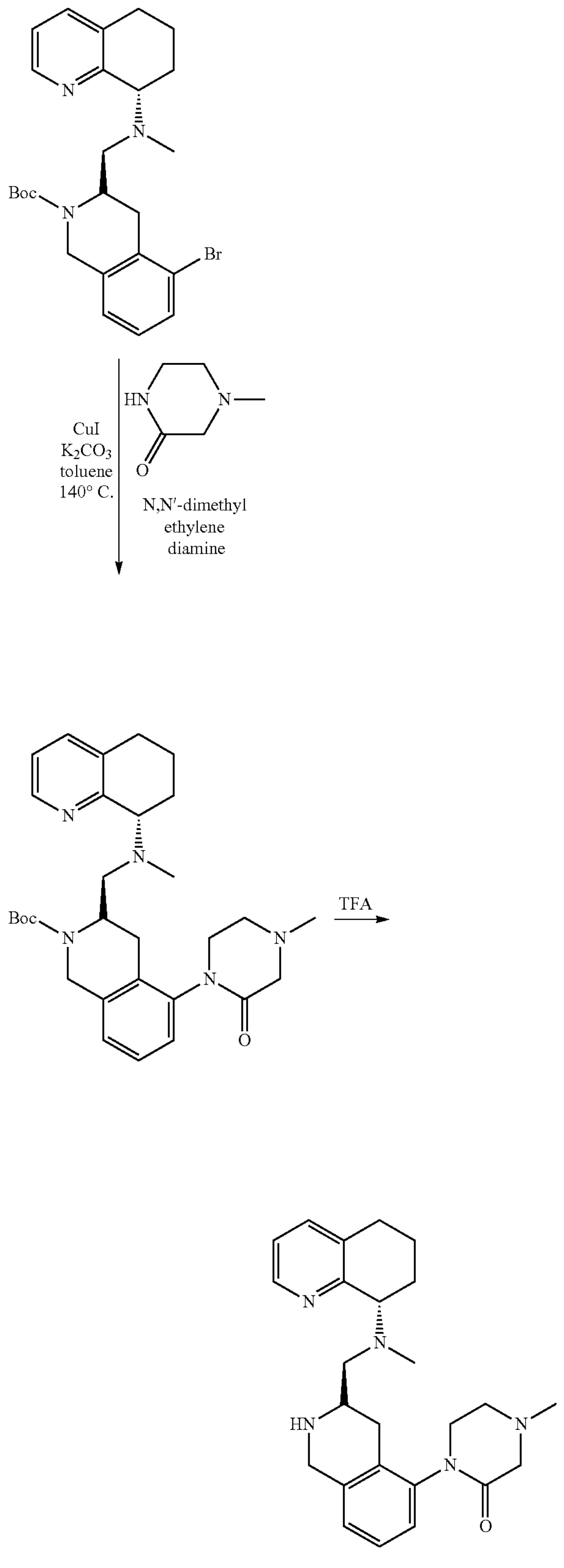

EMU-251

Example 2. Synthesis and Chemical Characterization of Exemplary Compounds

AA. Synthesis of (S)-5,6,7,8-tetrahydroquinolin-8-amine

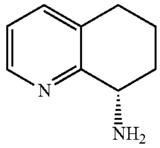 [SMILES: N[C@H]1CCCc2cccnc21]

(S)-5,6,7,8-Tetrahydroquinolin-8-amine was prepared according to Catalano, et al., *Bioorg Med Chem Lett,* 2010, 20(7), 2186-90.

AB. Synthesis of tert-butyl (tert-butoxycarbonyl)(4-oxobutyl)carbamate

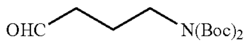

tert-Butyl (tert-butoxycarbonyl)(4-oxobutyl)carbamate was synthesized according to Iradier, et al., *Organic Letters,* 2001, 3(19), 2957-2960.

AC. Synthesis of 4-(1,3-dioxoisoindolin-2-yl)butanal

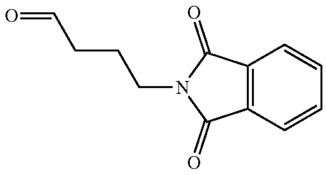 [SMILES: O=CCCCN1C(=O)c2ccccc2C1=O]

4-(1,3-Dioxoisoindolin-2-yl)butanal was prepared according to Truax, et al., *ACS Med. Chem. Lett.,* 2013, 4(11), 1025-1030.

AD. Synthesis of 2-(tert-butyl) 3-methyl (R)-5-morpholino-3,4-dihydroisoquinoline-2,3(1H)-dicarboxylate

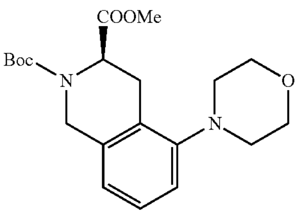 [SMILES: COC(=O)[C@H]1Cc2c(cccc2N2CCOCC2)CN1C(=O)OC(C)(C)C]

Procedure B was used starting with 2-(tert-butyl) 3-methyl (R)-5-bromo-3,4-dihydroisoquinoline-2,3(1H)-dicarboxylate. The residue was then subjected to column chromatography using a hexanes/ethyl acetate gradient to give a white foam (64% yield).

AE. Synthesis of tert-butyl (R)-3-formyl-5-morpholino-3,4-dihydroisoquinoline-2(1H)-carboxylate

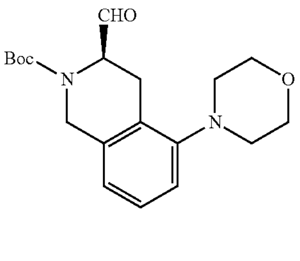 [SMILES: CC(C)(C)OC(=O)N1Cc2cccc(N3CCOCC3)c2C[C@@H]1C=O]

A solution of 0.444 g of 2-(tert-butyl) 3-methyl (R)-5-morpholino-3,4-dihydroisoquinoline-2,3(1H)-dicarboxylate in 10 mL of anhydrous toluene was cooled to −78° C. and then 3 mL of a 1 M diisobutyl aluminum hydride/toluene solution was added slowly over a 30-minute period. The reaction was stirred for an additional 3 hours at −78° C. Then an additional 3 mL of a DIBAL-H solution was added, and the reaction was stirred for an additional 30 minutes. Afterward, the reaction was quenched by the addition of 12 mL of ethyl acetate, 6 mL of acetone, and 6 mL of methanol. The reaction mixture was then warmed to room temperature and 50 mL of a $NH_4Cl$ solution was added followed by stirring overnight. The reaction was then extracted with additional ethyl acetate and the organic layers were combined and dried over anhydrous $Na_2SO_4$. Filtration and solvent removal gave a yellow viscous residue which was subjected to column chromatography (ISCO, 12 g column, hexanes:ethyl acetate gradient) to provide a clear viscous oil (77% yield).

AF. Synthesis of tert-butyl (R)-3-((methyl((S)-5,6,7,8-tetrahydroquinolin-8-yl)amino)methyl)-5-morpholino-3,4-dihydroisoquinoline-2(1H)-carboxylate

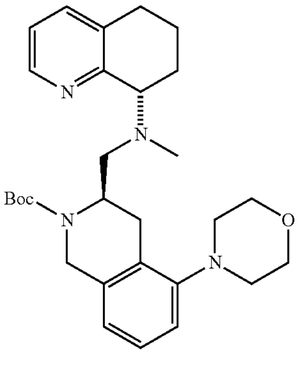

Procedure B was used starting with tert-butyl (R)-5-bromo-3-((methyl((S)-5,6,7,8-tetrahydroquinolin-8-yl)amino)methyl)-3,4-dihydroisoquinoline-2(1H)-carboxylate and morpholine to afford an off-white foam (73% yield).

AG. Synthesis of (S)—N-methyl-N—(((R)-5-morpholino-1,2,3,4-tetrahydroisoquinolin-3-yl)methyl)-5,6,7,8-tetrahydroquinolin-8-amine (EMU-172)

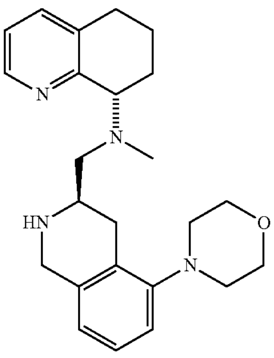

Procedure A was used to afford a white foam (63% yield). $^1H$ NMR (400 MHz, $CDCl_3$): δ 1.71 (m, 1H), 1.98 (m, 3H), 2.22 (m, 1H), 2.47 (s, 3H), 2.59 (m, 1H), 2.69 (m, 4H), 2.83 (m, 4H), 2.98 (m, 2H), 3.79 (m, 4H), 3.97 (m, 2H), 4.09 (d, 1H, J=16 Hz), 6.77 (d, 1H, J=8 Hz), 6.86 (d, 1H, J=8 Hz), 7.05 (dd, 1H, J=5 Hz, J=8 Hz), 7.1 (t, 1H, J=8 Hz), 7.34 (d, 1H, J=7 Hz), 8.44 (dd, 1H, J=1 Hz, J=4 Hz). $^{13}C$ NMR (101 MHz, $CDCl_3$): δ 21.28, 29.21, 29.9, 40.89, 48.34, 51.66, 52.21, 59.81, 64.47, 67.45, 74.79, 116.78, 121.57, 121.98, 126.17, 129.83, 133.88, 136.05, 136.73, 146.78, 151.07, 158.01. LC-MS: 100% at 0.449 min for 393.2 m/z [M+H]. HRMS: calc. for $C_{24}H_{33}ON_4$ 393.26489; found 393.26445 [M+H].

AH. Synthesis of tert-butyl (R)-3-((ethyl((S)-5,6,7,8-tetrahydroquinolin-8-yl)amino)methyl)-5-morpholino-3,4-dihydroisoquinoline-2(1H)-carboxylate

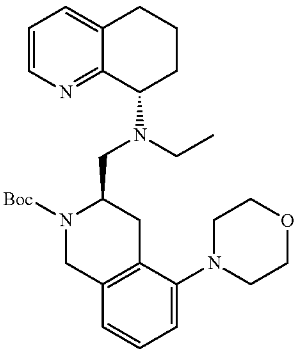 [SMILES: CCN(C[C@H]1Cc2c(cccc2N2CCOCC2)CN1C(=O)OC(C)(C)C)[C@H]1CCCc2cccnc21]

Procedure C was used starting with tert-butyl 5-morpholino-3-[[[(8S)-5,6,7,8-tetrahydroquinolin-8-yl]amino]methyl]-3,4-dihydro-1H-isoquinoline-2-carboxylate and acetaldehyde. The crude material was purified with column chromatography by starting with DCM and increasing the polarity with DCM:MeOH:$NH_3$ (in MeOH) (9:1:0.2) to yield the product as a yellowish foam (86% yield).

AI. Synthesis of (S)—N-ethyl-N—(((R)-5-morpholino-1,2,3,4-tetrahydroisoquinolin-3-yl)methyl)-5,6,7,8-tetrahydroquinolin-8-amine (EMU-250)

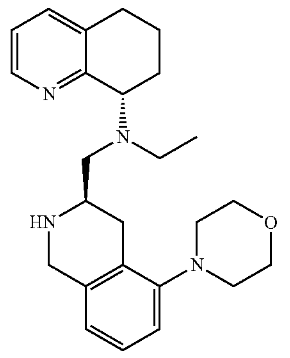 [SMILES: CCN(C[C@H]1Cc2c(cccc2N2CCOCC2)CN1)[C@H]1CCCc2cccnc21]

Procedure A was used to afford an off-white foam (48% yield). $^1H$ NMR (500 MHz, $CDCl_3$) δ 8.44 (d, J=4.9, 1.7 Hz, 1H), 7.35 (d, J=7.7 Hz, 1H), 7.13 (t, J=7.7 Hz, 1H), 7.07 (q, J=7.7, 4.7 Hz, 1H), 6.89 (d, J=7.8 Hz, 1H), 6.81 (d, J=7.6 Hz, 1H), 4.13-4.09 (m, 1H), 3.87-3.71 (m, 4H), 3.13 (d, J=13.4 Hz, 1H), 3.04-2.97 (m, 2H), 2.90 (d, J=16.9 Hz, 1H), 2.83-2.75 (m, 1H), 2.75-2.64 (m, 5H), 2.11-2.04 (m, 1H), 2.04-1.95 (m, 2H), 1.95-1.87 (m, 1H), 1.08 (t, J=7.0 Hz, 3H). $^{13}C$ NMR (101 MHz, $CDCl_3$) δ 158.76, 151.06, 146.57, 136.86, 134.01, 129.42, 126.41, 121.97, 121.57, 117.02, 67.42, 61.90, 56.74, 52.66, 52.17, 29.33, 28.41, 21.82, 15.12.

AJ. Synthesis of tert-butyl (R)-5-morpholino-3-((propyl((S)-5,6,7,8-tetrahydroquinolin-8-yl)amino)methyl)-3,4-dihydroisoquinoline-2(1H)-carboxylate

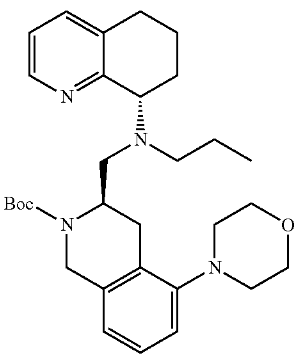 [SMILES: CCCN(C[C@H]1Cc2c(cccc2N2CCOCC2)CN1C(=O)OC(C)(C)C)[C@H]1CCCc2cccnc21]

Procedure C was used starting with tert-butyl (R)-5-morpholino-3-((((S)-5,6,7,8-tetrahydroquinolin-8-yl)amino)methyl)-3,4-dihydroisoquinoline-2(1H)-carboxylate and propionaldehyde. Crude material was purified with column chromatography by starting with DCM and increasing the polarity with DCM:MeOH:$NH_3$ (7 N in methanol) (9:1:0.2) to yield a yellowish foam (67% yield).

AK. Synthesis of (S)—N—(((R)-5-morpholino-1,2,3,4-tetrahydroisoquinolin-3-yl)methyl)-N-propyl-5,6,7,8-tetrahydroquinolin-8-amine (EMU-271)

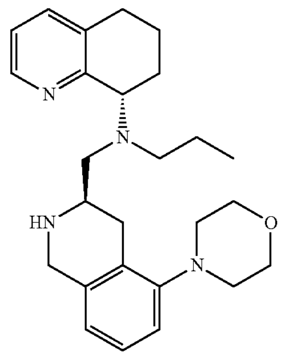 [SMILES: CCCN(C[C@H]1Cc2c(cccc2N2CCOCC2)CN1)[C@H]1CCCc2cccnc21]

Procedure A was used to afford the title compound as a white foam (68.34% yield). $^1H$ NMR (500 MHz, $CDCl_3$) δ 8.44 (d, J=4.7 Hz, 1H), 7.31 (d, J=7.7 Hz, 1H), 7.09 (t, J=7.7 Hz, 1H), 7.03 (dd, J=7.7, 4.7 Hz, 1H), 6.85 (d, J=7.8 Hz, 1H), 6.78 (d, J=7.6 Hz, 1H), 4.13-4.03 (m, 2H), 3.94 (d, J=15.2 Hz, 1H), 3.85-3.78 (m, 2H), 3.78-3.71 (m, 2H), 3.11-3.02 (m, 2H), 3.02-2.95 (m, 2H), 2.84 (dd, J=16.2, 3.1 Hz, 1H), 2.77 (ddd, J=16.3, 11.0, 4.9 Hz, 1H), 2.71-2.61 (m, 4H), 2.54 (dt, J=12.8, 7.7 Hz, 1H), 2.38 (t, J=13.1, 10.5 Hz, 1H), 2.19-2.03 (m, 2H), 2.02-1.94 (m, 1H), 1.96-1.85 (m, 1H), 1.76-1.64 (m, 1H), 1.52 (ddq, J=21.1, 13.9, 7.2 Hz, 2H), 0.88 (t, J=7.3 Hz, 3H). $^{13}C$ NMR (126 MHz, $CDCl_3$) δ 159.04, 151.08, 146.68, 136.85, 136.45, 133.91, 130.19, 126.07, 122.10, 121.32, 116.67, 77.37, 77.12, 76.86, 67.48, 61.47, 57.95, 56.59, 52.37, 52.18, 48.93, 30.21, 29.79, 29.46, 23.03, 22.04, 11.86. HRMS calculated for $C_{27}H_{38}N_4O$ 421.29485; found 421.29542 [M+H].

AL. Synthesis of tert-butyl (R)-3-((butyl((S)-5,6,7,8-tetrahydroquinolin-8-yl)amino)methyl)-5-morpholino-3,4-dihydroisoquinoline-2(1H)-carboxylate

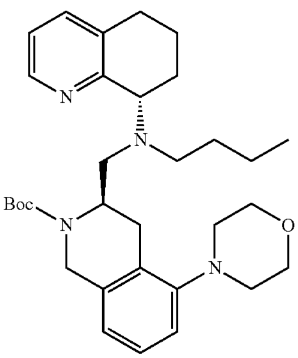 [SMILES: CCCCN(C[C@H]1Cc2c(cccc2N2CCOCC2)CN1C(=O)OC(C)(C)C)[C@H]1CCCc2cccnc21]

Procedure C was used starting with tert-butyl (R)-5-morpholino-3-((((S)-5,6,7,8-tetrahydroquinolin-8-yl)amino)methyl)-3,4-dihydroisoquinoline-2(1H)-carboxylate and butyraldehyde. Crude material was purified with column chromatography by starting with DCM and increasing the polarity with DCM:MeOH:$NH_3$ (7 N in methanol) (9:1:0.2) to produce a yellowish foam (50.34% yield).

AM. Synthesis of (S)—N-butyl-N—(((R)-5-morpholino-1,2,3,4-tetrahydroisoquinolin-3-yl)methyl)-5,6,7,8-tetrahydroquinolin-8-amine (EMU-272)

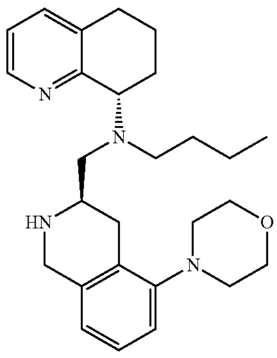 [SMILES: CCCCN(C[C@H]1Cc2c(cccc2N2CCOCC2)CN1)[C@H]1CCCc2cccnc21]

Procedure A was used to afford the title compound as an off-white foam (52% yield). $^1$H NMR (500 MHz, $CDCl_3$) δ 8.38 (d, J=4.7, 1.7 Hz, 1H), 7.42 (d, 1H), 7.22 (t, J=7.8 Hz, 1H), 7.12 (ddd, J=7.7, 4.8, 0.8 Hz, 1H), 6.98 (dd, J=8.1, 1.1 Hz, 1H), 6.87 (dd, J=7.7, 1.1 Hz, 1H), 4.58 (d, J=15.7 Hz, 1H), 4.25 (d, J=15.7 Hz, 1H), 4.14 (dd, J=10.6, 6.2 Hz, 1H), 3.90-3.72 (m, 4H), 3.29 (d, J=6.2 Hz, 3H), 3.08 (dd, J=16.9, 3.3 Hz, 1H), 3.05-2.97 (m, 2H), 2.92 (dd, J=16.9, 9.5 Hz, 1H), 2.84-2.71 (m, 4H), 2.64-2.54 (m, 1H), 2.49-2.45 (m, 1H), 2.16-2.08 (m, 1H), 2.02-1.95 (m, 1H), 1.87 (tdd, J=13.0, 10.5, 2.8 Hz, 1H), 1.80-1.69 (m, 1H), 1.40-1.29 (m, 1H), 1.31-1.22 (m, 1H), 1.24 (s, 1H), 1.22-1.10 (m, 2H), 0.76 (t, J=7.3 Hz, 3H). $^{13}$C NMR (126 MHz, $CDCl_3$) δ 158.26, 151.20, 146.14, 137.96, 134.41, 129.69, 127.59, 127.29, 122.27, 121.69, 118.30, 77.29, 77.04, 76.78, 67.32, 64.18, 54.17, 52.23, 43.62, 31.49, 29.11, 25.27, 21.76, 20.23, 13.86. HRMS calculated for $C_{27}H_{38}N_4O$ 435.31184; found 435.31121 [M+H].

AN. Synthesis of (S)—N-(4-((tert-butyldimethylsilyl)oxy)butyl)-5,6,7,8-tetrahydroquinolin-8-amine

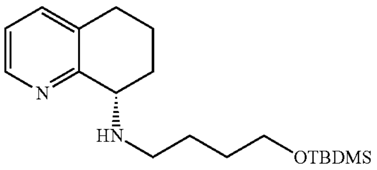 [SMILES: CC(C)(C)[Si](C)(C)OCCCCN[C@H]1CCCc2cccnc21]

(S)-5,6,7,8-Tetrahydroquinolin-8-amine (0.70 g, 4.7230 mmol), 4-((tert-butyldimethylsilyl)oxy)butanal (0.9559 g, 4.7233 mmol), and titanium isopropoxide (2.6849 g, 9.4467 mmol) were dissolved in 20 mL anhydrous THE and stirred for four hours at room temperature; then STAB (0.3574 g, 9.4467 mmol) was added to the reaction mixture, followed by stirring at room temperature overnight. The reaction was quenched with dropwise water until the bubbling finished. Afterward, more water and ethyl acetate were added, followed by stirring for another 1 hour. Aqueous phase was extracted with ethyl acetate twice. Combined organic layer was dried over anhydrous $MgSO_4$ and filtered, followed by solvent removal. The product was purified with column chromatography by starting with DCM and increasing the polarity with DCM:MeOH:$NH_3$ (7 N in methanol) (9:1:0.2) to afford a yellowish oil (34.8% yield).

AO. Synthesis of tert-butyl (R)-3-(((4-((tert-butyldimethylsilyl)oxy)butyl)((S)-5,6,7,8-tetrahydroquinolin-8-yl)amino)methyl)-5-morpholino-3,4-dihydroisoquinoline-2(1H)-carboxylate

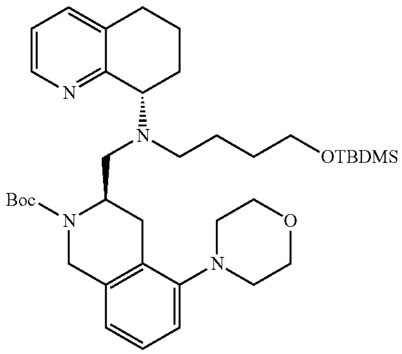 [SMILES: CC(C)(C)OC(=O)N1Cc2cccc(N3CCOCC3)c2C[C@@H]1CN(CCCCO[Si](C)(C)C(C)(C)C)[C@H]1CCCc2cccnc21]

(S)—N-(4-((tert-Butyldimethylsilyl)oxy)butyl)-5,6,7,8-tetrahydroquinolin-8-amine (0.51 g, 1.47 mmol), 2-(tert-butyl) 3-methyl (R)-5-morpholino-3,4-dihydroisoquinoline-2,3(1H)-dicarboxylate (0.49 g, 1.47 mmol), and titanium isopropoxyde (0.84 g, 2.95 mmol) were dissolved in 8 mL DCE. After stirring overnight, STAB (0.64 g, 2.95 mmol) was added and stirred for 6 hours at room temperature. The reaction was quenched with a saturated sodium bicarbonate solution and the aqueous phase was extracted with DCM. Combined organic layer was dried over anhydrous $MgSO_4$ and filtered, followed by solvent removal. The product was purified with column chromatography by starting with DCM and increasing the polarity with DCM:MeOH:$NH_3$ (7 N in methanol) (9:1:0.2) to afford the title compound (51.1% yield).

AP. Synthesis of 4-((((R)-5-morpholino-1,2,3,4-tetrahydroisoquinolin-3-yl)methyl)((S)-5,6,7,8-tetrahydroquinolin-8-yl)amino)butan-1-ol (EMU-274)

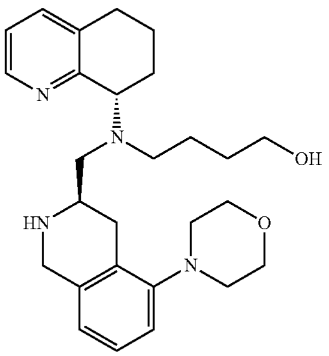 [SMILES: OCCCCN(C[C@H]1Cc2c(cccc2N2CCOCC2)CN1)[C@H]1CCCc2cccnc21]

Procedure A was used to afford the title compound as an off-white foam (25% yield). $^1$H NMR (500 MHz, $CDCl_3$) δ 8.53-8.24 (m, 1H), 7.45 (s, 1H), 7.17 (q, J=7.7 Hz, 2H), 6.94 (d, J=7.9 Hz, 1H), 6.81 (d, J=7.7 Hz, 1H), 4.48 (d, J=15.9 Hz, 1H), 4.36-3.99 (m, 2H), 3.78 (tddd, J=11.0, 8.9, 5.6, 2.4 Hz, 4H), 3.52 (dq, J=25.1, 6.1 Hz, 2H), 3.26 (d, J=11.7 Hz, 3H), 3.14-2.90 (m, 5H), 2.89-2.50 (m, 6H), 2.25-2.08 (m, 1H), 1.99 (d, J=13.0 Hz, 1H), 1.92-1.81 (m, 1H), 1.80-1.66 (m, 1H), 1.49 (d, J=39.0 Hz, 4H). $^{13}C$ NMR (126 MHz, $CDCl_3$) δ 157.82, 151.05, 145.95, 138.27, 134.61, 129.41, 127.58, 127.09, 122.54, 121.63, 118.21, 67.27, 63.80, 62.10, 55.21, 53.79, 53.45, 52.25, 51.56, 43.45, 30.27, 28.97, 25.81, 25.25, 21.67. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=451.2 [M+H], t=0.460 min, purity ≥95%. HRMS calculated for $C_{27}H_{39}N_4O_2$ 451.30675; found 451.30650 [M+H].

AQ. Synthesis of tert-butyl (R)-5-morpholino-3-((((S)-5,6,7,8-tetrahydroquinolin-8-yl)(4,4,4-trifluorobutyl)amino)methyl)-3,4-dihydroisoquinoline-2(1H)-carboxylate

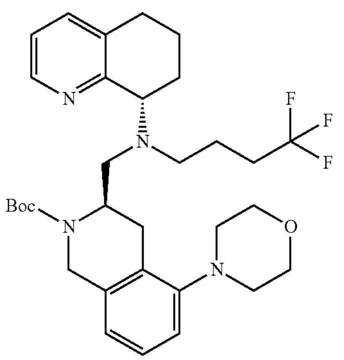 [SMILES: CC(C)(C)OC(=O)N1Cc2cccc(N3CCOCC3)c2C[C@@H]1CN(CCCC(F)(F)F)[C@H]1CCCc2cccnc21]

Procedure C was used starting with tert-butyl (R)-5-morpholino-3-((((S)-5,6,7,8-tetrahydroquinolin-8-yl)amino)methyl)-3,4-dihydroisoquinoline-2(1H)-carboxylate and 4,4,4-trifluorobutanal. The crude product was purified via column chromatography by starting with DCM and increasing the polarity with DCM:MeOH:$NH_3$ (7 N in methanol) (9:1:0.2) to afford the title compound as a colorless oil (89.1% yield).

AR. Synthesis of (S)—N—(((R)-5-morpholino-1,2,3,4-tetrahydroisoquinolin-3-yl)methyl)-N-(4,4,4-trifluorobutyl)-5,6,7,8-tetrahydroquinolin-8-amine (EMU-277)

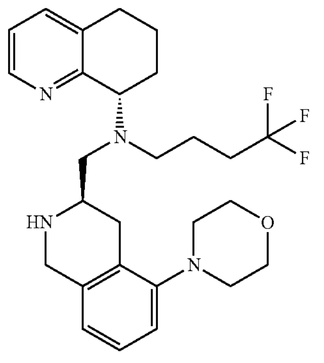 [SMILES: FC(F)(F)CCCN(C[C@H]1Cc2c(cccc2N2CCOCC2)CN1)[C@H]1CCCc2cccnc21]

Procedure A was used to afford the title compound as a yellowish foam (77% yield). $^1H$ NMR (600 MHz, $CDCl_3$) δ 8.46 (dd, J=4.8, 1.7 Hz, 1H), 7.36 (dd, J=7.7, 1.7 Hz, 1H), 7.13 (t, J=7.7 Hz, 1H), 7.08 (dd, J=7.7, 4.7 Hz, 1H), 6.90 (d, J=7.8 Hz, 1H), 6.82 (d, J=7.6 Hz, 1H), 4.16 (d, J=15.3 Hz, 1H), 4.08 (dd, J=10.4, 6.2 Hz, 1H), 3.97 (d, J=15.2 Hz, 1H), 3.89-3.82 (m, 2H), 3.82-3.75 (m, 2H), 3.18-3.10 (m, 1H), 3.08 (dd, J=13.4, 3.2 Hz, 1H), 3.04-2.96 (m, 2H), 2.92 (dd, J=16.2, 3.2 Hz, 1H), 2.86-2.64 (m, 6H), 2.57-2.47 (m, 1H), 2.34-2.07 (m, 4H), 2.06-1.97 (m, 1H), 1.97-1.86 (m, 1H), 1.84-1.66 (m, 3H). $^{13}C$ NMR (151 MHz, $CDCl_3$) δ 158.43, 151.12, 146.77, 136.62, 136.36, 133.96, 129.84, 127.52 (q, J: 276.0 Hz), 126.26, 122.09, 121.58, 116.89, 67.47, 61.70, 58.04, 53.06, 52.63, 52.23, 48.60, 31.46 (q, J=28.5 Hz), 29.97, 29.38, 28.96, 22.24 (d, J=2.2 Hz), 22.07. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=489.2 [M+H], t=0.496 min, purity ≥95%. HRMS calculated for $C_{27}H_{36}ON_4F_3$ 489.28357; found 489.28310 [M+H].

AS. Synthesis of tert-butyl (R)-3-(((2-((tert-butoxycarbonyl)amino)ethyl)((S)-5,6,7,8-tetrahydroquinolin-8-yl)amino)methyl)-5-morpholino-3,4-dihydroisoquinoline-2(1H)-carboxylate

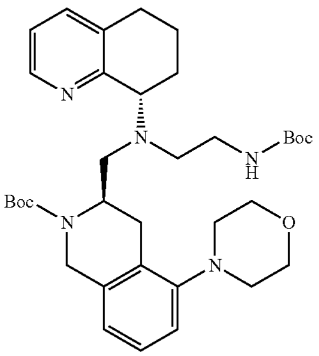 [SMILES: CC(C)(C)OC(=O)NCCN(C[C@H]1Cc2c(cccc2N2CCOCC2)CN1C(=O)OC(C)(C)C)[C@H]1CCCc2cccnc21]

Procedure C was used starting with tert-butyl (R)-5-morpholino-3-((((S)-5,6,7,8-tetrahydroquinolin-8-yl)amino)methyl)-3,4-dihydroisoquinoline-2(1H)-carboxylate and tert-butyl N-(2-oxoethyl)carbamate. The crude was purified with column chromatography by starting with DCM and increasing the polarity with DCM:MeOH:$NH_3$ (7 N in methanol) (9:1:0.2) to afford the title compound as a yellow foam (84.7% yield).

AT. Synthesis of N1-(((R)-5-morpholino-1,2,3,4-tetrahydroisoquinolin-3-yl)methyl)-N1-((S)-5,6,7,8-tetrahydroquinolin-8-yl)ethane-1,2-diamine (EMU-278)

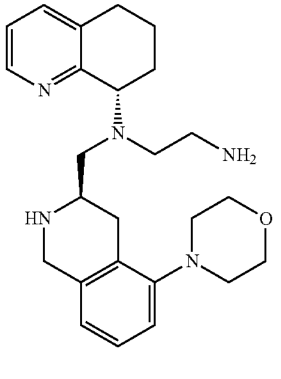 [SMILES: NCCN(C[C@H]1Cc2c(cccc2N2CCOCC2)CN1)[C@H]1CCCc2cccnc21]

Procedure A was used, and the product was crystallized over hexanes:DCM at a 5:1 ratio to afford the title compound as an amorphous solid (6.7% yield). $^1$H NMR (500 MHz, $CDCl_3$) δ 8.52-8.40 (m, 1H), 7.35 (d, J=7.8 Hz, 1H), 7.17-7.03 (m, 2H), 6.88 (d, J=7.9 Hz, 1H), 6.81-6.68 (m, 1H), 4.15 (d, J=16.1 Hz, 1H), 4.00 (dd, J=10.9, 5.8 Hz, 1H), 3.93-3.66 (m, 4H), 3.27 (s, 1H), 3.15-2.86 (m, 5H), 2.86-2.53 (m, 2H), 2.38 (s, 1H), 2.17 (d, J=35.5 Hz, 1H), 2.00 (s, 1H), 1.92-1.77 (m, 1H), 1.77-1.66 (m, 1H), 1.65-1.45 (m, 1H), 1.39-1.17 (m, 5H), 1.17-0.99 (m, 1H), 0.99-0.94 (m, 1H), 0.87-0.80 (m, 2H). $^{13}$C NMR (126 MHz, $CDCl_3$) δ 151.08, 146.77, 137.58, 136.10, 134.18, 128.67, 126.72, 122.23, 121.81, 117.29, 77.24, 67.36, 63.23, 57.15, 52.95, 52.23, 46.44, 38.63, 37.08, 28.98, 28.53, 25.30, 21.85. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=422.2 [M+H], t=0.414 min, purity ≥95%. HRMS calculated for $C_{25}H_{36}ON_5$ 422.29144; found 422.29135 [M+H].

AU. Synthesis of tert-butyl (R)-3-(((4-(1,3-dioxoisoindolin-2-yl)butyl)((S)-5,6,7,8-tetrahydroquinolin-8-yl)amino)methyl)-5-morpholino-3,4-dihydroisoquinoline-2(1H)-carboxylate

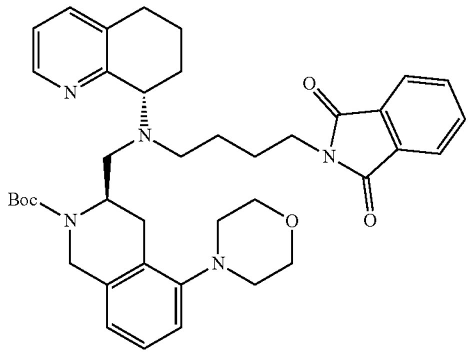

tert-Butyl tert-Butyl (R)-5-morpholino-3-((((S)-5,6,7,8-tetrahydroquinolin-8-yl)amino)methyl)-3,4-dihydroisoquinoline-2(1H)-carboxylate (0.6570 g, 1.3727 mmol), 4-(1,3-dioxoisoindolin-2-yl)butanal (0.4473 g, 2.059 mmol), and titanium (IV) isopropoxide (0.7803 g, 2.7453 mmol) was dissolved in 20 mL DCM and stirred at room temperature for two hours. STAB (0.5818 g, 1.3238 mmol) was added to the reaction mixture and stirred at room temperature overnight. The reaction was quenched with a saturated sodium bicarbonate solution and the aqueous phase was extracted with DCM twice. Combined organic layer was dried over anhydrous $MgSO_4$ and filtered, followed by solvent evaporation. The residue was purified via column chromatography by starting with DCM and increasing the polarity with DCM:MeOH:$NH_3$ (in methanol) (9:1:0.2) to afford the title compound as a colorless foam (96.4% yield).

AV. Synthesis of tert-butyl (R)-3-(((4-aminobutyl)((S)-5,6,7,8-tetrahydroquinolin-8-yl)amino)methyl)-5-morpholino-3,4-dihydroisoquinoline-2(1H)-carboxylate

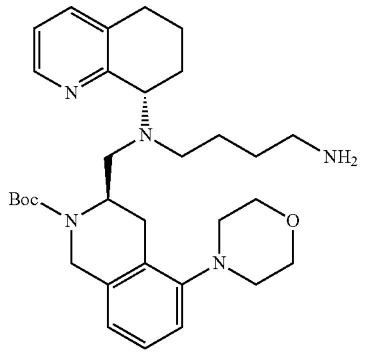

tert-Butyl tert-Butyl (R)-3-(((4-(1,3-dioxoisoindolin-2-yl)butyl)((S)-5,6,7,8-tetrahydroquinolin-8-yl)amino)methyl)-5-morpholino-3,4-dihydroisoquinoline-2(1H)-carboxylate was dissolved in 10 mL MeOH and 0.66 g (13.24 mmol) hydrazine hydrate was added at room temperature. The reaction mixture was stirred overnight. The solvent was evaporated. Then the residue was dissolved in water and extracted with DCM three times. Combined organic layer was dried over anhydrous $MgSO_4$ and filtered, followed by solvent evaporation. The resulting product (92.1% yield) was used for the next step without further purification.

AW. Synthesis of tert-butyl (R)-5-morpholino-3-((((S)-5,6,7,8-tetrahydroquinolin-8-yl)(4-ureidobutyl)amino)methyl)-3,4-dihydroisoquinoline-2(1H)-carboxylate

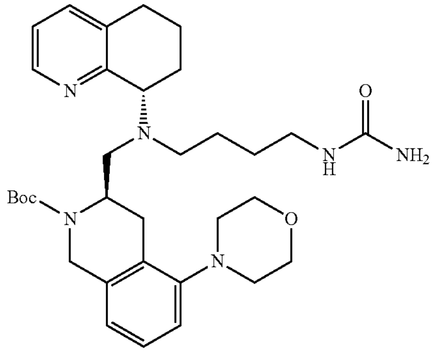

tert-Butyl tert-Butyl (R)-3-(((4-aminobutyl)((S)-5,6,7,8-tetrahydroquinolin-8-yl)amino)methyl)-5-morpholino-3,4-dihydroisoquinoline-2(1H)-carboxylate (0.68 g, 1.236 mmol), N,N-diisopropylethylamine (0.474 mL, 2.7212 mmol), and trimethylsilylisocyanate (0.2009 mL, 1.4843 mmol) were dissolved in 10 mL THE and stirred at room temperature overnight. The reaction was poured into water and the aqueous phase was extracted with DCM. Combined organic layer was dried over anhydrous $MgSO_4$ and filtered, followed by solvent evaporation. The crude was purified with column chromatography by starting with DCM and increasing the polarity with MeOH to 10% MeOH in DCM to afford the title compound as a colorless oil (72.3% yield).

AX. Synthesis of 1-(4-((((R)-5-morpholino-1,2,3,4-tetrahydroisoquinolin-3-yl)methyl)((S)-5,6,7,8-tetrahydroquinolin-8-yl)amino)butyl)urea (EMU-282)

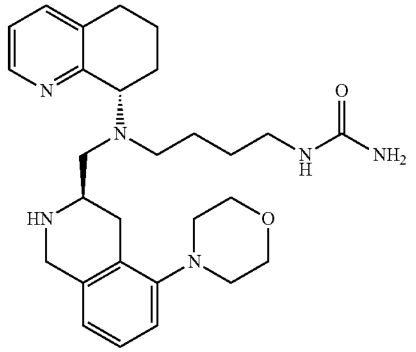 [SMILES: NC(=O)NCCCCN(C[C@H]1Cc2c(cccc2N2CCOCC2)CN1)[C@H]1CCCc2cccnc21]

Procedure A was used to afford the title compound as a colorless foam (77.4% yield). $^1H$ NMR (500 MHz, $CDCl_3$) δ 8.58-8.34 (m, 1H), 7.39-7.29 (m, 1H), 7.15-7.04 (m, 2H), 6.87 (d, J=7.8 Hz, 1H), 6.73 (dd, J=7.6, 1.1 Hz, 1H), 6.37 (s, 1H), 4.77 (s, 2H), 4.10-3.90 (m, 2H), 3.90-3.72 (m, 4H), 3.47 (d, J=15.4 Hz, 1H), 3.42-3.37 (m, 1H), 3.34-3.11 (m, 2H), 3.06 (dd, J=13.4, 3.0 Hz, 1H), 3.01-2.88 (m, 2H), 2.86-2.75 (m, 2H), 2.71-2.61 (m, 5H), 2.51 (dd, J=13.3, 10.5 Hz, 1H), 2.37 (s, 1H), 2.25-2.11 (m, 1H), 2.11-1.89 (m, 2H), 1.76-1.66 (m, 2H), 1.61 (s, 4H). $^{13}C$ NMR (126 MHz, $CDCl_3$) δ 159.39, 158.37, 151.04, 146.73, 137.04, 133.98, 129.41, 126.36, 122.06, 121.82, 117.05, 67.42, 61.57, 56.96, 56.89, 53.86, 52.24, 51.82, 47.92, 47.88, 40.33, 29.86, 29.53, 26.49, 26.43, 25.20, 22.03. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=493.2 (M+1), t=0.590 min, purity ≥95%. HRMS calculated for $C_{28}H_{41}O_2N_6$ 493.32855; found 498.32870 [M+H].

AY. Synthesis of 4-((4,4-difluorocyclohexyl)(methyl)amino)butanal

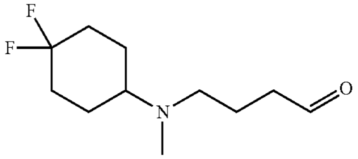

Step 1:

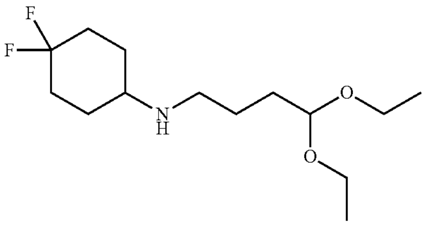 [SMILES: CCOC(CCCNC1CCC(F)(F)CC1)OCC]

A250 mL rb flask equipped with a magnetic stir bar and rubber septum was charged with 5.00 g of the amine (31.0 mmol, 1 equiv), 4.16 g of 4,4-difluorocyclohexan-1-one (31.0 mmol, 1 equiv), and 120 mL of DCE. Then 7.89 g of STAB (37.2 mmol, 1.2 equiv) was added. After stirring at room temperature for 2 h, the reaction mixture was quenched by the addition of a saturated $NaHCO_3$ solution, extracted with DCM (3×), and dried over $Na_2SO_4$. The organic layer was concentrated, and the crude product was used in the next step without purification.

Step 2:

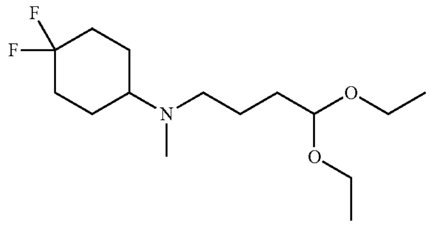 [SMILES: CCOC(CCCN(C)C1CCC(F)(F)CC1)OCC]

A 250 mL rb flask equipped with a magnetic stir bar and rubber septum was charged with 7.79 g of the amine (27.9 mmol, 1 equiv), 1.67 g of paraformaldehyde (55.8 mmol, 2 equiv), and 110 mL of DCE. Then 11.8 g of STAB (55.8 mmol, 2 equiv) was added. After stirring at room temperature for 12 h, no product was observed by LC-MS. Then 1.6 mL of acetic acid (27.9 mmol, 1 equiv) was added and the stirring was continued for 12 h. Some product was formed, but the reaction did not go to completion even when more paraformaldehyde and STAB were added. Then 2.50 mL of 37 w % formalin (33.5 mmol, 1.2 equiv) was added and the reaction was complete in 1 h. The reaction mixture was quenched by the addition of a saturated $NaHCO_3$ solution, extracted with DCM (3×), and dried over $Na_2SO_4$. The organic layer was concentrated, and the crude product was purified on a silica gel column (120 g) using 0 to 10% MeOH in EA as eluent, affording the product (with minor impurity) as a brown liquid as a brown liquid (88% combined yield).

Step 3:

A 100 mL rb flask equipped with a stir bar, reflux condenser, and septum was charged with 1.50 g of the acetal (5.11 mmol, 1 equiv), 1.96 mL of 6 M HCl (11.8 mmol, 2.3 equiv), and 13.0 mL of acetone. After stirring at 80° C. for 3 h, the reaction mixture was concentrated, quenched by the addition of a saturated $NaHCO_3$ solution, extracted with diethyl ether (3×), and dried over $Na_2SO_4$. The crude material was dissolved in hexanes and filtered, followed by solvent removal to afford the product as a yellow oil (40% yield).

AZ. Synthesis of tert-butyl (R)-3-(((4-((4,4-difluorocyclohexyl)(methyl)amino)butyl)((S)-5,6,7,8-tetrahydroquinolin-8-yl)amino)methyl)-5-morpholino-3,4-dihydroisoquinoline-2(1H)-carboxylate

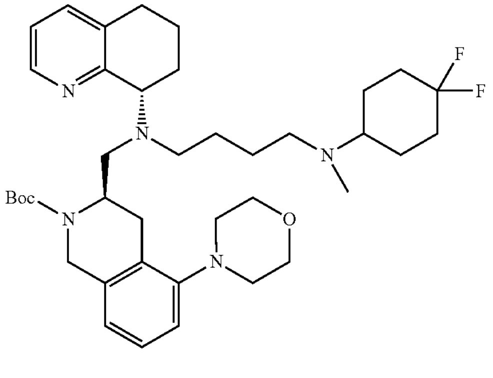 [SMILES: CN(CCCCN(C[C@H]1Cc2c(cccc2N2CCOCC2)CN1C(=O)OC(C)(C)C)[C@H]1CCCc2cccnc21)C1CCC(F)(F)CC1]

Procedure C was used starting with tert-butyl (R)-5-morpholino-3-((((S)-5,6,7,8-tetrahydroquinolin-8-yl)amino)methyl)-3,4-dihydroisoquinoline-2(1H)-carboxylate and 4-((4,4-difluorocyclohexyl)(methyl)amino)butanal. Crude material was purified with column chromatography by starting with DCM and increasing the polarity with DCM:MeOH:$NH_3$ (7 N in methanol) (9:1:0.2) to afford the title compound as a yellowish foam (26% yield).

BA. Synthesis of N1-(4,4-difluorocyclohexyl)-N1-methyl-N4-(((R)-5-morpholino-1,2,3,4-tetrahydroisoquinolin-3-yl)methyl)-N4-((S)-5,6,7,8-tetrahydroquinolin-8-yl)butane-1,4-diamine (EMU-273)

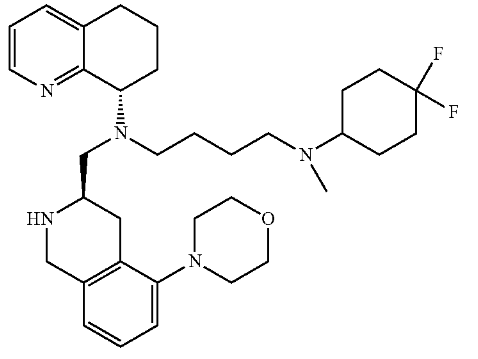 [SMILES: CN(CCCCN(C[C@H]1Cc2c(cccc2N2CCOCC2)CN1)[C@H]1CCCc2cccnc21)C1CCC(F)(F)CC1]

Procedure A was used to afford the title compound as an off-white foam (67% yield). $^1$H NMR (500 MHz, $CDCl_3$) δ 8.42 (d, J=4.8, 1.7 Hz, 1H), 7.34 (d, J=7.7, 1.8, 0.9 Hz, 1H), 7.11 (t, J=7.8 Hz, 1H), 7.05 (dd, J=7.6, 4.7, 0.6 Hz, 1H), 6.87 (d, J=7.9, 1.2 Hz, 1H), 6.79 (d, J=7.6, 1.1 Hz, 1H), 4.16 (d, J=15.3 Hz, 1H), 4.10 (dd, J=10.2, 6.3 Hz, 1H), 3.96 (d, J=15.3 Hz, 1H), 3.87-3.67 (m, 6H), 3.11 (dd, J=13.5, 2.9 Hz, 1H), 3.06-2.93 (m, 4H), 2.88 (dd, J=16.2, 3.2 Hz, 1H), 2.83-2.63 (m, 5H), 2.63-2.53 (m, 2H), 2.52-2.42 (m, 1H), 2.37 (t, J=6.6 Hz, 2H), 2.35-2.22 (m, 1H), 2.18-2.03 (m, 3H), 2.04-1.84 (m, 3H), 1.83-1.62 (m, 7H), 1.62-1.53 (m, 2H), 1.53-1.32 (m, 1H). $^{13}$C NMR (126 MHz, $CDCl_3$) δ 158.80, 151.08, 146.59, 136.77, 134.02, 129.60, 126.37, 123.17 (t, J: 96 Hz), 121.99, 121.53, 116.96, 77.33, 77.08, 76.83, 67.43, 61.96, 60.35, 57.51, 53.77, 52.72, 52.19, 37.84, 32.85 (d, J=10 Hz), 32.66 (d, J=10 Hz), 29.38, 28.97, 27.75, 25.56, 24.08 (d, J=3.5 Hz), 21.97. HRMS calculated for $C_{27}H_{38}N_4O$ 582.39646; found 582.39659 [M+H].

BB. Synthesis of tert-butyl (R)-3-(((3-(4-(tert-butoxycarbonyl)piperazin-1-yl)propyl)((S)-5,6,7,8-tetrahydroquinolin-8-yl)amino)methyl)-5-morpholino-3,4-dihydroisoquinoline-2(1H)-carboxylate

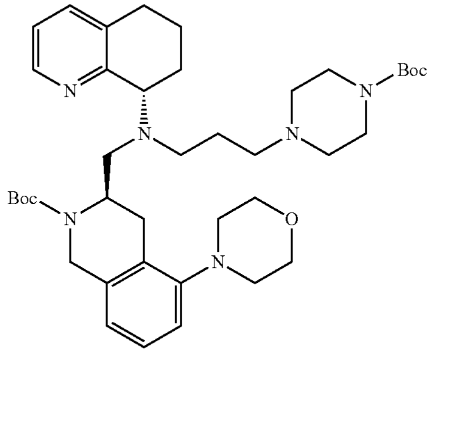 [SMILES: CC(C)(C)OC(=O)N1CCN(CCCN(C[C@H]2Cc3c(cccc3N3CCOCC3)CN2C(=O)OC(C)(C)C)[C@H]2CCCc3cccnc32)CC1]

Procedure C was used starting with tert-butyl (S)-4-(3-((5,6,7,8-tetrahydroquinolin-8-yl)amino)propyl)piperazine-1-carboxylate and tert-butyl (R)-3-formyl-5-morpholino-3,4-dihydroisoquinoline-2(1H)-carboxylate. The product was used for the next step without further purification.

BC. Synthesis of (S)—N—(((R)-5-morpholino-1,2,3,4-tetrahydroisoquinolin-3-yl)methyl)-N-(3-(piperazin-1-yl)propyl)-5,6,7,8-tetrahydroquinolin-8-amine (EMU-184)

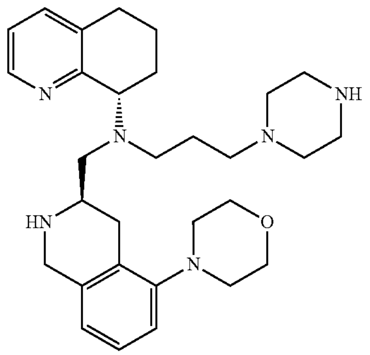 [SMILES: c1cnc2c(c1)CCC[C@@H]2N(CCCN1CCNCC1)C[C@H]1Cc2c(cccc2N2CCOCC2)CN1]

Procedure A was used to afford the title compound as an off-white foam (53% yield). $^1$H NMR (500 MHz, $CDCl_3$) δ 8.41 (dd, J=4.7, 1.8 Hz, 1H), 7.45-7.40 (m, 1H), 7.26-7.20 (m, 1H), 7.14 (dd, J=7.7, 4.7 Hz, 1H), 6.98 (dd, J=8.0, 1.3 Hz, 1H), 6.88 (dd, J=7.6, 1.2 Hz, 1H), 4.59 (d, J=16.2 Hz, 1H), 4.35-4.07 (m, 3H), 3.96-3.70 (m, 6H), 3.27 (s, 2H), 3.18 (d, J=16.9 Hz, 1H), 3.01 (dd, J=23.1, 16.0 Hz, 5H), 2.85-2.66 (m, 11H), 2.55 (s, 2H), 2.03 (d, J=12.3 Hz, 1H), 1.81 (dt, J=25.5, 13.3 Hz, 4H). LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=505.4 (M+H), t=0.597 min, purity ≥95% HRMS calculated for $C_{30}H_{45}N_6O$ (M+H): 505.35766, found: 505.36559.

BD. Synthesis of benzyl (S)-4-(3-((5,6,7,8-tetrahydroquinolin-8-yl)amino)propyl)piperazine-1-carboxylate

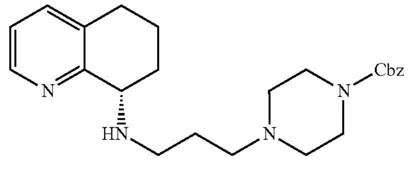 [SMILES: O=C(OCc1ccccc1)N1CCN(CCCN[C@H]2CCCc3cccnc32)CC1]

(8S)-5,6,7,8-Tetrahydroquinolin-8-amine (2.07 g, 13.968 mmol), benzyl 4-(3-bromopropyl)piperazine-1-carboxylate (4.333 g, 12.968 mmol), and N,N-diisopropyl-N-ethyl amine (4.102 g, 31.745 mmol) were mixed in 40 mL acetonitrile and stirred overnight. Saturated sodium bicarbonate solution (100 mL) and ethyl acetate (100 mL) were added to the reaction mixture and stirred for another 30 minutes. The phases were separated, and the aqueous phase was extracted with ethyl acetate twice. Combined organic layer was dried over anhydrous $MgSO_4$ and filtered, followed by solvent evaporation. The compound was purified with column chromatography by starting with DCM and increasing the polarity with DCM:MeOH:$NH_3$ (7 N in methanol) (9:1:0.2) to yield the title compound as a yellow sticky solid (28% yield).

BE. Synthesis of benzyl (S)-4-(3-((tert-butoxycarbonyl)(5,6,7,8-tetrahydroquinolin-8-yl)amino)propyl)piperazine-1-carboxylate

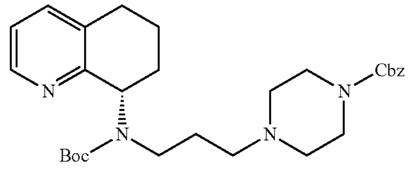 [SMILES: CC(C)(C)OC(=O)N(CCCN1CCN(C(=O)OCc2ccccc2)CC1)[C@H]1CCCc2cccnc21]

To the solution of 5.15 g (12.606 mmol) benzyl (S)-4-(3-((5,6,7,8-tetrahydroquinolin-8-yl)amino)propyl)piperazine-1-carboxylate and 5.5025 g (25.212 mmol) di-tert-butyl dicarbonate in 100 mL 1,4-dioxane, 63 mL (60.33 mmol) 1 M NaOH solution was added and stirred overnight. The reaction was diluted with ethyl acetate and extract with water. Organic layer was extracted with saturated $NaHCO_3$ solution, dried over anhydrous $MgSO_4$, and filtered, followed by solvent evaporation. Product was purified with column chromatography starting with DCM and increasing the polarity with DCM:MeOH:$NH_3$ (7 N in methanol) (9:1:0.2) to yield the title compound as a yellow oil (52% yield).

BF. Synthesis of tert-butyl (S)-(3-(piperazin-1-yl)propyl)(5,6,7,8-tetrahydroquinolin-8-yl)carbamate

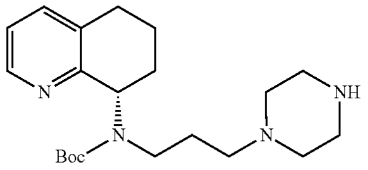 [SMILES: CC(C)(C)OC(=O)N(CCCN1CCNCC1)[C@H]1CCCc2cccnc21]

Benzyl 4-[3-[tert-butoxycarbonyl-[(8S)-5,6,7,8-tetrahydroquinolin-8-yl]amino]propyl]piperazine-1-carboxylate (3.36 g, 6.61 mmol) was dissolved in ethanol (100 mL) and palladium hydroxide on carbon (0.927 g) and ammonium formate (1.67 g) were added to the reaction mixture. It was heated to reflux for two hours. The reaction mixture was cooled to room temperature and filtered over celite. Filtrate was evaporated and used as it was for the next step.

BG. Synthesis of tert-butyl (S)-(3-(4-ethylpiperazin-1-yl)propyl)(5,6,7,8-tetrahydroquinolin-8-yl)carbamate

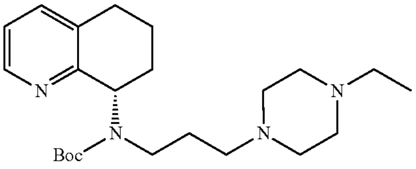 [SMILES: CCN1CCN(CCCN(C(=O)OC(C)(C)C)[C@H]2CCCc3cccnc32)CC1]

tert-Butyl (S)-(3-(piperazin-1-yl)propyl)(5,6,7,8-tetrahydroquinolin-8-yl)carbamate (2.45 g, 6.54 mmol) was dissolved in 1,2-DCE. STAB (2.77 g, 13.08 mmol) and acetaldehyde (0.288 g, 6.54 mmol) were added. The reaction mixture was stirred at room temperature overnight. It was quenched with a saturated sodium bicarbonate solution. The aqueous phase was extracted with DCM twice. Combined organic layer was dried over anhydrous $MgSO_4$ and filtered, followed by solvent evaporation. The product was purified with column chromatography by starting with DCM and increasing the polarity with DCM:MeOH:$NH_3$ (7 N in methanol) (9:1:0.2) to afford the title compound as a brownish oil (93% yield over two steps).

BH. Synthesis of (S)—N-(3-(4-ethylpiperazin-1-yl)propyl)-5,6,7,8-tetrahydroquinolin-8-amine

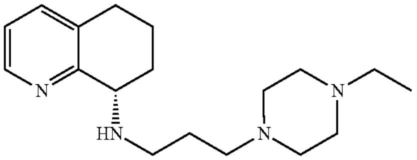 [SMILES: CCN1CCN(CCCN[C@H]2CCCc3cccnc32)CC1]

tert-Butyl N-[3-(4-ethylpiperazin-1-yl)propyl]-N-[(8S)-5,6,7,8-tetrahydroquinolin-8-yl]carbamate (1.4 g, 3.48 mmol) was dissolved in 20 mL dry DCM and 5.3 mL (69.55 mmol) TFA was added and stirred overnight. The reaction was quenched with 1 N NaOH solution to reach pH 12. The aqueous phase was extracted with DCM twice. Combined organic layer was dried over anhydrous $MgSO_4$ and filtered, followed by evaporation. The product was obtained as a brown oil (89% yield) and used as it was for the next step.

BI. Synthesis of tert-butyl (R)-3-(((3-(4-ethylpiperazin-1-yl)propyl)((S)-5,6,7,8-tetrahydroquinolin-8-yl)amino)methyl)-5-morpholino-3,4-dihydroisoquinoline-2(1H)-carboxylate

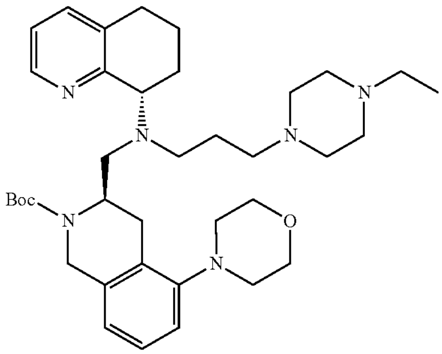 [SMILES: CCN1CCN(CCCN(C[C@H]2Cc3c(cccc3N3CCOCC3)CN2C(=O)OC(C)(C)C)[C@H]2CCCc3cccnc32)CC1]

(S)—N-(3-(4-Ethylpiperazin-1-yl)propyl)-5,6,7,8-tetrahydroquinolin-8-amine (0.3 g, 0.99 mmol), tert-butyl (R)-3-formyl-5-morpholino-3,4-dihydroisoquinoline-2(1H)-carboxylate (0.3436 g, 0.99 mmol), and titanium (IV) isopropoxide (0.5638 g, 1.98 mmol) were dissolved in 20 mL DCE. The reaction mixture was stirred overnight. STAB (0.4334 g, 1.98 mmol) was added to reaction mixture and stirred for four hours. It was quenched with a saturated sodium bicarbonate solution and extracted with DCM twice.

Combined organic layer was washed with brine solution, dried over anhydrous $MgSO_4$, and filtered, followed by solvent evaporation. Residue was then subjected to column chromatography by starting with DCM and increasing the polarity with DCM:MeOH:$NH_3$ (7 N in methanol) (9:1:0.2) to afford the title compound as a yellow oil (41% yield).

BJ. Synthesis of (S)—N-(3-(4-ethylpiperazin-1-yl)propyl)-N—(((R)-5-morpholino-1,2,3,4-tetrahydroisoquinolin-3-yl)methyl)-5,6,7,8-tetrahydroquinolin-8-amine (EMU-275)

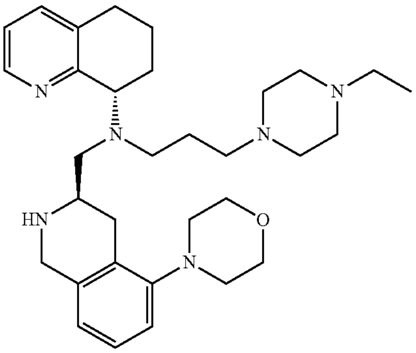 [SMILES: CCN1CCN(CCCN(C[C@H]2Cc3c(cccc3N3CCOCC3)CN2)[C@H]2CCCc3cccnc32)CC1]

Procedure A was used to afford the title compound as an off-white foam (76.4% yield). $^1H$ NMR (500 MHz, $CDCl_3$) δ 8.41 (d, J=4.7 Hz, 1H), 7.35 (d, J=7.7 Hz, 1H), 7.12 (t, J=7.8 Hz, 1H), 7.06 (dd, J=7.7, 4.7 Hz, 1H), 6.89 (d, J=7.9 Hz, 1H), 6.80 (d, J=7.6 Hz, 1H), 4.16 (s, 4H), 4.01 (d, J=15.0 Hz, 1H), 3.88-3.67 (m, 6H), 3.17-2.95 (m, 6H), 2.94-2.57 (m, 6H), 2.55-2.19 (m, 7H), 2.09 (d, J=12.5 Hz, 1H), 1.93 (ddd, J=35.5, 14.2, 9.9 Hz, 3H), 1.81-1.61 (m, 5H), 1.09-1.06 (m, 3H). $^{13}C$ NMR (126 MHz, $CDCl_3$) δ 158.75, 151.06, 146.50, 136.80, 135.08, 134.07, 129.48, 126.38, 121.94, 121.53, 117.02, 67.40, 61.82, 57.22, 56.47, 53.24, 52.72, 52.26, 52.17, 51.38, 47.65, 29.32, 29.07, 26.86, 21.93, 11.94. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=533.4 [M+H], t=0.421 min, purity ≥95% HRMS calculated for $C_{32}H_{49}N_6O$ 533.39624; found 533.39615 [M+H].

BK. Synthesis of tert-butyl 4-(3-oxopropyl)piperidine-1-carboxylate

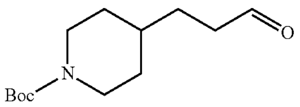 [SMILES: CC(C)(C)OC(=O)N1CCC(CCC=O)CC1]

4-(3-Hydroxy-propyl)-piperidine-1-carboxylicacid tert-butylester (0.28 g, 1.15 mmol) was dissolved in 5 mL DCM and the Dess-Martin reagent (0.732 g, 1.73 mmol) was added to the reaction mixture and stirred overnight. 30 mL saturated sodium thiosulfate, 30 mL saturated sodium bicarbonate, and some DCM was added and stirred for 30 minutes until the reaction mixture became clear. Aqueous phase was extracted with DCM twice and the combined organic layer was dried over anhydrous $MgSO_4$ and filtered, followed by solvent evaporation. The residue was used as it was without further purification.

BL. Synthesis of tert-butyl (R)-3-(((3-(1-(tert-butoxycarbonyl)piperidin-4-yl)propyl)((S)-5,6,7,8-tetrahydroquinolin-8-yl)amino)methyl)-5-morpholino-3,4-dihydroisoquinoline-2(1H)-carboxylate

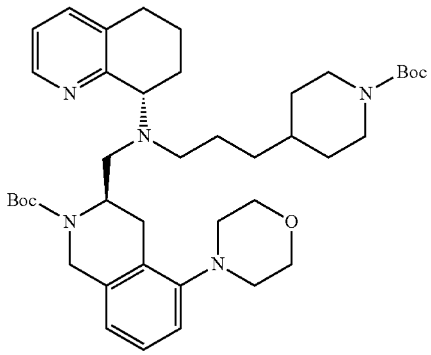 [SMILES: CC(C)(C)OC(=O)N1CCC(CCCN(C[C@H]2Cc3c(cccc3N3CCOCC3)CN2C(=O)OC(C)(C)C)[C@H]2CCCc3cccnc32)CC1]

Procedure C was used starting with tert-butyl (R)-5-morpholino-3-((((S)-5,6,7,8-tetrahydroquinolin-8-yl)amino)methyl)-3,4-dihydroisoquinoline-2(1H)-carboxylate and tert-butyl 4-(3-oxopropyl)piperidine-1-carboxylate. The residue was purified with column chromatography using DCM:MeOH:$NH_3$ (7 N in methanol) (9:1:0.2) in methanol to afford the title compound as a colorless oil (24.7% yield).

BM. Synthesis of (S)—N—(((R)-5-morpholino-1,2,3,4-tetrahydroisoquinolin-3-yl)methyl)-N-(3-(piperidin-4-yl)propyl)-5,6,7,8-tetrahydroquinolin-8-amine (EMU-279)

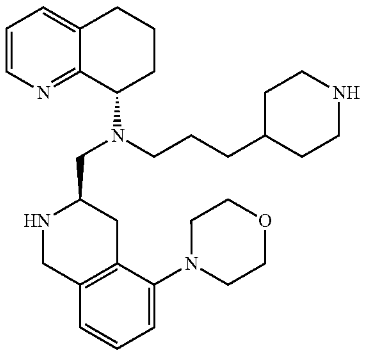 [SMILES: c1cnc2c(c1)CCC[C@@H]2N(CCCC1CCNCC1)C[C@H]1Cc2c(cccc2N2CCOCC2)CN1]

Procedure A was used to afford the title compound (61% yield). $^1H$ NMR (500 MHz, $CDCl_3$) δ 8.43 (dd, J=4.8, 1.7 Hz, 1H), 7.33 (ddt, J=7.7, 1.8, 0.9 Hz, 1H), 7.10 (t, J=7.7 Hz, 1H), 7.06-7.01 (m, 1H), 6.86 (dd, J=7.9, 1.2 Hz, 1H), 6.79 (dd, J=7.6, 1.1 Hz, 1H), 4.13 (d, J=15.2 Hz, 1H), 4.06 (dd, J=10.2, 6.1 Hz, 1H), 4.00-3.69 (m, 7H), 3.18-2.89 (m, 7H), 2.89-2.81 (m, 1H), 2.81-2.72 (m, 1H), 2.72-2.38 (m, 8H), 2.18 (dd, J=16.2, 10.8 Hz, 1H), 2.12-2.02 (m, 1H), 1.98 (ddt, J=13.0, 5.2, 3.2 Hz, 1H), 1.89 (tdd, J=13.0, 8.1, 2.9 Hz, 1H), 1.80-1.65 (m, 3H), 1.65-1.43 (m, 1H), 1.33-1.03 (m, 5H). $^{13}C$ NMR (126 MHz, $CDCl_3$) δ 158.87, 151.10, 146.66, 136.56, 136.29, 133.94, 129.95, 126.20, 122.10, 121.42, 116.86, 67.46, 61.75, 57.93, 54.45, 53.39, 52.60, 52.21, 48.55, 45.85, 35.53, 34.43, 32.10, 29.84, 29.41, 26.91, 22.00. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m/z=504.4 [M+H], t=0.438 min, purity ≥95%. HRMS calculated for $C_{31}H_{45}N_5O$ 504.36969, found 504.36921 [M+H].

BN. Synthesis of tert-butyl (R)-5-((1R,5S)-8-oxa-3-azabicyclo[3.2.1]octan-3-yl)-3-((methyl((S)-5,6,7,8-tetrahydroquinolin-8-yl)amino)methyl)-3,4-dihydroisoquinoline-2(1H)-carboxylate

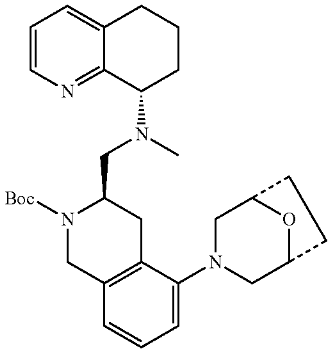 [SMILES: CN(C[C@H]1Cc2c(cccc2N2C[C@H]3CC[C@@H](C2)O3)CN1C(=O)OC(C)(C)C)[C@H]1CCCc2cccnc21]

Procedure B was used starting with tert-butyl (R)-5-bromo-3-((methyl((S)-5,6,7,8-tetrahydroquinolin-8-yl)amino)methyl)-3,4-dihydroisoquinoline-2(1H)-carboxylate and 8-oxa-3-azabicyclo[3.2.1]octane to afford the title compound as a white foam (40% yield).

BO. Synthesis of (S)—N—(((R)-5-((1R,5S)-8-oxa-3-azabicyclo[3.2.1]octan-3-yl)-1,2,3,4-tetrahydroisoquinolin-3-yl)methyl)-N-methyl-5,6,7,8-tetrahydroquinolin-8-amine (EMU-295)

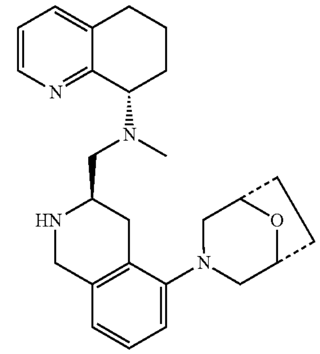 [SMILES: CN(C[C@H]1Cc2c(cccc2N2C[C@H]3CC[C@@H](C2)O3)CN1)[C@H]1CCCc2cccnc21]

Procedure A was used to afford the title compound as a white foam (38% yield). $^1H$ NMR (400 MHz, $CDCl_3$): δ 1.7 (m, 1H), 1.89-2.23 (m, 9H), 2.49 (s, 3H), 2.60 (q, 2H, J=11 Hz), 2.69-2.87 (m, 7H), 3.25 (dd, 1H, J=1.6 Hz, J=11 Hz), 3.95 (m, 1H), 3.97 (ABq, 2H, J=15 Hz, v=38 Hz), 4.3 (d, 1H, J=6 Hz), 4.39 (d, 1H, J=6 Hz), 6.76 (d, 1H, J=8 Hz), 6.89 (d, 1H, J=8 Hz), 7.05 (q, 1H, J=5 Hz), 7.06 (d, 1H, J=9 Hz), 7.33 (dd, 1H, J=1 Hz, J=8 Hz), 8.46 (dd, 1H, J=1 Hz, J=5 Hz). $^{13}C$ NMR (101 MHz, $CDCl_3$): δ 21.24, 26.21, 28.3, 28.56, 29.2, 30.18, 41.18, 48.75, 51.63, 56.41, 57.17, 60.14, 64.5, 74.91, 75.15, 117.83, 121.54, 122.2, 126.16, 130.35, 133.79, 136.68, 136.87, 146.81, 150.44, 158.06. LC-MS: 100% for 419.4 m/z [M+H]. HRMS: calculated for $C_{26}H_{35}ON_4$ 419.28054, found 419.28001 [M+H].

BP. Synthesis of tert-butyl (R)-3-((methyl((S)-5,6,7,8-tetrahydroquinolin-8-yl)amino)methyl)-5-(3-oxo-morpholino)-3,4-dihydroisoquinoline-2(1H)-carboxylate

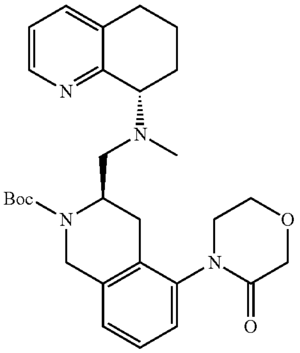 [SMILES: CN(C[C@H]1Cc2c(cccc2N2CCOCC2=O)CN1C(=O)OC(C)(C)C)[C@H]1CCCc2cccnc21]

A 20 mL microwave tube equipped with a stir bar was charged with 300 mg of tert-butyl (3R)-5-bromo-3-[[(3,5-dimethyl-2-pyridyl)methyl-methyl-amino]methyl]-3,4-dihydro-1H-isoquinoline-2-carboxylate (0.617 mmol, 1 equiv), 74.8 mg of the amide (0.740 mmol, 1.2 equiv), 170 mg of $K_2CO_3$ (1.23 mmol, 2 equiv), and 11.8 mg of CuI (0.0617 mmol, 0.1 equiv), and the system was set under argon. Then 6.1 mL of toluene (degassed by bubbling through argon for 1 h) and 13.0 μL of N,N'-dimethylethane-1,2-diamine (0.123 mmol, 0.2 equiv) was added. After stirring at 110° C. for 20 h, EA and water were added and the product was extracted with EA (3×) and dried over $Na_2SO_4$. The combined organic layer was concentrated, and the crude product was purified on a silica gel column (10 g) using EA as eluent, affording the title compound as a white foam (51% yield).

BQ. Synthesis of 4-((R)-3-((methyl((S)-5,6,7,8-tetrahydroquinolin-8-yl)amino)methyl)-1,2,3,4-tetrahydroisoquinolin-5-yl)morpholin-3-one (EMU-266)

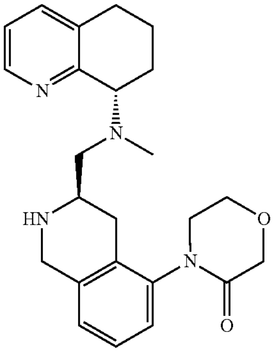 [SMILES: CN(C[C@H]1Cc2c(cccc2N2CCOCC2=O)CN1)[C@H]1CCCc2cccnc21]

Procedure A was used to afford the title compound as a white foam (89% yield). $^1H$ NMR (600 MHz, $CDCl_3$) δ 8.42 (dd, J=4.7, 1.8 Hz, 1H), 7.31 (dd, J=7.5, 1.7 Hz, 1H), 7.15 (t, J=7.9 Hz, 0.25H), 7.14 (t, J=7.9 Hz, 0.75H), 7.03 (dd, J=7.8, 4.5 Hz, 0.75H), 7.04-6.98 (m, 0.5H), 7.00 (d, J=7.7 Hz, 0.75H), 6.98 (d, J=7.6 Hz, 0.25H), 6.94 (d, J=7.7 Hz, 0.75H), 4.31 (A of AB, $J_{AB}$=17.5 Hz, 0.25H), 4.29 (s, 1.5H), 4.25 (B of AB, $J_{AB}$=16.5 Hz, 0.25H), 4.07 (A of AB, $J_{AB}$=15.8 Hz, 0.25H), 4.02-3.89 (m, 4H), 3.83 (B of AB, $J_{AB}$=15.2 Hz, 0.75H), 3.69 (dt, J=12.1, 5.2 Hz, 0.25H), 3.53 (ddd, J=12.1, 6.5, 4.1 Hz, 0.75H), 3.50-3.42 (m, 1H), 3.19 (br s, 2H), 2.96-2.89 (m, 0.25H), 2.81-2.71 (m, 2.75H), 2.64 (d, J=15.8 Hz, 1H), 2.55-2.42 (m, 1H), 2.46 (d, J=1.5 Hz, 2.25H), 2.42 (s, 0.75H), 2.26 (dd, J=16.7, 10.8 Hz, 0.25H), 2.16 (dd, J=16.2, 10.9 Hz, 0.75H), 2.05-1.82 (m, 3H), 1.72-1.61 (m, 1H). $^{13}$C NMR (151 MHz, $CDCl_3$) δ 166.31, 165.83 (minor isomer), 157.65, 157.58 (minor isomer), 146.66 (both isomers), 139.91 (minor isomer), 139.74, 137.66, 137.41 (minor isomer), 136.64, 136.59 (minor isomer), 133.86 (minor isomer), 133.66, 132.40 (minor isomer), 131.69, 126.73, 126.68, 126.57 (minor isomer), 126.15 (minor isomer), 124.77, 124.10 (minor isomer), 121.47, 121.44 (minor isomer), 68.27, 68.25 (minor isomer), 64.39 (minor isomer), 64.27, 64.05 (minor isomer), 63.93, 59.81 (minor isomer), 59.48, 51.13 (minor isomer), 50.95, 49.92 (minor isomer), 49.25, 48.46, 48.13 (minor isomer), 41.22, 40.16 (minor isomer), 29.29 (minor isomer), 29.10 (minor isomer), 29.06 (two signals), 25.44 (minor isomer), 25.32, 21.20 (minor isomer), 21.15. LC-MS (ESI-API, 254 nm) 50-95% MeOH in $H_2O$ (0.1% $HCO_2H$), 1.00 mL/min, C18 column (Agilent Zorbax XDB-18, 50 mm×4.6 mm, 3.5 μm), m z=429.2 [M+Na], 407.2 (M+H), 204.2 (M/2+H), t=0.460 min. HRMS calculated for $C_{24}H_{31}O_2N_4$ 407.2442; found: 407.2440 [M+H].

BR. Synthesis of tert-butyl-(R)-3-((methyl((S)-5,6,7,8-tetrahydroquinolin-8-yl)amino)methyl)-5-((S)-2-methylmorpholino)-3,4-dihydroisoquinoline-2(1H)-carboxylate

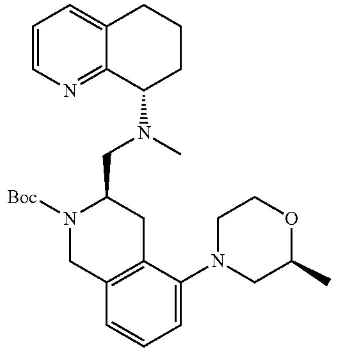 [SMILES: C[C@H]1CN(c2cccc3c2C[C@H](CN(C)[C@H]2CCCc4cccnc42)N(C(=O)OC(C)(C)C)C3)CCO1]

tert-Butyl (3R)-5-bromo-3-[[methyl-[(8S)-5,6,7,8-tetrahydroquinolin-8-yl]amino]methyl]-3,4-dihydro-1H-isoquinoline-2-carboxylate (402.00 mg, 0.83 mmol), (±)-2,2"-bis (diphenylphosphino)-1,1"-binaphthalene (77.19 mg, 0.12 mmol), tris(dibenzylideneacetone)dipalladium(0) (37.84 mg, 0.04 mmol), and cesium carbonate (376.97 mg, 1.16 mmol) were added to a microwave vial. Degassed toluene (5 mL) and (2S)-2-methylmorpholine (105.59 mg, 0.99 mmol) were added to the vial and degassed with argon for 30 minutes. Then the reaction was heated at 110° C. overnight. The reaction mixture was filtered over celite and washed with EtOAc. Combined filtrate was evaporated and purified with column chromatography with a EtOAc:hexanes solvent system to afford the title compound.

BS. Synthesis of (S)—N-methyl-N—(((R)-5-((S)-2-methylmorpholino)-1,2,3,4-tetrahydroisoquinolin-3-yl)methyl)-5,6,7,8-tetrahydroquinolin-8-amine (EMU-318)

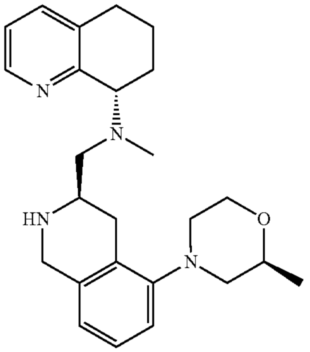 [SMILES: C[C@H]1CN(c2cccc3c2C[C@H](CN(C)[C@H]2CCCc4cccnc42)NC3)CCO1]

tert-Butyl (R)-3-((methyl((S)-5,6,7,8-tetrahydroquinolin-8-yl)amino)methyl)-5-((S)-2-methylmorpholino)-3,4-dihydroisoquinoline-2(1H)-carboxylate (0.33 g, 0.64 mmol) was dissolved in DCM (5 mL), followed by additional of trifluoroacetic acid (0.99 mL, 12.83 mmol). The reaction was stirred at room temperature overnight. Afterward, the reaction was basified with 1N NaOH to pH>12. The aqueous phase was extracted with DCM three times. Combined organic layer was dried over anhydrous $MgSO_4$ and filtered, followed by solvent removal. The product was purified with column chromatography by starting with DCM and increasing the polarity with DCM:MeOH:$NH_3$ (7 N in methanol) (9:1:0.2). $^1$H NMR (600 MHz, $CDCl_3$) δ 8.44 (dd, J=4.7, 1.7 Hz, 1H), 7.32 (ddd, J=7.6, 1.9, 0.9 Hz, 1H), 7.13-6.99 (m, 2H), 6.82 (d, J=7.8 Hz, 1H), 6.75 (d, J=7.6 Hz, 1H), 4.04 (d, J=15.4 Hz, 1H), 3.94-3.90 (m, 2H), 3.85 (ddd, J=11.0, 3.1, 1.5 Hz, 1H), 3.78 (td, J=11.1, 2.4 Hz, 1H), 3.72 (dtt, J=12.5, 6.4, 3.1 Hz, 1H), 2.87-2.73 (m, 7H), 2.70-2.64 (m, 2H), 2.51 (ddd, J=21.5, 10.6, 2.9 Hz, 3H), 2.47 (s, 3H), 2.16-2.08 (m, 1H), 2.08-1.88 (m, 2H), 1.68 (dtdd, J=13.1, 10.5, 5.0, 2.6 Hz, 1H), 1.18 (d, J=6.2 Hz, 3H). $^{13}$C NMR (151 MHz, $CDCl_3$) δ 158.06, 150.96, 146.85, 136.71, 133.89, 130.01, 126.12, 122.00, 121.58, 116.82, 72.34, 67.27, 64.53, 59.99, 58.00, 52.13, 51.61, 48.65, 41.14, 30.21, 29.25, 26.05, 21.31, 19.05. HRMS calculated for $C_{25}H_{35}N_4O$ 407.28054; found 407.28024 [M+H].

BT. Synthesis of tert-butyl (R)-5-((S)-2-(hydroxymethyl)morpholino)-3-((methyl((S)-5,6,7,8-tetrahydroquinolin-8-yl)amino)methyl)-3,4-dihydroisoquinoline-2(1H)-carboxylate

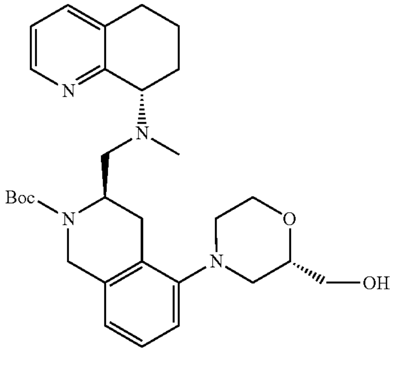 [SMILES: CN(C[C@H]1Cc2c(cccc2N2CCO[C@H](CO)C2)CN1C(=O)OC(C)(C)C)[C@H]1CCCc2cccnc21]

To the microwave vial tert-butyl (3R)-5-bromo-3-[[methyl-[(8S)-5,6,7,8-tetrahydroquinolin-8-yl]amino]methyl]-3,4-dihydro-1H-isoquinoline-2-carboxylate (248.00 mg, 0.51 mmol), [(2S)-morpholin-2-yl]methanol (71.67 mg, 0.61 mmol), (±)-2,2"-bis(diphenylphosphino)-1,1"-binaphthalene (47.62 mg, 0.0800 mmol), tris(dibenzylideneacetone)dipalladium(0) (23.34 mg, 0.03 mmol), and cesium carbonate (232.56 mg, 0.7100 mmol) were added and the cap was closed and degassed. Toluene (3 mL) was added to the system and degassed for another 30 minutes. Then the reaction mixture was heated to 110° C. for 28 hours, cooled to room temperature, filtered over celite, and washed with EtOAc. Combined filtrate was evaporated. The residue was purified with column chromatography by starting with DCM and increasing the polarity with DCM:MeOH:$NH_3$ (7 N in methanol) (9:1:0.2).

BU. Synthesis of ((S)-4-((R)-3-((methyl((S)-5,6,7,8-tetrahydroquinolin-8-yl)amino)methyl)-1,2,3,4-tetrahydroisoquinolin-5-yl)morpholin-2-yl)methanol (EMU-308)

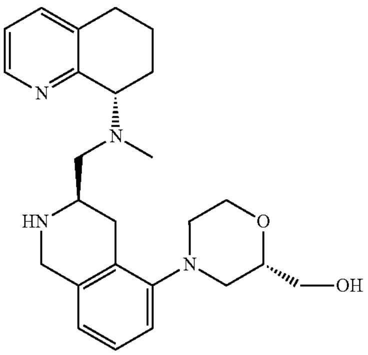 [SMILES: CN(C[C@H]1Cc2c(cccc2N2CCO[C@H](CO)C2)CN1)[C@H]1CCCc2cccnc21]

tert-Butyl (R)-5-((S)-2-(hydroxymethyl)morpholino)-3-((methyl((S)-5,6,7,8-tetrahydroquinolin-8-yl)amino)methyl)-3,4-dihydroisoquinoline-2(1H)-carboxylate (0.19 g, 0.37 mmol) was dissolved in DCM (3 mL) and added trifluoroacetic acid (0.28 mL, 3.67 mmol) at room temperature. The reaction was stirred at room temperature overnight. LC-MS showed the product mass. The reaction mixture was basified with 1 N NaOH to pH>12 and stirred for 15-20 minutes. Aqueous phase was extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in methanol) (9:1:0.2) to afford the title compound (54.76% yield). $^1$H NMR (400 MHz, $CDCl_3$) δ 8.42 (dd, J=4.7, 1.7 Hz, 1H), 7.45-7.41 (m, 1H), 7.20 (t, J=7.8 Hz, 1H), 7.14 (dd, J=7.7, 4.8 Hz, 1H), 7.00-6.91 (m, 1H), 6.87 (d, J=7.6 Hz, 1H), 4.39 (d, J=15.8 Hz, 1H), 4.22 (d, J=15.8 Hz, 1H), 4.12-3.97 (m, 2H), 3.88-3.73 (m, 2H), 3.73-3.56 (m, 2H), 3.33-2.93 (m, 6H), 2.89-2.62 (m, 5H), 2.52-2.44 (m, 1H), 2.31 (s, 3H), 2.15-1.83 (m, 2H), 1.82-1.66 (m, 1H), 1.39-1.02 (m, 2H). $^{13}$C NMR (151 MHz, $CDCl_3$) δ 157.28, 151.04, 146.13, 136.96, 134.02, 131.78, 128.08, 127.19, 122.14, 121.92, 118.00, 76.53, 67.00, 65.54, 64.09, 57.95, 54.23, 52.34, 51.22, 45.00, 29.71, 29.14, 26.63, 24.75, 21.37. HRMS calculated for $C_{25}H_{35}N_4O_2$ 423.27545; found 423.27517 [M+H].

BV. Synthesis of (R)-5-((R)-3-methylmorpholino)-3,3a,4,9-tetrahydro-2H-isoxazolo[2,3-b]isoquinolin-2-one

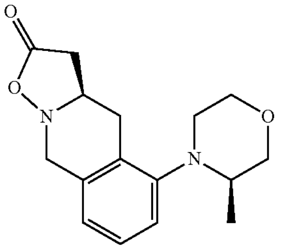 [SMILES: C[C@@H]1COCCN1c1cccc2c1C[C@@H]1CC(=O)ON1C2]

(10aR)-9-Bromo-1,5,10,10a-tetrahydrooxazolo[3,4-b]isoquinolin-3-one (0.50 g, 1.86 mmol), (±)-2,2"-bis(diphenylphosphino)-1,1"-binaphthalene (0.17 g, 0.28 mmol), tris(dibenzylideneacetone)dipalladium(0) (0.09 g, 0.09 mmol), and cesium carbonate (0.85 g, 2.61 mmol) were added to a microwave vial. Then (3R)-3-methylmorpholine (0.25 mL, 2.24 mmol) was added and degassed. Toluene (4 mL) were added and degassed for one hour. The reaction was heated at 110° C. for 36 hours, cooled to room temperature, filtered over celite, and washed with EtOAc. The combined filtrate was evaporated and the product was purified with column chromatography by starting with DCM and increasing the polarity with DCM:MeOH:$NH_3$ (7 N in methanol) (9:1:0.2) to afford the title compound (39.98% yield).

BW. Synthesis of ((R)-5-((R)-3-methylmorpholino)-1,2,3,4-tetrahydroisoquinolin-3-yl)methanol

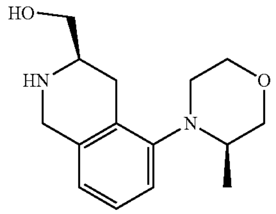 [SMILES: C[C@@H]1COCCN1c1cccc2c1C[C@H](CO)NC2]

(R)-5-((R)-3-Methylmorpholino)-3,3a,4,9-tetrahydro-2H-isoxazolo[2,3-b]isoquinolin-2-one was dissolved in methanol (3 mL) and added sodium hydroxide (1.24 mL, 7.46 mmol). The reaction mixture was heated at 100° C. for three hours and cooled to room temperature. The solvent was evaporated. The residue was suspended in 5 mL water and stirred overnight. The precipitates were filtered and used for the next step without further purification.

BX. Synthesis of tert-butyl (R)-3-(hydroxymethyl)-5-((R)-3-methylmorpholino)-3,4-dihydroisoquinoline-2(1H)-carboxylate

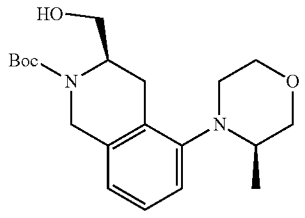 [SMILES: C[C@@H]1COCCN1c1cccc2c1C[C@H](CO)N(C(=O)OC(C)(C)C)C2]

[(3R)-5-[(3R)-3-methylmorpholin-4-yl]-1,2,3,4-tetrahydroisoquinolin-3-yl]methanol (0.20 g, 0.74 mmol) was dissolved in THE (3 mL) and sodium carbonate (0.24 g, 2.23 mmol) was added. Di-tert-butyl dicarbonate (0.26 mL, 1.11 mmol) was added to the reaction mixture and continued to stir at room temperature overnight. The reaction mixture was diluted with DCM and extracted with water. Organic phase was dried with anhydrous $MgSO_4$ and filtered, followed by solvent evaporation. The residue was purified with column chromatography by starting with hexanes and increasing the polarity with EtOAc to afford the title compound at a 9.2795% yield.

BY. Synthesis of tert-butyl (R)-3-formyl-5-((R)-3-methylmorpholino)-3,4-dihydroisoquinoline-2(1H)-carboxylate

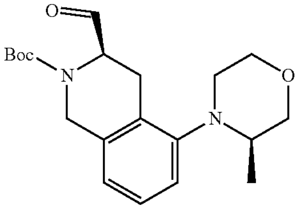 [SMILES: C[C@@H]1COCCN1c1cccc2c1C[C@H](C=O)N(C(=O)OC(C)(C)C)C2]

To a solution of tert-butyl (3R)-3-(hydroxymethyl)-5-[(3R)-3-methylmorpholin-4-yl]-3,4-dihydro-1H-isoquinoline-2-carboxylate (0.22 g, 0.6 mmol) in DCM (1.7 mL), triethylamine (0.42 mL, 2.99 mmol) was added and the mixture was cooled to 0° C. with an ice bath. A solution of pyridine sulfur trioxide (0.38 g, 2.39 mmol) in DMSO (1.7 mL) was added to the reaction mixture at 0° C. The reaction was stirred at 0° C. for 4 hours. Sodium bicarbonate solution was added to the reaction mixture, diluted with EtOAc, and stirred for 30 minutes. The phases were separated and the aqueous phase was extracted with EtOAc. Combined organic layer was dried over anhydrous $MgSO_4$ and filtered, followed by solvent evaporation. The product was used for the next step without further purification.

BZ. Synthesis of tert-butyl (R)-3-((methyl((S)-5,6,7,8-tetrahydroquinolin-8-yl)amino)methyl)-5-((R)-3-methylmorpholino)-3,4-dihydroisoquinoline-2(1H)-carboxylate

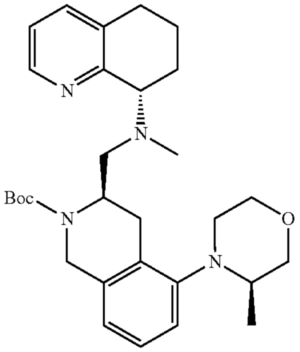 [SMILES: C[C@@H]1COCCN1c1cccc2c1C[C@H](CN(C)[C@H]1CCCc3cccnc31)N(C(=O)OC(C)(C)C)C2]

(8S)—N-methyl-5,6,7,8-tetrahydroquinolin-8-amine (106.44 mg, 0.66 mmol) was dissolved in DCM (5 mL) and added sodium triacetoxyborohydride (316.04 mg, 1.49 mmol) and acetic acid (0.03 mL, 0.6 mmol). The reaction was stirred for a few minutes and then tert-butyl (3R)-3-formyl-5-[(3R)-3-methylmorpholin-4-yl]-3,4-dihydro-1H-isoquinoline-2-carboxylate (215 mg, 0.6 mmol) was added to the reaction mixture and stirred overnight at room temperature. The reaction was quenched with a saturated $NaHCO_3$ solution. The phases were separated, and the aqueous phase was extracted with DCM three times. Combined organic layer was dried over anhydrous $MgSO_4$ and filtered, followed by solvent evaporation. The residue was purified with column chromatography by starting with hexanes and increasing the polarity with EtOAc. The title compound was obtained at a 72.5% yield.

CA. Synthesis of (S)—N-methyl-N—(((R)-5-((R)-3-methylmorpholino)-1,2,3,4-tetrahydroisoquinolin-3-yl)methyl)-5,6,7,8-tetrahydroquinolin-8-amine (EMU-338)

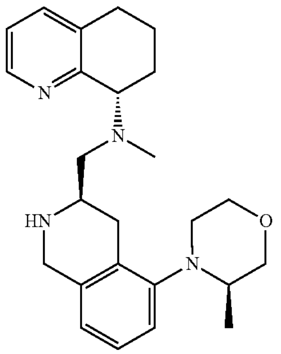 [SMILES: C[C@@H]1COCCN1c1cccc2c1C[C@H](CN(C)[C@H]1CCCc3cccnc31)NC2]

tert-Butyl (3R)-5-[(3R)-3-methylmorpholin-4-yl]-3-[[methyl-[(8S)-5,6,7,8-tetrahydroquinolin-8-yl]amino]methyl]-3,4-dihydro-1H-isoquinoline-2-carboxylate (0.22 g, 0.43 mmol) was dissolved in DCM (4 mL) and trifluoroacetic acid (0.33 mL, 4.32 mmol) was added to the solution. The reaction was stirred at room temperature overnight. The reaction mixture was basified to pH>12 with 1 N NaOH. Aqueous phase was extracted with DCM twice. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in methanol) (9:1:0.2) to afford the title compound at a 37% yield. $^1$H NMR (400 MHz, $CDCl_3$) δ 8.50 (dd, J=4.8, 1.7 Hz, 1H), 7.37 (dd, J=7.7, 1.7 Hz, 1H), 7.15-7.02 (m, 3H), 6.87 (d, J=7.4 Hz, 1H), 4.08-3.90 (m, 3H), 3.84 (ddd, J=14.2, 9.9, 2.8 Hz, 3H), 3.73 (td, J=10.9, 2.5 Hz, 1H), 3.31 (dd, J=10.9, 9.6 Hz, 1H), 3.19-3.04 (m, 1H), 2.85-2.77 (m, 4H), 2.76-2.64 (m, 3H), 2.59 (s, 3H), 2.48 (dd, J=13.1, 10.1 Hz, 1H), 2.38-2.25 (m, 1H), 2.17-1.87 (m, 3H), 1.81-1.61 (m, 1H), 0.65 (d, J=6.2 Hz, 3H). $^{13}$C NMR (101 MHz, $CDCl_3$) δ 158.25, 149.57, 146.84, 136.87, 136.67, 133.89, 133.32, 125.96, 123.61, 121.55, 120.73, 73.63, 67.95, 64.47, 59.63, 54.51, 51.69, 48.76, 41.75, 30.09, 29.72, 29.27, 26.79, 21.40, 14.89. HRMS calculated for $C_{25}H_{35}NO$ 407.28054; found 407.28068 [M+H].

CB. Synthesis of (R)-5-((S)-3-methylmorpholino)-3,3a,4,9-tetrahydro-2H-isoxazolo[2,3-b]isoquinolin-2-one

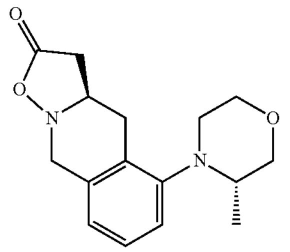 [SMILES: C[C@H]1COCCN1c1cccc2c1C[C@@H]1CC(=O)ON1C2]

(10aR)-9-Bromo-1,5,10,10a-tetrahydrooxazolo[3,4-b]isoquinolin-3-one (1.00 g, 3.73 mmol), (±)-2,2"-bis(diphenylphosphino)-1,1"-binaphthalene (0.35 g, 0.56 mmol), (1E,4E)-1,5-diphenylpenta-1,4-dien-3-one;palladium (0.17 g, 0.19 mmol), and cesium carbonate (1.70 g, 5.22 mmol) were added to a microwave vial. Then (3S)-3-methylmorpholine (0.51 mL, 4.48 mmol) and degassed toluene (8 mL) were added and degassed for another hour. The reaction was heated at 110° C. over the weekend, cooled to room temperature, filtered over celite, and washed with EtOAc. The combined filtrate was evaporated and the residue was purified with column chromatography using EtOAc:hexanes to yield the title compound at a 57.4% yield.

CC. Synthesis of ((R)-5-((S)-3-methylmorpholino)-1,2,3,4-tetrahydroisoquinolin-3-yl)methanol

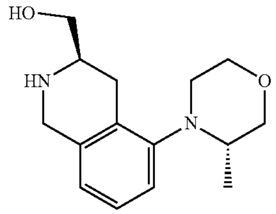 [SMILES: C[C@H]1COCCN1c1cccc2c1C[C@H](CO)NC2]

(R)-5-((S)-3-methylmorpholino)-3,3a,4,9-tetrahydro-2H-isoxazolo[2,3-b]isoquinolin-2-one (0.62 g, 2.14 mmol) was suspended in methanol (14.023 mL), followed by the addition of sodium hydroxide (3.57 mL, 21.4 mmol). The reaction mixture was heated at 100° C. for two hours. The reaction mixture was then cooled to room temperature and there were some precipitates. The solvent was evaporated. The residue was suspended in 5 mL water and stirred overnight. The precipitates were filtered and used for the next step without further purification.

CD. Synthesis of tert-butyl (R)-3-(hydroxymethyl)-5-((S)-3-methylmorpholino)-3,4-dihydroisoquinoline-2(1H)-carboxylate

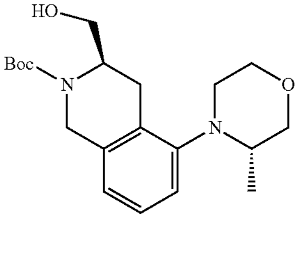 [SMILES: C[C@H]1COCCN1c1cccc2c1C[C@H](CO)N(C(=O)OC(C)(C)C)C2]

[(3R)-5-[(3S)-3-Methylmorpholin-4-yl]-1,2,3,4-tetrahydroisoquinolin-3-yl]methanol (0.56 g, 2.14 mmol) was dissolved in THE (10 mL) and sodium carbonate (907 mg, 8.56 mmol) was added and stirred for a few minutes. Then di-tert-butyl dicarbonate (0.89 mL, 3.85 mmol) was added to the reaction mixture and continued to stir at room temperature overnight. The reaction was diluted with DCM and extracted with water. Organic phase was dried over anhydrous $MgSO_4$ and filtered, followed by solvent evaporation. The residue was purified with column chromatography with hexanes:EtOAc to afford the title compound at a 57.1% yield.

CE. Synthesis of tert-butyl (R)-3-formyl-5-((S)-3-methylmorpholino)-3,4-dihydroisoquinoline-2(1H)-carboxylate

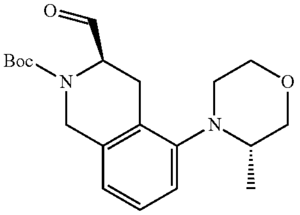 [SMILES: C[C@H]1COCCN1c1cccc2c1C[C@H](C=O)N(C(=O)OC(C)(C)C)C2]

To the solution of tert-butyl (3R)-3-(hydroxymethyl)-5-[(3S)-3-methylmorpholin-4-yl]-3,4-dihydro-1H-isoquinoline-2-carboxylate (0.23 g, 0.62 mmol) in DCM (2 mL), triethylamine (0.43 mL, 3.1 mmol) was added, and the mixture was cooled to 0° C. with an ice bath. A solution of pyridine sulfur trioxide (0.40 g, 2.48 mmol) in DMSO (2 mL) was added to the reaction mixture at 0° C. The reaction was stirred at 0° C. for 4 hours. Sodium bicarbonate solution was added to the reaction mixture, diluted with EtOAc, and stirred for 30 minutes. The phases were separated, and the aqueous phase was extracted with EtOAc. Combined organic layer was dried over anhydrous $MgSO_4$ and filtered, followed by solvent evaporation.

CF. Synthesis of tert-butyl (R)-3-((methyl((S)-5,6,7,8-tetrahydroquinolin-8-yl)amino)methyl)-5-((S)-3-methylmorpholino)-3,4-dihydroisoquinoline-2(1H)-carboxylate

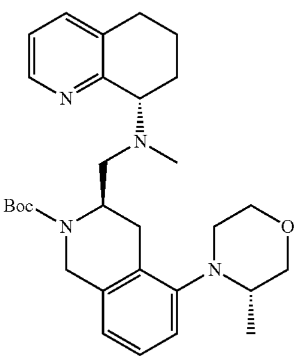 [SMILES: C[C@H]1COCCN1c1cccc2c1C[C@H](CN(C)[C@H]1CCCc3cccnc31)N(C(=O)OC(C)(C)C)C2]

(8S)—N-Methyl-5,6,7,8-tetrahydroquinolin-8-amine (0.11 g, 0.68 mmol) was dissolved in DCM (5 mL), and sodium triacetoxyborohydride (0.26 g, 1.24 mmol) and acetic acid (0.04 mL, 0.62 mmol) were added to the solution. Then tert-butyl (3R)-3-formyl-5-[(3S)-3-methylmorpholin-4-yl]-3,4-dihydro-1H-isoquinoline-2-carboxylate (0.22 g, 0.62 mmol) was added to the reaction at room temperature, and the reaction mixture was stirred at room temperature overnight. The reaction was quenched with a saturated $NaHCO_3$ solution. Aqueous phase was extracted with DCM. Combined organic layer was dried over anhydrous $MgSO_4$ and filtered, followed by solvent evaporation. The residue was purified with column chromatography using EtOAc: hexanes to afford the title compound at a 79.1% yield.

CG. Synthesis of (S)—N-methyl-N—(((R)-5-((S)-3-methylmorpholino)-1,2,3,4-tetrahydroisoquinolin-3-yl)methyl)-5,6,7,8-tetrahydroquinolin-8-amine (EMU-339)

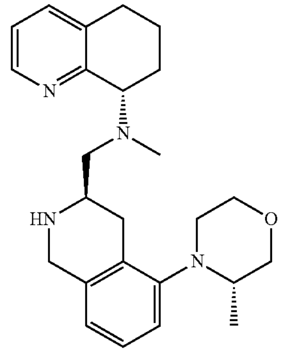 [SMILES: C[C@H]1COCCN1c1cccc2c1C[C@H](CN(C)[C@H]1CCCc3cccnc31)NC2]

tert-Butyl 5-[(3S)-3-methylmorpholin-4-yl]-3-[[methyl-[(8S)-5,6,7,8-tetrahydroquinolin-8-yl]amino]methyl]-3,4-dihydro-1H-isoquinoline-2-carboxylate (0.25 g, 0.49 mmol) was dissolved in DCM (5 mL) and added trifluoroacetic acid (0.38 mL, 4.89 mmol) at room temperature. The reaction was stirred at room temperature overnight. The reaction was basified with 1 N NaOH to pH>12 and the aqueous phase was extracted with DCM twice. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in methanol) (9:1:0.2) to afford the title compound at a 73% yield. $^1$H NMR (400 MHz, $CDCl_3$) δ 8.49 (dd, J=4.8, 1.7 Hz, 1H), 7.39 (dd, J=7.7, 1.7 Hz, 1H), 7.14 (d, J=7.7 Hz, 1H), 7.10 (dd, J=7.8, 4.8 Hz, 1H), 6.97 (d, J=7.8 Hz, 1H), 6.85 (d, J=7.5 Hz, 1H), 4.14 (d, J=15.3 Hz, 1H), 4.05-3.96 (m, 2H), 3.81 (dddd, J=28.2, 20.4, 10.9, 2.8 Hz, 3H), 3.53-3.31 (m, 2H), 3.23 (dqd, J=9.2, 6.2, 2.9 Hz, 1H), 3.04 (dd, J=16.6, 3.2 Hz, 1H), 2.96-2.77 (m, 4H), 2.77-2.58 (m, 2H), 2.55 (s, 3H), 2.26-1.88 (m, 5H), 1.74 (dddd, J=13.3, 10.4, 8.7, 4.5 Hz, 1H), 0.79 (d, J=6.2 Hz, 3H). $^{13}$C NMR (101 MHz, $CDCl_3$) δ 158.16, 149.13, 146.79, 136.83, 136.25, 133.97, 131.94, 125.94, 122.68, 121.64, 119.91, 73.31, 67.88, 64.45, 59.67, 52.75, 51.92, 50.57, 48.53, 30.45, 29.77, 29.25, 26.47, 21.38, 14.26. HRMS calculated for $C_{25}H_{35}NO$ 407.28054; found 407.28014 [M+H].

CH. Synthesis of tert-butyl (R)-3-((methyl((S)-5,6,7,8-tetrahydroquinolin-8-yl)amino)methyl)-5-((R)-2-methylmorpholino)-3,4-dihydroisoquinoline-2(1H)-carboxylate

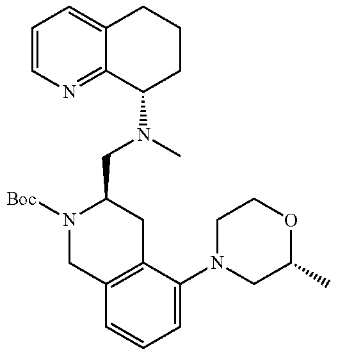 [SMILES: C[C@@H]1CN(c2cccc3c2C[C@H](CN(C)[C@H]2CCCc4cccnc42)N(C(=O)OC(C)(C)C)C3)CCO1]

A 5 mL microwave vial equipped with a stir bar was charged with 250 mg of the bromide (0.514 mmol, 1 equiv), 48.0 mg of BINAP (0.0772 mmol, 0.15 equiv), 335 mg of $Cs_2CO_3$ (1.03 mmol, 2 equiv), and 23.5 mg of $Pd_2(dba)_3$ (0.0257 mmol, 0.05 equiv), and the system was set under argon. Then 67.6 mg of the amine (0.668 mmol, 1.3 equiv) and 2.6 mL of toluene (degassed by bubbling argon for 1.5 h) were added. After stirring at 125° C. for 12 h, EA was added and the suspension was filtered through a celite plug. The organics were concentrated, and the crude product was purified on a silica gel column (80 g) using 0 to 50% EA in hexanes as eluent affording the product as a yellow foam.

CI. Synthesis of (S)—N-methyl-N—(((R)-5-((R)-2-methylmorpholino)-1,2,3,4-tetrahydroisoquinolin-3-yl)methyl)-5,6,7,8-tetrahydroquinolin-8-amine (EMU-317)

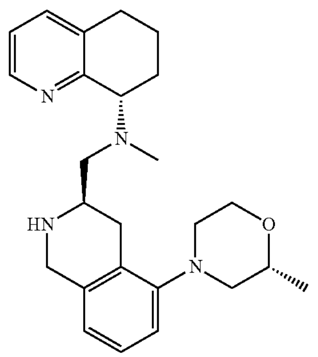 [SMILES: C[C@@H]1CN(c2cccc3c2C[C@H](CN(C)[C@H]2CCCc4cccnc42)NC3)CCO1]

A 20 mL vial equipped with a stir bar was charged with 110 mg of the amine (0.217 mmol, 1 equiv) dissolved in 2.2 mL of $CH_2Cl_2$. Then 0.50 mL of $CF_3COOH$ (6.51 mmol, 30 equiv) was added. After stirring at room temperature for 12 h, the reaction mixture was cooled in an ice bath and quenched by addition of a saturated $Na_2CO_3$ solution, extracted with $CH_2Cl_2$ (3×), and dried over $Na_2SO_4$. The crude material was purified on a silica gel column (12 g) using 0 to 30% solvent 5 (solvent 5=0.5 M $NH_3$ in 30% MeOH in $CH_2Cl_2$) in $CH_2Cl_2$ as eluent affording the product as a white sticky foam. $^1$H NMR (400 MHz, $CDCl_3$) δ 8.48

(dd, J=4.6, 1.4 Hz, 1H), 7.35 (d, J=7.5 Hz, 1H), 7.09 (t, J=7.9 Hz, 1H), 7.07 (dd, J=7.8, 4.6 Hz, 1H), 6.86 (d, J=7.8 Hz, 1H), 6.78 (d, J=7.3 Hz, 1H), 4.05 (A of AB, $J_{AB}$=15.4 Hz, 1H), 3.99-3.89 (m, 3H), 3.81-3.73 (m, 2H), 3.02 (td, J=11.2, 3.1 Hz, 1H), 2.92 (dt, J=11.9, 1.9 Hz, 1H), 2.89-2.65 (m, 5H), 2.55 (s, 3H), 2.54-2.44 (m, 2H), 2.23 (dd, J=12.0, 9.8 Hz, 1H), 2.19-1.92 (m, 4H), 1.79-1.64 (m, 1H), 1.61 (br s, 1H), 1.14 (d, J=6.3 Hz, 3H). $^{13}C$ NMR (151 MHz, $CDCl_3$) δ 158.18, 151.00, 146.85, 137.08, 136.63, 133.82, 130.11, 126.06, 122.03, 121.52, 116.76, 72.09, 67.27, 64.47, 59.95, 59.14, 51.65, 50.93, 48.84, 41.58, 30.29, 29.23, 26.29, 21.27, 18.86. LC-MS (ESI-API, 254 nm) 10-95% MeOH in $H_2O$ (0.1% $HCO_2H$), 0.6 mL/min, C18 column (Agilent Zorbax XDB-C18, 50 mm×2.1 mm, 3.5 μm), m z=407.5 (M+H), 204.4 (M/2+H), t=3.572 min. HRMS (ESI+) calculated for $C_{25}H_{35}ON_4$ ([M+H]+): 407.28054; found: 407.28018.

CJ. Synthesis of tert-butyl (R)-5-((R)-2-(hydroxymethyl)morpholino)-3-((methyl((S)-5,6,7,8-tetrahydroquinolin-8-yl)amino)methyl)-3,4-dihydroisoquinoline-2(1H)-carboxylate

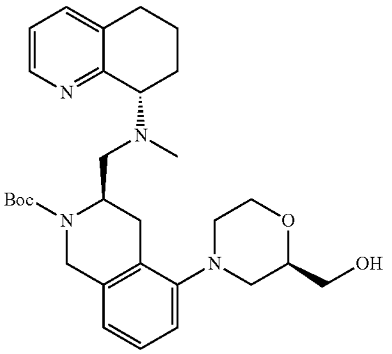 [SMILES: CN(C[C@H]1Cc2c(cccc2N2CCO[C@@H](CO)C2)CN1C(=O)OC(C)(C)C)[C@H]1CCCc2cccnc21]

A 5 mL microwave vial equipped with a stir bar was charged with 196 mg of the amine salt (1.28 mmol, 2.5 equiv) and 123 mg of NaOtBu (1.28 mmol, 2.5 equiv) and the vial was set under argon. Then 4.0 mL of dry dioxane was added and the suspension was stirred at 100° C. for 16 h. The reaction mixture was cooled and let to sit for 3 h. The clear liquid was separated by syringe and filtered (syringe filter) to another 5 mL microwave vial, and the solution was degassed by bubbling argon for 1.5 h. A third 5 mL microwave vial equipped with a stir bar was charged with 250 mg of the bromide (0.514 mmol, 1 equiv), 48.0 mg of BINAP (0.0772 mmol, 0.15 equiv), 419 mg of $Cs_2CO_3$ (1.28 mmol, 2.5 equiv), and 23.5 mg of $Pd_2(dba)_3$ (0.0257 mmol, 0.05 equiv), and the system was set under argon. Then the dioxane solution was added. After stirring at 120° C. for 12 h, EA was added and the suspension was filtered through a celite plug. The organics were concentrated and the crude product was purified on a silica gel column (40 g) using 0 to 100% EA in hexanes as eluent affording the product as a yellow foam.

CK. Synthesis of ((R)-4-((R)-3-((methyl((S)-5,6,7,8-tetrahydroquinolin-8-yl)amino)methyl)-1,2,3,4-tetrahydroisoquinolin-5-yl)morpholin-2-yl)methanol (EMU-322)

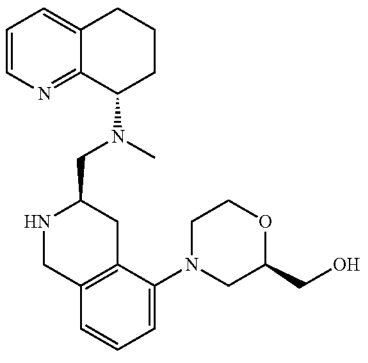 [SMILES: CN(C[C@H]1Cc2c(cccc2N2CCO[C@@H](CO)C2)CN1)[C@H]1CCCc2cccnc21]

A 20 mL vial equipped with a stir bar was charged with 110 mg of the amine (0.211 mmol, 1 equiv) dissolved in 2.1 mL of $CH_2Cl_2$. Then 0.49 mL of $CF_3COOH$ (6.31 mmol, 30 equiv) was added. After stirring at room temperature for 12 h, the reaction mixture was cooled in an ice bath, quenched by addition of a saturated $Na_2CO_3$ solution, extracted with $CH_2Cl_2$ (3×), and dried over $Na_2SO_4$. The crude material was purified on a silica gel column (12 g) using 0 to 30% Solvent 5 (solvent 5=0.5 M $NH_3$ in 30% MeOH in $CH_2Cl_2$) in $CH_2Cl_2$ as eluent affording the title compound as a white foam (87% yield). $^1H$ NMR (600 MHz, $CDCl_3$) δ 8.48 (d, J=3.2 Hz, 1H), 7.35 (dd, J=7.7, 1.6 Hz, 1H), 7.10 (t, J=7.8 Hz, 1H), 7.07 (dd, J=7.7, 4.7 Hz, 1H), 6.85 (d, J=7.8 Hz, 1H), 6.79 (d, J=7.6 Hz, 1H), 4.06 (A of AB, $J_{AB}$=15.4 Hz, 1H), 3.98-3.92 (m, 3H), 3.83 (td, J=10.8, 2.5 Hz, 1H), 3.80-3.74 (m, 2H), 3.69-3.65 (m, 1H), 2.96-2.74 (m, 8H), 2.69 (dt, J=16.4, 4.7 Hz, 1H), 2.59 (td, J=12.4, 11.4, 3.0 Hz, 1H), 2.52 (s, 3H), 2.25 (br s, 1H), 2.18-2.12 (m, 1H), 2.10-1.92 (m, 3H), 1.77-1.67 (m, 1H), 1.70 (br s, 1H). $^{13}C$ NMR (151 MHz, $CDCl_3$) δ 158.09, 150.83, 146.85, 137.02, 136.66, 133.87, 130.06, 126.11, 122.11, 121.54, 116.72, 76.30, 66.88, 64.20, 63.81, 59.88, 52.73, 52.29, 51.58, 48.83, 41.50, 30.39, 29.26, 25.99, 21.32. LC-MS (ESI-API, 254 nm) 10-95% MeOH in $H_2O$ (0.1% $HCO_2H$), 0.6 mL/min, C18 column (Agilent Zorbax XDB-C18, 50 mm×2.1 mm, 3.5 μm), m z=423.5 (M+H), 212.3 (M/2+H), t=2.672 min. HRMS (ESI+) calculated for $C_{25}H_{35}O_2N_4$ ([M+H]+): 423.27545; found: 423.27599.

CL. Synthesis of tert-butyl (R)-5-((1S,4R)-2-oxa-6-azabicyclo[2.2.1]heptan-6-yl)-3-((methyl((S)-5,6,7,8-tetrahydroquinolin-8-yl)amino)methyl)-3,4-dihydroisoquinoline-2(1H)-carboxylate

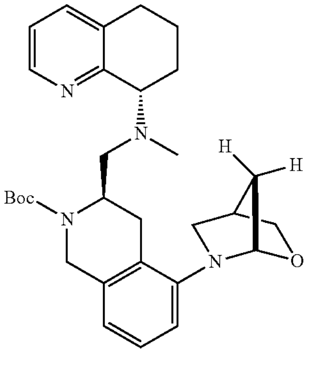 [SMILES: CN(C[C@H]1Cc2c(cccc2N2CC3CO[C@@H]2C3)CN1C(=O)OC(C)(C)C)[C@H]1CCCc2cccnc21]

To a 5 mL microwave vial was added 249.5 mg (0.51 mmol) of tert-butyl (3R)-5-bromo-3-[[methyl-[(8S)-5,6,7,8-tetrahydroquinolin-8-yl]amino]methyl]-3,4-dihydro-1H-isoquinoline-2-carboxylate, 101 mg (1.02 mmol) of (1R, 4R)-2-oxa-5-azabicyclo[2.2.1]heptane, 16.2 mg (0.051 mmol) of (±)-2,2'-bis(diphenylphosphino)-1,1'-binaphthyl, 21.5 mg (0.024 mmol) of tris(dibenzylideneacetone)dipalladium, and 204.7 mg (0.63 mmol) of cesium carbonate. The solids were diluted with 3 mL of degassed, dry toluene and the resulting solution was degassed further with argon for 1.5 hours. The vial was then heated for three 24-hour periods at 100° C. The vial was cooled, diluted with ethyl acetate, and stirred with silica gel. The solution was then filtered over a pad of silica gel with additional ethyl acetate, followed by solvent removal. The residue was then subjected to column chromatography (Teledyne ISCO Combiflash, 24 g silica gel column, hexanes/ethyl acetate gradient) to afford the title compound as a light-yellow foam (59.1% yield).

CM. Synthesis of (S)—N—(((R)-5-((1S,4R)-2-oxa-6-azabicyclo[2.2.1]heptan-6-yl)-1,2,3,4-tetrahydroisoquinolin-3-yl)methyl)-N-methyl-5,6,7,8-tetrahydroquinolin-8-amine (EMU-324)

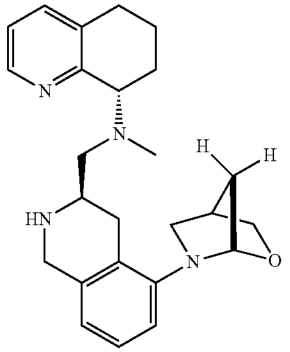 [SMILES: CN(C[C@H]1Cc2c(cccc2N2CC3CO[C@@H]2C3)CN1)[C@H]1CCCc2cccnc21]

tert-Butyl (R)-5-((1S,4R)-2-oxa-6-azabicyclo[2.2.1]heptan-6-yl)-3-((methyl((S)-5,6,7,8-tetrahydroquinolin-8-yl)amino)methyl)-3,4-dihydroisoquinoline-2(1H)-carboxylate (188.1 mg, 0.36 mmol) was dissolved in 5 mL trifluoroacetic acid. The mixture was stirred at room temperature overnight. Then 6 mL of a 6 M NaOH solution was added followed by 10 mL of DCM and the reaction was stirred for 10 minutes. The organic layer was separated and washed with a NaCl solution. The aqueous layer was re-extracted with DCM. Combined organic layer was combined and dried over $Na_2SO_4$. Filtration and solvent removal gave a dark yellow viscous oil. The residue was basified by adding 6 mL of 6 M NaOH (aq) until the pH reached 14. The aqueous layer was extracted with $Et_2O$. The ether layer was separated and washed with a NaCl solution, followed by separation and drying over $N_2SO_4$. Filtration, solvent removal, and column chromatography (DCM/[80% DCM, 20% (MeOH—$NH_3$ (7N))] gradient) gave the title compound as an off-white foam (80% yield). $^1$H NMR ($CDCl_3$, 400 MHz) δ 1.68 (m, 1H), 1.86 (m, 1H), 1.93 (m, 2H), 2.01 (m, 1H), 2.22 (ABX, J=10.8 Hz, z=5.2 Hz), 2.46 (s, 3H), 2.54 (m, 1H), 2.69 (m, 2H), 2.74 (m, 1H), 2.93 (d, 1H, J=9.2 Hz), 3.65 (dd, 1H, J=2 Hz, J=9.6 Hz), 3.83 (dd, 1H, J=1.6 Hz, J=7.6 Hz), 3.94 (m, 2H), 4.06 (d, 2H, J=9.2 Hz), 4.22 (d, 1H, J=7.6 Hz), 4.51 (s, 1H), 6.49 (d, 1H, J=8 Hz), 6.57 (d, 1H, J=7.2 Hz), 6.98 (t, 1H, J=8 Hz), 7.02 (dd, 1H, J=4.8 Hz, J=7.6 Hz), 7.32 (d, 1H, J=8 Hz), 8.42 (dd, 1H, J=1.6 Hz, J=4.8 Hz). $^{13}$C NMR ($CDCl_3$, 100 MHz) δ 21.3, 25.36, 29.25, 32.49, 36.33, 40.96, 48.69, 51.67, 59.7, 60.19, 64.44, 71.05, 76.96, 76.99, 113.22, 118.36, 121.56, 125.44, 125.56, 133.93, 136.71, 136.86, 146.83, 147.89, 157.88. HRMS: $C_{25}H_{33}N_4O$, calculated 405.26489; found, 405.26552. LC-MS: 95.82% (75-95% CAN, 254 nm); 99.07% TIC (M+H$^+$ for 405 m/z).

CN. Synthesis of tert-butyl (R)-5-((1R,4R)-2-oxa-5-azabicyclo[2.2.1]heptan-5-yl)-3-((methyl((S)-5,6,7,8-tetrahydroquinolin-8-yl)amino)methyl)-3,4-dihydroisoquinoline-2(1H)-carboxylate

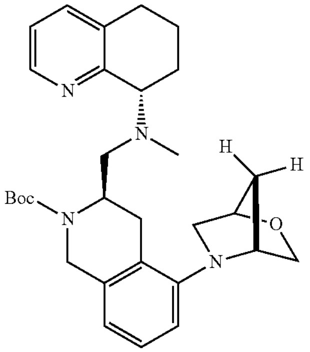

To a 5 mL microwave vial was added 257.8 mg (0.53 mmol) of tert-butyl (3R)-5-bromo-3-[[methyl-[(8S)-5,6,7,8-tetrahydroquinolin-8-yl]amino]methyl]-3,4-dihydro-1H-isoquinoline-2-carboxylate, 107 mg (0.97 mmol) of (1S,4S)-2-oxa-5-azabicyclo[2.2.1]heptane, 18.3 mg (0.029 mmol) of (±)-2,2'-bis(diphenylphosphino)-1,1'-binaphthyl, 21.9 mg (0.024 mmol) of tris(dibenzylideneacetone)dipalladium, and 215.1 mg (0.66 mmol) of cesium carbonate. The solids were diluted with 3 mL of degassed, dry toluene and the resulting solution was degassed further with argon for 1.5 hours. The vial was then heated for three 24-hour periods at 100° C. The vial was cooled, diluted with ethyl acetate, and stirred with silica gel. The solution was then filtered over a pad of silica gel with additional ethyl acetate, followed by solvent removal. The residue was then subjected to column chromatography (Teledyne ISCO Combiflash, 24 g silica gel column, hexanes/ethyl acetate gradient) to afford the title compound as an orange foam (60.4% yield).

CO. Synthesis of (S)—N—(((R)-5-((1R,4R)-2-oxa-5-azabicyclo[2.2.1]heptan-5-yl)-1,2,3,4-tetrahydroisoquinolin-3-yl)methyl)-N-methyl-5,6,7,8-tetrahydroquinolin-8-amine (EMU-325)

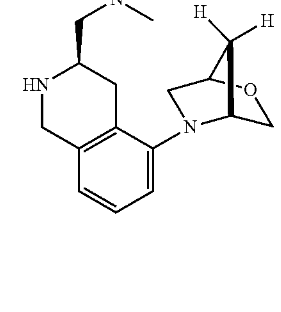

tert-Butyl (R)-5-((1R,4R)-2-oxa-5-azabicyclo[2.2.1]heptan-5-yl)-3-((methyl((S)-5,6,7,8-tetrahydroquinolin-8-yl)amino)methyl)-3,4-dihydroisoquinoline-2(1H)-carboxylate was dissolved in 3 mL of 1,4-dioxane and then 0.6 mL of a 4 M HCl/1,4-dioxane solution was added. The mixture was stirred for 1.5 hours during which time a clumpy, light-yellow solid had formed. Next, 20 drops of $H_2O$ were added and the clumpy solid dissolved then turned into a slurry over the course of an additional hour of stirring. Then an additional 0.6 mL of the HCl/dioxane solution was added. The slurry dissolved immediately, and the resulting light-yellow solution was stirred overnight. Next, 5 mL of a 6 M NaOH solution was added, adjusting the pH of the resulting solution to 14, followed by the addition of 20 mL of $Et_2O$. The ether layer was separated and washed with a NaCl solution, followed by drying over $Na_2SO_4$. The aqueous layer was re-extracted two more times. Combined organic layer was dried over $Na_2SO_4$, followed by solvent removal. Column chromatography (DCM/[80% DCM, 20% (MeOH—$NH_3$ (7N))] gradient) followed by solvent removal gave the title compound as a white foam (86.5% yield). $^1$H NMR ($CDCl_3$, 400 MHz) δ 1.7 (m, 1H), 1.89 (m, 2H), 1.92 (m, 2H), 1.99 (m, 2H), 2.44 (s, 3H), 2.67 (m, 1H), 2.76 (m, 2H), 2.86 (m, 2H), 3.48 (d, 1H, J=9.6 Hz), 3.74 (dd, 1H, J=2.4 Hz, J=7.6), 3.88 (d, 1H, J=7.2 Hz), 3.98 (m, 1H), 4.11 (m, 2H), 4.55 (s, 1H), 6.65 (d, 1H, J=7.6 Hz), 6.83 (d, 1H, J=8 Hz), 7.03 (t, 1H, J=7.6 Hz), 7.06 (m, 1H), 7.33 (d, 1H, J=8 Hz), 8.43 (dd, 1H, J=1.6 Hz, J=4.8 Hz). $^{13}$C NMR ($CDCl_3$, 100 MHz) δ 21.32, 25.13, 29.26, 31.52, 35.39, 40.65, 48.42, 51.7, 59.77, 59.85, 60.65, 64.5, 73.43, 77.76, 77.79, 114.45, 119.74, 121.57, 125.73, 127.74, 133.89, 136.75, 146.82, 149.39, 157.78. HRMS: $C_{25}H_{33}N_4O$, calculated 405.26489; found, 405.26558. LC-MS: 99.67%, 10-95% MeOH at 254 nm; 96.27% TIC (M+H 405 m/z).

CP. Synthesis of ethyl 3-(8-oxo-5,6,7,8-tetrahydroquinolin-7-yl)propanoate

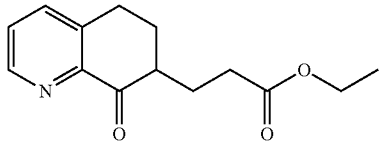 [SMILES: CCOC(=O)CCC1CCc2cccnc2C1=O]

The title compound was synthesized via a procedure described in PCT Patent Application Publication No. WO2006/096444. To a solution of 6,7-dihydro-5H-quinolin-8-one (12.00 g, 81.54 mmol) in benzene (300 mL) was added p-toluenesulfonic acid monohydrate (1.55 g, 8.15 mmol) and pyrrolidine (13.49 mL, 163.08 mmol). The reaction mixture was heated to reflux under Dean-Stark trap for 16 hours. The reaction mixture was cooled down to room temperature and concentrated down. The residue was taken up in toluene, concentrated, and dried under vacuum. The residue was dissolved in ethanol (300 mL) and ethyl prop-2-enoate (12.45 mL, 114.15 mmol) was added. The reaction solution was heated at 78° C. for 4 hours and allowed to cool to room temperature. The reaction mixture was concentrated to almost half volume, followed by the addition of 150 mL water and extraction with DCM (100 mL) three times. Combined organic layer was dried over anhydrous $MgSO_4$ and filtered, followed by solvent evaporation. The residue was purified with column chromatography by starting with hexanes:EtOAc (1:1) and increasing the polarity to 100% EtOAc to give the title compound as a brown oil (50% yield).

CQ. Synthesis of ethyl 3-((7R,8S)-8-(((S)-1-(4-methoxyphenyl)ethyl)amino)-5,6,7,8-tetrahydroquinolin-7-yl)propanoate

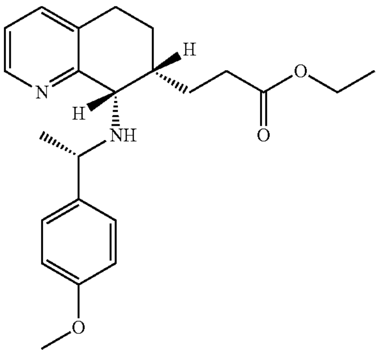 [SMILES: CCOC(=O)CC[C@H]1CCc2cccnc2[C@H]1N[C@@H](C)c1ccc(OC)cc1]

To a solution of ethyl 3-(8-oxo-6,7-dihydro-5H-quinolin-7-yl)propanoate (10.00 g, 40.44 mmol) in toluene (350 mL) was added p-toluenesulfonic acid monohydrate (0.77 g, 4.04 mmol) and rac-(1S)-1-(4-methoxyphenyl)ethanamine (8.96 mL, 60.66 mmol). The reaction mixture was refluxed under a Dean-Stark trap for 4 hours. The reaction mixture was cooled to room temperature and evaporated and the residue was dissolved in DCE (350 mL). Sodium triacetoxyborohydride (25.71 g, 121.32 mmol) was added and stirred at room temperature overnight. The reaction mixture was diluted with DCE (350 mL) and washed with water. Organic phase was dried over anhydrous $Na_2SO_4$ and filtered, followed by solvent evaporation. The residue was purified with column chromatography by starting with hexanes:EtOAc (5:1) and increasing the polarity with EtOAc to give the product (55% yield).

CR. Synthesis of 3-((7R,8S)-8-(((S)-1-(4-methoxyphenyl)ethyl)amino)-5,6,7,8-tetrahydroquinolin-7-yl)propan-1-ol

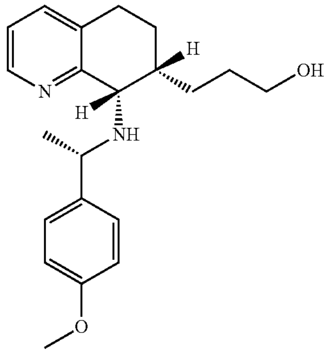 [SMILES: COc1ccc([C@H](C)N[C@@H]2c3ncccc3CC[C@@H]2CCCO)cc1]

To a 0° C. solution of ethyl 3-[(7R,8S)-8-[[(1S)-1-(4-methoxyphenyl)ethyl]amino]-5,6,7,8-tetrahydroquinolin-7-yl]propanoate (8.55 g, 22.35 mmol) in THF (250 mL) was added dropwise 2 M solution of lithium aluminum hydride (11.18 ml, 22.35 mmol) in THF. The reaction mixture was stirred for 1 hour at 0° C. and sequentially quenched with 0.33 mL water, 0.33 mL 1 N NaOH solution, and 0.99 ml water. The mixture was diluted with 250 mL THE and allowed to warm to room temperature. The reaction mixture was stirred at room temperature for 30 minutes and solids filtered off. The filtrate was concentrated and the residue was purified with column chromatography by starting with DCM and increasing the polarity with DCM:MeOH:$NH_3$ (7 N in methanol) (9:1:0.2) to give a yellow color oil.

CS. Synthesis of (4aR,10bS)-1-((S)-1-(4-methoxyphenyl)ethyl)-1,2,3,4,4a,5,6,10b-octahydro-1,10-phenanthroline

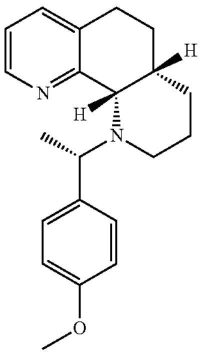 [SMILES: COc1ccc([C@H](C)N2CCC[C@H]3CCc4cccnc4[C@H]32)cc1]

To a solution of 3-[(7R,8S)-8-[[(1S)-1-(4-methoxyphenyl)ethyl]amino]-5,6,7,8-tetrahydroquinolin-7-yl]propan-1-ol (5.60 g, 16.45 mmol) and N,N-diisopropylethylamine (4.30 mL, 24.67 mmol) in DCM (75 mL) was added methanesulfonyl chloride (1.67 mL, 21.38 mmol) dropwise. 4-Dimethylaminopyridine (0.20 g, 1.64 mmol) was added to the reaction mixture and stirred for 16 hours at room temperature. The reaction mixture was diluted with 100 mL water. Aqueous phase was extracted with DCM twice. Combined organic layer was dried over anhydrous $Na_2SO_4$ and filtered, followed by solvent evaporation. The residue was purified with column chromatography by starting with DCM and increasing the polarity with DCM:MeOH:$NH_3$ (7 N in methanol) (9:1:0.2).

CT. Synthesis of (4aR,10bS)-1,2,3,4,4a,5,6,10b-octahydro-1,10-phenanthroline

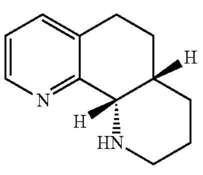 [SMILES: c1cnc2c(c1)CC[C@@H]1CCCN[C@H]21]

rac-(4aR,10bS)-1-[rac-(1S)-1-(4-Methoxyphenyl)ethyl]-3,4,4a,5,6,10b-hexahydro-2H-1,10-phenanthroline (0.75 g, 2.33 mmol) was dissolved in DCM (5 mL), and trifluoroacetic acid (3.58 mL, 46.52 mmol) was added to the reaction solution. It was stirred at room temperature overnight. The reaction mixture was diluted with EtOAc and water and stirred for 30 minutes. The phases were separated. The organic phase was washed with water. Combined water phase was basified with 1 N NaOH to reach pH>12 and extracted with DCM several times. Combined organic layer was dried over anhydrous $MgSO_4$ and filtered, followed by solvent evaporation. The product was used as it was for the next step.

CU. Synthesis of tert-butyl (R)-5-bromo-3-(((4aR,10bS)-3,4,4a,5,6,10b-hexahydro-1,10-phenanthrolin-1(2H)-yl)methyl)-3,4-dihydroisoquinoline-2(1H)-carboxylate

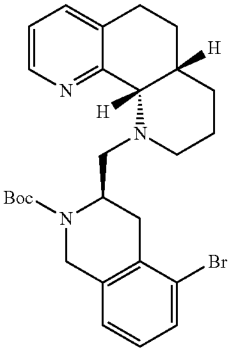 [SMILES: CC(C)(C)OC(=O)N1Cc2cccc(Br)c2C[C@@H]1CN1CCC[C@H]2CCc3cccnc3[C@H]21]

(4aR,10bS)-1,2,3,4,4a,5,6,10b-Octahydro-1,10-phenanthroline (0.43 g, 2.29 mmol) was dissolved in DCM (10 mL) and added sodium triacetoxyborohydride (0.88 g, 4.17 mmol) and acetic acid (0.12 mL, 2.09 mmol). The reaction mixture was stirred for a few minutes and then added tert-butyl (3R)-5-bromo-3-formyl-3,4-dihydro-1H-isoquinoline-2-carboxylate (0.71 g, 2.09 mmol). It was stirred overnight at room temperature. The reaction was quenched with a saturated $NaHCO_3$ solution. Aqueous phase was extracted with DCM twice. Combined organic layer was dried over anhydrous $MgSO_4$ and filtered off, followed by solvent evaporation. The residue was purified using column chromatography with hexanes:EtOAc (1:1) to yield the title compound (85.4% yield).

CV. Synthesis of tert-butyl (R)-3-(((4aR,10bS)-3,4,4a,5,6,10b-hexahydro-1,10-phenanthrolin-1(2H)-yl)methyl)-5-(3-oxomorpholino)-3,4-dihydroisoquinoline-2(1H)-carboxylate

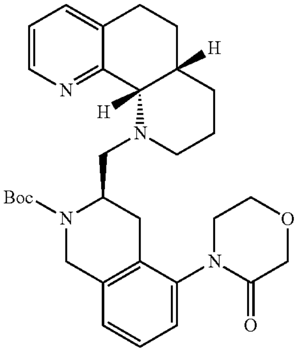 [SMILES: CC(C)(C)OC(=O)N1Cc2cccc(N3CCOCC3=O)c2C[C@@H]1CN1CCC[C@H]2CCc3cccnc3[C@H]21]

A mixture of tert-butyl (3R)-3-[[(4aR,10bS)-3,4,4a,5,6,10b-hexahydro-2H-1,10-phenanthrolin-1-yl]methyl]-5-bromo-3,4-dihydro-1H-isoquinoline-2-carboxylate (0.34 g, 0.67 mmol), morpholin-3-one (0.08 g, 0.8 mmol), N,N- dimethylethane-1,2-diamine (0.01 mL, 0.13 mmol), potassium carbonate (0.18 g, 1.33 mmol), and copper(I) iodide (0.01 g, 0.07 mmol) in anhydrous, degassed toluene (3 mL) was heated at 110° C. with stirring overnight. The reaction was poured to water and extracted with EtOAc twice. Combined organic layer was dried over anhydrous $MgSO_4$ and filtered, followed by solvent evaporation. The product was purified with column chromatography by starting with hexanes:EtOAc and increasing the polarity to 100% EtOAc and then to 10% MeOH in EtOAc to give the title compound (53.3% yield).

CW. Synthesis of 4-((R)-3-(((4aR,10bS)-3,4,4a,5,6,10b-hexahydro-1,10-phenanthrolin-1(2H)-yl)methyl)-1,2,3,4-tetrahydroisoquinolin-5-yl)morpholin-3-one (EMU-342)

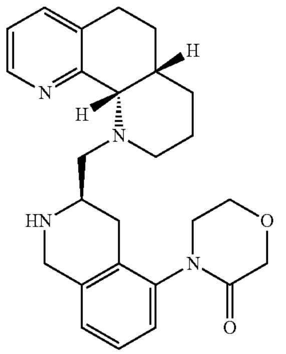 [SMILES: O=C1COCCN1c1cccc2c1C[C@H](CN1CCC[C@H]3CCc4cccnc4[C@H]31)NC2]

tert-Butyl (3R)-3-[[(4aR,10bS)-3,4,4a,5,6,10b-hexahydro-2H-1,10-phenanthrolin-1-yl]methyl]-5-(3-oxomorpholin-4-yl)-3,4-dihydro-1H-isoquinoline-2-carboxylate (0.19 g, 0.3500 mmol) was dissolved in DCM (5 mL) and added trifluoroacetic acid (0.27 mL, 3.55 mmol) at room temperature. It was stirred at room temperature overnight. The reaction mixture was basified with 1 N NaOH to pH>12 and extracted with DCM twice. Combined organic layer was dried over anhydrous $MgSO_4$ and filtered, followed by solvent evaporation. Residue was purified by starting with DCM and increasing the polarity with DCM:MeOH:$NH_3$ (7 N in methanol) (9:1:0.2). $^1$H NMR (600 MHz, $CDCl_3$) δ 8.41 (dd, J=4.9, 1.6 Hz, 0.25H), 8.39 (dd, J=4.7, 1.6 Hz, 0.75H), 7.42 (dd, J=7.6, 1.6 Hz, 1H), 7.17 (t, J=7.8 Hz, 1H), 7.11 (td, J=7.2, 4.7 Hz, 1H), 7.03-6.96 (m, 2H), 4.74 (s, 1.5H), 4.37 (dd, J=5.0, 2.5 Hz, 0.25H), 4.34 (d, J=2.2 Hz, 1.75H), 4.32 (d, J=4.9 Hz, 0.25H), 4.29 (s, 0.25H), 4.10-3.92 (m, 5H), 3.76-3.69 (ddd, J=11.6, 7.2, 4.0 Hz, 0.25H), 3.58 (ddd, J=11.6, 7.2, 4.0 Hz, 0.75H), 3.54-3.38 (m, 2H), 3.06 (m, 2H), 3.00-2.91 (m, 0.75H), 2.91-2.81 (m, 0.25H), 2.85-2.64 (m, 3H), 2.55 (dd, J=16.2, 3.7 Hz, 0.75H), 2.48 (dd, J=16.2, 3.7 Hz, 0.25H), 2.43-1.99 (m, 3H), 1.82-1.57 (m, 5H). $^{13}$C NMR (151 MHz, $CDCl_3$) δ 166.48, 165.93 (minor isomer), 157.45, 157.35 (minor isomer), 146.13 (minor isomer), 145.90, 140.10 (minor isomer), 139.99, 137.13, 136.98 (minor isomer), 133.67, 133.45 (minor isomer), 132.07, 126.85 (minor isomer), 126.82, 126.58, 126.55 (minor isomer), 124.87, 124.46, 124.30 (minor isomer), 122.53, 122.42 (minor isomer), 74.85, 68.47, 67.37, 66.92 (minor isomer), 64.23 (minor isomer), 63.60, 58.93, 51.27, 50.92 (minor isomer), 49.83 (minor isomer), 49.42, 34.13, 31.24, 29.31, 29.12 (minor isomer), 27.10, 26.97, 23.47 (minor isomer), 23.14, 22.03 (minor isomer), 21.82. HRMS calculated for $C_{26}H_{33}N_4O_2$ 433.2598; found 433.25934 [M+H].

CX. Synthesis of tert-butyl (R)-3-((((3,5-dimethylpyridin-2-yl)methyl)(methyl)amino)methyl)-5-(3-oxomorpholino)-3,4-dihydroisoquinoline-2(1H)-carboxylate

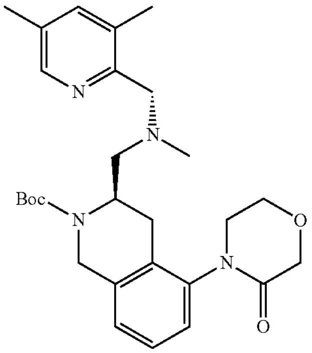

A mixture of tert-butyl (3R)-5-bromo-3-[[(3,5-dimethyl-2-pyridyl)methyl-methyl-amino]methyl]-3,4-dihydro-1H-isoquinoline-2-carboxylate (0.33 g, 0.6900 mmol), morpholin-3-one (0.08 g, 0.83 mmol), N,N-dimethylethane-1,2-diamine (0.01 mL, 0.14 mmol), potassium carbonate (0.19 g, 1.39 mmol), and copper(I) iodide (0.01 g, 0.07 mmol) in anhydrous degassed toluene (3 mL) was heated at 110° C. with stirring overnight. The reaction was poured to water and extracted with EtOAc twice. Combined organic layer was dried over anhydrous $MgSO_4$ and filtered, followed by solvent evaporation. The product was purified with column chromatography by starting with hexanes:EtOAc and increasing the polarity to 100% EtOAc and then to 10% MeOH in EtOAc.

CY. Synthesis of (R)-4-(3-((((3,5-dimethylpyridin-2-yl)methyl)(methyl)amino)methyl)-1,2,3,4-tetrahydroisoquinolin-5-yl)morpholin-3-one (EMU-340)

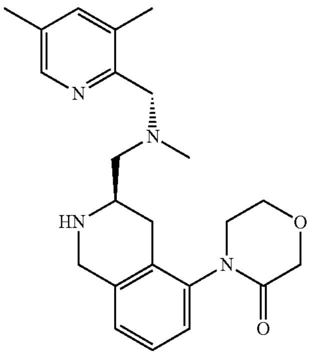

tert-Butyl (3R)-3-[[(3,5-dimethyl-2-pyridyl)methyl-methyl-amino]methyl]-5-(3-oxomorpholin-4-yl)-3,4-dihydro-1H-isoquinoline-2-carboxylate (0.25 g, 0.5 mmol) was dissolved in DCM (5 mL) and added trifluoroacetic acid (0.39 mL, 5.03 mmol) at room temperature. The reaction was stirred at room temperature overnight. The reaction was basified with 1 N NaOH solution to pH>12 and extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in methanol) (9:1:0.2) to isolate the title compound. $^1H$ NMR (400 MHz, $CDCl_3$) δ 8.22 (d, J=2.2 Hz, 1H), 7.29 (s, 1H), 7.22 (td, J=7.7, 3.8 Hz, 1H), 7.11-6.96 (m, 2H), 4.37 (s, 2H), 4.35 (d, J=3.9 Hz, 1H), 4.11-3.92 (m, 4H), 3.81-3.67 (m, 1H), 3.67-3.55 (m, 2H), 3.50 (dddd, J=17.9, 12.3, 5.7, 3.9 Hz, 1H), 3.03 (tt, J=10.2, 3.6 Hz, 1H), 2.70-2.43 (m, 3H), 2.41 (s, 3H), 2.33-2.27 (m, 7H). $^{13}C$ NMR (101 MHz, $CDCl_3$) δ 166.51, 153.74, 146.65, 140.01, 137.64, 132.14, 131.87, 130.80, 127.06, 126.89, 126.36, 125.08, 68.49, 64.12, 62.87, 51.04, 50.13, 49.46, 48.63, 43.23, 29.19, 18.33, 17.96. HRMS calculated for $C_{23}H_{31}N_4O_2$ 395.24415; found 395.24320 [M+H].

CZ. Synthesis of (S)—N—((S)-1-(4-methoxyphenyl)ethyl)-3,4-dihydro-2H-pyrano[3,2-b]pyridin-4-amine

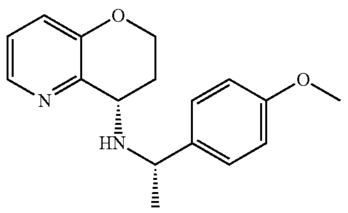 [SMILES: COc1ccc([C@H](C)N[C@H]2CCOc3cccnc32)cc1]

To a solution of 2,3-dihydropyrano[3,2-b]pyridin-4-one (2.38 g, 15.96 mmol) in anhydrous THE (50 mL), titanium (IV) isopropoxide (9.45 mL, 31.91 mmol) and (1S)-1-(4-methoxyphenyl)ethanamine (2.59 mL, 17.55 mmol) were added and stirred for four hours at room temperature. Sodium triacetoxyborohydride (10.68 g, 47.87 mmol) and methanol (12.5 mL) were added to the reaction mixture and stirred overnight at room temperature. The reaction mixture was quenched with a saturated $NaHCO_3$ solution, supplemented with EtOAc, and stirred for 30 minutes at room temperature. The phases were separated, and the aqueous phase was extracted with EtOAc three times. Combined organic layer was dried over anhydrous $Na_2SO_4$ and filtered, followed by solvent evaporation. The residue was purified with column chromatography using EtOAc:hexanes to afford the title compound (28.7% yield).

DA. Synthesis of (S)—N—((S)-1-(4-methoxyphenyl)ethyl)-N-methyl-3,4-dihydro-2H-pyrano[3,2-b]pyridin-4-amine

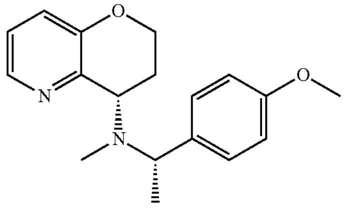 [SMILES: COc1ccc([C@H](C)N(C)[C@H]2CCOc3cccnc32)cc1]

To a solution of (4S)—N-[rac-(1S)-1-(4-methoxyphenyl)ethyl]-3,4-dihydro-2H-pyrano[3,2-b]pyridin-4-amine (1.20 g, 4.22 mmol) in DCE (12 mL) was added formaldehyde aqueous solution (0.94 mL, 12.66 mmol) and acetic acid (0.36 mL, 6.33 mmol). The reaction mixture was stirred for 15 minutes, and then sodium triacetoxyborohydride (1.79 g, 8.44 mmol) was added and stirred at room temperature for a few hours. The reaction mixture was diluted with DCM and quenched with saturated sodium bicarbonate solution. The organic layer was separated, dried over anhydrous $MgSO_4$, and filtered, followed by solvent evaporation, to afford the title compound (99.3% yield).

DB. Synthesis of (S)—N-methyl-3,4-dihydro-2H-pyrano[3,2-b]pyridin-4-amine

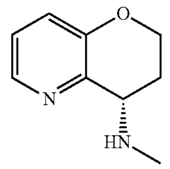

(4S)—N-Methyl-N-[rac-(1S)-1-(4-methoxyphenyl)ethyl]-3,4-dihydro-2H-pyrano[3,2-b]pyridin-4-amine (1.25 g, 4.19 mmol) was added to a flask and added trifluoroacetic acid (6.45 mL, 83.79 mmol) at room temperature and stirred at room temperature overnight. The reaction mixture was diluted with EtOAc and water and stirred for 30 minutes. The phases were separated, and the organic phase was washed with water. Combined water phase was basified with 1 N NaOH to pH>12 and extracted with DCM several times. Combined organic layer was dried over anhydrous $MgSO_4$ and filtered, followed by solvent evaporation. The product was used for the next step without further purification.

DC. Synthesis of tert-butyl (R)-5-bromo-3-((((S)-3,4-dihydro-2H-pyrano[3,2-b]pyridin-4-yl)(methyl)amino)methyl)-3,4-dihydroisoquinoline-2(1H)-carboxylate

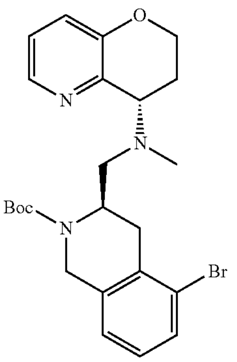 [SMILES: CN(C[C@H]1Cc2c(Br)cccc2CN1C(=O)OC(C)(C)C)[C@H]1CCOc2cccnc21]

(4S)—N-methyl-3,4-Dihydro-2H-pyrano[3,2-b]pyridin-4-amine (0.69 g, 4.2 mmol) was dissolved in DCM (10 mL) and added sodium triacetoxyborohydride (2.02 g, 9.55 mmol) and acetic acid (0.22 mL, 3.82 mmol). The reaction mixture was stirred for a few minutes and then added tert-butyl (3R)-5-bromo-3-formyl-3,4-dihydro-1H-isoquinoline-2-carboxylate (1.30 g, 3.82 mmol). The reaction was stirred at room temperature overnight. The reaction was quenched with a saturated $NaHCO_3$ solution. The aqueous phase was extracted with DCM three times. Combined organic layer was dried over anhydrous $MgSO_4$ and filtered, followed by solvent evaporation. The residue was purified with column chromatography by starting with hexanes and increasing the polarity with EtOAc.

DD. Synthesis of tert-butyl (R)-3-((((S)-3,4-dihydro-2H-pyrano[3,2-b]pyridin-4-yl)(methyl)amino)methyl)-5-(3-oxomorpholino)-3,4-dihydroisoquinoline-2(1H)-carboxylate

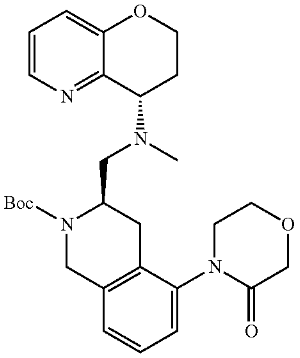 [SMILES: CN(C[C@H]1Cc2c(cccc2N2CCOCC2=O)CN1C(=O)OC(C)(C)C)[C@H]1CCOc2cccnc21]

A mixture of tert-butyl (3R)-5-bromo-3-[[[(4S)-3,4-dihydro-2H-pyrano[3,2-b]pyridin-4-yl]-methyl-amino]methyl]-3,4-dihydro-1H-isoquinoline-2-carboxylate (0.33 g, 0.67 mmol), morpholin-3-one (0.08 g, 0.8 mmol), N,N-dimethylethane-1,2-diamine (0.01 mL, 0.13 mmol), potassium carbonate (0.18 g, 1.33 mmol), and copper(I) iodide (0.01 g, 0.07 mmol) in anhydrous degassed toluene (3 mL) was heated to 110° C. with stirring overnight. The reaction was poured to water and extracted with EtOAc twice. Combined organic layer was dried over anhydrous $MgSO_4$ and filtered, followed by solvent evaporation. The product was purified with column chromatography by starting with hexanes:EtOAc and increasing the polarity to 100% EtOAc and then to 10% MeOH in EtOAc to give the title compound (83.0% yield).

DE. Synthesis of 4-((R)-3-((((S)-3,4-dihydro-2H-pyrano[3,2-b]pyridin-4-yl)(methyl)amino)methyl)-1,2,3,4-tetrahydroisoquinolin-5-yl)morpholin-3-one (EMU-341)

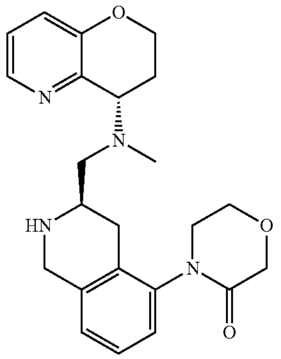 [SMILES: CN(C[C@H]1Cc2c(cccc2N2CCOCC2=O)CN1)[C@H]1CCOc2cccnc21]

tert-Butyl (3R)-3-[[[(4S)-3,4-dihydro-2H-pyrano[3,2-b]pyridin-4-yl]-methyl-amino]methyl]-5-(3-oxomorpholin-4-yl)-3,4-dihydro-1H-isoquinoline-2-carboxylate (0.28 g, 0.55 mmol) was dissolved in DCM (5 mL) and added trifluoroacetic acid (0.43 mL, 5.52 mmol) at room temperature. It was stirred at room temperature overnight. The reaction mixture was basified with 1 N NaOH to pH>12 and extracted with DCM twice. Combined organic layer was dried over anhydrous $MgSO_4$ and filtered, followed by solvent evaporation. Purification with column chromatography by starting with DCM and increasing the polarity with DCM:MeOH:$NH_3$ (7 N in methanol) (9:1:0.2) yielded the title compound. $^1$H NMR (600 MHz, $CDCl_3$) δ 8.21 (dd, J=3.9, 2.2 Hz, 0.25H), 8.19 (dd, J=3.9, 2.2 Hz, 0.75H), 7.20 (td, J=7.7, 4.2 Hz, 1H), 7.10 (dd, J=4.9, 2.5 Hz, 2H), 7.07-7.04 (m, 1H), 7.03 (d, J=7.7 Hz, 0.25H), 7.01 (d, J=7.7 Hz, 0.75H), 4.37 (ddd, J=12.6, 6.0, 2.8 Hz, 1H), 4.31 (A of AB, $J_{AB}$=17.5 Hz, 0.25H), 4.29 (s, 1.5H), 4.25 (B of AB, $J_{AB}$=16.5 Hz, 0.25H), 4.07 (A of AB, $J_{AB}$=15.8 Hz, 0.25H), 4.23-3.90 (m, 6H), 3.83 (B of AB, $J_{AB}$=15.2 Hz, 0.75H), 3.73 (ddd, J=12.3, 6.1, 4.3 Hz, 0.25H), 3.59 (ddd, J=12.3, 6.7, 4.0 Hz, 0.75H), 3.54-3.45 (m, 1H), 3.06-2.96 (m, 1H), 2.83 (d, J=12.7 Hz, 0.75H), 2.73 (dd, J=13.0, 4.3 Hz, 0.25H), 2.64-2.50 (m, 2H), 2.46 (s, 2H), 2.45 (s, 1H), 2.41-2.15 (m, 2H), 2.13-2.01 (m, 1H). $^{13}$C NMR (151 MHz, $CDCl_3$) δ 166.52, 166.02 (minor isomer), 152.58, 152.53 (minor isomer), 144.33 (minor isomer), 144.21, 141.39 (minor isomer), 141.22, 140.16 (minor isomer), 140.01, 132.36, 131.58, 127.19 (minor isomer), 126.86, 126.31, 125.28, 124.48, 124.27 (minor isomer), 123.53, 123.46 (minor isomer), 74.86, 68.49, 65.00, 64.25 (minor isomer), 64.13, 60.30 (minor isomer), 60.24, 59.65 (minor isomer), 59.27, 53.42, 51.52, 51.33 (minor isomer), 50.13, 48.96, 25.65, 25.54 (minor isomer). HRMS calculated for $C_{23}H_{29}N_4O_3$ 409.22342; found 582.39659 [M+H].

DF. Synthesis of tert-butyl 3-((((S)-3,4-dihydro-2H-pyrano[3,2-b]pyridin-4-yl)(methyl)amino)methyl)-5-morpholino-3,4-dihydroisoquinoline-2(1H)-carboxylate

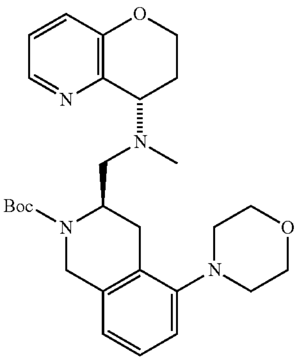

A 5 mL microwave vial equipped with a stir bar was charged with tert-butyl (R)-5-bromo-3-((((S)-3,4-dihydro-2H-pyrano[3,2-b]pyridin-4-yl)(methyl)amino)methyl)-3,4-dihydroisoquinoline-2(1H)-carboxylate (0.251 g, 0.514 mmol, 1 equiv), 48.0 mg of BINAP (0.0772 mmol, 0.15 equiv), 335 mg of $Cs_2CO_3$ (1.03 mmol, 2 equiv), and 23.5 mg of $Pd_2(dba)_3$ (0.0257 mmol, 0.05 equiv), and the system was set under argon atmosphere. Then 0.06 mL of morpholine (0.668 mmol, 1.3 equiv) and 2.6 mL of toluene (degassed by bubbling argon for 1.5 h) were added. After stirring at 125° C. for 12 h, EA was added, and the suspension was filtered through a celite plug. The organics were concentrated, and the residue was purified with EtOAc: hexanes to afford the title compound (81% yield).

DG. Synthesis of (4S)—N-methyl-N-((5-morpholino-1,2,3,4-tetrahydroisoquinolin-3-yl)methyl)-3,4-dihydro-2H-pyrano[3,2-b]pyridin-4-amine (EMU-319)

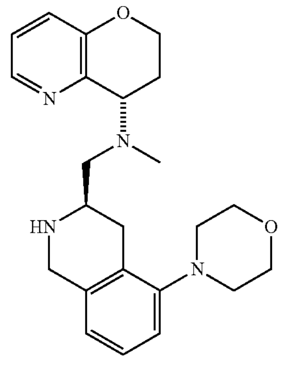

tert-Butyl (3R)-3-[[[(4S)-3,4-dihydro-2H-pyrano[3,2-b]pyridin-4-yl]-methyl-amino]methyl]-5-(4-methylpiperazin-1-yl)-3,4-dihydro-1H-isoquinoline-2-carboxylate (0.207 g, 0.42 mmol) was dissolved in DCM (5 mL), and trifluoroacetic acid (0.56 mL, 4.2 mmol) was added to the solution. The reaction was stirred overnight at room temperature. The reaction was basified with 1 N NaOH to pH>12 and the phases were separated. The aqueous phase was extracted with DCM three times. Combine organic layer was dried over anhydrous $MgSO_4$ and filtered, followed by solvent evaporation. The residue was purified with column chromatography by starting with DCM and increasing the polarity with DCM:MeOH:$NH_3$ (7 N in MeOH) (90:10:2) to afford the title compound (64.06% yield). $^1H$ NMR (600 MHz, $CDCl_3$) δ 8.18 (t, J=3.0 Hz, 1H), 7.28 (t, J=7.8 Hz, 1H), 7.25 (d, J=3.0 Hz, 2H), 7.13 (dd, J=8.0, 1.1 Hz, 1H), 7.03 (dd, J=7.7, 1.1 Hz, 1H), 4.44-4.38 (m, 3H), 4.23 (dd, J=10.4, 6.0 Hz, 1H), 4.17 (td, J=11.3, 2.2 Hz, 1H), 3.69 (tt, J=10.5, 4.2 Hz, 1H), 3.29-3.28 (m, 1H), 3.26 (d, J=4.5 Hz, 1H), 3.17-3.10 (m, 2H), 3.05-3.02 (m, 8H), 3.00-2.93 (m, 1H), 2.76 (dd, J=17.3, 10.5 Hz, 1H), 2.66 (s, 3H), 2.27 (dddd, J=14.1, 11.4, 10.3, 3.9 Hz, 1H), 2.11 (s, 3H). $^{13}C$ NMR (151 MHz, MeOD) δ 153.66, 150.05, 143.07, 140.78, 129.61, 127.69, 127.02, 125.47, 123.98, 122.73, 119.29, 72.97, 65.39, 61.13, 57.58, 54.25, 51.64, 43.80, 42.98, 33.60, 25.32, 20.51. HRMS calculated for $C_{24}H_{34}N_5O$ 408.27579, found 408.27576 [M+H].

DH. Synthesis of (R)—N-(4-morpholinobutyl)-N—(((S)-5,6,7,8-tetrahydro-1,6-naphthyridin-7-yl) methyl)-5,6,7,8-tetrahydroquinolin-8-amine (EMU-204)

The title compound was synthesized according to the scheme below (reagents and conditions: (i) $CH_3COOH$, $NaBH(OAc)_3$, DCE, room temperature, 70-93%; (ii) $CF_3COOH$, $CH_2Cl_2$, rt, 40-100%). $^1H$ NMR (600 MHz, $CDCl_3$) δ 8.49 (d, J=4.4 Hz, 1H), 8.35 (d, J=4.5 Hz, 1H), 7.33 (d, J=6.9 Hz, 1H), 7.32 (d, J=6.9 Hz, 1H), 7.04 (dd, J=7.6, 4.7 Hz, 1H), 7.02 (dd, J=7.7, 4.7 Hz, 1H), 4.07-4.00 (m, 3H), 3.69 (t, J=4.7 Hz, 4H), 2.99-2.92 (m, 1H), 2.82-2.75 (m, 3H), 2.72-2.48 (m, 5H), 2.41 (br s, 4H), 2.30 (t, J=7.1 Hz, 2H), 2.17-2.11 (m, 1H), 2.04-1.98 (m, 1H), 1.88-1.65 (m, 3H), 1.58-1.43 (m, 4H). $^{13}C$ NMR (400 MHz, $CDCl_3$) δ 157.84, 155.32, 147.20, 147.10, 136.42, 134.18, 134.04, 131.26, 121.60, 120.66, 66.89, 61.01, 58.81, 57.82, 53.62, 52.85, 52.14, 47.85, 37.08, 29.33, 27.15, 24.29, 24.23, 21.48. HRMS (ESI+) calculated for $C_{26}H_{38}N_5O$ ([M+H]+) 436.3071, found 436.3066. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m z=436.2 (M+H), 218.6 (M/2+H), t=0.535 min.

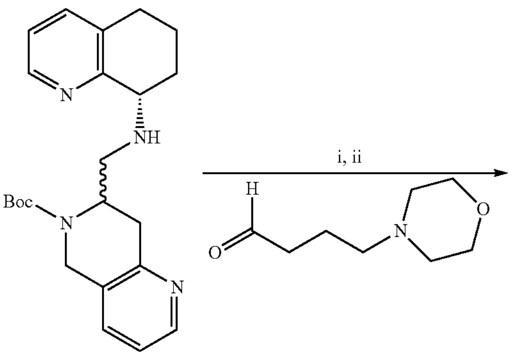

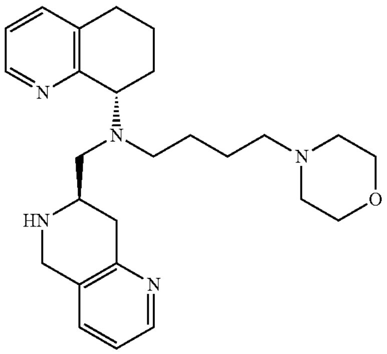

EMU-204

DI. Synthesis of tert-butyl (R)-5-((2S,6R)-2,6-dimethylmorpholino)-3-((methyl((S)-5,6,7,8-tetrahydroquinolin-8-yl)amino)methyl)-3,4-dihydroisoquinoline-2(1H)-carboxylate

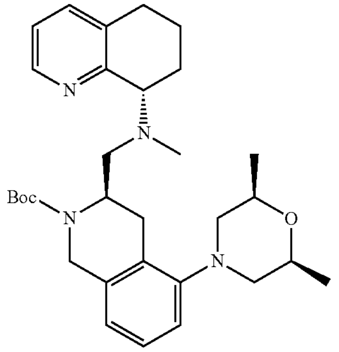 [SMILES: C[C@@H]1CN(c2cccc3c2C[C@H](CN(C)[C@H]2CCCc4cccnc42)N(C(=O)OC(C)(C)C)C3)C[C@H](C)O1]

Procedure B was used starting with tert-butyl (R)-5-bromo-3-((methyl((S)-5,6,7,8-tetrahydroquinolin-8-yl)amino)methyl)-3,4-dihydroisoquinoline-2(1H)-carboxylate and (2R,6S)-2,6-dimethylmorpholine to afford the title compound as a light-yellow foam (24% yield).

DJ. Synthesis of (S)—N—(((R)-5-((2S,6R)-2,6-dimethylmorpholino)-1,2,3,4-tetrahydroisoquinolin-3-yl)methyl)-N-methyl-5,6,7,8-tetrahydroquinolin-8-amine (EMU-247)

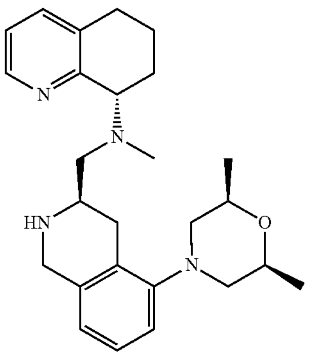 [SMILES: C[C@@H]1CN(c2cccc3c2C[C@H](CN(C)[C@H]2CCCc4cccnc42)NC3)C[C@H](C)O1]

Procedure A was used to afford the title compound as a white foam (81% yield). $^{1}$H NMR (400 MHz, $CDCl_3$) δ 8.43 (dd, J=4.7, 1.9 Hz, 1H), 7.32 (dd, J=7.7, 1.7 Hz, 1H), 7.12-7.01 (m, 2H), 6.81 (d, J=7.6 Hz, 1H), 6.74 (d, J=7.6 Hz, 1H), 4.07 (d, J=15.5 Hz, 1H), 4.00-3.86 (m, 2H), 3.77 (ddtd, J=16.0, 12.4, 6.2, 2.2 Hz, 2H), 2.87-2.76 (m, 6H), 2.71-2.47 (m, 3H), 2.42 (s, 3H), 2.35-2.08 (m, 3H), 2.04-1.91 (m, 2H), 1.76-1.56 (m, 1H), 1.23-1.19 (m, 1H), 1.17 (d, J=5.2 Hz, 3H), 1.13 (d, J=6.3 Hz, 3H). $^{13}$C NMR (101 MHz, $CDCl_3$) δ 156.77, 151.29, 145.81, 137.99, 135.70, 134.73, 129.73, 126.18, 121.86, 121.61, 116.93, 72.19, 72.03, 64.51, 59.84, 58.45, 57.26, 51.63, 48.16, 40.44, 29.73, 29.20, 25.47, 21.26, 19.08, 18.90. HRMS calculated for $C_{26}H_{37}N_4O$ 421.3478, found: 421.3472 [M+H].

DK. Synthesis of tert-butyl (R)-3-((((3,5-dimethylpyridin-2-yl)methyl)(methyl)amino)methyl)-5-morpholino-3,4-dihydroisoquinoline-2(1H)-carboxylate

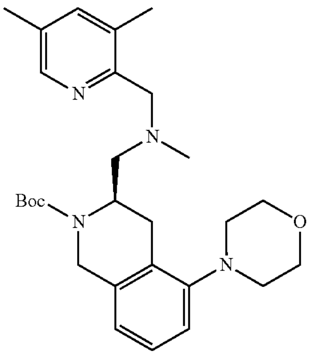 [SMILES: Cc1cnc(CN(C)C[C@H]2Cc3c(cccc3N3CCOCC3)CN2C(=O)OC(C)(C)C)c(C)c1]

Procedure B was used starting with tert-butyl (R)-5-bromo-3-((((3,5-dimethylpyridin-2-yl)methyl)(methyl)amino)methyl)-3,4-dihydroisoquinoline-2(1H)-carboxylate and morpholine. The crude material was purified with column chromatography using 0-5% DCM/MeOH to afford the title compound as an orange powder (80.2% yield).

DL. Synthesis of (R)-1-(3,5-dimethylpyridin-2-yl)-N-methyl-N-((5-morpholino-1,2,3,4-tetrahydroisoquinolin-3-yl)methyl)methanamine (EMU-260)

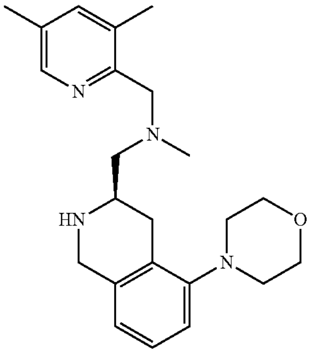 [SMILES: Cc1cnc(CN(C)C[C@H]2Cc3c(cccc3N3CCOCC3)CN2)c(C)c1]

Procedure A was used to prepare the title compound. $^{1}$H NMR (399 MHz, $CDCl_3$) δ 8.18 (d, J=1.5 Hz, 1H), 7.26 (d, J=2.1 Hz, 1H), 7.11 (t, J=7.8 Hz, 1H), 6.88 (d, J=7.7 Hz, 1H), 6.78 (d, J=7.6 Hz, 1H), 4.25 (br s, 1H), 4.11 (A of AB, $J_{AB}$=15.4 Hz, 1H), 4.06 (B of AB, $J_{AB}$=15.5 Hz, 1H), 3.86-3.74 (m, 4H), 3.70 (A of AB, $J_{AB}$=13.1 Hz, 1H), 3.61 (B of AB, $J_{AB}$=13.0 Hz, 1H), 3.07-2.90 (m, 4H), 2.76-2.69 (m, 2H), 2.65 (dd, J=12.7, 10.3 Hz, 1H), 2.56 (dd, J=12.4, 3.7 Hz, 1H), 2.37-2.22 (m, 1H), 2.36 (s, 3H), 2.31 (s, 3H), 2.26 (s, 3H). $^{13}$C NMR (100 MHz, $CDCl_3$) δ 153.75, 151.02, 146.43, 138.94, 135.41, 131.93, 131.76, 129.36, 126.33, 121.88, 116.95, 67.36, 62.54, 62.28, 52.16, 51.28, 47.63, 43.18, 29.27, 18.22, 17.86. HRMS calculated for $C_{23}H_{33}ON_4$ 381.26489, found: 381.26489 [M+H].

DM. Synthesis of tert-butyl (R)-5-bromo-3-((methyl((S)-5,6,7,8-tetrahydroquinolin-8-yl)amino)methyl)-3,4-dihydroisoquinoline-2(1H)-carboxylate

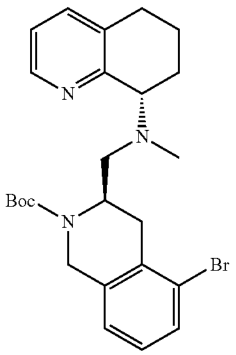 [SMILES: CN(C[C@H]1Cc2c(Br)cccc2CN1C(=O)OC(C)(C)C)[C@H]1CCCc2cccnc21]

(8S)—N-Methyl-5,6,7,8-tetrahydroquinolin-8-amine (5.7 g, 35.14 mmol) was dissolved in DCE (100 mL) and added sodium triacetoxyborohydride (19.19 g, 87.84 mmol) and stirred 30 minutes at room temperature. Then tert-butyl (3R)-5-bromo-3-formyl-3,4-dihydro-1H-isoquinoline-2-carboxylate (11.95 g, 35.14 mmol) was added to the reaction mixture and continued to stir at room temperature overnight.

The reaction was quenched with saturated $NaHCO_3$ solution. Aqueous phase was extracted with DCM twice. Combined organic layer was dried over anhydrous $MgSO_4$ and filtered, followed by solvent evaporation. The product was purified with column chromatography by starting with hexanes and increasing the polarity with EtOAc.

DN. Synthesis of tert-butyl (R)-5-(4-acetylpiperazin-1-yl)-3-((methyl((S)-5,6,7,8-tetrahydroquinolin-8-yl)amino)methyl)-3,4-dihydroisoquinoline-2(1H)-carboxylate

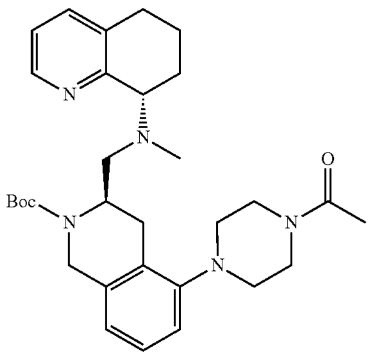 [SMILES: CC(=O)N1CCN(c2cccc3c2C[C@H](CN(C)[C@H]2CCCc4cccnc42)N(C(=O)OC(C)(C)C)C3)CC1]

tert-Butyl 5-bromo-3-[[methyl-[(8S)-5,6,7,8-tetrahydroquinolin-8-yl]amino]methyl]-3,4-dihydro-1H-isoquinoline-2-carboxylate (0.45 g, 0.9300 mmol), 1-acetylpiperazine (0.14 g, 1.11 mmol), tris(dibenzylideneacetone)dipalladium (0) (0.04 g, 0.0500 mmol), (±)-2,2''-bis(diphenylphosphino)-1,1''-binaphthalene (0.09 g, 0.1400 mmol), and cesium carbonate (0.42 g, 1.3 mmol) were suspended in degassed toluene (7 mL) in a microwave vial. Then the reaction was heated at 140° C. for two days. The reaction mixture was filtered over celite, washed with EtOAc, evaporated, and purified with column chromatography by starting with hexanes and increasing the polarity with EtOAc and then with MeOH.

DO. Synthesis of 1-(4-((R)-3-((methyl((S)-5,6,7,8-tetrahydroquinolin-8-yl)amino)methyl)-1,2,3,4-tetrahydroisoquinolin-5-yl)piperazin-1-yl)ethan-1-one (EMU-262)

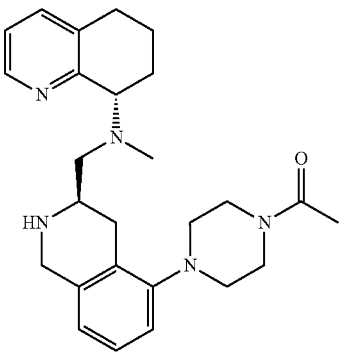 [SMILES: CC(=O)N1CCN(c2cccc3c2C[C@H](CN(C)[C@H]2CCCc4cccnc42)NC3)CC1]

tert-Butyl 5-(4-acetylpiperazin-1-yl)-3-[[methyl-[(8S)-5,6,7,8-tetrahydroquinolin-8-yl]amino]methyl]-3,4-dihydro-1H-isoquinoline-2-carboxylate (0.38 g, 0.7100 mmol) was dissolved in DCM (3 mL) and added trifluoroacetic acid (1.1 mL, 14.24 mmol) to the solution. The reaction solution was stirred at room temperature overnight. The reaction was basified with 1 N NaOH solution. Aqueous phase was extracted with DCM three times. Combine organic layer was dried over anhydrous $MgSO_4$ and filtered, followed by solvent evaporation. The product was purified with column chromatography by starting with DCM and increasing the polarity with DCM:MeOH:$NH_3$ (9:1:0.2). $^1H$ NMR (500 MHz, $CDCl_3$) δ 8.42 (d, J=4.0 Hz, 1H), 7.47 (d, J=7.7 Hz, 1H), 7.21 (t, J=7.8 Hz, 1H), 7.16 (dd, J=7.8, 4.8 Hz, 1H), 6.95 (d, J=7.9 Hz, 1H), 6.89 (d, J=7.7 Hz, 1H), 4.51 (d, J=15.8 Hz, 1H), 4.32 (d, J=15.8 Hz, 1H), 4.13-4.01 (m, 1H), 3.59 (t, J=16.4 Hz, 3H), 3.40 (d, J=10.3 Hz, 1H), 3.29 (t, J=12.7 Hz, 1H), 3.19-3.08 (m, 2H), 3.00-2.86 (m, 4H), 2.86-2.66 (m, 5H), 2.25 (s, 3H), 2.13 (s, 3H), 2.11-2.04 (m, 1H), 2.03-1.97 (m, 1H), 1.90 (tdd, J=12.8, 10.3, 2.8 Hz, 1H), 1.80-1.67 (m, 1H). $^{13}C$ NMR (126 MHz, $CDCl_3$) δ 169.20, 150.76, 146.12, 138.28, 134.67, 129.88, 127.60, 127.29, 122.45, 122.11, 118.60, 64.41, 57.74, 52.56, 52.38, 51.37, 46.73, 43.47, 41.85, 29.68, 28.95, 25.16, 21.36. HRMS calculated for $C_{26}H_{35}ON_5$ 434.29144; found 434.29173 [M+H].

DP. Synthesis of tert-butyl (R)-3-((methyl((S)-5,6,7,8-tetrahydroquinolin-8-yl)amino)methyl)-5-(4-(methylsulfonyl)piperazin-1-yl)-3,4-dihydroisoquinoline-2(1H)-carboxylate

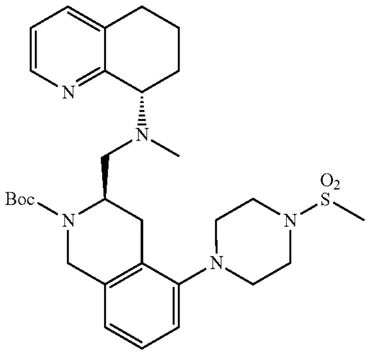 [SMILES: CN(C[C@H]1Cc2c(cccc2N2CCN(S(C)(=O)=O)CC2)CN1C(=O)OC(C)(C)C)[C@H]1CCCc2cccnc21]

tert-Butyl 5-bromo-3-[[methyl-[(8S)-5,6,7,8-tetrahydroquinolin-8-yl]amino]methyl]-3,4-dihydro-1H-isoquinoline-2-carboxylate (0.45 g, 0.9300 mmol), 1-methylsulfonylpiperazine (0.18 g, 1.11 mmol), tris(dibenzylideneacetone) dipalladium(0) (0.04 g, 0.0500 mmol), (±)-2,2''-bis (diphenylphosphino)-1,1''-binaphthalene (0.09 g, 0.1400 mmol), cesium carbonate (0.42 g, 1.3 mmol) were suspended in degassed toluene (7 mL) in a microwave vial. The reaction was heated at 140° C. for 2 days. Then it was filtered off over celite and washed with EtOAc, evaporated, and purified with column chromatography by starting hexanes and increasing the polarity with EtOAc.

DQ. Synthesis of (S)—N-methyl-N—(((R)-5-(4-(methylsulfonyl)piperazin-1-yl)-1,2,3,4-tetrahydroisoquinolin-3-yl)methyl)-5,6,7,8-tetrahydroquinolin-8-amine (EMU-263)

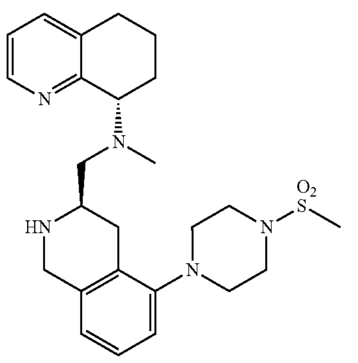 [SMILES: CN(C[C@H]1Cc2c(cccc2N2CCN(S(C)(=O)=O)CC2)CN1)[C@H]1CCCc2cccnc21]

tert-Butyl 5-(4-methylsulfonylpiperazin-1-yl)-3-[[methyl-[(8S)-5,6,7,8-tetrahydroquinolin-8-yl]amino]methyl]-3,4-dihydro-1H-isoquinoline-2-carboxylate (0.4 g, 0.7 mmol) and trifluoroacetic acid (1.08 mL, 14.04 mmol) were dissolved in DCM (3 mL) and stirred at room temperature overnight. The reaction was basified with 1 N NaOH to pH>12 and the aqueous phase was extracted with DCM three times. Combined organic layer was dried over anhydrous $MgSO_4$ and filtered, followed by solvent evaporation. The product was purified with column chromatography by starting with DCM and increasing the polarity with DCM:MeOH:$NH_3$ (9:1:0.2). $^1H$ NMR (500 MHz, $CDCl_3$) δ 8.42 (d, J=4.5 Hz, 1H), 7.40 (d, J=8.0 Hz, 1H), 7.18 (t, J=7.8 Hz, 1H), 7.11 (dd, J=7.7, 4.7 Hz, 1H), 6.95 (d, J=7.5 Hz, 1H), 6.87 (d, J=7.6 Hz, 1H), 4.32 (d, J=15.7 Hz, 1H), 4.20-4.11 (m, 1H), 4.04 (dd, J=9.9, 6.0 Hz, 1H), 3.44-3.25 (m, 4H), 3.19-3.11 (m, 1H), 3.07 (ddd, J=9.7, 7.4, 4.0 Hz, 2H), 3.01-2.93 (m, 3H), 2.92-2.86 (m, 1H), 2.85 (s, 3H), 2.84-2.75 (m, 1H), 2.75-2.67 (m, 1H), 2.61 (dd, J=16.7, 10.4 Hz, 1H), 2.37 (s, 3H), 2.07 (dqd, J=15.6, 5.0, 2.4 Hz, 1H), 2.00 (ddt, J=13.6, 5.3, 3.0 Hz, 1H), 1.97-1.87 (m, 1H), 1.74 (ddtd, J=16.1, 11.2, 5.1, 2.7 Hz, 1H), 1.28-1.19 (m, 2H). $^{13}C$ NMR (126 MHz, $CDCl_3$) δ 157.57, 150.47, 146.54, 137.42, 134.26, 128.53, 127.02, 122.50, 122.00, 118.11, 109.99, 64.43, 58.63, 52.12, 51.40, 46.33, 45.62, 34.66, 29.69, 29.11, 27.24, 25.39, 21.34. HRMS calculated for $C_{25}H_{35}O_2N_5S$ 470.25842; found 470.25848 [M+H].

DR. Synthesis of tert-butyl (R)-5-(4-(ethoxycarbonyl)piperazin-1-yl)-3-((methyl((S)-5,6,7,8-tetrahydroquinolin-8-yl)amino)methyl)-3,4-dihydroisoquinoline-2(1H)-carboxylate

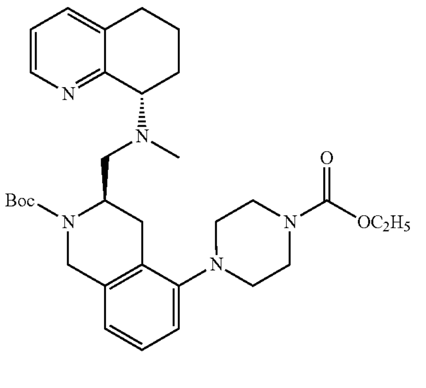 [SMILES: CCOC(=O)N1CCN(c2cccc3c2C[C@H](CN(C)[C@H]2CCCc4cccnc42)N(C(=O)OC(C)(C)C)C3)CC1]

tert-Butyl 5-bromo-3-[[methyl-[(8S)-5,6,7,8-tetrahydroquinolin-8-yl]amino]methyl]-3,4-dihydro-1H-isoquinoline-2-carboxylate (0.400 g, 0.8200 mmol), ethyl piperazine-1-carboxylate (156.11 mg, 0.9900 mmol), tris (dibenzylideneacetone)dipalladium(0) (0.038 g, 0.0400 mmol), (±)-2,2"-bis(diphenylphosphino)-1,1"-binaphthalene (0.077 g, 0.1200 mmol), cesium carbonate (0.376 g, 1.15 mmol) were suspended in degassed toluene (7 mL) in a microwave vial. Then the reaction was heated at 140° C. for two days. The reaction mixture was filtered over celite, washed with EtOAc, evaporated, and purified with column chromatography by starting hexanes and increasing the polarity with EtOAc and then with MeOH.

DS. Synthesis of ethyl 4-((R)-3-((methyl((S)-5,6,7,8-tetrahydroquinolin-8-yl)amino)methyl)-1,2,3,4-tetrahydroisoquinolin-5-yl)piperazine-1-carboxylate (EMU-261)

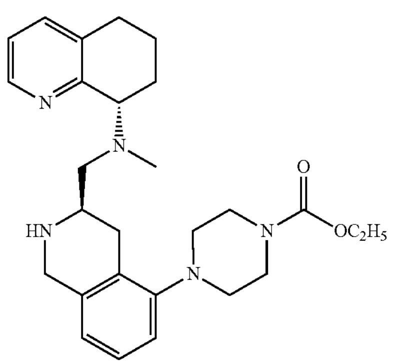 [SMILES: CCOC(=O)N1CCN(c2cccc3c2C[C@H](CN(C)[C@H]2CCCc4cccnc42)NC3)CC1]

tert-Butyl 5-(4-ethoxycarbonylpiperazin-1-yl)-3-[[methyl-[(8S)-5,6,7,8-tetrahydroquinolin-8-yl]amino]methyl]-3,4-dihydro-1H-isoquinoline-2-carboxylate (0.25 g, 0.4400 mmol) was dissolved in DCM (3 mL) and added trifluoroacetic acid (0.68 mL, 8.87 mmol) to the solution. It was stirred at room temperature overnight. The reaction was basified with 1 N NaOH solution. Aqueous phase was extracted with DCM three times. Combine organic layer was dried over anhydrous $MgSO_4$ and filtered, followed by solvent evaporation. The product was purified with column chromatography by starting with DCM and increasing the polarity with DCM:MeOH:$NH_3$ (9:1:0.2). $^1H$ NMR (500 MHz, $CDCl_3$) δ 8.40 (dd, J=4.8, 1.7 Hz, 1H), 7.43 (dd, J=7.8, 1.6 Hz, 1H), 7.20 (t, J=7.8 Hz, 1H), 7.13 (dd, J=7.7, 4.7 Hz, 1H), 6.94 (d, J=7.9 Hz, 1H), 6.87 (d, J=7.7 Hz, 1H), 4.47 (d, J=15.8 Hz, 1H), 4.27 (d, J=15.8 Hz, 1H), 4.17 (q, J=7.1 Hz, 2H), 4.06 (dd, J=10.2, 5.9 Hz, 1H), 3.89-3.39 (m, 5H), 3.34 (h, J=4.1 Hz, 1H), 3.18 (t, J=12.5 Hz, 1H), 3.09 (dt, J=14.2, 3.9 Hz, 2H), 2.93 (dd, J=11.6, 6.7 Hz, 2H), 2.85-2.66 (m, 5H), 2.28 (s, 3H), 2.12-2.05 (m, 1H), 2.05-1.95 (m, 1H), 1.90 (tdd, J=12.8, 10.2, 2.8 Hz, 1H), 1.80-1.66 (m, 1H), 1.28 (t, J=7.1 Hz, 3H). $^{13}C$ NMR (126 MHz, $CDCl_3$) δ 161.99, 157.26, 155.58, 151.10, 146.44, 137.82, 134.42, 127.40, 126.46, 122.24, 121.94, 118.38, 64.49, 61.46, 57.95, 52.43, 51.82, 44.19, 43.95, 29.68, 29.05, 25.70, 24.64, 21.40, 14.67. HRMS calculated for $C_{27}H_{37}O_2N_5$ 464.30200; found 464.30228 [M+H].

DT. Synthesis of tert-butyl (R)-5-(4-((benzyloxy) carbonyl)piperazin-1-yl)-3-((methyl((S)-5,6,7,8-tetrahydroquinolin-8-yl)amino)methyl)-3,4-dihydroisoquinoline-2(1H)-carboxylate

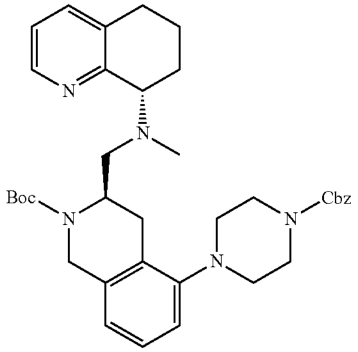 [SMILES: CN(C[C@H]1Cc2c(cccc2N2CCN(C(=O)OCc3ccccc3)CC2)CN1C(=O)OC(C)(C)C)[C@H]1CCCc2cccnc21]

To a solution of (8S)—N-methyl-5,6,7,8-tetrahydroquinolin-8-amine (3.03 g, 18.65 mmol) in DCE (75 mL) was added sodium triacetoxyborohydride (6.08 g, 28.69 mmol) and stirred for 10 minutes and then added the solution of tert-butyl (3R)-5-(4-benzyloxycarbonylpiperazin-1-yl)-3-formyl-3,4-dihydro-1H-isoquinoline-2-carboxylate (6.88 g, 14.35 mmol) in DCE (25 mL). The reaction mixture was stirred at room temperature overnight. The reaction was quenched with a saturated $NaHCO_3$ solution. Aqueous phase was extracted with DCM three times. Combined organic layer was dried over anhydrous $Na_2SO_4$ and filtered, followed by solvent evaporation. The product was purified with column chromatography using a EtOAc:hexanes (1:1) solvent system.

DU. Synthesis of tert-butyl (R)-3-((methyl((S)-5,6,7,8-tetrahydroquinolin-8-yl)amino)methyl)-5-(piperazin-1-yl)-3,4-dihydroisoquinoline-2(1H)-carboxylate

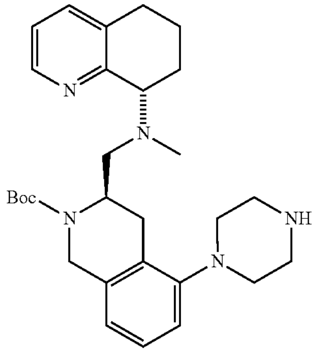 [SMILES: CN(C[C@H]1Cc2c(cccc2N2CCNCC2)CN1C(=O)OC(C)(C)C)[C@H]1CCCc2cccnc21]

tert-Butyl (3R)-5-(4-benzyloxycarbonylpiperazin-1-yl)-3-[[methyl-[(8S)-5,6,7,8-tetrahydroquinolin-8-yl]amino] methyl]-3,4-dihydro-1H-isoquinoline-2-carboxylate (0.50 g, 0.8 mmol) and palladium hydroxide on carbon (0.06 g, 0.08 mmol) were added to a round bottom flask in inert atmosphere and then ethanol (8 mL) was added, followed by ammonium formate (1.01 g, 15.98 mmol). The reaction mixture was heated to 45° C. and stirred for two hours. It was cooled to room temperature and filtered with celite. The filtrate was evaporated. The residue was dissolved in DCM and extracted with saturated sodium carbonate solution. Organic layer was dried over anhydrous $MgSO_4$ and filtered, followed by solvent evaporation. The product was used for the next reaction without further purification.

DV. Synthesis of tert-butyl (R)-5-(4-carbamoylpiperazin-1-yl)-3-((methyl((S)-5,6,7,8-tetrahydroquinolin-8-yl)amino)methyl)-3,4-dihydroisoquinoline-2(1H)-carboxylate

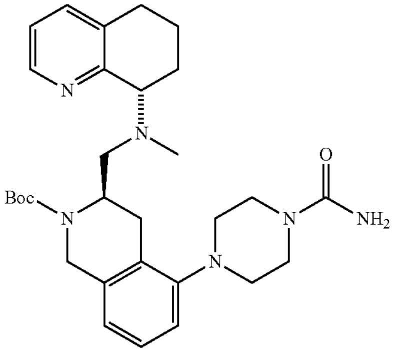 [SMILES: CN(C[C@H]1Cc2c(cccc2N2CCN(C(N)=O)CC2)CN1C(=O)OC(C)(C)C)[C@H]1CCCc2cccnc21]

To a solution of tert-butyl (3R)-3-[[methyl-[(8S)-5,6,7,8-tetrahydroquinolin-8-yl]amino]methyl]-5-piperazin-1-yl-3,4-dihydro-1H-isoquinoline-2-carboxylate (0.19 g, 0.39 mmol) in THF (4 mL), N,N-diisopropylethylamine (0.13 mL, 0.77 mmol) was added and then trimethylsilylisocyanate (0.08 mL, 0.5800 mmol) was added to the solution and stirred at room temperature overnight. The reaction was diluted with DCM and quenched with saturated $NH_4Cl$ solution and extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in MeOH) (90:10:2) to afford the title compound (86.6% yield).

DW. Synthesis of 4-((R)-3-((methyl((S)-5,6,7,8-tetrahydroquinolin-8-yl)amino)methyl)-1,2,3,4-tetrahydroisoquinolin-5-yl)piperazine-1-carboxamide (EMU-326)

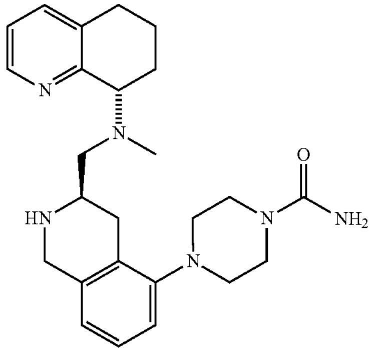 [SMILES: CN(C[C@H]1Cc2c(cccc2N2CCN(C(N)=O)CC2)CN1)[C@H]1CCCc2cccnc21]

tert-Butyl (3R)-5-(4-carbamoylpiperazin-1-yl)-3-[[methyl-[(8S)-5,6,7,8-tetrahydroquinolin-8-yl]amino]methyl]-3,4-dihydro-1H-isoquinoline-2-carboxylate (0.18 g, 0.33 mmol) was dissolved in DCM (5 mL) and trifluoroacetic acid (0.52 mL, 6.7 mmol) was added to the reaction solution and stirred at room temperature overnight. The reaction was basified with 1 N NaOH to pH>12. Aqueous phase was extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in MeOH) (80:20:3) to give the title compound (59.8% yield). $^1$H NMR (600 MHz, $CDCl_3$) δ 8.38 (dd, J=4.7, 1.7 Hz, 1H), 7.40 (dd, J=7.8, 1.7 Hz, 1H), 7.17 (t, J=7.8 Hz, 1H), 7.11 (dd, J=7.6, 4.7 Hz, 1H), 6.92-6.89 (m, 1H), 6.85 (d, J=7.6 Hz, 1H), 4.72 (s, 2H), 4.38 (d, J=15.6 Hz, 1H), 4.20 (d, J=15.6 Hz, 1H), 4.06 (dd, J=10.0, 6.1 Hz, 1H), 3.59-3.41 (m, 4H), 3.32-3.18 (m, 1H), 3.12-2.97 (m, 3H), 2.97-2.86 (m, 2H), 2.84-2.56 (m, 6H), 2.36 (s, 3H), 2.12-2.03 (m, 1H), 2.03-1.84 (m, 2H), 1.74 (ddtd, J=16.1, 11.3, 5.0, 2.8 Hz, 1H). $^{13}$C NMR (151 MHz, $CDCl_3$) δ 206.50, 158.16, 157.81, 150.98, 146.51, 137.63, 134.36, 128.09, 127.20, 122.16, 122.05, 120.66, 118.14, 64.34, 58.20, 53.44, 52.65, 51.61, 44.49, 29.70, 29.08, 26.32, 25.70, 21.43. HRMS: calculated for $C_{25}H_{35}N_6O$ 435.28669; found 435.28781 [M+H].

DX. Synthesis of tert-butyl (R)-5-(4-(dimethylcarbamoyl)piperazin-1-yl)-3-((methyl((S)-5,6,7,8-tetrahydroquinolin-8-yl)amino)methyl)-3,4-dihydroisoquinoline-2(1H)-carboxylate

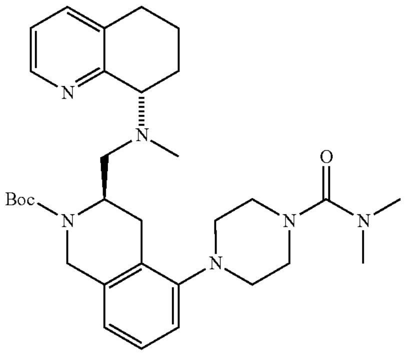 [SMILES: CN(C)C(=O)N1CCN(c2cccc3c2C[C@H](CN(C)[C@H]2CCCc4cccnc42)N(C(=O)OC(C)(C)C)C3)CC1]

tert-Butyl (3R)-3-[[methyl-[(8S)-5,6,7,8-tetrahydroquinolin-8-yl]amino]methyl]-5-piperazin-1-yl-3,4-dihydro-1H-isoquinoline-2-carboxylate (0.19 g, 0.39 mmol) was dissolved in DCM (4 mL), added N,N-diisopropylethylamine (0.13 mL, 0.77 mmol) and cooled to 0° C., and then added dimethylcarbamoyl chloride (0.05 mL, 0.58 mmol). The reaction mixture was warmed up to room temperature and stirred overnight. The reaction was basified with 1 N NaOH solution to pH>9. The aqueous layer was extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in MeOH) (90:10:2) to give the title compound (87% yield).

DY. Synthesis of N,N-dimethyl-4-((R)-3-((methyl((S)-5,6,7,8-tetrahydroquinolin-8-yl)amino)methyl)-1,2,3,4-tetrahydroisoquinolin-5-yl)piperazine-1-carboxamide (EMU-327)

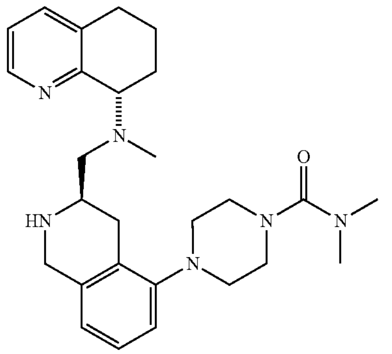 [SMILES: CN(C)C(=O)N1CCN(c2cccc3c2C[C@H](CN(C)[C@H]2CCCc4cccnc42)NC3)CC1]

tert-Butyl (3R)-5-[4-(dimethylcarbamoyl)piperazin-1-yl]-3-[[methyl-[(8S)-5,6,7,8-tetrahydroquinolin-8-yl]amino]methyl]-3,4-dihydro-1H-isoquinoline-2-carboxylate (0.19 g, 0.34 mmol) was dissolved in DCM (5 mL) and added trifluoroacetic acid (0.52 mL, 6.72 mmol) and stirred at room temperature overnight. The reaction mixture was basified with 1 N NaOH to pH>12. Aqueous phase was extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (80:20:3) to give the title compound (51.488% yield). $^1$H NMR (600 MHz, $CDCl_3$) δ 8.44 (d, J=4.4, 2.2 Hz, 1H), 7.31 (dd, J=7.7, 3.5 Hz, 1H), 7.04 (dtd, J=11.9, 7.8, 3.5 Hz, 2H), 6.81 (dd, J=7.6, 2.0 Hz, 1H), 6.74 (dd, J=7.6, 2.0 Hz, 1H), 4.70-4.65 (m, OH), 4.02 (dd, J=15.3, 3.0 Hz, 1H), 3.95-3.88 (m, 2H), 3.88-3.84 (m, OH), 3.41-3.18 (m, 5H), 2.99-2.90 (m, 3H), 2.87-2.82 (m, 1H), 2.81 (d, J=3.5 Hz, 6H), 2.80-2.74 (m, 3H), 2.73-2.69 (m, OH), 2.69-2.62 (m, 3H), 2.50 (d, J=3.9 Hz, 3H), 2.46 (ddd, J=12.7, 10.1, 3.0 Hz, 1H), 2.17-2.09 (m, 1H), 2.07-1.85 (m, 2H), 1.70-1.64 (m, 1H). $^{13}$C NMR (151 MHz, $CDCl_3$) δ 164.87, 162.84, 158.19, 151.11, 146.87, 136.65, 133.83, 130.09, 126.06, 122.08, 121.55, 116.90, 74.87, 64.47, 59.82, 51.68, 48.81, 47.30, 41.79, 38.56, 30.25, 29.26, 26.50, 21.34. HRMS calculated for $C_{27}H_{39}N_6O$ 463.31799; found 463.31894 [M+H].

DZ. Synthesis of tert-butyl (R)-3-((methyl((S)-5,6,7,8-tetrahydroquinolin-8-yl)amino)methyl)-5-(4-methyl-3-oxopiperazin-1-yl)-3,4-dihydroisoquinoline-2(1H)-carboxylate

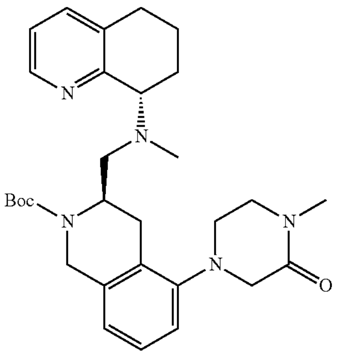 [SMILES: CN1CCN(c2cccc3c2C[C@H](CN(C)[C@H]2CCCc4cccnc42)N(C(=O)OC(C)(C)C)C3)CC1=O]

A 5 mL microwave tube equipped with a stir bar was charged with 250 mg of the bromide (0.510 mmol, 1 equiv), 76.3 mg of 1-methylpiperazin-2-one (0.670 mmol, 1.3 equiv), 48.0 mg of BINAP (0.080 mmol, 0.15 equiv), 0.251 g of $Cs_2CO_3$ (0.770 mmol, 1.5 equiv), and 23.5 mg of $Pd_2(dba)_3$ (0.030 mmol, 0.05 equiv), and the system was set under argon atmosphere. Then 3.0 mL of dioxane (degassed by bubbling through argon for 1 h) was added. After stirring at 140° C. for 2 h in the microwave reactor, EA was added, and the suspension was filtered through a celite plug and the plug was washed with EA. The organics were concentrated, and the crude product was purified on a silica gel column (10 g) using 0-15% MeOH in EA as eluent affording the product as a yellow foam (89% yield).

EA. Synthesis of 1-methyl-4-((R)-3-((methyl((S)-5,6,7,8-tetrahydroquinolin-8-yl)amino)methyl)-1,2,3,4-tetrahydroisoquinolin-5-yl)piperazin-2-one (EMU-255)

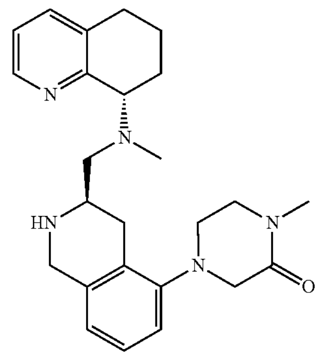 [SMILES: CN1CCN(c2cccc3c2C[C@H](CN(C)[C@H]2CCCc4cccnc42)NC3)CC1=O]

A 20 mL vial equipped with a stir bar was charged with 110 mg of the amine (0.210 mmol, 1 equiv) dissolved in 2.1 mL of $CH_2Cl_2$. Then 0.489 mL of $CF_3COOH$ (6.35 mmol, 30 equiv) was added. After stirring at room temperature for 12 h, the reaction mixture was quenched by the addition of 2 N NaOH solution, extracted with $CH_2Cl_2$ (3×) and dried over $Na_2SO_4$. The organics were concentrated, and the crude material was purified on a silica gel column using 0 to 30% Solvent 2 (Solvent 2=70% $CH_2Cl_2$, 30% MeOH, 3% $NH_4OH$) in $CH_2Cl_2$ as eluent affording the product as a white foam (92% yield). $^{1}H$ NMR (600 MHz, $CDCl_3$) δ 8.42 (dd, J=4.7, 1.8 Hz, 1H), 7.32 (dd, J=7.5, 1.8 Hz, 1H), 7.07 (t, J=7.8 Hz, 1H), 7.03 (dd, J=7.7, 4.6 Hz, 1H), 6.80-6.77 (m, 2H), 4.03 (A of AB, $J_{AB}$=15.5 Hz, 1H), 3.93 (dd, J=9.2, 5.6 Hz, 1H), 3.90 (B of AB, $J_{AB}$=15.9 Hz, 2H), 3.66 (A of AB, $J_{AB}$=16.5 Hz, 1H), 3.41 (B of AB, $J_{AB}$=16.5 Hz, 1H), 3.37-3.30 (m, 2H), 3.20 (dtd, J=11.0, 5.4, 4.6, 2.2 Hz, 1H), 3.12 (br s, 2H), 3.02-2.98 (m, 1H), 2.98 (s, 3H), 2.82-2.61 (m, 4H), 2.48 (ddd, J=13.6, 9.8, 3.4 Hz, 1H), 2.42 (s, 3H), 2.15 (dd, J=16.1, 10.4 Hz, 1H), 2.05-1.86 (m, 3H), 1.71-1.61 (m, 1H). $^{13}C$ NMR (151 MHz, $CDCl_3$) δ 167.37, 157.56, 148.58, 146.70, 136.92, 136.66, 133.80, 129.85, 126.10, 122.51, 121.49, 116.67, 64.43, 59.78, 55.49, 51.25, 48.83, 48.58, 48.37, 40.47, 33.87, 30.02, 29.13, 25.00, 21.20. LC-MS (ESI-API, 254 nm) 50-95% MeOH in $H_2O$ (0.1% $HCO_2H$), 1.00 mL/min, C18 column (Agilent Zorbax XDB-18, 50 mm×4.6 mm, 3.5 μm), m z=420.2 (M+H), 210.7 (M/2+H), t=0.465 min. HRMS (ESI+) calculated for $C_{25}H_{34}ON_5$ ([M+H]+): 420.2758, found: 420.2763.

EB. Synthesis of tert-butyl (R)-3-((methyl((S)-5,6,7,8-tetrahydroquinolin-8-yl)amino)methyl)-5-(3-oxopiperazin-1-yl)-3,4-dihydroisoquinoline-2(1H)-carboxylate

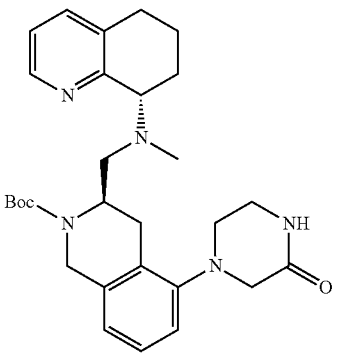 [SMILES: CN(C[C@H]1Cc2c(cccc2N2CCNC(=O)C2)CN1C(=O)OC(C)(C)C)[C@H]1CCCc2cccnc21]

A 5 mL microwave tube equipped with a stir bar was charged with 250 mg of the bromide (0.510 mmol, 1 equiv), 66.9 mg of the piperazin-2-one (0.670 mmol, 1.3 equiv), 48.0 mg of BINAP (0.080 mmol, 0.15 equiv), 0.251 g of $Cs_2CO_3$ (0.770 mmol, 1.5 equiv), and 23.5 mg of $Pd_2(dba)_3$ (0.030 mmol, 0.05 equiv), and the system was set under argon atmosphere. Then 3.0 mL of dioxane (degassed by bubbling argon for 1 h) was added. After stirring at 140° C. for 3 h in the microwave reactor. Then EA was added and the suspension was filtered through a celite plug and the plug was washed with EA. The organics were concentrated, and the crude product was purified a on silica gel column (30 g) using 0-30% MeOH in EA as eluent to afford the product as a brownish foam (45% yield).

EC. Synthesis of 4-((R)-3-((methyl((S)-5,6,7,8-tetrahydroquinolin-8-yl)amino)methyl)-1,2,3,4-tetrahydroisoquinolin-5-yl)piperazin-2-one (EMU-254)

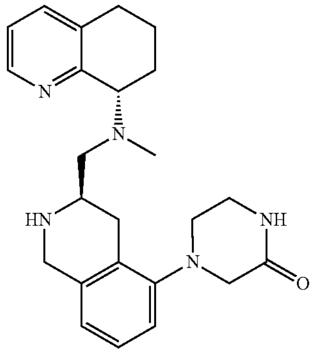 [SMILES: CN(C[C@H]1Cc2c(cccc2N2CCNC(=O)C2)CN1)[C@H]1CCCc2cccnc21]

A 20 mL vial equipped with a stir bar was charged with 102 mg of the amine (0.200 mmol, 1 equiv) dissolved in 2.0 mL of $CH_2Cl_{22}$. Then 0.466 mL of $CF_3COOH$ (6.05 mmol, 30 equiv) was added. After stirring at room temperature for 12 h, the reaction mixture was cooled in an ice bath, quenched by addition of 2 N NaOH solution to reach pH 11, extracted with $CH_2Cl_2$ (3×), and dried over $Na_2SO_4$. The organics were concentrated, and the crude material was purified on a silica gel column using 0 to 30% Solvent 2

(Solvent 2=70% $CH_2Cl_2$, 30% MeOH, 3% $NH_4OH$) in $CH_2Cl_2$ as eluent, affording the product as a white foam (81% yield). $^1H$ NMR (600 MHz, $CDCl_3$) δ 8.43 (dd, J=4.6, 2.1 Hz, 1H), 7.32 (d, J=7.6 Hz, 1H), 7.08 (t, J=7.8 Hz, 1H), 7.03 (dd, J=7.6, 4.7 Hz, 1H), 6.99 (s, 1H), 6.83 (d, J=6.5 Hz, 1H), 6.80 (d, J=7.5 Hz, 1H), 4.04 (A of AB, $J_{AB}$=15.6 Hz, 1H), 3.96-3.91 (m, 1H), 3.91 (B of AB, $J_{AB}$=16.3 Hz, 1H), 3.66 (A of AB, $J_{AB}$=16.7 Hz, 1H), 3.42 (B of AB, $J_{AB}$=17.2 Hz, 1H), 3.42-3.33 (m, 1H), 3.19-3.13 (m, 1H), 3.05-2.94 (m, 3H), 2.81 (d, J=16.1 Hz, 1H), 2.78-2.70 (m, 3H), 2.65 (d, J=16.6 Hz, 1H), 2.53-2.46 (m, 1H), 2.42 (s, 3H), 2.16 (dd, J=16.1, 10.6 Hz, 1H), 2.05-1.94 (m, 2H), 1.94-1.86 (m, 1H), 1.71-1.62 (m, 1H). $^{13}C$ NMR (151 MHz, $CDCl_3$) δ 170.00, 157.58, 148.75, 146.76, 136.97, 136.73, 133.85, 130.01, 126.18, 122.64, 121.55, 116.98, 64.50, 59.85, 55.26, 51.32, 48.39, 48.34, 41.34, 40.43, 30.04, 29.19, 24.95, 21.26. LC-MS (ESI-API, 254 nm) 75-95% MeOH in $H_2O$ (0.1% $HCO_2H$), 1.00 mL/min, C18 column (Agilent Zorbax XDB-18, 50 mm×4.6 mm, 3.5 μm), m z=428.2 (M+Na), 406.2 (M+H), 203.6 (M/2+H), t=0.450 min. HRMS (ESI+) calculated for $C_{24}H_{32}ON_5$ ([M+H]+): 406.2601, found 406.2607.

ED. Synthesis of tert-butyl (R)-5-((R)-hexahydropyrazino[2,1-c][1,4]oxazin-8(1H)-yl)-3-((methyl ((S)-5,6,7,8-tetrahydroquinolin-8-yl)amino)methyl)-3,4-dihydroisoquinoline-2(1H)-carboxylate

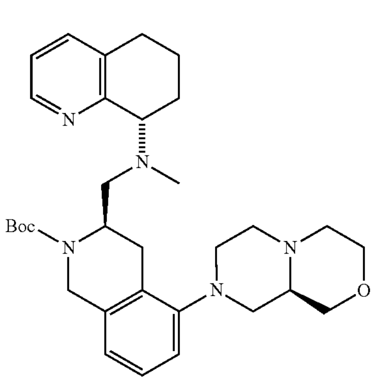 [SMILES: CN(C[C@H]1Cc2c(cccc2N2CCN3CCOC[C@H]3C2)CN1C(=O)OC(C)(C)C)[C@H]1CCCc2cccnc21]

224.4 mg (1.04 mmol) (R)-Octahydropyrazino[2,1-c][1,4]oxazine dihydrochloride and 245 mg (2.55 mmol) sodium t-butoxide were diluted with 5 mL of degassed 1,4-dioxane. The solution was heated for 24 h, resulting in a yellow solution. The solids were filtered off and the solution was added to a 5 mL microwave vial charged with 257.8 mg tert-butyl (3R)-5-bromo-3-[[methyl-[(8S)-5,6,7,8-tetrahydroquinolin-8-yl]amino]methyl]-3,4-dihydro-1H-isoquinoline-2-carboxylate, 45.8 mg (+/−)-2,2'-bis(diphenylphosphino)-1,1'-binaphthalene (rac-BINAP), 30.4 mg tris (dibenzylideneacetone)-di-palladium(0), and 217.4 mg of cesium carbonate. The resulting solution was degassed further with argon for 1.5 h. The vial was then heated for four 24-hour periods at 100° C. The vial was cooled, diluted with ethyl acetate, and stirred with silica gel. The solution was then filtered over a pad of silica gel with additional ethyl acetate, followed by solvent removal. The residue was then subjected to column chromatography the afford the product as an off-white foam (33% yield).

EE. Synthesis of (S)—N—(((R)-5-((R)-hexahydropyrazino[2,1-c][1,4]oxazin-8(1H)-yl)-1,2,3,4-tetrahydroisoquinolin-3-yl)methyl)-N-methyl-5,6,7,8-tetrahydroquinolin-8-amine (EMU-343)

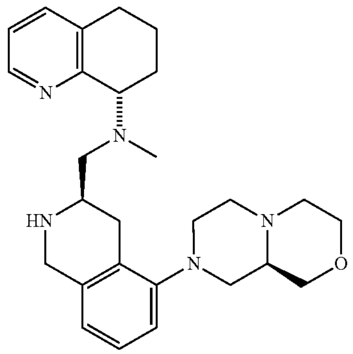 [SMILES: CN(C[C@H]1Cc2c(cccc2N2CCN3CCOC[C@H]3C2)CN1)[C@H]1CCCc2cccnc21]

151 mg (0.276 mmol) of tert-butyl (3R)-5-[(9aR)-3,4,6,7,9,9a-hexahydro-1H-pyrazino[2,1-c][1,4]oxazin-8-yl]-3-[[methyl-[(8S)-5,6,7,8-tetrahydroquinolin-8-yl]amino]methyl]-3,4-dihydro-1H-isoquinoline-2-carboxylate was dissolved in 3 mL of 1,4-dioxane. Next, 0.25 mL of HCl (conc.) was added and the mixture stirred for 24 hours. The reaction was then quenched and basified to pH 14 with NaOH solution (5 M) with a precipitate forming. The resulting slurry was then extracted with $Et_2O$ (solids dissolved) followed by washing with NaOH (0.5 M) and NaCl solutions. The aqueous layer was re-extracted with $Et_2O$ and the organic layer was combined and dried over $MgSO_4$. Filtration and solvent removal were followed by column chromatography (24 g GOLD ISCO column, 80/20 DCM/MeOH (1 N $NH_3$)) which gave the title compound as a white foam (54.1% yield). $^1H$ NMR (600 MHz, $CDCl_3$) δ 8.45 (d, J=4.7 Hz, 1H), 7.34 (d, J=7.6 Hz, 1H), 7.06 (m, 2H), 6.83 (d, J=7.9 Hz, 1H), 6.76 (d, J=7.6 Hz, 1H), 4.08 (d, J=15.4 Hz, 1H), 3.95 (m, 1H), 3.94 (d, J=16.0 Hz, 1H), 3.85 (dd, J=11.4, 3.2 Hz, 1H), 3.72 (td, J=11.4, 2.3 Hz, 1H), 3.67 (dd, J=11.0, 2.9 Hz, 1H), 3.33 (t, J=10.6 Hz, 1H), 3.33 (t, 1H, J=12 Hz), 3.27 (bs, 2H), 2.99 (dd, J=11.6, 2.9 Hz, 1H), 2.87-2.62 (m, 11H), 2.58 (dd, J=12.6, 9.8 Hz, 1H), 2.50 (td, J=11.2, 2.9 Hz, 1H), 2.44 (s, 4H), 2.21 (dd, J=16.1, 10.3 Hz, 1H), 2.04 (m, 2H), 1.94 (td, J=12.1, 9.5 Hz, 1H), 1.7 (m, 1H). $^{13}C$ NMR (151 MHz, $CDCl_3$) δ 158.01, 151.07, 146.89, 136.88, 136.39, 134.01, 129.96, 126.24, 122.06, 121.70, 116.99, 69.30, 67.17, 64.62, 60.62, 60.05, 54.83, 54.14, 52.38, 52.28, 51.74, 48.38, 40.55, 29.91, 29.32, 25.68, 21.39. HRMS: calculated for $C_{27}H_{38}N_5O$ 448.30709, found 448.30683. LC-MS (UV, 254 nm, $[M+H^+]$ 448): 100% (MeCN/$H_2O$), 98% (MeOH/$H_2O$).

EF. Synthesis of tert-butyl 3-((((S)-3,4-dihydro-2H-pyrano[3,2-b]pyridin-4-yl)(methyl)amino)methyl)-5-(4-methylpiperazin-1-yl)-3,4-dihydroisoquinoline-2(1H)-carboxylate

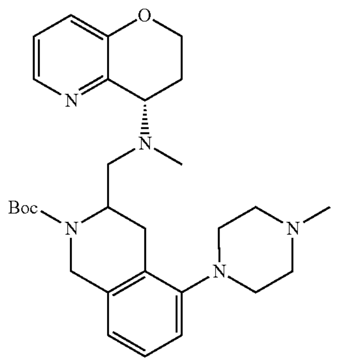 [SMILES: CN1CCN(c2cccc3c2CC(CN(C)[C@H]2CCOc4cccnc42)N(C(=O)OC(C)(C)C)C3)CC1]

(4S)—N-methyl-3,4-dihydro-2H-pyrano[3,2-b]pyridin-4-amine (135.00 mg, 0.82 mmol) was dissolved in DCM (5 mL) and sodium triacetoxyborohydride (366.84 mg, 1.64 mmol) was added to the solution. Then tert-butyl (3R)-3-formyl-5-(4-methylpiperazin-1-yl)-3,4-dihydro-1H-isoquinoline-2-carboxylate (295.54 mg, 0.8200 mmol) and acetic acid (47.07 μL, 0.82 mmol) were added to the reaction mixture and it was stirred overnight. The reaction was basified with 1 N NaOH to pH>12 and the phases were separated. The aqueous phase was extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in MeOH) (80:20:6) to afford the title compound (83.854% yield).

EG. Synthesis of (4S)—N-methyl-N-((5-(4-methylpiperazin-1-yl)-1,2,3,4-tetrahydroisoquinolin-3-yl)methyl)-3,4-dihydro-2H-pyrano[3,2-b]pyridin-4-amine (EMU-320)

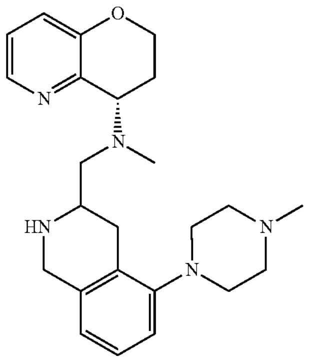 [SMILES: CN1CCN(c2cccc3c2CC(CN(C)[C@H]2CCOc4cccnc42)NC3)CC1]

tert-Butyl (3R)-3-[[[(4S)-3,4-dihydro-2H-pyrano[3,2-b]pyridin-4-yl]-methyl-amino]methyl]-5-(4-methylpiperazin-1-yl)-3,4-dihydro-1H-isoquinoline-2-carboxylate (0.35 g, 0.69 mmol) was dissolved in DCM (5 mL), and trifluoroacetic acid (1.06 mL, 13.79 mmol) was added to the solution. The reaction was stirred overnight at room temperature. The reaction was basified with 1 N NaOH to pH>12 and the phases were separated. The aqueous phase was extracted with DCM three times. Combined organic layer was dried over anhydrous $MgSO_4$ and filtered, followed by solvent evaporation. The residue was purified with column chromatography by starting with DCM and increasing the polarity with DCM:MeOH:$NH_3$ (7 N in MeOH) (90:10:2) to afford the title compound (64.063% yield). $^1$H NMR (600 MHz, $CDCl_3$) δ 8.18 (t, J=3.0 Hz, 1H), 7.28 (t, J=7.8 Hz, 1H), 7.25 (d, J=3.0 Hz, 2H), 7.13 (dd, J=8.0, 1.1 Hz, 1H), 7.03 (dd, J=7.7, 1.1 Hz, 1H), 4.44-4.38 (m, 3H), 4.23 (dd, J=10.4, 6.0 Hz, 1H), 4.17 (td, J=11.3, 2.2 Hz, 1H), 3.69 (tt, J=10.5, 4.2 Hz, 1H), 3.29-3.28 (m, 1H), 3.26 (d, J=4.5 Hz, 1H), 3.17-3.10 (m, 2H), 3.05-3.02 (m, 8H), 3.00-2.93 (m, 1H), 2.76 (dd, J=17.3, 10.5 Hz, 1H), 2.66 (s, 3H), 2.27 (dddd, J=14.1, 11.4, 10.3, 3.9 Hz, 1H), 2.11 (s, 3H). $^{13}$C NMR (151 MHz, MeOD) δ 153.66, 150.05, 143.07, 140.78, 129.61, 127.69, 127.02, 125.47, 123.98, 122.73, 119.29, 72.97, 65.39, 61.13, 57.58, 54.25, 51.64, 43.80, 42.98, 33.60, 25.32, 20.51. HRMS calculated for $C_{24}H_{34}N_5O$ 408.27579, found 408.27576 [M+H].

EH. Synthesis of tert-butyl (S)-3-((methyl((S)-5,6,7,8-tetrahydroquinolin-8-yl)amino)methyl)-5-(4-methyl-2-oxopiperazin-1-yl)-3,4-dihydroisoquinoline-2(1H)-carboxylate

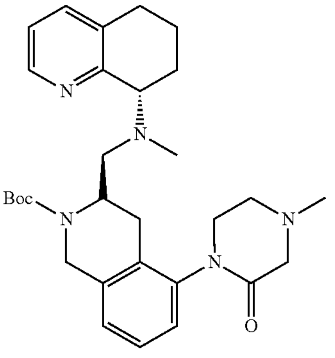

A mixture of tert-butyl (3R)-5-bromo-3-[[methyl-[(8S)-5,6,7,8-tetrahydroquinolin-8-yl]amino]methyl]-3,4-dihydro-1H-isoquinoline-2-carboxylate (0.4 g, 0.8200 mmol), 4-methylpiperazin-2-one (0.19 g, 1.64 mmol), N,N-dimethylethane-1,2-diamine (8.85 μL, 0.0800 mmol), potassium carbonate (0.23 g, 1.64 mmol), and copper(i) iodide (0.01 g, 0.0400 mmol) in anhydrous toluene was heated to 120° C. with stirring for five days. After cooling to room temperature, the reaction was poured to water and extracted with EtOAc twice. Combined organic layer was dried over anhydrous $MgSO_4$ and filtered, followed by solvent evaporation. The product was purified with column chromatography by first starting with hexanes:EtOAc and increasing the polarity to 100% EtOAc and then to 10% MeOH in EtOAc.

EL. Synthesis of 4-methyl-1-((S)-3-((methyl((S)-5,6,7,8-tetrahydroquinolin-8-yl)amino)methyl)-1,2,3,4-tetrahydroisoquinolin-5-yl)piperazin-2-one (EMU-251)

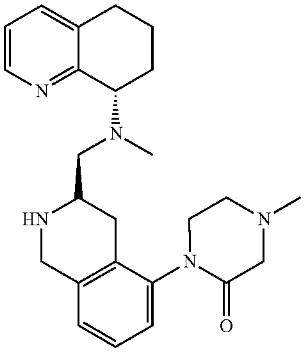

tert-Butyl (S)-3-((methyl((S)-5,6,7,8-tetrahydroquinolin-8-yl)amino)methyl)-5-(4-methyl-2-oxopiperazin-1-yl)-3,4-dihydroisoquinoline-2(1H)-carboxylate (100 mg, 0.19 mmol) was dissolved in 2 mL DCM and added TFA (0.30 mL, 3.84 mmol) and stirred at room temperature overnight. The mixture was basified with 1 N NaOH to pH>10-12 and extracted with DCM three times. Combined organic layer was dried over anhydrous $MgSO_4$ and filtered, followed by solvent evaporation. The product was purified with column chromatography using DCM:MeOH:$NH_3$ (9:1:0.2) to afford a white-color foam (38% yield). $^1$H NMR (600 MHz, $CDCl_3$) δ 8.44-8.36 (m, 1H), 7.49 (d, J=7.7 Hz, 1H), 7.33-7.24 (m, 1H), 7.20-7.15 (m, 1H), 7.15-7.07 (m, 2H), 4.57 (d, J=15.5 Hz, 1H), 4.32-4.17 (m, 2H), 3.64-3.56 (m, 1H), 3.55-3.41 (m, 2H), 3.38-3.27 (m, 2H), 3.19 (dd, J=16.6, 11.5 Hz, 1H), 3.12 (dd, J=14.2, 3.1 Hz, 1H), 3.08-2.94 (m, 1H), 2.88-2.77 (m, 2H), 2.77-2.67 (m, 3H), 2.41 (s, 3H), 2.26 (s, 3H), 2.15-2.06 (m, 1H), 2.06-1.95 (m, 1H), 1.94-1.82 (m, 1H), 1.34-1.14 (m, 2H). $^{13}$C NMR (151 MHz, $CDCl_3$) δ 166.93, 156.96, 145.77, 140.58, 138.62, 134.93, 130.49, 129.80, 128.26, 126.84, 126.60, 122.48, 65.30, 64.06, 59.49, 53.03, 51.93, 49.82, 45.12, 44.62, 29.68, 28.96, 25.07, 24.26, 21.31. HRMS calculated for $C_{25}H_{38}N_3O$ 420.27579, found 420.27572 [M+H].

EJ. Synthesis of EMU-178 and EMU-291

EMU-178

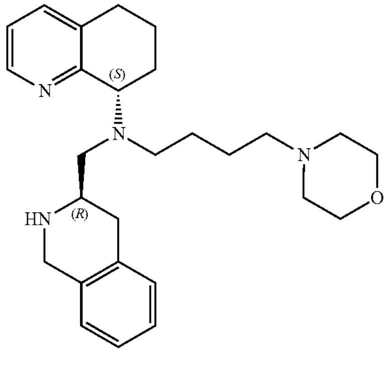

-continued

EMU-291

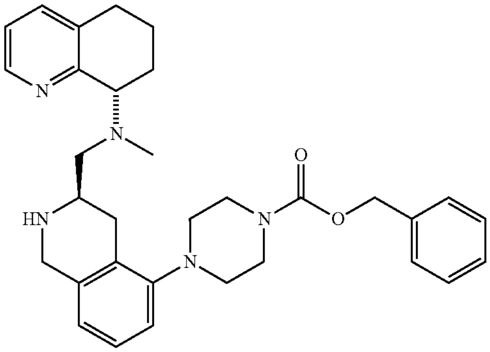

EMU-178 was synthesized using a method similar to EMU-204. EMU-291 was synthesized using a method similar to EMU-261.

Example 3. Bioanalytical Studies

A. Materials and Methods

Calcium Flux Assay

Calcium flux assay was performed by Eurofins or Bristol Myers Squibb. The method used by Eurofins is described below. The method used by Bristol Myers Squibb is described in Jecs, et al., *J. Med. Chem.*, 2022, 65, 5, 4058-4084.

Compound plate preparation: Vehicle controls and positive controls were prepared to ensure all assays were properly controlled. All wells were prepared using the Eurofins Discovery Services GPCRProfiler® Assay Buffer. The GPCRProfiler® Assay Buffer was a modified Hanks Balanced Salt Solution (HBSS) where HBSS was supplemented to contain 20 mM HEPES and 2.5 mM Probenecid at pH 7.4.

| Reference Controls | | | | |
|---|---|---|---|---|
| GPCR Target | Reference Agonist | $E_{max}$ | Reference Antagonist | $I_{max}$ |
| CXCR4 | SDF-1α | 1.25 μM | AMD3100 | 10 μM |

Agonist assay (first addition): Compound(s) supplied were plated in duplicate for each concentration assayed. During the agonist assay, the concentration(s) reflects accommodation for the dilution of compound during the antagonist assay. Please see below for further details. Reference agonist for each GPCR assayed was prepared in a similar manner to serve as assay control. The reference agonist for each GPCR was included at $E_{max}$ (the concentration where the reference agonist elicited a maximal response). The agonist assay was conducted on a FLIPR$^{TETRA}$ instrument where the test compound(s), vehicle controls, and reference agonist were added to the assay plate after a fluorescence/luminescence baseline was established. The agonist assay was a total of 180 seconds and was used to assess each compound's ability to activate each GPCR assayed. Upon completion of the three minute agonist assay, the assay plate was incubated at 25° C. for a further two minutes. After the incubation period the antagonist assay was initiated.

Antagonist assay (second addition): Using a challenge potency value requested by the customer, all pre-incubated compound wells were challenged with a 16 nM concentration of reference agonist after establishment of a fluorescence/luminescence baseline. The antagonist assay was conducted using the same assay plate that was used for the agonist assay. The antagonist assay was conducted on a FLIPR$^{TETRA}$ instrument where vehicle controls and challenge concentration of reference agonist were added to appropriate wells. The antagonist assay was a total of 180 seconds and was used to assess each compound's ability to inhibit each GPCR assayed.

Data Processing—All plates were subjected to appropriate baseline corrections. Once baseline corrections were processed, maximum fluorescence/luminescence values were exported, and data manipulated to calculate percentage activation and percentage inhibition. Negative values of 0-30% may be the result of biological variance. Data manipulation calculation is as followed: ((Max RLU)−(Baseline Avg.))/((Positive Avg.)−(Baseline Avg.)).

cAMP Assay cAMP assay was performed using a method adapted from DiRaddo et al., *J. Pharmacol. Exp. Ther.,* 2014, 349:373-382.

Materials, reagents, and instrument—Advanced DMEM (Gibco), trypsin EDTA (0.05%, phenol red), L-glutamine, HBSS buffer with and without $Ca^{2+}/Mg^{2+}$ (Gibco), antibiotic-antimycotic (Gibco), hygromycin B, and geneticin selective antibiotic (G418 sulfate) were purchased from Invitrogen. Forskolin (Tocris), SDF-1α (R&D Systems), HEPES (Sigma Aldrich), FBS (Atlanta Biologicals), D-luciferin (Gold Biotechnology), sterile 60 mm tissue culture dishes, and 96-well sterile tissue culture plates were purchased from Corning. Buffer: Loke's buffer (HBSS with $Ca^{2+}/Mg^{2+}$+20 mM HEPES); D-luciferin: 4 mM (final concentration); running buffer: Locke-Luc buffer (Loke's buffer+D-Luciferin); forskolin: 3 μM (final concentration); SDF-1a: 6.25 nM (final concentration, $EC_{80}$); positive control: AMD3100; plate reader: Biotek Synergy Neo2 multiplate reader.

The assay targeted CXCR4 expressed in CHO-gloSensor cells. It monitored GPCR activation based on forskolin-stimulated cAMP production in cells. The assay used a genetically encoded biosensor with its cAMP binding domain fused to luciferase. Binding of cAMP to the cAMP binding domain changed the conformation of the biosensor, leading to the activation of luciferase. The intensity of the luciferase signal (light output) resulted from the oxidation of D-luciferin to oxyluciferin is proportional to the amount of cAMP produced in the cells.

The assay was performed in triplicate using live cells in 96-well tissue culture plates. Cells were pre-incubated in the dark at room temperature for one hour in the presence of D-luciferin. Bioluminescence was quantified before and after the agonist/antagonist addition. Stock solution of forskolin and SDF-1a, was prepared in Locke-Luc buffer. Stock solutions of the test compounds were prepared in DMSO (10 mM); they were diluted by Locke's buffer for use in the assay.

CHO-Glo cells, a cell line stably expressing the GloSensor cAMP biosensor (Promega), were transfected with cDNA encoding human CXCR4 in Pires-AcGFP1 (Clontech) and a stable cell line was isolated (CXCR4-CHO-Glo cells). The CXCR4-CHO-Glo cells were grown to confluency on 60 mm tissue culture dishes. After trypsinization, the cells were plated on 96-well plates and incubated overnight. The next day, culture media in each well was aspirated and replaced with 100 μL Locke's buffer containing 4 mM D-luciferin, followed by incubation in the dark for one hour. Before the addition of agonist/antagonist, each plate was read five times at 2 min intervals to obtain basal bioluminescence values from each well. The average of these five pre-readings was used to normalize each well's response to account for differences in GloSensor expression and cell density. After five pre-readings, cAMP formation was initiated with the addition of 50 μL solution of test compound (TC) in Locke Luc buffer containing forskoline and SDF-1α. The final concentrations of forskolin and SDF-1α in the assay were 3 μM and 6.25 nM, respectively. Luminescence was measured immediately after the addition of the antagonist solution. The measurements were taken every two minutes for 30 minutes in kinetics mode after antagonist addition. $IC_{50}$ values were calculated from the 4-parameter logistic equation using Prism GraphPad.

Fluorometric CYP450 Inhibition Assay

Fluorometric CYP450 inhibition assay was performed at Emory University's Department of Chemistry or by Bristol Myers Squibb. The method used by Emory University's Department of Chemistry is described below. The method used by Bristol Myers Squibb is described in Jecs, et al., *J. Med. Chem.,* 2022, 65, 5, 4058-4084.

The CYP450 inhibition assays utilized microsomes from insect cells expressing human recombinant individual cDNA-expressed CYP isoforms 3A4 and 2D6, as well as the fluorogenic probe that produces fluorescent metabolite. Standard inhibitors were co-incubated with fluorogenic substrates and their inhibitory potential ($IC_{50}$) was determined. Assay conditions in terms of CYP450 protein concentration and time of incubation were standardized, enzyme kinetics parameters of each fluorescent probe substrate were estimated and $IC_{50}$ values of inhibitors were determined and validated on different days to check reproducibility.

Test compounds were prepared in 100% DMSO or 100% MeOH and did not exceed a final concentration of <0.2% in the final reaction. A 100 mM sodium phosphate buffer was prepared and adjusted to pH 7.4. In a separate falcon tube, a 2× enzyme/substrate (E/S) solution was prepared in phosphate buffer. The final concentration of CYP2D6 (CORNING®) and 7-amido-4-methyl coumaric acid (AMMC) was 10 nM and 4 μM, and CYP3A4 (CORNING®) and 7-benzyloxy-4-(trifluoromethyl) coumarin (BFC) was 20 nM and 40 μM, respectively. In a separate falcon tube, a 2×NADPH regenerating system (NRS) was prepared in phosphate buffer. The final concentration for each component in the assay was as follows:

CYP2D6 assay: 0.008 mM NADPH, 3.3 mM glucose 6-phosphate, 0.4 U of glucose-6-phosphate dehydrogenase per mL CYP3A4 assay: 2.45 mM NADPH, 24.7 mM glucose 6-phosphate, 1.25 U of glucose-6-phosphate dehydrogenase per mL Both enzymatic assays were conducted in a 96-well microtiter plate (Black, CORNING® COSTAR®) with a final volume of 100 μL. Preparation of the plate began with the addition of 74 μL of the E/S in the first well, and 50 μL to all subsequent wells (from 2-11). The test compounds (1 μL) were dissolved in the first well to give the first row a final volume of 75 μL. A 1:3 serial dilution of the test compound was conducted by removing 25 μL from the first well and diluting it with the second and so forth until the tenth row. Final concentrations yielded a range from 200 μM-0.01 μM. Well no. 11 contained no inhibitor, and well no. 12 contained no enzyme. Both were used as controls for background fluorescence. The plate was incubated for 30 min at 37° C. After incubation, the reaction was initiated by the addition of 50 μL of the 2×NRS to each well.

Immediately (within 1 min) the fluorescence was measured using a microplate reader (BIOTEK® Synergy Neo2). CYP2D6 was monitored at Ex/Em=410/460 nm, and CYP3A4 monitored at Ex/Em=410/538 nm in kinetic mode that scanned every 5 min for 60 mins. Data was exported and analyzed using Graph Pad Prism 7. Fluorescence readout was normalized to the fluorescence intensity of the reaction in the absence of the test substance (well no. 11, 0% inhibition) and the mixture of reaction components in the presence of "Inhibitor Cocktail" (well no. 12, 100% inhibition). The $IC_{50}$ value was derived after the data was fitted on a 10-point curve using a four-parameter logistic regression model.

Metabolic Stability Assay

Metabolic stability assay was performed at Emory University's Department of Chemistry or by Bristol Myers Squibb. The method used by Emory University's Department of Chemistry is described below. The method used by Bristol Myers Squibb is described in Jecs, et al., *J Med. Chem.*, 2022, 65, 5, 4058-4084.

The LC-MS/MS analysis was performed using Agilent 1260 Infinity II HPLC, coupled with an Agilent G6460 triple quadrupole mass spectrometer (Agilent Technologies, USA). All the data were acquired employing Agilent 6460 Quantitative Analysis data processing software.

Reverse-phase HPLC separation for each compound was achieved either on an Agilent Porshell 120 EC-$C_8$ column (2.1×50 mm, 2.7 μm), or on an Agilent Zorbax XDB C18 column (2.1×50 mm, 3.5 μm) with a mobile phase composed of methanol-water-formic acid or acetonitrile-water-formic acid (0.1%) at a flow rate of 0.5 mL/min (changes for some compounds). Each method was developed in the presence of an internal standard (ISTD) $d_5$-7-ethoxy coumarin. The column temperature was maintained at 40° C. for most of the samples otherwise noted. The detection was operated in the Agilent JetStream electrospray positive ionization using multiple reaction monitoring mode (MRM).

Other MS conditions were as follows: dwell time 100 ms; gas flow 10 L/min; nebulizer pressure 45 psi; delta EMV 200 V; fragmentor voltage and collision energy for individual compounds vary.

Test compounds were dissolved in 100% DMSO or 100% MeOH to make 10 mM stock solutions. Verapamil (Sigma Aldrich) aided as a positive control and was dissolved in 100% DMSO to make 10 mM stock solutions. The 10 mM stock solution of test and control compounds were further diluted in potassium phosphate buffer (100 mM, pH 7.4) to 500 μM to ensure the organic solvent content was <0.2%. Human liver microsomes (HLMs) were purchased from Xenotech at 20 mg/mL. NADPH (Sigma Aldrich) 10 mM stocks were prepared in deionized water.

The HLM assay was prepared in a 1.5 mL Eppendorf tube with a final volume of 1100 μL for duplicate runs. Each reaction contained phosphate buffer (928.4 μL), liver microsomes (55 μL), and test compound resulting in a final concentration of 3 μM (6.6 μL of 500 μM). The reaction was initiated with 110 μL of 10 mM NADPH. Aliquots (100 μL) were removed in duplicate at 0, 15, 30, 60, 120 min (for prodrug compounds) and 0, 5, 10, 15, 30 min (verapamil, positive control compound) time intervals and quenched in cold 100 mL of 100% methanol which contained internal standard (ISTD: $d_5$-7-ethoxy coumarin 4 μM). Before centrifugation each of the aliquoted tubes were vortexed to make sure compounds were in the solution. The aliquots were centrifuged at 12,000 g for 5 min and the supernatant removed and placed in an LC-MS vial. Each time point was assessed using LC-MS and the area, based on the extracted ion, was integrated with respect to the ISTD. Positive controls were conducted at a final volume of 550 μL to give each time point in a single run. A no-NADPH negative control with test or control compound was performed in a single run (150 μL) at the longest time point. Controls were processed and analyzed like the test compounds. Each time point was run in duplicates followed by in-between blank washes to avoid the carryover and to equilibrate the column.

The MLM assay was performed using the same procedures as those described above for the HLM assay.

PAMPA Assay

PAMPA assay was performed by BioAssay Systems Services or Bristol Myers Squibb. The method used by BioAssay Systems Services is described below. The method used by Bristol Myers Squibb is described in Jecs, et al., *J. Med. Chem.*, 2022, 65, 5, 4058-4084.

Stock solutions in DMSO for all compounds (10 mM) were thawed. The assay was performed in duplicate by following the PAMPA-096 procedure for sample plating. 4% Lecithin in dodecane solution was prepared by resuspending the dried lecithin with 750 μL dodecane. PBS pH 7.4 was used as the diluent. Two sets of plates and equilibrium solutions were incubated for 4 hours at room temperature. Acceptor and equilibrium solutions were analyzed in a UV plate. $OD_{280}$ nm was used for High Permeability Control (chloramphenicol). $OD_{270\ nm}$ was used for Medium Permeability Control (diclofenac) and Low Permeability Control (theophylline). $OD_{254\ nm}$ was used for the test compounds.

Data analysis was performed by using the peak absorbance for each respective test compound and Permeability Control to determine the Permeability Rate ($P_e$) via the following equation:

$$P_e = C \times -\ln(1 - \frac{OD_A}{OD_E})\text{cm/s}$$

where $OD_A$ is the absorbance of Acceptor Solution, $OD_E$ is the absorbance of the Equilibrium Standard, and C is determined by the equation below:

$$C = \frac{V_D \times V_A}{(V_D + V_A) \times \text{Area} \times \text{time}}\text{cm/s}$$

where Donor Volume ($V_D$) is 0.2 $cm^3$, Acceptor Volume ($V_A$) is 0.3 $cm^3$, and Membrane Area (Area) is 0.24 $cm^2$.

B. Results

TABLE 1

Bioanalytical characterization of exemplary CXCR4 antagonists

| Compd. No. | CXCR4 $Ca^{+2}$ Flux $IC_{50}$ (nM) | CXCR4 cAMP $IC_{50}$ (nM) | CYP450 $IC_{50}$ (μM) 3A4 | 2D6 | Liver Microsomes % rem. @ 10 min. or $T_{1/2}$ (min) H | M | PAMPA pH 7.4 (nm/s) |
|---|---|---|---|---|---|---|---|
| EMU-172 | 23.8 | 8.25 | >20 | 4.28 | 46.0 | 0.71 | 936 |
| EMU-250 | 9.6 | 76.6 | >20 | 3.10 | 17.9 | 17.3 | NA |
| EMU-271 | 88 | 453 | 17.1 | 18.9 | 12.3 | 65.9 | NA |
| EMU-272 | 120 | 281 | 8.10 | 2.58 | 19.3 | 61.1 | NA |
| EMU-274 | 26 | 1053 | 17.3 | >20 | 31.8 | 45.6 | NA |
| EMU-277 | 130 | 444 | 9.60 | >20 | 19.4 | 36.4 | NA |
| EMU-278 | 250 | 177 | 12.4 | >20 | 97.2 | 100 | NA |
| EMU-282 | 41 | 187 | 9.57 | >20 | 33.5 | 68.5 | NA |
| EMU-273 | 61 | 377 | >20 | >20 | 30.2 | 78.5 | 226 |
| EMU-184 | 145 | 103.9 | >20 | >20 | 80.7 | 99.7 | 30 |
| EMU-275 | 19 | 387 | 17.3 | >20 | 56.6 | 84 | 100 |
| EMU-279 | 18 | 136 | >20 | >20 | 72.8 | 87.3 | 101 |
| EMU-317 | 40 | 23.19 | >20 | 6.2 | 37.6 | 29.0 | 155 |
| EMU-318 | 270 | 172.60 | 6.0 | 11.1 | 26.4 | 10.0 | 166 |
| EMU-339 | 57 | 51.7 | 9.3 | >20 | 9.7 | 49.7 | 171 |
| EMU-338 | 32 | 81.7 | 17.3 | >20 | 5.3 | 29.3 | 157 |
| EMU-247 | 4705 | 1206 | 15.8 | 4.90 | 13.8 | 6.3 | NA |
| EMU-295 | 80 | 42.0 | 16.8 | 9.8 | 36.8 | 38.7 | 165 |
| EMU-308 | 78 | 37.75 | 14.9 | >20 | 94.4 | 38.0 | 138 |
| EMU-322 | 50 | 82.38 | 16.0 | >20 | 80.6 | 42.6 | 131 |
| EMU-266 | 68.9 | 48.26 | 32.6 | >50 | 79.1 | 83.2 | 197 |
| EMU-324 | 31 | 55.00 | 3.5 | >20 | 48.5 | 36.9 | 106 |
| EMU-325 | 120 | 164.66 | 6.0 | >20 | 63.6 | 29.7 | 123 |
| EMU-260 | 28 | 412 | 12.2 | 13.0 | 43.2 | 54.5 | 192 |
| EMU-319 | 26 | 83.76 | 4.6 | 10.4 | 73.5 | 80.9 | 160 |
| EMU-340 | 1000 | 7110 | 17.4 | >20 | 81.4 | 73.5 | NA |
| EMU-341 | 650 | 1600 | >20 | >20 | 84.7 | 87.2 | NA |
| EMU-342 | 2700 | 327 | >20 | >20 | 61.5 | 69.3 | NA |
| EMU-178 | 82.51 | NA | >20 | 0.44 | 52.6 | 3.68 | 212 |
| EMU-204 | 270 | NA | >20 | >20 | 100 | 19.6 | 215 |
| EMU-251 | 205 | 244 | 48.4 | >50 | $T_{1/2}$ = 288 | $T_{1/2}$ = 126 | 146 |
| EMU-254 | 52 | 31.61 | 14.3 | 8.1 | $T_{1/2}$ = 37 | $T_{1/2}$ = 35 | 118 |
| EMU-255 | 224 | 69.3 | 13.7 | 43.1 | $T_{1/2}$ = 16 | $T_{1/2}$ = 17 | 136 |
| EMU-261 | 990 | 3.7 | 7.82 | 4.47 | $T_{1/2}$ = 4.9 | $T_{1/2}$ = 7.4 | 146 |
| EMU-262 | 56 | 14.6 | 16.26 | >50 | $T_{1/2}$ = 16 | $T_{1/2}$ = 5.5 | 146 |
| EMU-263 | 312 | 48.3 | 24.12 | 34.39 | $T_{1/2}$ = 10 | $T_{1/2}$ = 3.0 | 134 |
| EMU-291 | NA | 2320 | >20 | >20 | 35.6 | 66.4 | NA |
| EMU-326 | NA | 491.5 | NA | NA | 87.1 | 78.3 | 76 |
| EMU-327 | NA | 683.7 | NA | NA | 11.00 | 38.10 | 122 |
| EMU-320 | 13 | 28.88 | 3.2 | NA | 74.7 | 91.6 | 167 |
| EMU-343 | 4.4 | 6.15 | >20 | 4.1 | 23.7 | 33.8 | NA |

What is claimed is:

1. A compound of Formula I or a pharmaceutically acceptable salt thereof,

Formula I

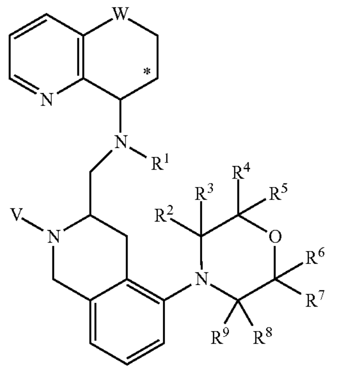

wherein W is $CH_2$ or O;

wherein Vis hydrogen, an optionally substituted $C_1$-$C_4$ alkyl, or an optionally substituted $C_1$-$C_4$ haloalkyl;

wherein:

(1) $R^1$ is an optionally substituted $C_1$-$C_4$ alkyl, an optionally substituted $C_1$-$C_4$ haloalkyl, an optionally substituted $C_1$-$C_4$ alkenyl, an optionally substituted $C_1$-$C_4$ haloalkenyl, an optionally substituted carbocyclyl, or an optionally substituted halocarbocyclyl, or (2) $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle;

wherein the pair of $R^8$ and $R^9$ is =O or =S;

wherein $R^2$, $R^3$, $R^4$, $R^5$, $R^6$, and $R^7$ are independently hydrogen, halogen, amino, optionally substituted hydroxyl, optionally substituted alkyl, or optionally substituted haloalkyl;

optionally wherein one or more of the following pairs—$R^2$ and $R^3$, $R^4$ and $R^5$, and $R^6$ and $R^7$—are independently =O or =S; and optionally wherein two of $R^2$, $R^3$, $R^4$, $R^5$, $R^6$, and $R^7$ joint together to form a bridge on the morpholine ring or a carbocycle or heterocycle that is connected to the morpholine ring in a spiro manner (i.e., the two rings are connected through a single common atom) or in a fused manner (i.e., the two rings share two adjacent atoms; in other words, the two rings share one covalent bond).

2. The compound of claim 1, wherein Formula I is in the following configuration.

Formula I′

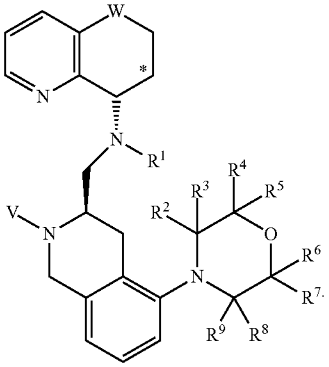

3. The compound of claim 1, wherein Wis $CH_2$ and Vis hydrogen.

4. The compound of claim 1, wherein $R^1$ is methyl.

5. The compound of claim 1, wherein $R^1$ is —$R^{10}$—$R^{11}$, wherein $R^{10}$ is an optionally substituted, bridging $C_1$-$C_4$ alkylene (alkyl bridge), an optionally substituted, bridging $C_1$-$C_4$ haloalkylene (haloalkyl bridge), an optionally substituted, bridging $C_1$-$C_4$ alkenylene (alkenyl bridge), an optionally substituted, bridging $C_1$-$C_4$ haloalkenylene (haloalkenyl bridge), an optionally substituted, bridging carbocyclylene (carbocyclyl bridge), or an optionally substituted, bridging halocarbocyclylene (halocarbocyclyl bridge), and wherein $R^{11}$ is hydrogen, halogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, —$NR^aR^b$, —$NR^c[C(=O)R^d]$, or —$OR^f$, wherein $R^a$, $R^b$, $R^c$, $R^d$, and $R^f$ are independently hydrogen, alkyl, haloalkyl, alkenyl, haloalkenyl, alkynyl, haloalkynyl, carbocyclyl, alkylcarbocyclyl, haloalkylcarbocyclyl, halocarbocyclyl, heterocyclyl, alkylheterocyclyl, haloalkylheterocyclyl, haloheterocyclyl, aryl, alkylaryl, haloalkylaryl, haloaryl, heteroaryl, alkylheteroaryl, haloalkylheteroaryl, or haloheteroaryl.

6. The compound of claim 5, wherein $R^1$ is selected from the group consisting of: ethyl, propyl, isopropyl, butyl, isobutyl, —$(CH_2)_2OH$, —$(CH_2)_2NH_2$, —$(CH_2)_3OH$, —$(CH_2)_3NH_2$, —$(CH_2)_4OH$, —$(CH_2)_4NH_2$, —$(CH_2)_3CF_3$,

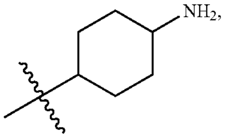

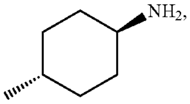

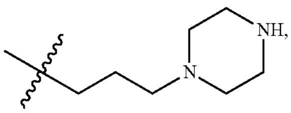

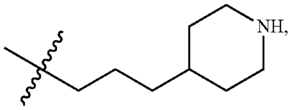

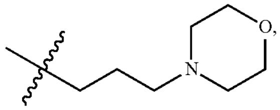

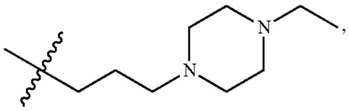

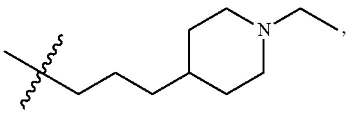

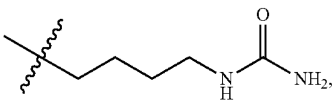

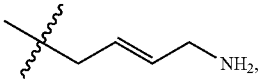

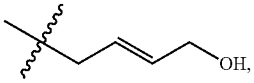

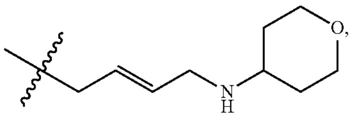

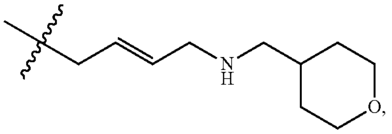

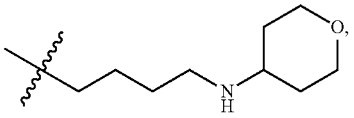

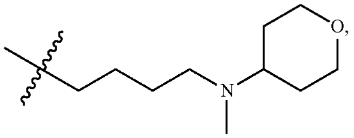

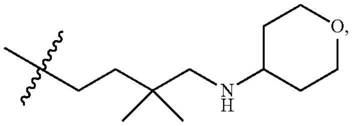

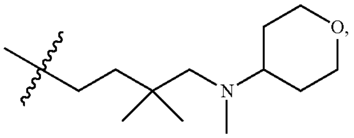

-continued

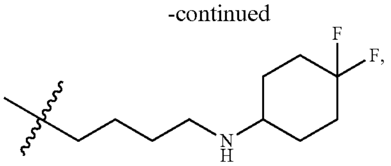

and

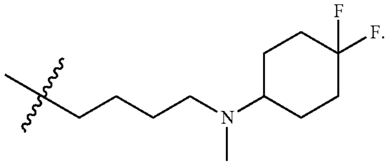

7. The compound of claim 1, wherein $R^1$ is an optionally substituted, bridging $C_1$-$C_4$ alkyl, an optionally substituted, bridging $C_1$-$C_4$ haloalkyl, an optionally substituted, bridging $C_1$-$C_4$ alkenyl, or an optionally substituted, bridging $C_1$-$C_4$ haloalkenyl, joining the carbon atom labeled by the "*" sign to form an optionally substituted heterocycle, wherein the optionally substituted heterocycle is five- or six-membered.

8. The compound of claim 7, wherein the optionally substituted heterocycle is a piperidine.

9. The compound of claim 1, selected from the group consisting of:

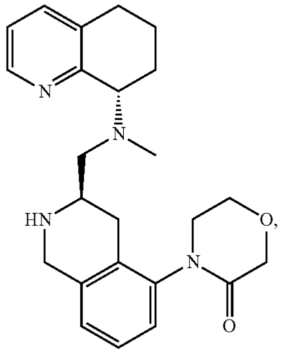

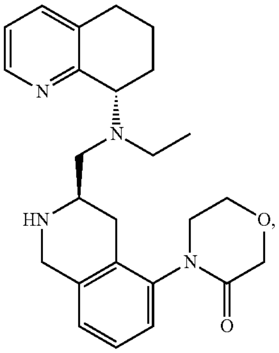

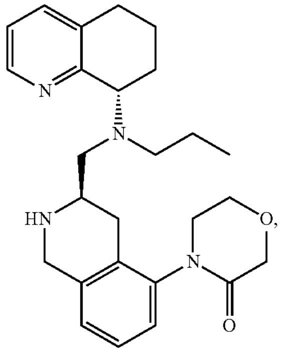

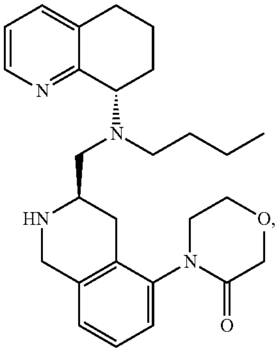

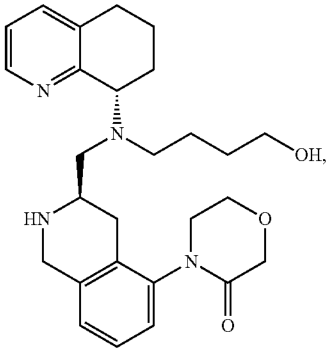

-continued

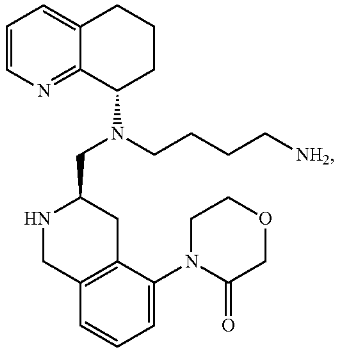

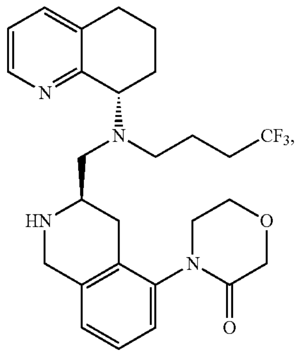

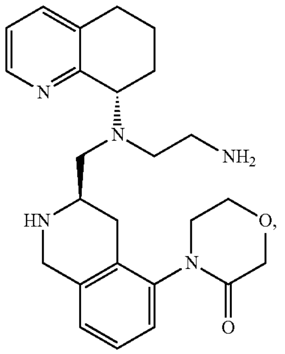

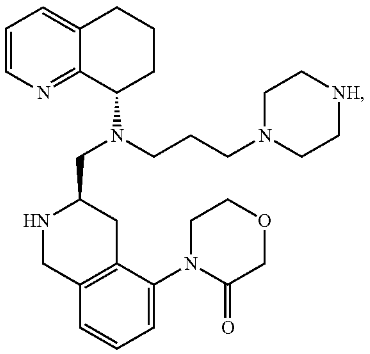

-continued
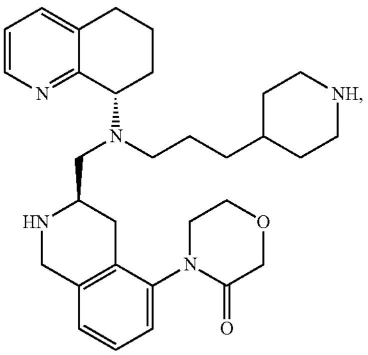
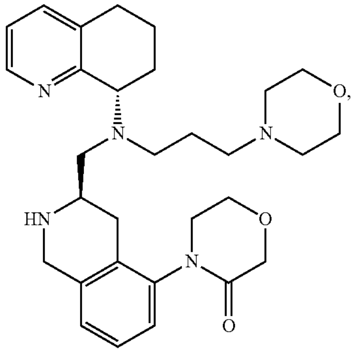
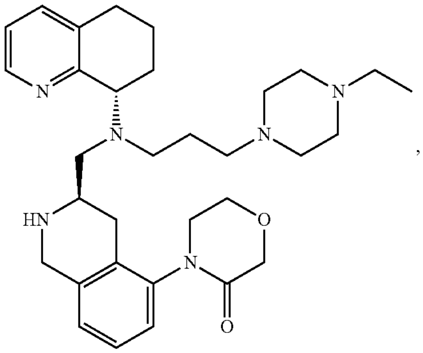
,
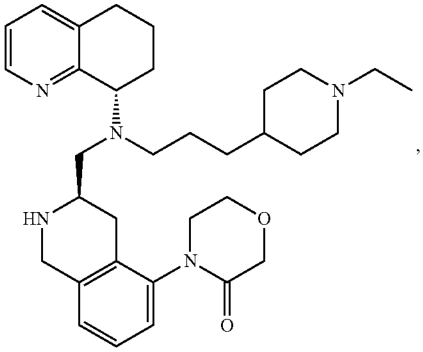
,
-continued
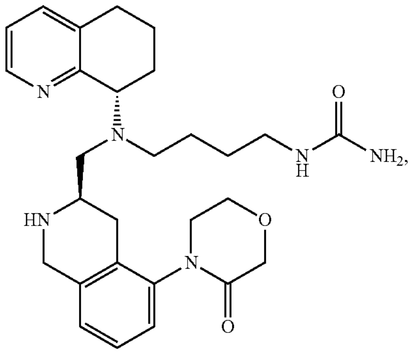
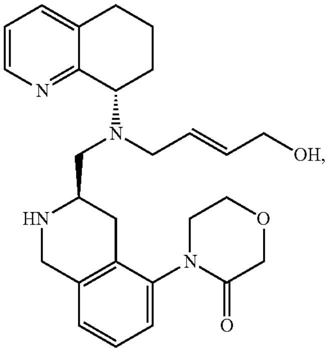
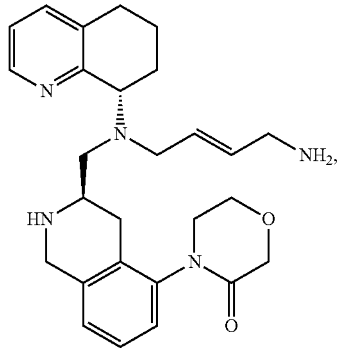
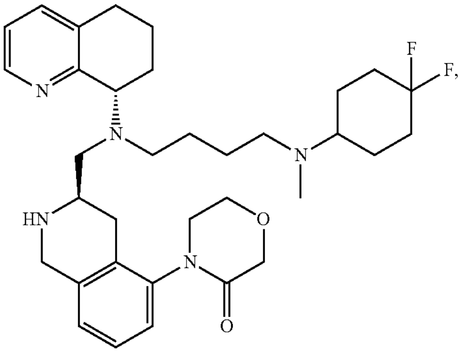

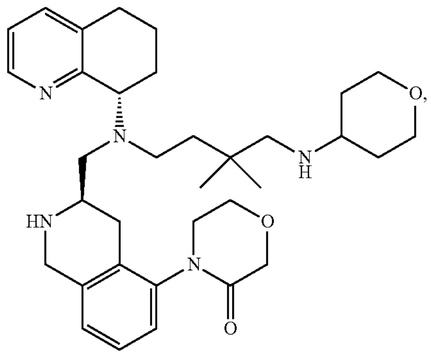
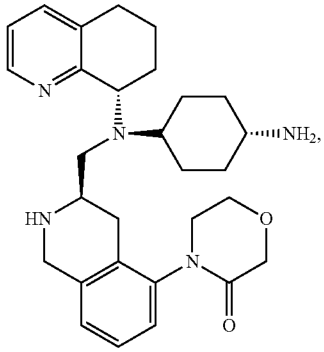
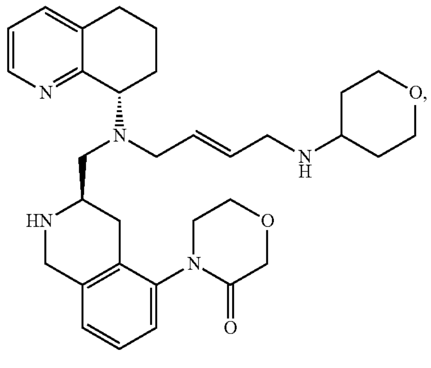
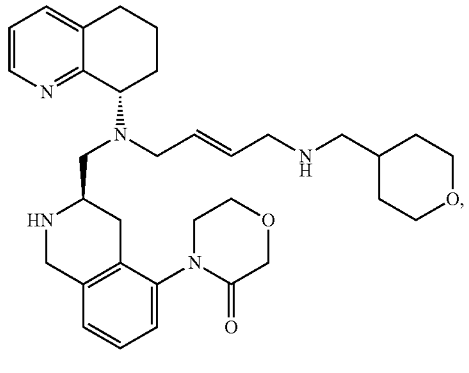
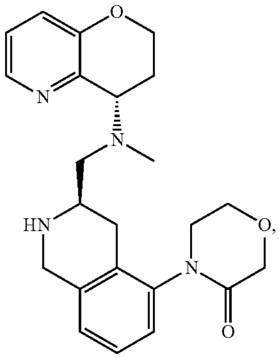
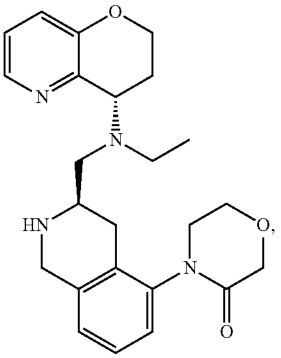
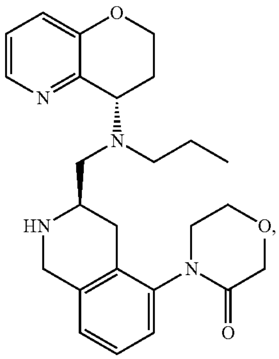
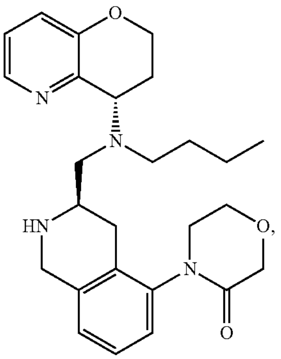
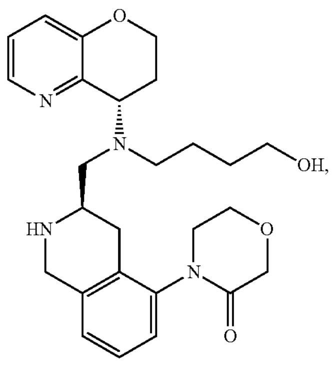
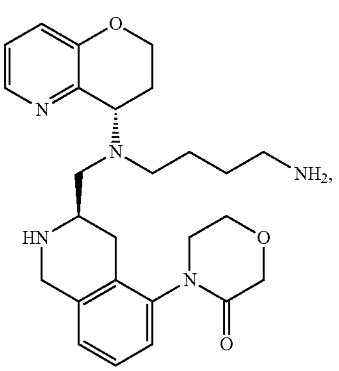

-continued
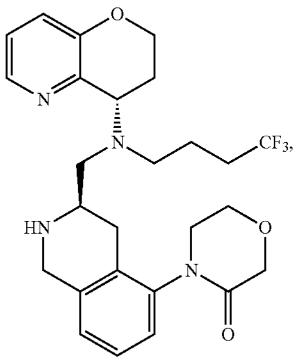
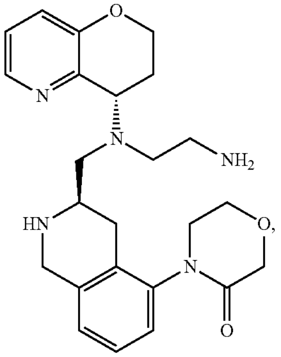
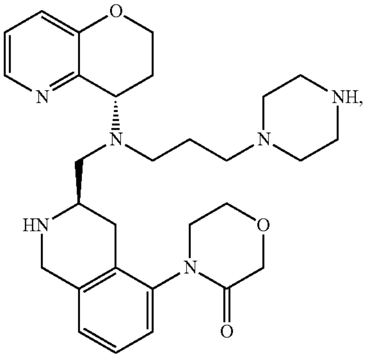
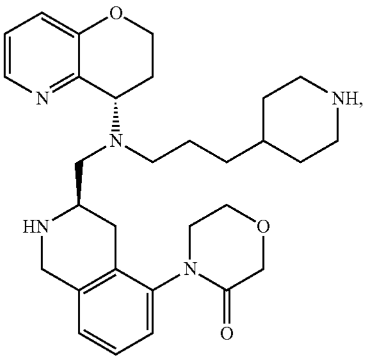
-continued
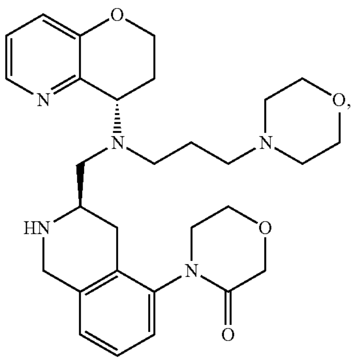
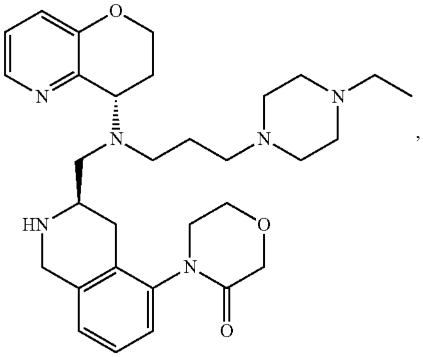
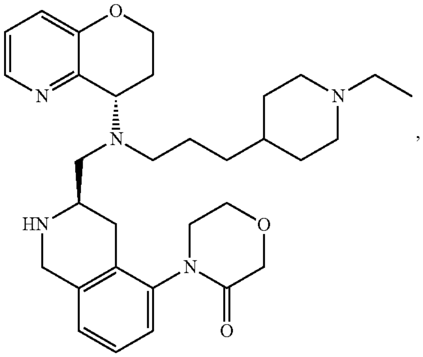
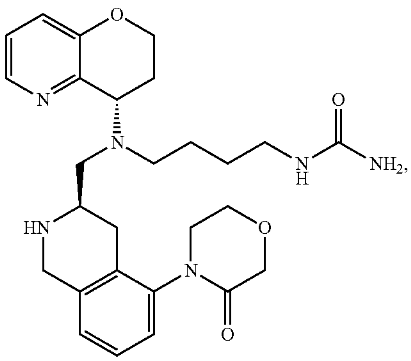

-continued
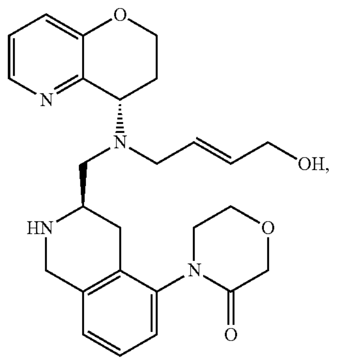
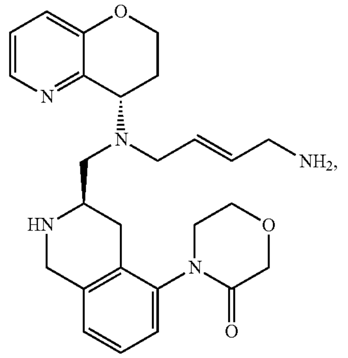
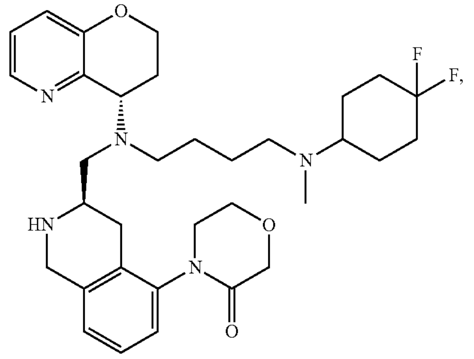
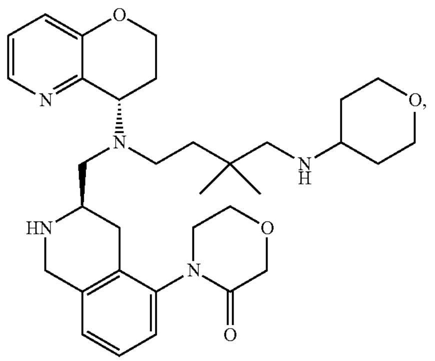
-continued
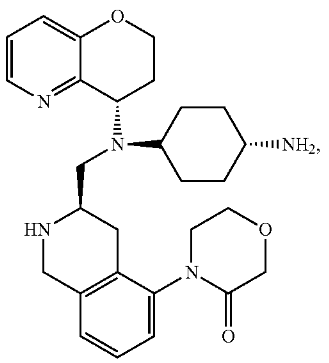
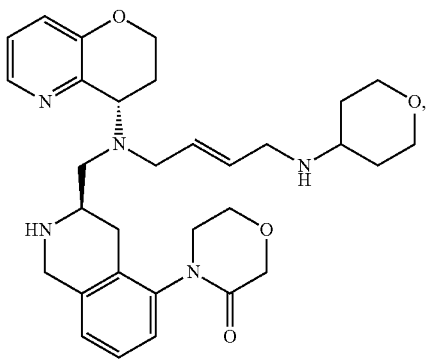
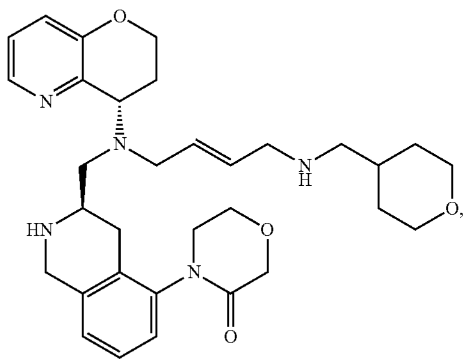
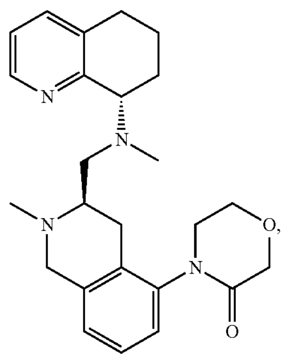
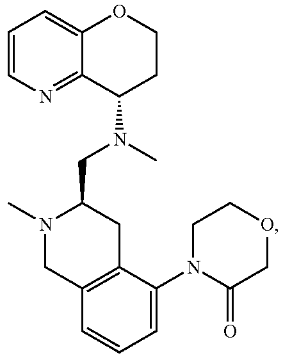

-continued

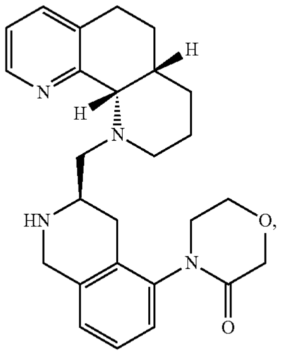

and

-continued

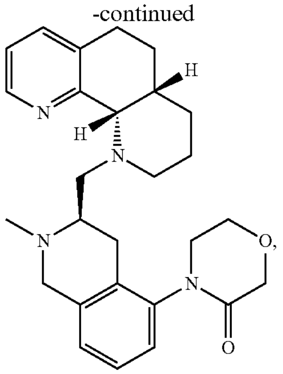

or is a pharmaceutically acceptable salt thereof.

10. A pharmaceutical formulation, comprising the compound of claim 1 and a pharmaceutically acceptable carrier.

11. The pharmaceutical formulation of claim 10, wherein the pharmaceutical formulation is in the form of tablet, capsule, pill, gel, cream, granule, solution, suspension, emulsion, or nanoparticulate formulation.

12. The pharmaceutical formulation of claim 10, wherein the pharmaceutical formulation is an oral formulation.

* * * * *